(12) United States Patent
Andrews et al.

(10) Patent No.: US 7,893,058 B2
(45) Date of Patent: Feb. 22, 2011

(54) IMIDAZOLOPYRAZINE COMPOUNDS USEFUL FOR THE TREATMENT OF DEGENERATIVE AND INFLAMMATORY DISEASES

(75) Inventors: Martin James Inglis Andrews, Mechelen (BE); Paul Edwards, Laval (CA); Philip Huxley, Freeland (GB); Wolfgang Schmidt, Saffron Walden (GB); Veronique Birault, Warren Terrace (GB); Mark Stuart Chambers, Saffron Walden (GB); Clifford John Harris, Eynsford (GB); Angus MacLeod, Saffron Walden (GB); Kim Louise Hirst, Saffron Walden (GB); Juha Andrew Clase, Mechelen (BE); Gregory Bar, Mechelen (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/803,015

(22) Filed: May 11, 2007

(65) Prior Publication Data

US 2007/0281943 A1 Dec. 6, 2007

Related U.S. Application Data

(60) Provisional application No. 60/747,223, filed on May 15, 2006, provisional application No. 60/928,539, filed on May 10, 2007, provisional application No. 60/928,600, filed on May 10, 2007, provisional application No. 60/928,639, filed on May 10, 2007, provisional application No. 60/928,568, filed on May 10, 2007.

(51) Int. Cl.
C07D 487/04 (2006.01)
A61K 31/4985 (2006.01)
(52) U.S. Cl. .................... 514/233.2; 514/249; 544/117; 544/350
(58) Field of Classification Search ................. 544/117, 544/350; 514/233.2, 249
See application file for complete search history.

(56) References Cited

U.S. PATENT DOCUMENTS

| | | | |
|---|---|---|---|
| 6,316,444 | B1 | 11/2001 | Hunt et al. |
| 7,157,460 | B2 | 1/2007 | Sun et al. |
| 7,186,832 | B2 | 3/2007 | Sun et al. |
| 2004/0220189 | A1 | 11/2004 | Sun et al. |
| 2005/0009832 | A1 | 1/2005 | Sun et al. |
| 2008/0090818 | A1 | 4/2008 | Andrews |

FOREIGN PATENT DOCUMENTS

| WO | WO 02/005688 | | 7/2002 |
|---|---|---|---|
| WO | WO 02/060492 | * | 8/2002 |
| WO | WO 2004/037814 | | 5/2004 |
| WO | WO 2004/072081 | | 8/2004 |
| WO | WO 2005/014599 | * | 2/2005 |
| WO | WO 2005/120513 | | 12/2005 |
| WO | WO 2006/053121 | | 5/2006 |
| WO | WO 2006/086545 | | 8/2006 |

OTHER PUBLICATIONS

Aberg, E, et al, Regulation of MAPK-activated Protein Kinase 5 Activity and Subcellular Localizatio by the Atypical MAPK ERK4/MAPK4, 2006, Jour. of Bio. Chem, pp. 35499-35510.
Bain, J, et al, The specificiies of protein kinase inhibitors: an update, 2003, Biochem, J., pp. 199-204.
Folmer, F, et al, Inhibition of TNFα-induced activation of nuclear factor κB by kava (Piper Methysticum) derivatives, 2006, Biochemical Pharmacology, pp. 1206-1218.
Gaestel, M, MAPKAP Kinases—Mks—Two's company, three's a crowd, 2006, Nature, pp. 120-130.
Kant, S, et al, Characterization of the Atypical MAPK ERK4 and its Activation of the MAPK-activated Protein Kinase MK5, 2006, Jour of Bio Chem, pp. 35511-35519.
New, Liguo, et al, PRAK, a novel protein kinase regulated by the p38 MAP Kinase, 1998, The EMBO Journal, pp. 3372-3384.
New, Liguo, et al, Regulation of PARK Subcellular Location by p38 MAP Kinases, 2003, Molecular Bio of the Cell, pp. 2603-2616.
Ni, H, et al, MAPKAPK5, a Novel Mitogen-Activated Protein Kinase (MAPK)-Activated Protein Kinase, Is a Substrate of the Extracellular-Regulated Kinase (ERK) and p38 Kinase, 1998, Biochem & Biophys Research Comm, pp. 492-496.
Schumacher, S, et al, Scaffolding by ERK3 regulates MK5 in development, 2004, The EMBO Journal, pp. 4770-4779.
Seternes, O, et al, Activation of MK5/PRAK by the atypical MAP kinase ERK3 defines a novel signal transduction pathway, 2004, The EMBO Journal, pp. 4780-4791.
Seternes, O, et al, Both Binding and Activationof p38 Mitogen-Activated Protein Kinase (MAPK) Play Esstential Roles in Regulation of the Nucleocytoplasmic Distribution of MAPK-Activated Protein Kinase 5 by Cellular Stress, 2002, Molecular and Cellular Biology, pp. 6931-6945.

(Continued)

Primary Examiner—Deepak Rao

(57) ABSTRACT

Novel imidazo[1,2-a]pyrazine compounds are disclosed that have a formula represented by the following:

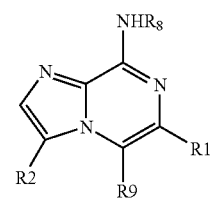

The compounds may be prepared as pharmaceutical compositions, and may be used for the prevention and treatment of a variety of conditions in mammals including humans, including by way of non-limiting example, arthritis, inflammation, and others.

55 Claims, 5 Drawing Sheets

OTHER PUBLICATIONS

Shi, Y, et al, Elimination of Protein Kinase MK5/PRAK Activity by Targeted Homologous Recombination, 2003, Molecular and Cellular Biology, pp. 7732-7741.

Sun, P, et al, PRAK Is Essential for ras-Induced Senescence and Tumor Suppression, 2007, Cell, pp. 295-308.

PubChem Public Chemical Database—K00159—Apr. 14, 2006.

PubChem Public Chemical Database—BioFocus 190_0027-7467—Oct. 20, 2006.

N. Gerits, et al., "Protein Kinase Inhibitors" Encyclopedia of Molecular Pharmacology (2007) ISBN 978-3-540-38916-3.

S. Kostenko, et al., "The Roles of Mammalian Mitogen-Activated Protein Kinase-Activating Protein Kinases (MAPKAPKs) in Cell Cycle Control" Progress in Cell Cycle Control Research, K.L. Chen (editor) (2008) ISBN: 978-1-60456-797-7.

Search Results, 2010.

* cited by examiner

Schematic view of a normal joint and its changes in rheumatoid arthritis
(From Smolen and Steiner, 2003).

Increased expression of MMP1 by SFs triggered with cytokines involved in rheumatoid arthritis pathology.

Dose-dependent inhibition of the "TNF-α -based trigger"-induced expression of MMP1 by SFs by a known anti-inflammatory compound.

Reduction, at the protein level, of the expression of MAPKAPK5 in SFs by infection of the cells with Ad-siRNA virus targeting MAPKAPK5.

Reduction of 'complex trigger' induced levels of MMP1 expression by SFs by an Ad-siRNA virus targeting MAPKAPK5.

IMIDAZOLOPYRAZINE COMPOUNDS USEFUL FOR THE TREATMENT OF DEGENERATIVE AND INFLAMMATORY DISEASES

CROSS REFERENCE TO RELATED APPLICATIONS

The present application claims the priority of co-pending provisional application U.S. Ser. No. 60/747,223 filed on May 15, 2006, and Ser. Nos. 60/928,539, 60/928,600 60/928,639 and 60/928,568, all bearing the same title as the present application, and filed on May 10, 2007, and the disclosures of such applications are incorporated by reference herein in their entireties. Applicants claim the benefits of such applications under 35 U.S.C. §119(e).

FIELD OF THE INVENTION

The present invention relates to a class of imidazolopyrazine compounds capable of binding to the active site of a serine/threonine kinase, the expression of which is involved in the pathway resulting in the degradation of extra-cellular matrix (ECM), joint degeneration and diseases involving such degradation and/or inflammation.

Diseases involving the degradation of extra-cellular matrix include, but are not limited to, psoriatic arthritis, juvenile arthritis, early arthritis, reactive arthritis, osteoarthritis, ankylosing spondylitis, osteoporosis, muskulo skeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, and ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Although it is widely accepted that RA is an auto-immune disease, there is no consensus concerning the precise mechanisms driving the 'initiation stage' of the disease. What is known is that the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). When the disease progresses, the cellular activation and cytokine production cascade becomes self-perpetuating. At this early stage, the destruction of joint structures is already very clear at this early stage. Thirty percent of the patients have radiographic evidence of bony erosions at the time of diagnosis and this proportion increases to 60 percent after two years.

Histological analysis of the joints of RA patients clearly evidences the mechanisms involved in the RA-associated degradative processes. This analysis shows that the main effector responsible for RA-associated joint degradation is the pannus, where the synovial fibroblast, by producing diverse proteolytic enzymes, is the prime driver of cartilage and bone erosion. A joint classically contains two adjacent bones that articulate on a cartilage layer and are surrounded by the synovial membrane and joint capsule. In the advanced RA patient, the synovium of joint increases in size to form the pannus, due to the proliferation of the synovial fibroblasts and the infiltration of mononuclear cells such as T-cells, B-cells, monocytes, macrophages and neutrophils. The pannus mediates the degradation of the adjacent cartilage, leading to the narrowing of the joint space, and has the potential to invade adjacent bone and cartilage. As bone and cartilage tissues are composed mainly of collagen type I or II, respectively, the pannus destructive and invasive properties are mediated by the secretion of collagenolytic proteases, principally the matrix metallo proteinases (MMPs). The erosion of the bone under and adjacent to the cartilage is also part of the RA process, and results principally from the presence of osteoclasts at the interface of bone and pannus. Osteoclasts are multinucleated cells that, upon adhesion to the bone tissue, form a closed compartment, within which the osteoclasts secrete proteases (Cathepsin K, MMP9) that degrade the bone tissue. The osteoclast population in the joint is abnormally increased by osteoblast formation from precursor cells induced by the secretion of the receptor activator of NFκB ligand (RANKL) by activated SFs and T-cells.

Various collagen types have a key role in defining the stability of the extracellular matrix (ECM). Collagens type I and collagen type II, for example, are the main components of bone and cartilage, respectively. Collagen proteins typically organise into multimeric structures referred to as collagen fibrils. Native collagen fibrils are very resistant to proteolytic cleavage. Only a few types of ECM-degrading proteins have been reported to have the capacity to degrade native collagen: MMPs and Cathepsins. Among the Cathepsins, cathepsin K, which is active mainly in osteoclasts, is the best characterised. Among the MMPs, MMP1, MMP2, MMP8 MMP13 and MMP14 are known to have collagenolytic properties. The correlation between an increased expression of MMP1 by synovial fibroblasts (SFs) and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation. Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, muscular skeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reiff et al., 2005), cardio-vascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

The 471-amino acid serine/threonine kinase identified as Mitogen-Activated Protein Kinase-Activated Protein Kinase 5 (MAPKAPK5 or PRAK) is expressed in a wide panel of tissues. The protein contains its catalytic domain at the N-terminal end and both a nuclear localization signal (NLS) and nuclear export signal (NES) at its C-terminal end. Endogenous MAPKAPK5 is predominantly present in the cytoplasm, but stress or cytokine activation of the cells mediates its translocation into the nucleus (New et al., 2003). This event is dependent on phosphorylation of MAPKAPK5. Thr182 is the regulatory phosphorylation site of MAPKAPK5. Although the p38α kinase is able to phosphorylate MAPKAPK5 in an overexpression setting, experiments with endogenous MAPKAPK5 do not support this hypothesis (Shi et al., 2003). MAPKAPK5 knock-out mice have been generated that are viable and fertile. The phenotype of these mice is quite different from that of mice deficient for MAPKAPK2, a MAPKAPK5 related kinase that is regulated by p38α (Shi et al., 2003). This indicates that the function of each protein is distinct and that neither kinase can compensate for the other's activity. Taken together, MAPKAPK5 and MAPKAPK2 represent distinct targets with a non-redundant role. MAPK6 (also referred to as ERK3) has recently been identified as a physiologically relevant substrate for MAPKAPK5, defining a novel signal transduction pathway (Seternes et al., 2004).

BACKGROUND OF THE INVENTION

NSAIDS (Non-steroidal anti-inflammatory drugs) are used to reduce the pain associated with RA and improve life quality of the patients. These drugs will not, however, put a brake on the RA-associated joint destruction.

Corticosteroids were found to decrease the progression of RA as detected radiographically and are used at low doses to treat part of the RA patients (30 to 60%). Serious side effects, however, are associated with long corticosteroid use (Skin thinning, osteoporosis, cataracts, hypertension, hyperlipidemia).

Synthetic DMARDs (Disease-Modifying Anti-Rheumatic Drugs) (e.g. methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve an ACR40 score after 24 months treatment with methotrexate. This means that, according to the American College of Rheumatology, only 30% of the patients do achieve a 50% improvement of their symptoms (O'Dell et al., 1996). In addition, the precise mechanism of action of DMARDs is often unclear.

Biological DMARDs (Infliximab, Etanercept, Adalimumab, Rituximab, CTLA4-Ig) are therapeutic proteins that do inactivate cytokines (e.g. TNF-α) or cells (e.g. T-cells or B-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR40) in disease symptoms in 50-60% of patients after 12 months therapy (St Clair et al., 2004). Some adverse events warnings for anti-TNF-α drugs exist, shedding a light on the side effects associated to this type of drugs. Increased risk for infections (tuberculosis) hematologic events and demyelinating disorders have been described for the TNF-α blockers (see also Gomez-Reino et al., 2003). Besides the serious side effects, the TNF-α blockers do also share the general disadvantages of the biological class of therapeutics, which are the unpleasant way of administration (frequent injections accompanied by infusion site reactions) and the high production cost. Newer agents in late development phase target T-cell costimulatory molecules and B-cells. The efficacy of these agents is expected to be similar to that of the TNF-α blockers. The fact that a variety of targeted therapies have similar but limited efficacies, suggests that there is a multiplicity of pathogenic factors for RA. This is also indicative for the deficiencies in our understanding of pathogenic events relevant to RA.

The current therapies for RA are not satisfactory due to a limited efficacy (No adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

US 2005/0009832 describes substituted imidazolo[1,2-a] pyrazine-8-yl-amines as modulators of protein kinases, including MAPKAPK5. W002/056888 describes inhibitors of MAPKAPK5 as TNF modulators able to regulate the expression of certain cytokines. Neither of these prior art references discloses any compound within the scope of the class of compounds described herein below.

SUMMARY OF THE INVENTION

The present invention is based on the discovery of that MAPKAPK5 functions in the pathway that results in the expression of MMP1, and that inhibitors of MAPKAPK5 activity, such as the compounds of the present invention, are useful for the treatment of diseases involving the abnormally high expression of MMP activity.

The present matrix metallo proteinase inhibiting compounds of the present invention may be described generally as imidazo[1,2-a]pyrazine-8-yl-amines substituted in the 5-position by an aromatic group capable of donating electrons to, and an 8-amino substituent capable of accepting electrons from, the imidazo[12.a]pyrazine ring. In particular, the 5-substituent group is characterized as having a hydrogen bond donor-acceptor functionality, whereas the substituent on the 8-amino group must be sufficiently electron-withdrawing to polarise the N-H bond of the 8-substituent, or alternatively, the 8-NH group is capable of participating in pi-conjugation with the substituent group on the 8-NH group.

The compounds of the present invention may show less toxicity, good absorption, good half-life, good solubility, low protein binding affinity, less drug-drug interaction, and good metabolic stability.

More particularly, the present invention relates to compounds having matrix metallo proteinase inhibiting properties in a mammalian cell, according to formula (I):

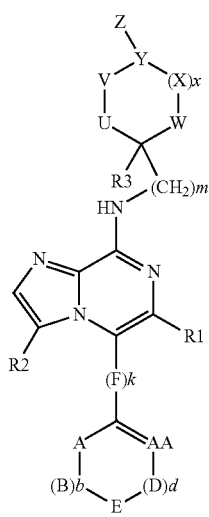

(I)

wherein:
A and B are independently CR4R", NR", oxygen or sulfur;
AA is CR4 or N;
D is C=O, CR4R" or NR";
E is NH or CR"R6, when k is zero, and is NH or CR"R6a, when k is one;
F is sulfur, oxygen or NH;
T is oxygen or NR;
U, V, W and X are independently CR"R7 or NR";
Y is CR" or N;
Z is hydrogen, amino, hydroxyl, lower alkoxy, carbamoyl, carboxyl, SO$_2$Rz, SO$_2$NRRz, —NR(CO)(CH2)d-Rz, —NRRz, —(CO)—ORz, —(CO)—NR(CH2)d-Rz, or

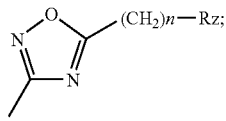

R is independently hydrogen or lower alkyl;
R' is independently hydrogen or lower alkyl;
R" is H or forms a double bond with an adjacent atom;
R1 is H; R4; or lower alkyl, lower cycloalkyl and lower alkyl-lower cycloalkyl, optionally substituted with one or more R4;
R2 is H; lower alkyl, lower cycloalkyl and lower alkyl-lower cycloalkyl, optionally substituted with one or more of F and Cl;
R3 is H or forms a double bond with an adjacent R";
R4 is H, F, Cl; CN; COOR5; OR5; C(O)N(R5R5a); S(O)$_2$N(R5R5a); lower alkyl; O— lower NH-lower alkyl; S-lower alkyl; COO— lower alkyl; OC(O)— lower alkyl; C(O)N(R5)-lower alkyl; S(O)$_2$N(R5)-lower alkyl; S(O)N(R5)-lower alkyl; S(O)$_2$-lower alkyl; S(O)-lower alkyl; N(R5)S(O)$_2$-lower alkyl; and N(R5)S(O)-lower alkyl; wherein each lower alkyl is optionally substituted with one or more of F and Cl;
R5 and R5a are independently
    H; F, Cl; or lower alkyl, lower cycloalkyl, or lower alkyl-lower cycloalkyl optionally substituted with one or more of F and Cl;

R6 is hydrogen, amino, hydroxyl, carbamoyl, carboxyl, SO$_2$R, NRR', —(CO)—OR, or —CO)—NRR';
R6a is R6, Cl, F, lower alkoxy, cyano, trifluoromethoxy; or together with the adjacent be —(CHR")$_n$—NR—(CHR")$_p$—, and form a five or six member heterocyclic ring fused to the ring to which they are bonded;
R7 is independently hydrogen, halogen, lower alkyl or lower alkoxy;
Rz is hydrogen, lower alkyl, lower alkanoyl, phenyl, 1-lower alkyl pyrrolidin-3-yl, pyrazol-4-yl, pyrazol-2-yl, or lower alkyl, lower alkanoyl, phenyl, 1-loweralkyl pyrrolidin-3-yl, pyrazol-4-yl, pyrazol-2-yl or pyrid-3-yl substituted by one or more of hydroxyl, amino, mono- or di-loweralkylamino, acetamidyl, lower alkanoyl, lower alkyl, 4-hydroxy-phenyl, 3-aminomethylphenyl, lower alkyl sulfonyl, 4-diloweralkylaminophenyl, pyrid-3-yl, 1H-indol-3-yl, morpholin-4-yl,;
R and Rz together may be —(CHR)$_q$-T-(CHR)$_r$— and form a five or six member heterocyclic ring with the nitrogen to which they are bonded;
Rz and R7 together may be —(CHR")$_n$—NR—(CHR")$_p$—, and form a five or six member heterocyclic ring fused to the ring to which they are bonded;
b and d are independently 0 or 1; provided at least one of b or d is 1;
k is 0 or 1;
m is 0 or 1;
n and p are independently 0, 1 or 2;
q and r are 1 or 2;
x is o or 1;
with the provisos that: (1) when m is zero, and (a) either U or W is NR", then Z is not carbamoyl; and
    (b) x is 1 and U is NR", then W is not NR";
    (2) (a) when m is 1, or (b) when U, V, W, X and Y form phenyl and X is C-lower alkoxy, or (c) when Rz together with R7 form indolyl, then R6 is not carbamoyl; and
    (3) at least one of R7 is other than hydrogen;

or a pharmaceutically acceptable salt, hydrate, solvate or prodrug thereof.

A preferred aspect of the present invention is a subclass of compounds according to formula II,

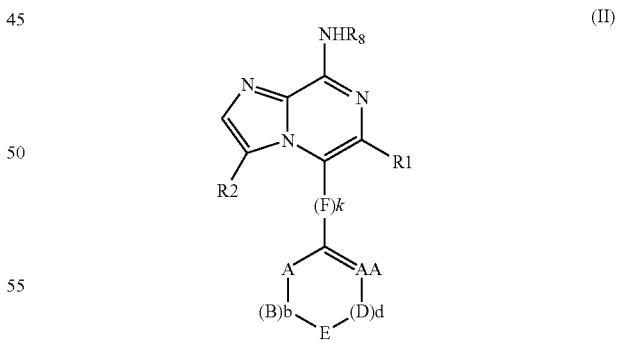

(II)

wherein
A and B are independently CR4R", NR", oxygen or sulfur;
AA is CR4 or N;
D is C=O, CR4R" or NR";
E is NH or CR"R6, when k is zero, and is NH or CR"R6a, when k is one;
F is sulfur, oxygen or NH;
T is oxygen or NR;

R" is H or forms a double bond with an adjacent atom;

R is independently hydrogen or lower alkyl;

R' is independently hydrogen or lower alkyl;

R1 is H; R4; or lower alkyl, lower cycloalkyl and lower alkyl-lower cycloalkyl, optionally substituted with one or more R4;

R2 is H; lower alkyl, lower cycloalkyl and lower alkyl-lower cycloalkyl, optionally substituted with one or more of F and Cl;

R4 is H, F, Cl; CN; COOR5; OR5; C(O)N(R5R5a); S(O)$_2$N(R5R5a); lower alkyl; O— -lower alkyl NH-lower alkyl; S-lower alkyl; COO— lower alkyl; OC(O)— lower alkyl; C(O)N(R5)— lower alkyl; S(O)$_2$N(R5)-lower alkyl; S(O)N(R5)-lower alkyl; S(O)$_2$-lower alkyl; S(O)-lower alkyl; N(R5)S(O)$_2$-lower alkyl; and N(R5)S(O)-lower alkyl; wherein each lower alkyl is optionally substituted with one or more of F and Cl;

R5 and R5a are independently
  H; F, Cl; or lower alkyl, lower cycloalkyl, or lower alkyl-lower cycloalkyl optionally substituted with one or more of F and Cl;

R6 is hydrogen, amino, hydroxyl, carbamoyl, carboxyl, SO$_2$R, NRR', —(CO)—OR, or —(CO)—NRR';

R6a is R6, Cl, F, lower alkoxy, cyano, trifluoromethoxy; or together with the adjacent be —(CHR")$_n$—NR—(CHR")$_p$—, and form a five or six member heterocyclic ring fused to the ring to which they are bonded;

R8 is phenyl independently substituted by R$_a$ in the ortho-position, by R$_b$ in the meta-position, and by R$_c$ in the para-position; pyrid-3-yl; pyrid-3-yl substituted by R$_c$ in the 5-position; or cyclohexyl independently substituted by R$_a$ in the 2-position, and by R$_d$ in the 4-position;

R$_a$ is hydrogen, halogen, lower alkyl, trifluoromethyl or lower alkoxy;

R$_b$ is hydrogen, trifluoromethyl, lower alkoxy, lower alkyl sulfonamide, carboxyl, —NR$_e$R$_f$, —(CO)—OR, or —(CO)—NR$_e$R$_f$;

R$_c$ is hydrogen, amino, hydroxyl, lower alkoxy, carbamoyl, carboxyl, SO$_2$R, SO$_2$NR$_e$R$_f$, NR$_e$R$_f$, —(CO)—OR, or —(CO)—NR$_e$R$_f$; or R$_b$ and R$_c$ can together form a benzdiazole, or indole substituted in the 3-position by R';

R$_d$ is hydroxyl, halogen, amino, lower alkoxy, or NR$_e$R$_f$;

R$_e$ and R$_f$ are independently hydrogen, 1-loweralkyl pyrrolidin-3-yl, 1-R-pyrazol-4-yl, lower alkanoyl, phenyl, or lower alkyl optionally substituted by one or more of 4-hydroxy-phenyl, 3-aminomethylphenyl, lower alkyl sulfonyl, 4-diloweralkylaminophenyl, pyrid-3-yl, 1H-indol-3-yl, morpholin-4-yl, hydroxyl, amino, mono- or di-loweralkylamino, or by lower alkanoyl; or R' and R" together are —(CHR)$_n$-T-(CHR)$_n$— and form a five or six member heterocyclic ring with the nitrogen to which they are bonded;

m is 0, 1, or2;

n is 1 or 2;

with the proviso that (1) (a) when R8 is pyridy-3-yl, or (b) when R$_b$ is lower alkoxy or (c) together with R$_c$ are indolyl, then R$_e$ is not carbamoyl;

(2) when R$_e$ is hydroxyl, then R$_g$ is not lower alkyl; and (3) at least one of R$_a$, R$_b$ and R$_c$ is other than hydrogen;

or a pharmaceutically acceptable salt, hydrate, solvate or prodrug thereof.

Another aspect of the present invention is compounds according to formula III:

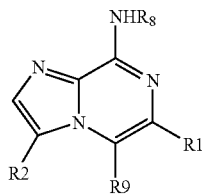

wherein

R$^1$ is H, or substituted or unsubstituted alkyl; R$^2$ is H, lower alkyl, lower cycloalkyl and lower alkyl-lower cycloalkyl, optionally substituted with one or more of F and Cl; R$^8$ is selected from substituted or unsubstituted cycloalkyl, substituted or unsubstituted heterocycloalkyl, substituted or unsubstituted aryl, substituted or unsubstituted pyridyl, substituted or unsubstituted pyrimidine, and substituted or unsubstituted pyrazine, substituted or unsubstituted pyrrole, substituted or unsubstituted pyrazole and substituted or unsubstituted imidazole; and R$^9$ is selected from substituted or unsubstituted cycloalkyl, substituted or unsubstituted heterocycloalkyl, substituted or unsubstituted aryl, substituted or unsubstituted heteroaryl; or a pharmaceutically acceptable salt, solvate or prodrug thereof; and stereoisomers, isotopic variants and tautomers thereof.

In one embodiment, with respect to compounds of formula III, R$^1$ is H, Me, Et, i-Pr or CF$_3$.

In one embodiment, with respect to compounds of formula III, R$^1$ is H.

In one embodiment, with respect to compounds of formula III, R$^2$ is H, Me, Et, i-Pr or CF$_3$.

In one embodiment, with respect to compounds of formula III, R$^2$ is H.

Another aspect of the present invention relates to compounds according to formula IVa, IVb, IVc, or IVd:

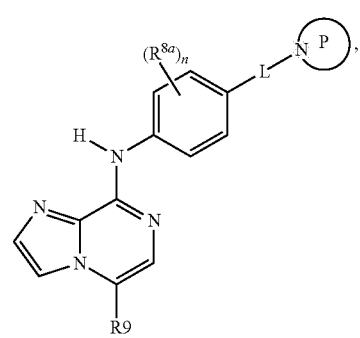

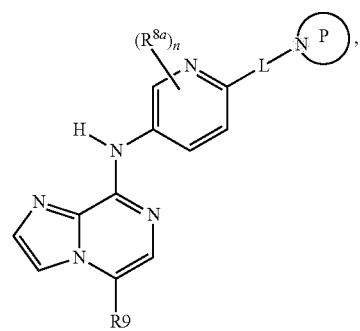

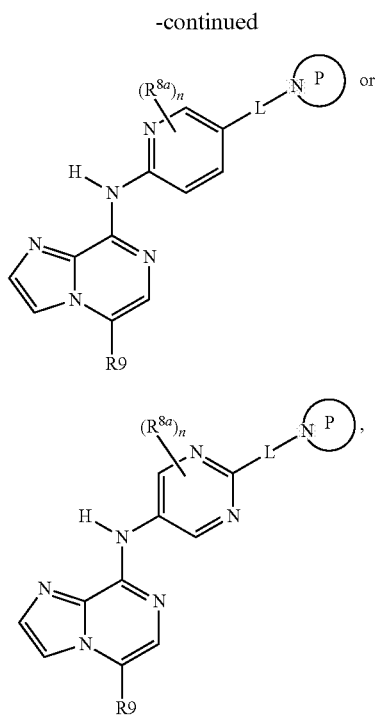

and wherein L is a bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; the ring P is substituted or unsubstituted heterocycloalkyl; the subscript n is selected from 1-4; each $R^{8a}$ is independently selected from hydrogen, substituted or unsubstituted alkyl, alkoxy, cyano, carbamoyl, CHO, and halo; and $R^9$ is independently selected from substituted or unsubstituted aryl and heteroaryl; or a pharmaceutically acceptable salt, solvate or prodrug thereof; and stereoisomers, isotopic variants and tautomers thereof.

In a one embodiment, with respect to compounds of formulae III-IVd, $R^9$ is substituted or unsubstituted aryl. In another embodiment, $R^9$ is substituted or unsubstituted phenyl.

In a one embodiment, with respect to compounds of formulae III-IVd, $R^9$ is substituted or unsubstituted heteroaryl. In another embodiment, $R^9$ is substituted or unsubstituted pyridyl.

In a one embodiment, with respect to compounds of formulae III-IVd, $R^9$ is selected from substituted or unsubstituted phenyl, indolyl, isoinolyl, pyrrolyl, furanyl, thienyl, pyrazolyl, oxazolyl, and thiazolyl.

In a further aspect, the present invention provides pharmaceutical compositions comprising an imidazolopyrazine compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

Another aspect of this invention relates to the use of the present compound in a therapeutic method, a pharmaceutical composition, and the manufacture of such composition, useful for the treatment of diseases involving inflammation, collagen degradation, and in particular, diseases characteristic of abnormal matrix metallo protease (MMP1) and/or Mitogen-Activated Protein-Kinase Activated Protein Kinase 5 (MAPKAPK5) activity, of which rheumatoid arthritis (RA) is a particular such disease. This invention also relates to processes for the preparation of the present compounds.

Other objects and advantages will become apparent to those skilled in the art from a consideration of the ensuing detailed description, considered in conjunction with the following illustrative drawings.

DETAILED DESCRIPTION OF THE INVENTION

Definitions

Figure 1:
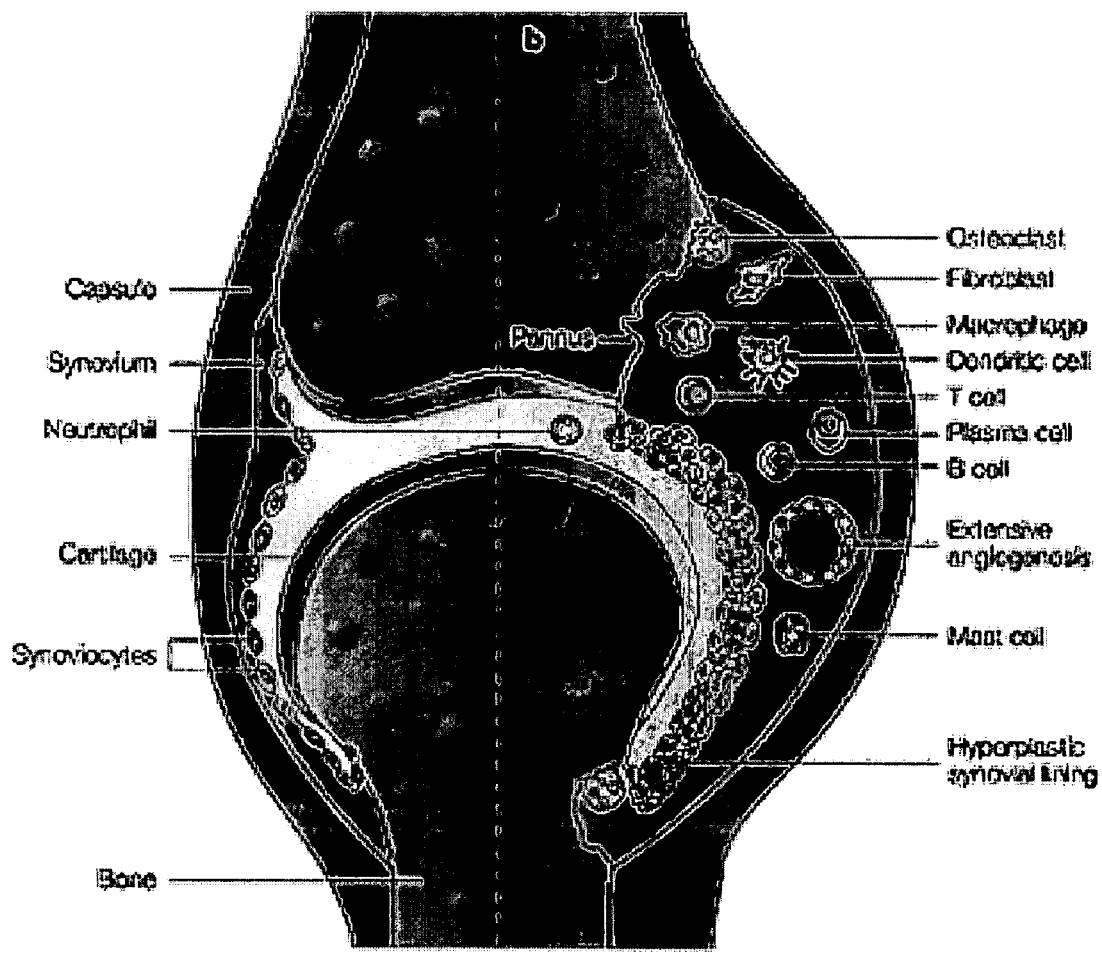
FIG. 1. This diagram shows the striking histological differences between a healthy joint and that of a RA patient ((From Smolen and Steiner, 2003).

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_2$-C$_6$ alkenyl, C$_3$-C$_6$ alkynyl, C$_1$-C$_6$ alkoxy, aryl and di-C$_1$-C$_6$ alkylamino. It should be further understood that the terms "groups" and "radicals" can be considered interchangeable when used herein.

"Alkoxy" means alkyl-O—. Exemplary alkoxy includes methoxy, ethoxy, n-propoxy, i-propoxy, n-butoxy, and heptoxy. Preferred alkoxy groups are lower alkoxy.

"Alkyl" means straight or branched aliphatic hydrocarbon having 1 to about 20 carbon atoms. Preferred alkyl has 1 to about 12 carbon atoms. More preferred is lower alkyl. Branched means that one or more lower alkyl groups such as methyl, ethyl or propyl is attached to a linear alkyl chain.

"Alkyl amino" means alkyl-NH—. Preferred alkyl amino is (C$_1$-C$_6$)-alkyl amino. Exemplary alkyl amino includes methylamino and ethylamino.

"Amino lower alkanoyl" means NH$_2$—R—CO—, where R is lower alkylene. Preferred groups include aminoethanoyl and aminoacetyl.

"Carbamoyl lower alkyl" means the radical NH$_2$CO-lower alkyl-. Preferred groups include carbamoylethyl and carbamoylmethyl.

"Carboxy lower alkyl ester" means a lower alkyl ester of a carboxy radical, —COO— group.

"Compounds of the present invention", and equivalent expressions, are meant to embrace compounds of Formula (I, II or III) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

"Expression" means endogenous expression.

"Halo" or "halogen" means fluoro, chloro, bromo, or iodo.

"Hydrogen" means in the context of a substituent that —H is present at the compound position and also includes its isotope, deuterium.

"Lower alkanoyl amino" means an amino group with an organic functional group R—CO—, where R represents a lower alkyl group.

"Lower alkyl" means 1 to about 6 carbon atoms in a linear alkyl chain that may be straight or branched.

"Lower alkoxy" means 1 to about 6 carbon atoms in a linear alkyl chain that may be straight or branched, and that is bonded by an oxygen atom.

"Lower alkyl sulphonamide" refers to a lower alkyl amide of sulphonamide of the formula —SO$_2$NR*R*, where R* is hydrogen or lower alkyl, and at least one R* is lower alkyl.

"Prophylaxis" means a measure taken for the prevention of a disease.

"Solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. Conventional solvents include water, ethanol, acetic acid and the like, therefore, representative solvates include hydrates, ethanolates and methanolates.

"Substituted" means that one atom or group of atoms in a molecule is replaced by another atom or group.

"Sulphonamide" refers to a group of compounds containing the chemical group —SO$_2$NH$_2$.

"Therapeutically effective amount" means that amount of a drug or pharmaceutical agent that will elicit the biological or medical response of a subject that is being sought by a medical doctor or other clinician. The "therapeutically effective amount" can vary depending on the compound, the disease and its severity, and the age, weight, etc., of the subject to be treated. In particular, with regard to treating an disease condition characterized by the degradation of extracellular matrix, the term "effective matrix metallo-protease inhibiting amount" is intended to mean that effective amount of an compound of the present invention that will bring about a biologically meaningful decrease in the production of MMP-1 in the subject's disease affected tissues such that extracellular matrix degradation is meaningfully reduced. A compound having matrix metallo-protease inhibiting properties or a "matrix metallo-protease inhibiting compound" means a compound of the present invention that provided to a cell in effective amounts is able to cause a biologically meaningful decrease in the production of MMP-1 in such cells.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein. In a specific embodiment, the term "carbamoyl" refers to —C(O)—NH$_2$.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

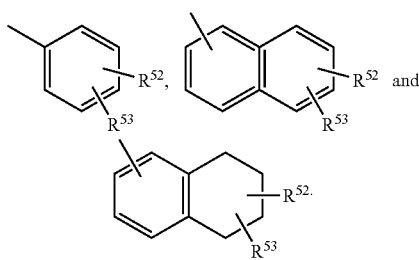

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

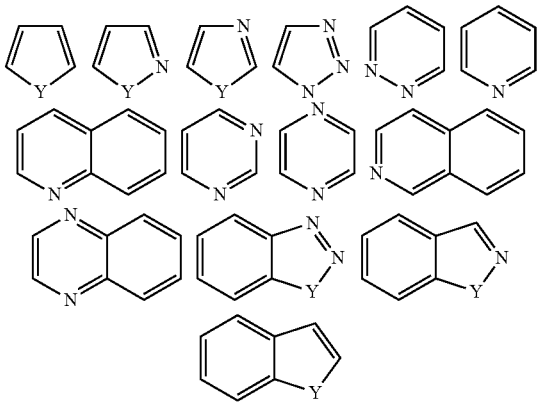

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

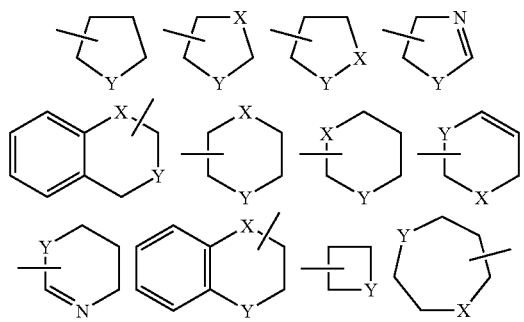

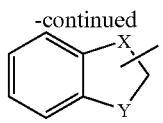

wherein each X is selected from $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

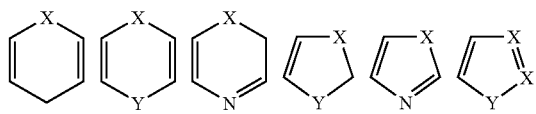

wherein each X is selected from $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

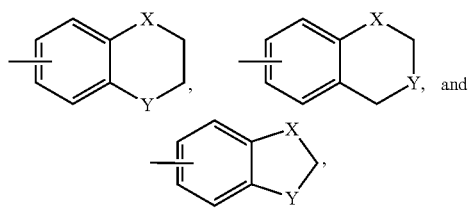

wherein each X is selected from C—$R^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to the non-toxic, inorganic and organic acid addition salts, and base addition salts, of compounds of the present invention, in particular they are a salt of a compound of the invention that is pharmaceutically acceptable and that possesses the desired pharmacological activity of the parent compound. These salts can be prepared in situ during the final isolation and purification of compounds useful in the present invention. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Subject" includes humans. The terms "human," "patient" and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is based on the discovery of that MAPKAPK5 functions in the pathway that results in the expression of MMP1, and that inhibitors of MAPKAPK5 activity, such as the compounds of the present invention, are useful for the treatment of diseases involving the abnormally high expression of MMP activity.

The present matrix metallo proteinase inhibiting compounds of the present invention may be described generally as imidazo[1,2-a]pyrazine-8-yl-amines substituted in the 5-position by an aryl and heteroaryl group, and an in the 8-position by an arylamino or a heteroarylamino group.

More particularly, the present invention relates to compounds having matrix metallo proteinase inhibiting properties in a mammalian cell, according to formula (I):

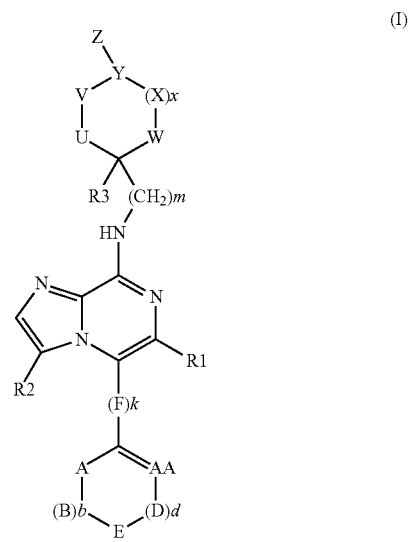

wherein:
A and B are independently CR4R", NR", oxygen or sulfur;
AA is CR4 or N;
D is C=O, CR4R" or NR";

E is NH or CR"R6, when k is zero, and is NH or CR"R6a, when k is one;
F is sulfur, oxygen or NH;
T is oxygen or NR;
U, V, W and X are independently CR"R7 or NR";
Y is CR" or N;
Z is hydrogen, amino, hydroxyl, lower alkoxy, carbamoyl, carboxyl, SO$_2$Rz, SO$_2$NRRz, —NR(CO)(CH2)d-Rz, —NRRz, —(CO)—ORz, —(CO)—NR(CH2)d-Rz, or

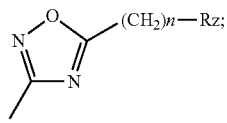

R is independently hydrogen or lower alkyl;
R' is independently hydrogen or lower alkyl;
R" is H or forms a double bond with an adjacent atom;
R1 is H; R4; or lower alkyl, lower cycloalkyl and lower alkyl-lower cycloalkyl, optionally substituted with one or more R4;
R2 is H; lower alkyl, lower cycloalkyl and lower alkyl-lower cycloalkyl, optionally substituted with one or more of F and Cl;
R3 is H or forms a double bond with an adjacent R";
R4 is H, F, Cl; CN; COOR5; OR5; C(O)N(R5R5a); S(O)$_2$N(R5R5a); lower alkyl; O— lower alkyl; NH-lower alkyl; S-lower alkyl; COO— lower alkyl; OC(O)— lower alkyl; C(O)N(R5)— lower alkyl; S(O)$_2$N(R5)-lower alkyl; S(O)N(R5)-lower alkyl; S(O)$_2$-lower alkyl; S(O)-lower alkyl; N(R5)S(O)$_2$-lower alkyl; and N(R5)S(O)-lower alkyl; wherein each lower alkyl is optionally substituted with one or more of F and Cl;
R5 and R5a are independently
  H; F, Cl; or lower alkyl, lower cycloalkyl, or lower alkyl-lower cycloalkyl optionally substituted with one or more of F and Cl;
R6 is hydrogen, amino, hydroxyl, carbamoyl, carboxyl, SO$_2$R, NRR', —(CO)—OR, or —(CO)—NRR';
R6a is R6, Cl, F, lower alkoxy, cyano, trifluoromethoxy; or together with the adjacent be —(CHR")$_n$—NR—(CHR")$_p$—, and form a five or six member heterocyclic ring fused to the ring to which they are bonded;
R7 is independently hydrogen, halogen, lower alkyl or lower alkoxy;
Rz is hydrogen, lower alkyl, lower alkanoyl, phenyl, 1-loweralkyl pyrrolidin-3-yl, pyrazol-4-yl, pyrazol-2-yl, or lower alkyl, lower alkanoyl, phenyl, 1-loweralkyl pyrrolidin-3-yl, pyrazol-4-yl, pyrazol-2-yl or pyrid-3-yl substituted by one or more of hydroxyl, amino, mono- or di-loweralkylamino, acetamidyl, lower alkanoyl, lower alkyl, 4-hydroxy-phenyl, 3-aminomethylphenyl, lower alkyl sulfonyl, 4-diloweralkylaminophenyl, pyrid-3-yl, 1H-indol-3-yl, morpholin-4-yl,;
R and Rz together may be —(CHR)$_q$-T-(CHR)$_r$, and form a five or six member heterocyclic ring with the nitrogen to which they are bonded;
Rz and R7 together may be —(CHR")$_n$—NR—(CHR")$_p$—, and form a five or six member heterocyclic ring fused to the ring to which they are bonded;
b and d are independently 0 or 1; provided at least one of b or d is 1;
k is 0 or 1;
m is 0 or 1;
n and p are independently 0, 1 or 2;

q and r are 1 or 2;
x is 0 or 1;
with the provisos that: (1) when m is zero, and (a) either U or W is NR", then Z is not carbamoyl; and
  (b) x is 1 and U is NR", then W is not NR";
(2) (a) when m is 1, or (b) when U, V, W, X and Y form phenyl and X is C-lower alkoxy, or (c) when Rz together with R7 form indolyl, then R6 is not carbamoyl; and
(3) at least one of :R7 is other than hydrogen;

or a pharmaceutically acceptable salt, hydrate, solvate or prodrug thereof.

A preferred aspect of the present invention is a subclass of compounds according to formula II,

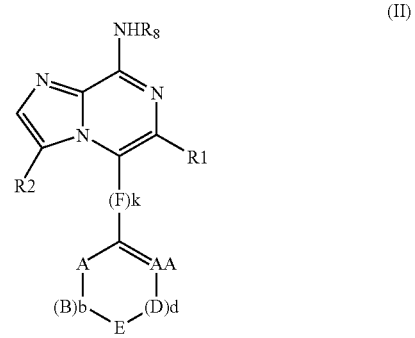

(II)

wherein
A and B are independently CR4R", NR", oxygen or sulfur;
AA is CR4 or N;
D is C=O, CR4R" or NR";
E is NH or CR"R6, when k is zero, and is NH or CR"R6a, when k is one;
F is sulfur, oxygen or NH;
T is oxygen or NR;
R is independently hydrogen or lower alkyl;
R' is independently hydrogen or lower alkyl;
R" is H or forms a double bond with an adjacent atom;
R1 is H; R4; or lower alkyl, lower cycloalkyl and lower alkyl-lower cycloalkyl, optionally substituted with one or more R4;
R2 is H; lower alkyl, lower cycloalkyl and lower alkyl-lower cycloalkyl, optionally substituted with one or more of F and Cl;
R4 is H, F, Cl; CN; COOR5; OR5; C(O)N(R5R5a); S(O)$_2$N(R5R5a); lower alkyl; O— lower alkyl; NH-lower alkyl; S-lower alkyl; COO— lower alkyl; OC(O)— lower alkyl; C(O)N(R5)— lower alkyl; S(O)$_2$N(R5)-lower alkyl; S(O)N(R5)-lower alkyl; S(O)$_2$-lower alkyl; S(O)-lower alkyl; N(R5)S(O)$_2$-lower alkyl; and N(R5)S(O)-lower alkyl; wherein each lower alkyl is optionally substituted with one or more of F and Cl;
R5 and R5a are independently
  H; F, Cl; or lower alkyl, lower cycloalkyl, or lower alkyl-lower cycloalkyl optionally substituted with one or more of F and Cl;
R6 is hydrogen, amino, hydroxyl, carbamoyl, carboxyl, SO$_2$R, NRR', —(CO)—OR, or —(CO)—NRR';
R6a is R6, Cl, F, lower alkoxy, cyano, trifluoromethoxy; or together with the adjacent be —(CHR")$_n$—NR—(CHR")$_p$—, and form a five or six member heterocyclic ring fused to the ring to which they are bonded;

R8 is phenyl independently substituted by $R_a$ in the ortho-position, by $R_b$ in the meta-position, and by $R_c$ in the para-position; pyrid-3-yl; pyrid-3-yl substituted by $R_c$ in the 5-position; or cyclohexyl independently substituted by $R_a$ in the 2-position, and by $R_d$ in the 4-position;

$R_a$ is hydrogen, halogen, lower alkyl, trifluoromethyl or lower alkoxy;

$R_b$ is hydrogen, trifluoromethyl, lower alkoxy, lower alkyl sulfonamide, carboxyl, —$NR_eR_f$, —(CO)—OR or —(CO)—$NR_eR_f$;

$R_c$ is hydrogen, amino, hydroxyl, lower alkoxy, carbamoyl, carboxyl, $SO_2R$, $SO_2NR_eR_f$, $NR_eR_f$, —(CO)—OR, or —(CO)—$NR_eR_f$; or $R_b$ and $R_c$ can together form a benzdiazole, or indole substituted in the 3-position by R';

$R_d$ is hydroxyl, halogen, amino, lower alkoxy, or $NR_eR_f$;

$R_e$ and $R_f$ are independently hydrogen, 1-loweralkyl pyrrolidin-3-yl, 1-R-pyrazol-4-yl, lower alkanoyl, phenyl, or lower alkyl optionally substituted by one or more of 4-hydroxy-phenyl, 3-aminomethylphenyl, lower alkyl sulfonyl, 4-diloweralkylaminophenyl, pyrid-3-yl, 1H-indol-3-yl, morpholin-4-yl, hydroxyl, amino, mono- or di-loweralkylamino, or by lower alkanoyl; or R' and R" together are —(CHR)$_n$-T-(CHR)$_n$— and form a five or six member heterocyclic ring with the nitrogen to which they are bonded;

m is 0, 1, or2;

n is 1 or 2;

with the proviso that: (1) (a) when R8 is pyridy-3-yl, or (b) when $R_b$ is lower alkoxy or (c) together with $R_c$ are indolyl, then $R_e$ is not carbamoyl;
(2) when $R_e$ is hydroxyl, then $R_g$ is not lower alkyl; and
(3) at least one of $R_a$, $R_b$ and $R_c$ is other than hydrogen;

or a pharmaceutically acceptable salt, hydrate, solvate or prodrug thereof.

Another aspect of the present invention relates to compounds according to formula III:

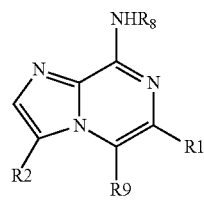

(III)

wherein $R^1$ is H, or substituted or unsubstituted alkyl; $R^2$ is H, lower alkyl, lower cycloalkyl and lower alkyl-lower cycloalkyl, optionally substituted with one or more of F and Cl; $R^8$ is selected from substituted or unsubstituted cycloalkyl, substituted or unsubstituted heterocycloalkyl, substituted or unsubstituted aryl, substituted or unsubstituted pyridyl, substituted or unsubstituted pyrimidine, and substituted or unsubstituted pyrazine, substituted or unsubstituted pyrrole, substituted or unsubstituted pyrazole and substituted or unsubstituted imidazole; and $R^9$ is selected from substituted or unsubstituted cycloalkyl, substituted or unsubstituted heterocycloalkyl, substituted or unsubstituted aryl, substituted or unsubstituted heteroaryl; or a pharmaceutically acceptable salt, solvate or prodrug thereof; and stereoisomers, isotopic variants and tautomers thereof.

In one embodiment, with respect to compounds of formula III, $R^1$ is H, Me, Et, i-Pr or $CF_3$.

In one embodiment, with respect to compounds of formula III, R' is H.

In one embodiment, with respect to compounds of formula III, $R^2$ is H, Me, Et, i-Pr or $CF_3$.

In one embodiment, with respect to compounds of formula III, $R^2$ is H.

In one embodiment, with respect to compounds of formula III, $R^8$ is selected from substituted or unsubstituted cycloalkyl.

In another embodiment, with respect to compounds of formula III, $R^8$ is selected from substituted or unsubstituted cyclohexyl or cyclopentyl.

In one embodiment, with respect to compounds of formula III, $R^8$ is selected from substituted or unsubstituted heterocycloalkyl.

In another embodiment, with respect to compounds of formula III, $R^8$ is selected from substituted or unsubstituted piperidinyl, morpholinyl, or pyrrolidinyl.

In one embodiment, with respect to compounds of formula III, $R^8$ is selected from substituted or unsubstituted phenyl, pyridyl or pyrimidine.

In one embodiment, with respect to compounds of formula III, $R^8$ is selected from substituted phenyl, substituted pyridyl, and substituted pyrimidine; and the substitution is -L-$R^{8d}$; and wherein L is selected from a bond, alkylene, heteroalkylene, —O—, —N($R^{8e}$)—, —CO—, —$CO_2$—, —SO—, —$SO_2$—, —CON($R^{8e}$)—, —$SO_2$N($R^{8e}$)—, —N($R^{8e}$)CO—, —N($R^{8e}$)$SO_2$—, —N($R^{8e}$)CO N($R^{8e}$)—, —N($R^{8e}$)$SO_2$N($R^{8e}$)—; and $R^{8d}$ is selected from substituted or unsubstituted alkyl, substituted or unsubstituted cycloalkyl, substituted or unsubstituted aryl, substituted or unsubstituted heterocycloalkyl, substituted or unsubstituted heteroaryl, substituted or unsubstituted amino, substituted or unsubstituted aralkyl, substituted or unsubstituted heteroarylalkyl and substituted or unsubstituted aminoalkyl; and $R^{8e}$ is selected from H, substituted or unsubstituted alkyl and substituted or unsubstituted cycloalkyl.

In one embodiment, with respect to compounds of formula III, $R^8$ is

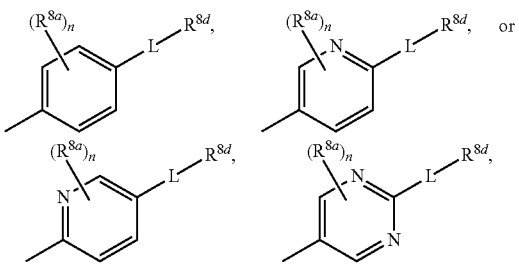

wherein L, and $R^{8d}$ are as described in the preceding paragraph; the subscript n is selected from 1-4; and each $R^{8a}$, is independently selected from hydrogen, substituted or unsubstituted alkyl, alkoxy, cyano, and halo.

In one embodiment, with respect to compounds of formula III, $R^8$ is as described above and the subscript n is 1 and R8a is Me, Et, Pr, iso-Pr, Cl, F, CN, OMe, or $CF_3$. In another embodiment, $R^8$, is at 2-(ortho to -L) position. In yet another embodiment, $R^{8a}$ is 2-Cl, 2-F, 2-Me or 2-$CF_3$.

In one embodiment, with respect to compounds of formula III, $R^8$ is as described above and L is —CON($R^{8e}$)— or $SO_2N(R^{8e})$—;

$R^{8d}$ is selected from substituted or unsubstituted alkyl, substituted or unsubstituted cycloalkyl, substituted or unsubstituted aryl, substituted or unsubstituted heterocycloalkyl, substituted or unsubstituted heteroaryl, substituted or unsubstituted aralkyl, substituted or unsubstituted heteroarylalkyl and substituted or unsubstituted aminoalkyl; and $R^{8e}$ is selected from H, substituted or unsubstituted alkyl.

In one embodiment, with respect to compounds of formula III, $R^8$ is as described above and L is —CONH— or $SO_2NH$—; and $R^{8d}$ is selected from H, alkylaminoethyl, dialkylaminoethyl, cycloalkyl, heterocycloalkyl, arylalkyl, and heteroarylalkyl.

In one embodiment, with respect to compounds of formula III, $R^8$ is as described above and L is —CONH— or $SO_2NH$—; and $R^{8d}$ is selected from methylaminoethyl, ethylaminoethyl, dimethylaminoethyl, diethylaminoethyl, substituted or unsubstituted pyrrolidinyl, benzyl and pyridylmethyl.

In one embodiment, with respect to compounds of formula III, $R^8$ is as described above and L is a bond, —CO—, $SO_2$, —$(CH_2)_{m1}$—, —$O(CH_2)_{m1}$—, —$NH(CH_2)_{m1}$—, —$CON(H)(CH_2)_{m1}$—, or —$SO_2NH(CH_2)_{m1}$—; the subscript m1 is selected from 1-4; and $R^{8d}$ is

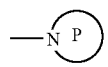

and wherein the ring P is substituted or unsubstituted heterocycloalkyl.

In one embodiment, with respect to compounds of formula III, $R^8$ is as described above; L is a bond; and the ring P is substituted or unsubstituted heterocycloalkyl.

In one embodiment, with respect to compounds of formula III, $R^8$ is as described above; L is a bond; and the ring P is substituted or unsubstituted piperidine, substituted or unsubstituted piperazine, and substituted or unsubstituted piperidine, morpholine.

In one embodiment, with respect to compounds of formula III, $R^8$ is as described above; L is CO or $SO_2$; and the ring P is substituted or unsubstituted heterocycloalkyl.

In one embodiment, with respect to compounds of formula III, $R^8$ is as described above; L is CO or $SO_2$; and the ring P is substituted or unsubstituted piperidine, substituted or unsubstituted piperazine, and substituted or unsubstituted piperidine, morpholine.

In one embodiment, with respect to compounds of formula III, $R^8$ is as described above; L is —$(CH_2)_{m1}$—, —$O(CH_2)_{m1}$—, or —$NH(CH_2)_{m1}$-; the subscript m1 is selected from 1-4; and the ring P is substituted or unsubstituted heterocycloalkyl.

In one embodiment, with respect to compounds of formula III, $R^8$ is as described above; L is —$(CH_2)_{m1}$—, —$O(CH_2)_{m1}$—, or —$NH(CH_2)_{m1}$—; the subscript m1 is 2 or 3; and the ring P is substituted or unsubstituted piperidine, substituted or unsubstituted piperazine, and substituted or unsubstituted piperidine, morpholine.

In one embodiment, with respect to compounds of formula III, $R^8$ is as described above; L is —$CON(H)(CH_2)_{m1}$—, or —$SO_2NH(CH_2)_{m1}$—; the subscript m1 is selected from 1-4; and the ring P is substituted or unsubstituted heterocycloalkyl.

In one embodiment, with respect to compounds of formula III, $R^8$ is as described above; L is —$CON(H)(CH_2)_{m1}$—, or —$SO_2NH(CH_2)_{m1}$—; the subscript m1 is 2 or 3; and the ring P is substituted or unsubstituted piperidine, substituted or unsubstituted piperazine, and substituted or unsubstituted piperidine, morpholine.

In one embodiment, with respect to compounds of formula III, the compound is according to formula IVa, IVb, IVc, or IVd:

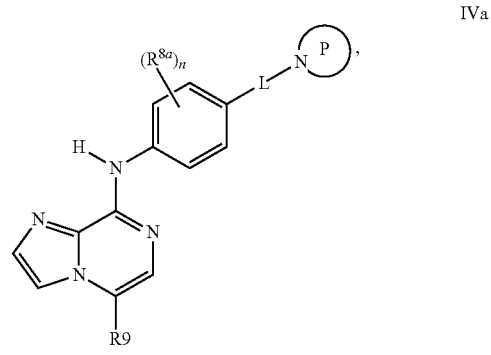

IVa

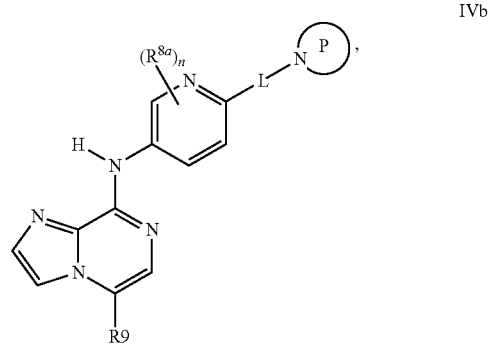

IVb

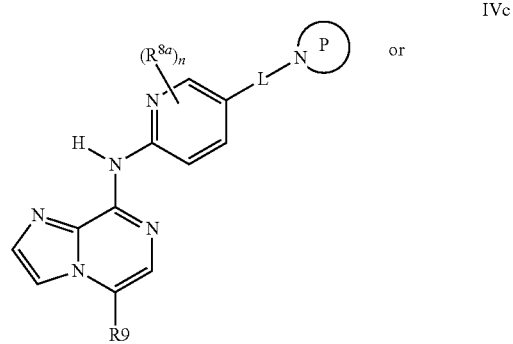

IVc or

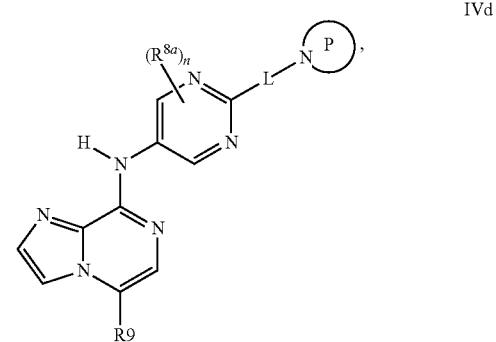

IVd and wherein L is a bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; the ring P is substituted or unsubstituted heterocycloalkyl; the subscript n is selected from 1-4; each R$^{8a}$ is independently selected from hydrogen, substituted or unsubstituted alkyl, alkoxy, cyano, and halo; and R$^9$ is independently selected from substituted or unsubstituted aryl and heteroaryl; or a pharmaceutically acceptable salt, solvate or prodrug thereof; and stereoisomers, isotopic variants and tautomers thereof.

In one embodiment, with respect to compounds of formulae IVa-IVd, L is a bond.

In one embodiment, with respect to compounds of formulae IVa-IVd, L is methylene, ethylene, propylene, and butylene.

In one embodiment, with respect to compounds of formulae IVa-IVd, L is —CO—.

In one embodiment, with respect to compounds of formulae IVa-IVd, L is —SO$_2$—.

In one embodiment, with respect to compounds of formulae IVa-IVd, L is —CON(H)—CH$_2$—CH$_2$—, or —SO$_2$NH—CH$_2$—CH$_2$—.

In one embodiment, with respect to compounds of formulae IVa-IVd, L is —OCH$_2$—CH$_2$— or —NHCH$_2$—CH$_2$—.

In a preferred embodiment L is a bond, CO or SO$_2$.

In one embodiment, with respect to compounds of formulae IVa-IVd, the ring P is substituted or unsubstituted piperidine, morpholine or piperazine.

In one embodiment, with respect to compounds of formulae IVa-IVd, L and the ring P are as described above; the subscript n is 4 and each R$^{8a}$ is H.

In one embodiment, with respect to compounds of formulae IVa-IVd, L and the ring P are as described above; the subscript n is 1 and R$^{8a}$ is Me, Et, Pr, iso-Pr, Cl, F, CN, OMe, or CF$_3$. In another embodiment, R$^{8a}$ is at 2-(ortho to -L) position. In yet another embodiment, R$^{8a}$ is 2-Cl, 2-F, 2-Me or 2-CF$_3$.

In a further embodiment, with respect to compounds of formula III, R$^8$ is

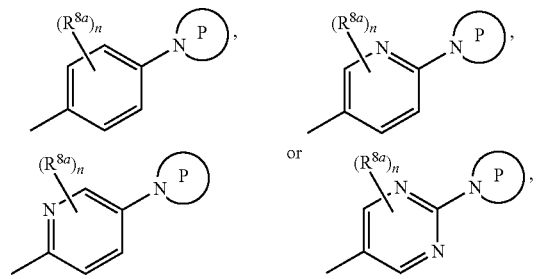

and wherein the ring P is substituted or unsubstituted heterocycloalkyl; the subscript n is selected from 1-4 and each R$^{8a}$ is independently selected from hydrogen, substituted or unsubstituted alkyl, alkoxy, cyano, and halo.

In one embodiment, with respect to compounds of formula III, R$^8$ is as described above and the ring P is substituted or unsubstituted piperidine, morpholine or piperazine.

In one embodiment, with respect to compounds of formula III, R$^8$ is as described above and the subscript n is 4 and each R$^{8a}$ is H.

In one embodiment, with respect to compounds of formula III, R$^8$ is as described above and the subscript n is 1 and R$^{8a}$ is Me, Et, Pr, iso-Pr, Cl, F, CN, OMe, or CF$_3$. In another embodiment, R$^{8a}$ is at the 2-(ortho to N-ring P) position. In yet another embodiment, R$^{8a}$ is 2-Cl, 2-F, 2-Me or 2-CF$_3$.

In a further embodiment, with respect to compounds of formula III, R$^8$ is

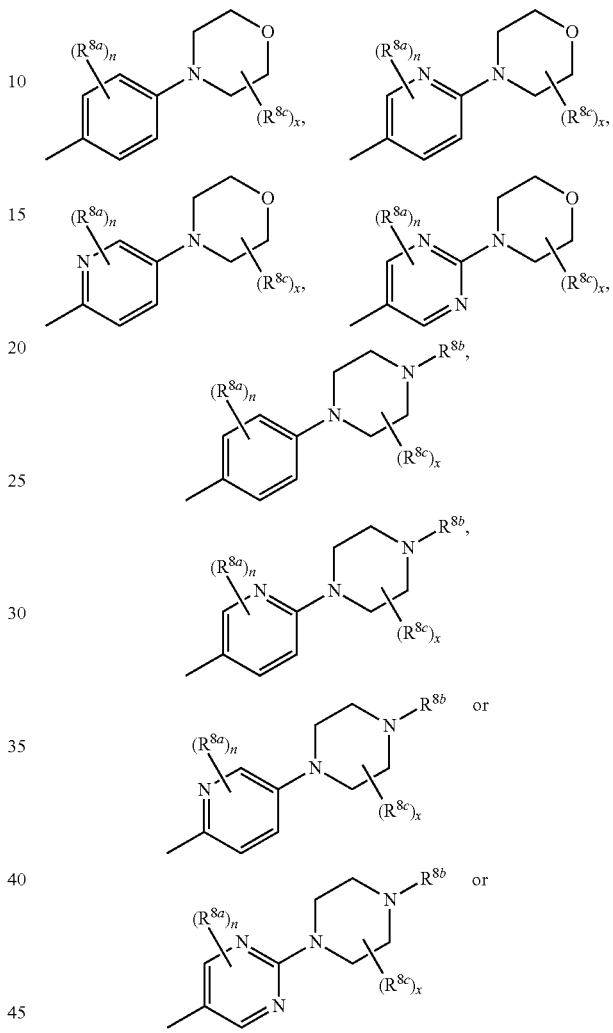

and wherein the subscript n is selected from 1-4; each R$^{8a}$ is independently selected from hydrogen, substituted or unsubstituted alkyl, alkoxy, cyano, and halo; R$^{8b}$ is hydrogen, substituted or unsubstituted alkyl or substituted or unsubstituted cycloalkyl; R$^{8c}$ is hydrogen, substituted or unsubstituted alkyl and the subscript x is selected from 1-8.

In a further embodiment, with respect to compounds of formula III, R$^8$ is

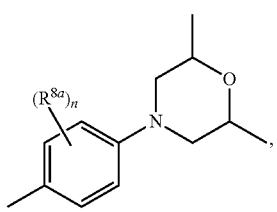

-continued

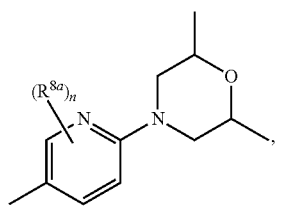

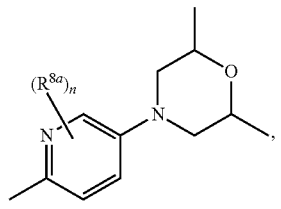

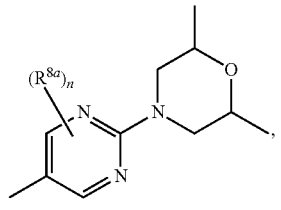

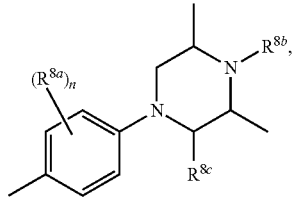

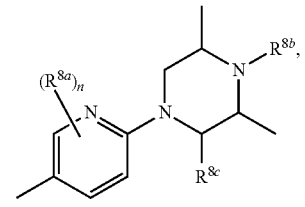

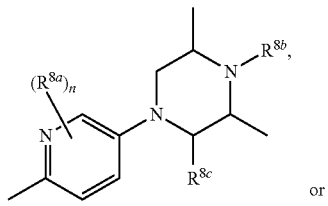

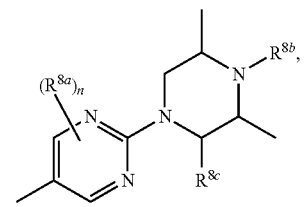

or

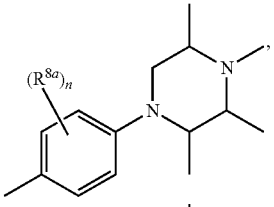

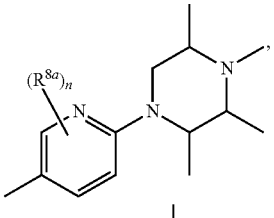

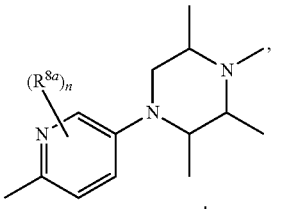

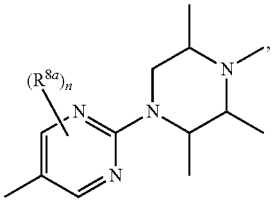

or and wherein the subscript n is selected from 1-4; each $R^{8a}$ is independently selected from hydrogen, substituted or unsubstituted alkyl, alkoxy, cyano, and halo.

In a further embodiment, with respect to compounds of formula III, $R^8$ is

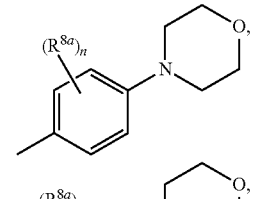

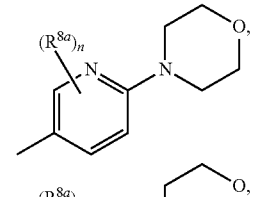

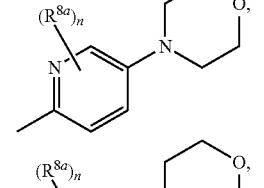

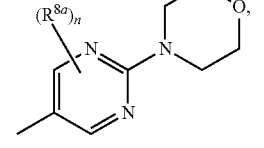

and wherein the subscript n is selected from 1-4; each $R^{8a}$ is independently selected from hydrogen, substituted or unsubstituted alkyl, alkoxy, cyano, and halo; $R^{8b}$ is hydrogen, substituted or unsubstituted alkyl or substituted or unsubstituted cycloalkyl; $R^{8c}$ is hydrogen or Me.

In a further embodiment, with respect to compounds of formula III, $R^8$ is

-continued

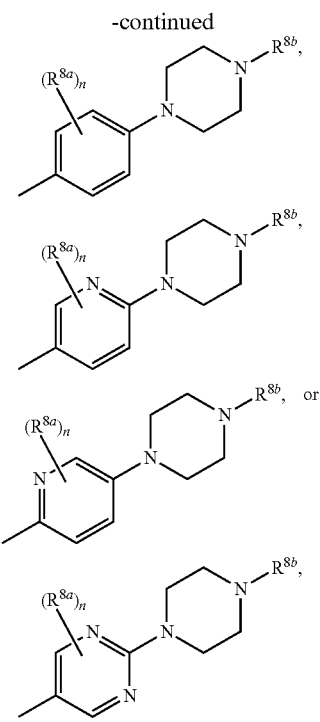

and wherein the subscript n is selected from 1-4; each $R^{8a}$ is independently selected from hydrogen, substituted or unsubstituted alkyl, alkoxy, cyano, and halo; and $R^{8b}$ is hydrogen, substituted or unsubstituted alkyl or substituted or unsubstituted cycloalkyl.

In one embodiment, with respect to compounds of formula III, $R^8$ is as described above and the subscript n is 4 and each $R^{8a}$ is H.

In one embodiment, with respect to compounds of formula III, $R^8$ is as described above and the subscript n is 1 and $R^{8a}$ is Me, Et, Pr, iso-Pr, Cl, F, CN, OMe, or $CF_3$. In another embodiment, $R^{8a}$ is at 2-(ortho to N-ringP) position. In yet another embodiment, $R^{8a}$ is 2-Cl, 2-F, 2-Me or 2-$CF_3$.

In one embodiment, with respect to compounds of formula III, $R^8$ is as described above and $R^{8b}$ is H.

In one embodiment, with respect to compounds of formula III, $R^8$ is as described above and $R^{8b}$ substituted or unsubstituted alkyl.

In one embodiment, with respect to compounds of formula III, $R^8$ is as described above and $R^{8b}$ substituted or unsubstituted cycloalkyl.

In one embodiment, with respect to compounds of formula III, $R^8$ is as described above and $R^{8b}$ is Me, Et, Pr, i-Pr, t-Bu, i-Bu, $CH_2CF_3$, $CF_3$, $CH_2CONH_2$, cyclopropyl or cyclopropylmethyl.

In one particular embodiment, with respect to compounds of formula III, $R^8$ is as described above and $R^{8b}$ is i-Pr.

In a further embodiment, with respect to compounds of formulae IVa-IVd, $R^{8a}$ is independently selected from hydrogen, substituted or unsubstituted alkyl, alkoxy, cyano, carbamoyl, CHO, and halo. In one embodiment, $R^{8a}$ is H, Me, F, or Cl. In a preferred embodiment $R^{8a}$ is H.

In one embodiment, with respect to compounds of formulae IVa-IVd, the compound is according to formula Va, Vb, Vc, Vd, Ve, or Vf:

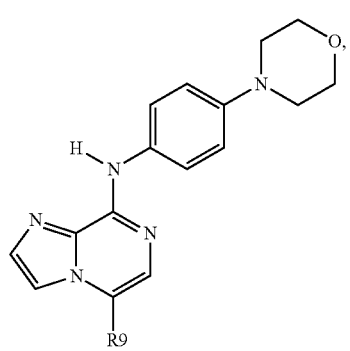

Va

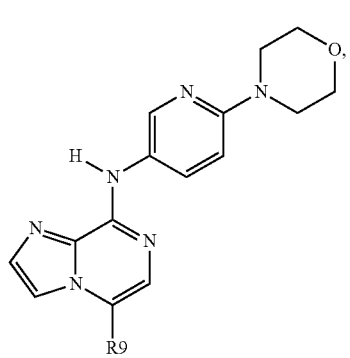

Vb

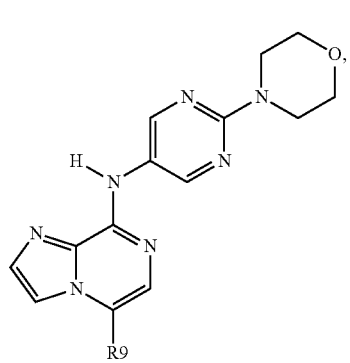

Vc

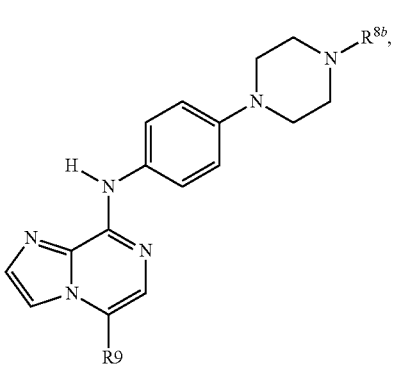

Vd

-continued

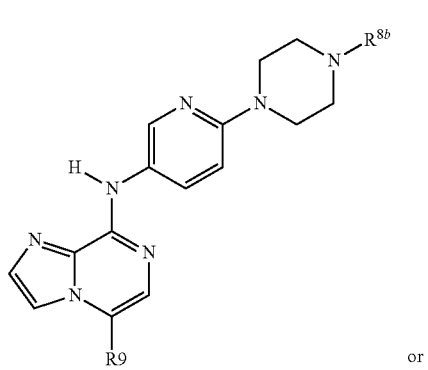

Ve or

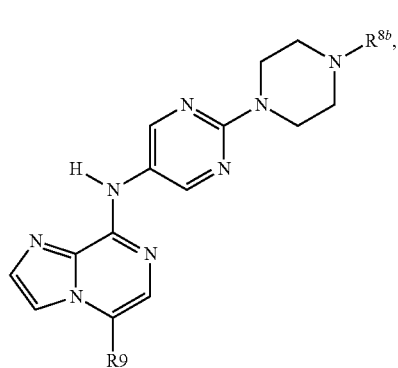

Vf and wherein $R^9$ is as described for formula III and $R^{8b}$ is hydrogen, substituted or unsubstituted alkyl or substituted or unsubstituted cycloalkyl.

In one embodiment, with respect to compounds of formulae Va-Vf, $R^{8b}$ is H.

In one embodiment, with respect to compounds of formulae Va-Vf, $R^{8b}$ is substituted or unsubstituted alkyl.

In one embodiment, with respect to compounds of formulae Va-Vf, $R^{8b}$ is substituted or unsubstituted cycloalkyl.

In one embodiment, with respect to compounds of formulae Va-Vf, $R^{8b}$ is Me, Et, Pr, i-Pr, t-Bu, i-Bu, $CH_2CF_3$, $CF_3$, $CH_2CONH_2$, cyclopropyl or cyclopropylmethyl.

In one particular embodiment, with respect to compounds of formulae Va-Vf, $R^{8b}$ is i-Pr.

In a one embodiment, with respect to compounds of formulae III-VF, $R^9$ is substituted or unsubstituted aryl. In another embodiment, $R^9$ is substituted or unsubstituted phenyl.

In a one embodiment, with respect to compounds of formulae III-VF, $R^9$ is substituted or unsubstituted heteroaryl. In another embodiment, $R^9$ is substituted or unsubstituted pyridyl.

In a one embodiment, with respect to compounds of formulae III-VF, $R^9$ is selected from substituted or unsubstituted phenyl, indolyl, isoinolyl, pyrrolyl, furanyl, thienyl, pyrazolyl, oxazolyl, and thiazolyl.

In one embodiment, with respect to compounds of formulae III-Vf, $R^9$ is

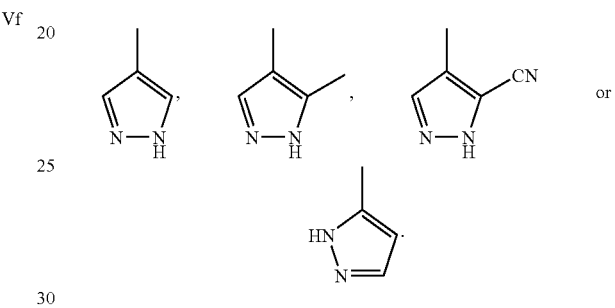

and each of $A^1$, $A^2$ and $A^3$ is independently selected from S, O, N, $NR^{9a}$, and $CR^{9a}$; each of $R^{9a}$ is independently H or substituted or unsubstituted alkyl; and $R^{9b}$ is $CONH_2$, CONHMe, or CN.

In further embodiment, with respect to compounds of formulae III-Vf, $R^9$ is

In further embodiment, with respect to compounds of formulae III-Vf, $R^9$ is

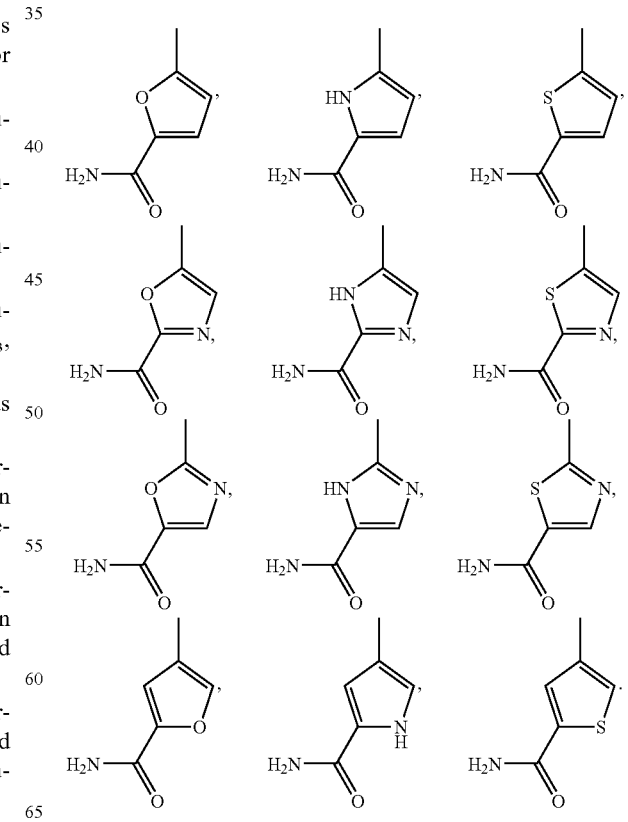

In further embodiment, with respect to formulae III-Vf, $R^9$ is

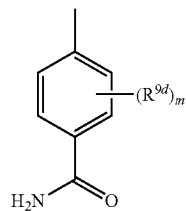

and wherein the subscript m is selected from 1-4 and each $R^{9d}$ is independently H, substituted or unsubstituted alkyl or halo.

In further embodiment, with respect to compounds of formulae III-Vf, $R^9$ is

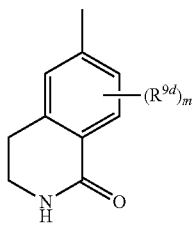 or 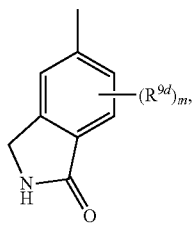

and wherein the subscript m is selected from 1-4 and each $R^{9d}$ is independently H, substituted or unsubstituted alkyl or halo.

In a further embodiment, with respect to compounds of formulae III-VF, $R^9$ is

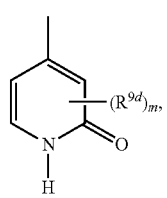, 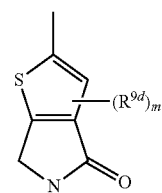 or

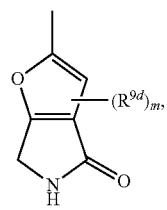

and wherein the subscript m is selected from 1-3 and each $R^{9d}$ is independently H, substituted or unsubstituted alkyl or halo.

In a further embodiment, with respect to compounds of formulae III-VF, $R^9$ is as described above; and each $R^{9d}$ is H.

In a further embodiment, with respect to compounds of formulae III-VF, $R^9$ is as described above; m is 1 or 2 and each $R^{9d}$ is independently Me, Cl or F.

In one embodiment, with respect to compounds of formula III, the compound is according to formula VIa, VIb, VIc, VId, VIe or VIf:

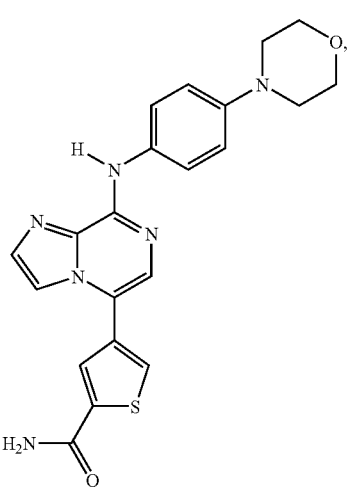

VIa

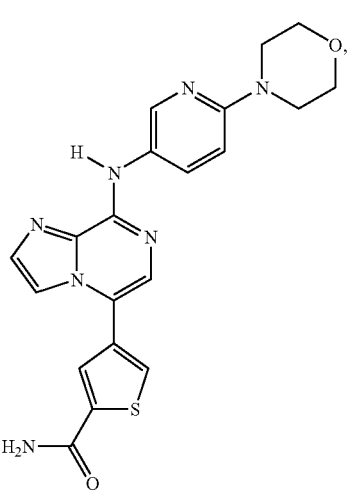

VIb

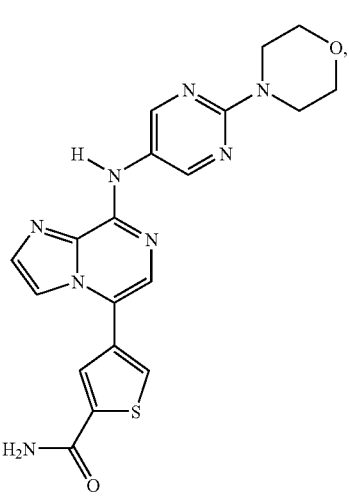

VIc

-continued

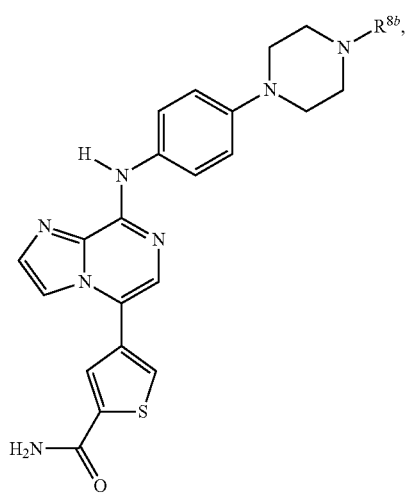

VId

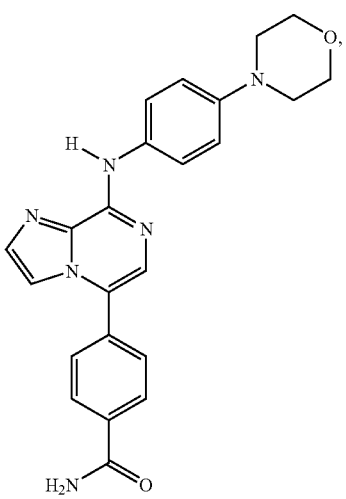

VIe

VIf and $R^{8b}$ is hydrogen, substituted or unsubstituted alkyl or substituted or unsubstituted cycloalkyl.

In a further embodiment, with respect to compounds of formulae VIa-VIf, $R^{8b}$ is H.

In a further embodiment, with respect to compounds of formulae VIa-VIf, $R^{8b}$ is cycloalkyl.

In a further embodiment, with respect to compounds of formulae VIa-VIf, $R^{8b}$ is cyclopropyl.

In a further embodiment, with respect to compounds of formulae VIa-VIf, $R^{8b}$ is substituted or unsubstituted alkyl.

In a further embodiment, with respect to compounds of formulae VIa-VIf, $R^{8b}$ is Me, Et, Pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula VIIa, VIb, VIIc, VIIc, VId, VIIe or VIIf:

VIIa

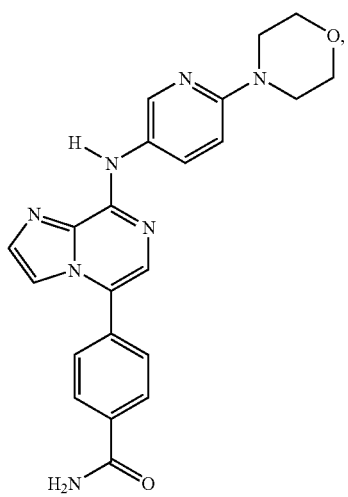

VIIb

-continued

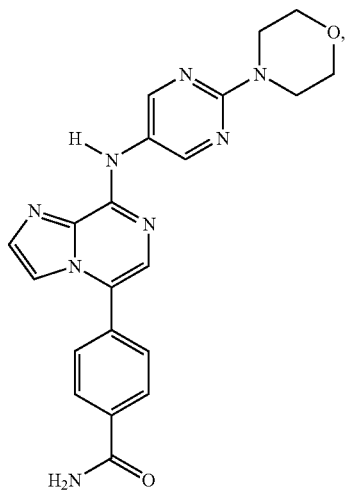
VIIc

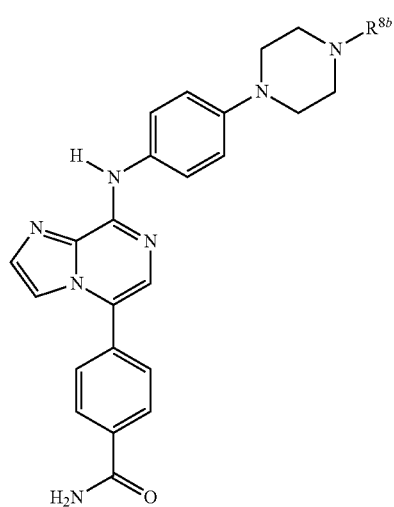
VIId

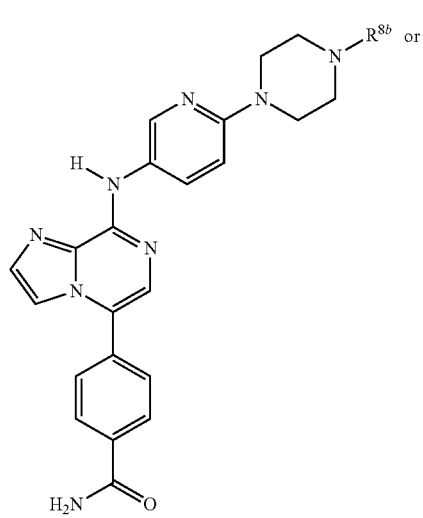
VIIe or

-continued

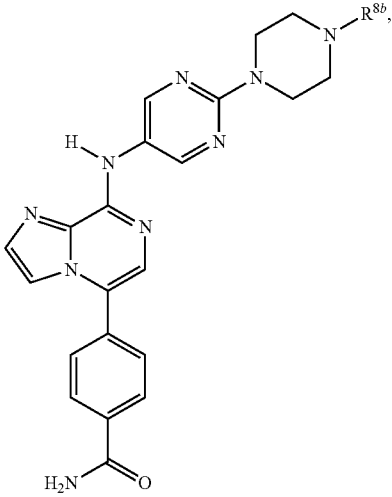
VIIf and $R^{8b}$ is hydrogen, substituted or unsubstituted alkyl or substituted or unsubstituted cycloalkyl.

In a further embodiment, with respect to compounds of formulae VIIa-VIId, $R^{8b}$ is H.

In a further embodiment, with respect to compounds of formulae VIIa-VIIIf, $R^8b$ is cycloalkyl.

In a further embodiment, with respect to compounds of formulae VIIa-VIIf, $R^{8b}$ is cyclopropyl.

In a further embodiment, with respect to compounds of formulae VIIa-VIIf, $R^{8b}$ is substituted or unsubstituted alkyl.

In a further embodiment, with respect to compounds of formulae VIa-VIIf, $R^{8b}$ is Me, Et, Pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula VIIa, VIIb, VIIc, VIId, VIIe or VIIIf:

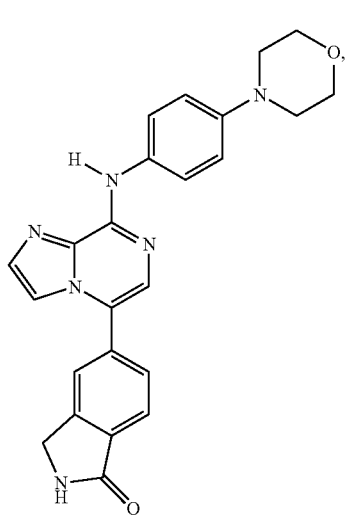
VIIIa

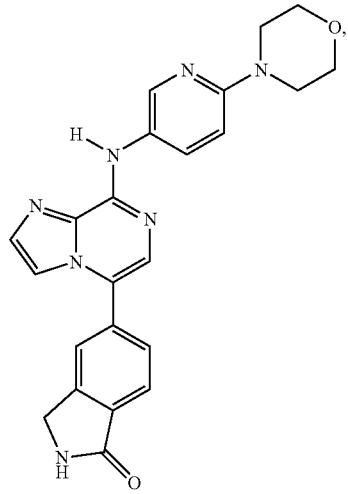
VIIIb

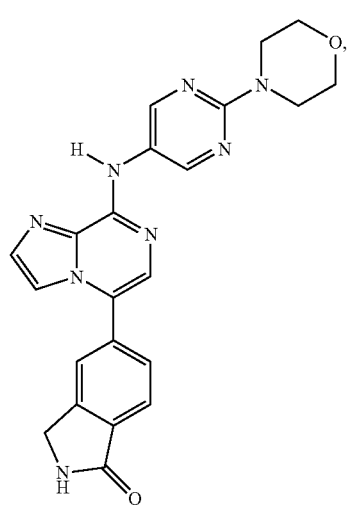
VIIIc

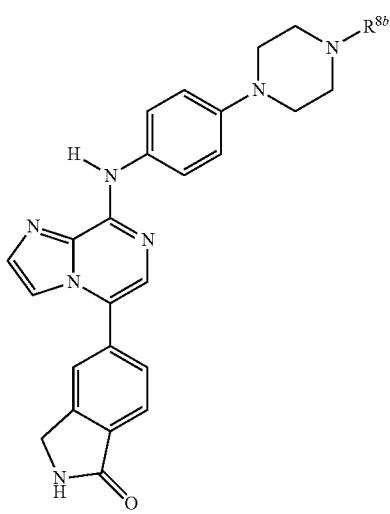
VIIId

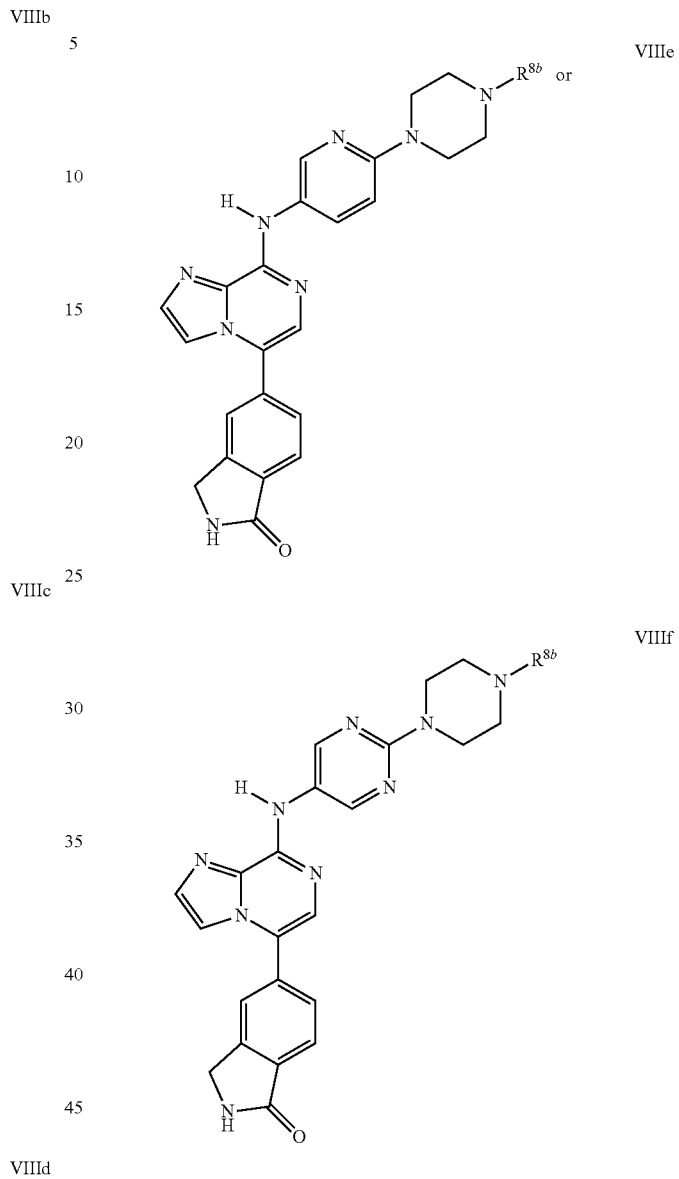

and $R^{8b}$ is hydrogen, substituted or unsubstituted alkyl or substituted or unsubstituted cycloalkyl.

In a further embodiment, with respect to compounds of formulae VIIIa-VIIIf, $R^{8b}$ is H.

In a further embodiment, with respect to compounds of formulae VIIIa-VIIIf, $R^{8b}$ is cycloalkyl.

In a further embodiment, with respect to compounds of formulae VIIIa-VIIIf, $R^{8b}$ is cyclopropyl.

In a further embodiment, with respect to compounds of formulae VIIIa-VIIIf, $R^{8b}$ is substituted or unsubstituted alkyl.

In a further embodiment, with respect to compounds of formulae VIIIa-VIIIf, $R^{8b}$ is Me, Et, Pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula IXa, IXb, IXc, IXd, IXe, or IXf:

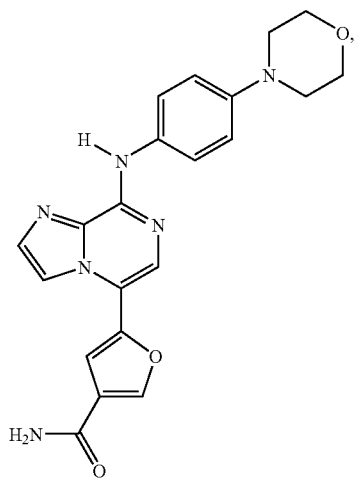
IXa
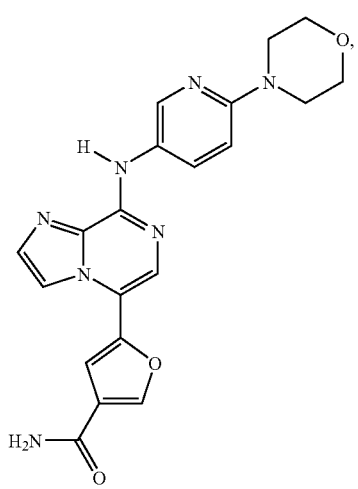
IXb
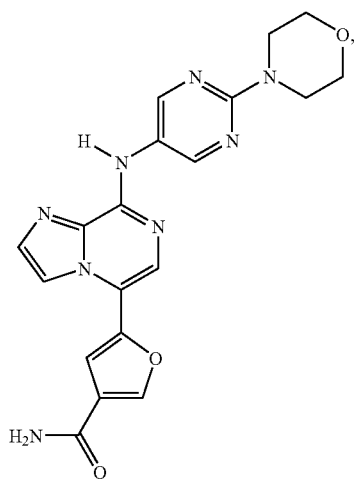
IXc
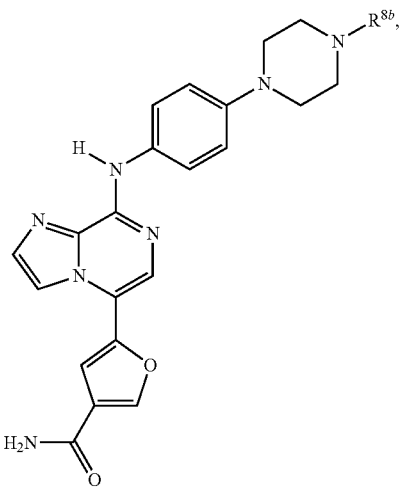
IXd
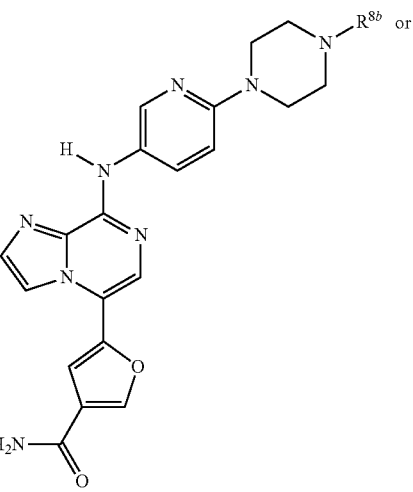
IXe
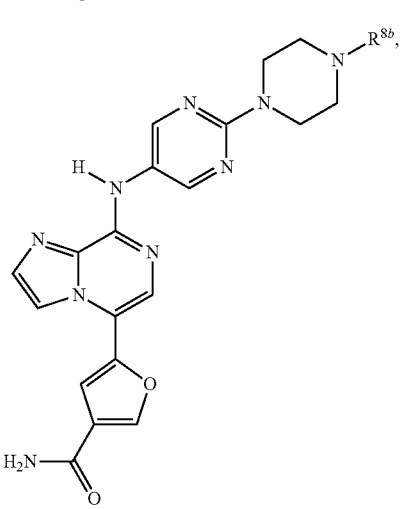
IXf
and $R^{8b}$ is hydrogen, substituted or unsubstituted alkyl or substituted or unsubstituted cycloalkyl.
In a further embodiment, with respect to compounds of formulae IXa-IXf, $R^{8b}$ is H.
In a further embodiment, with respect to compounds of formulae IXa-IXf, $R^{8b}$ is cycloalkyl.

In a further embodiment, with respect to compounds of formulae Ixa-IXf, $R^{8b}$ is cyclopropyl.

In a further embodiment, with respect to compounds of formulae IXa-IXf, $R^{8b}$ is substituted or unsubstituted alkyl.

In a further embodiment, with respect to compounds of formulae IXa-IXf, $R^{8b}$ is Me, Et, Pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula Xa, Xb, Xc, Xd, Xe, or Xf:

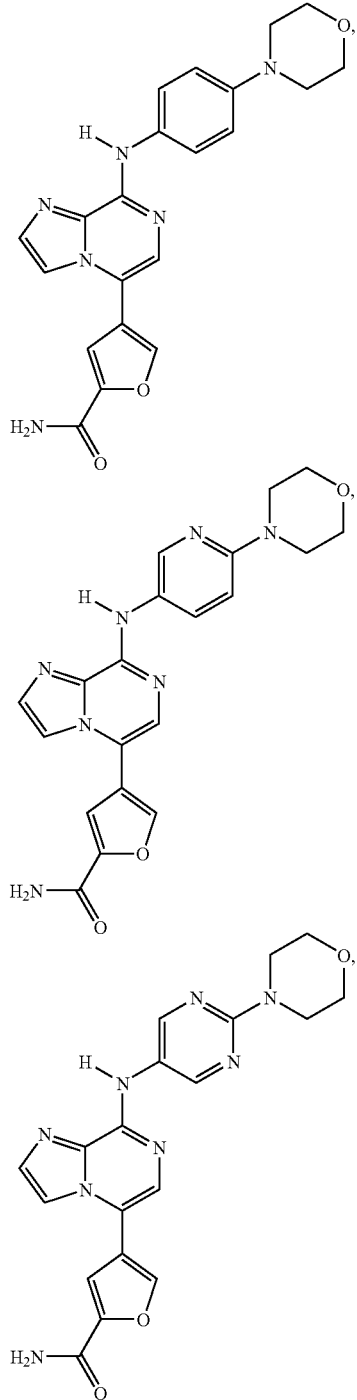

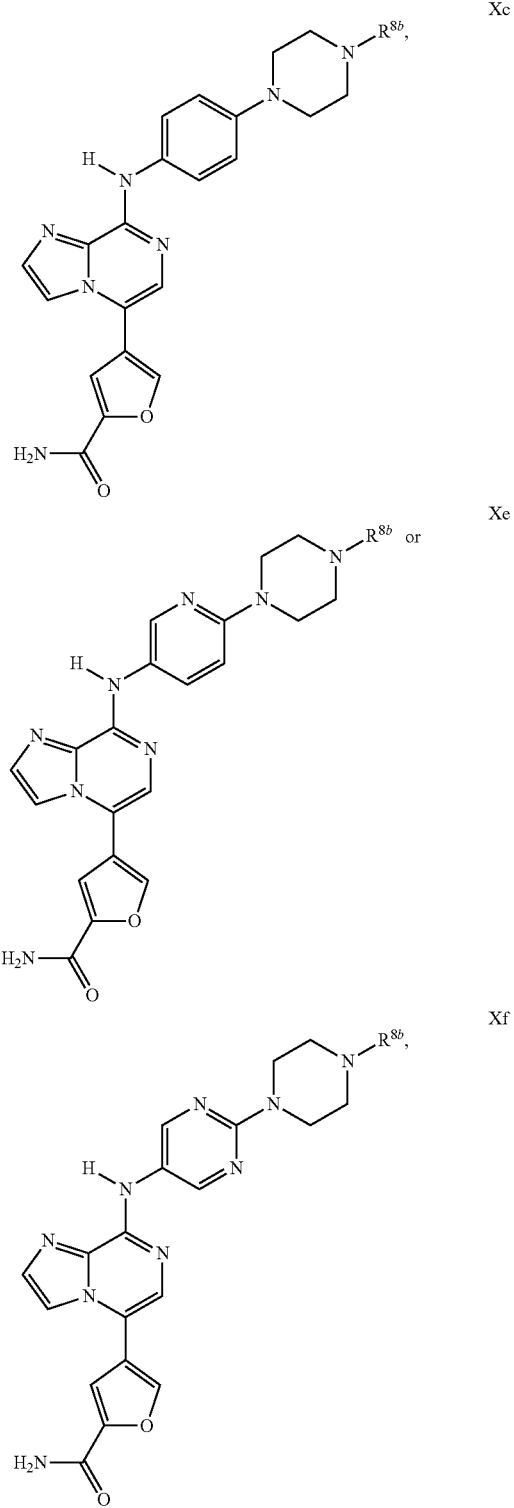

and $R^{8b}$ is hydrogen, substituted or unsubstituted alkyl or substituted or unsubstituted cycloalkyl.

In a further embodiment, with respect to compounds of formulae Xa-Xf, $R^{8b}$ is H.

In a further embodiment,.with respect to compounds of formulae Xa-Xf, $R^{8b}$ is cycloalkyl.

In a further embodiment, with respect to compounds of formulae Xa-Xf, $R^{8b}$ is cyclopropyl.

In a further embodiment, with respect to compounds of formulae Xa-Xf, $R^{8b}$ is substituted or unsubstituted alkyl.

In a further embodiment, with respect to compounds of formulae Xa-Xf, $R^{8b}$ is Me, Et, Pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula XIa, XIb, XIc, XId, XIe or XIf:

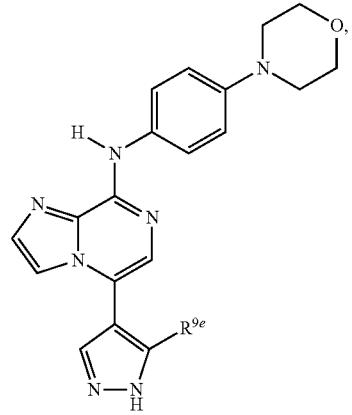

XIa

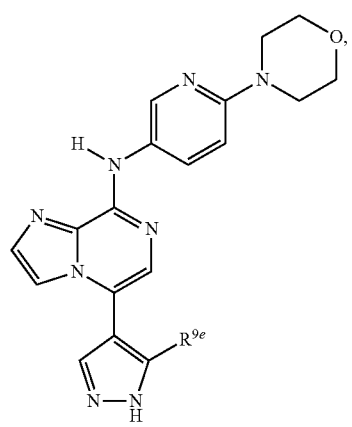

XIb

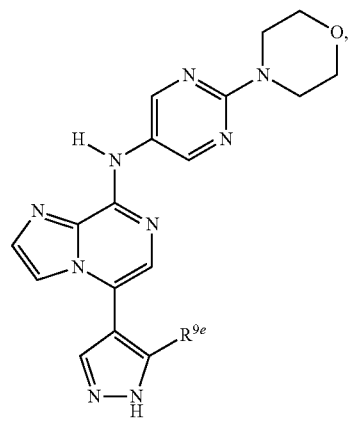

XIc

-continued

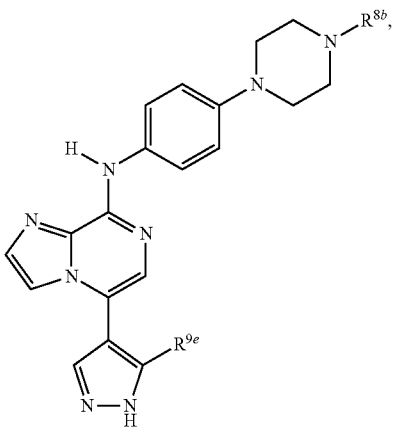

XId

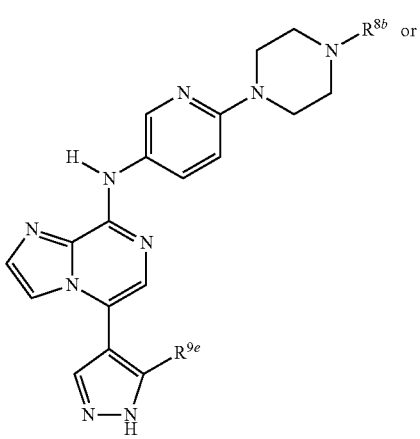

XIe

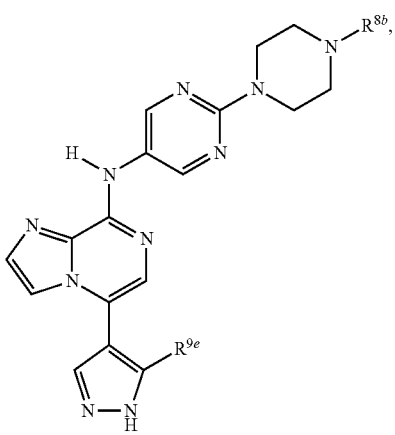

XIf and $R^{8b}$ is hydrogen, substituted or unsubstituted alkyl or substituted or unsubstituted cycloalkyl; and $R^{9e}$ is hydrogen, Me, or CN.

In one embodiment, with respect to compounds of formulae XIa-XIf, $R^{9e}$ is H.

In one embodiment, with respect to compounds of formulae XIa-XIf, $R^{9e}$ is Me.

In one embodiment, with respect to compounds of formulae XIa-XIf, $R^{9e}$ is CN.

In a further embodiment, with respect to compounds of formulae XIa-XIf, $R^{8b}$ is H.

In a further embodiment, with respect to compounds of formulae XIa-XIf, $R^{8b}$ is cycloalkyl.

In a further embodiment, with respect to compounds of formulae XIa-XIf, $R^{8b}$ is cyclopropyl.

In a further embodiment, with respect to compounds of formulae XIa-XIf, $R^{8b}$ is substituted or unsubstituted alkyl.

In a further embodiment, with respect to compounds of formulae XIa-XIf, $R^{8b}$ is Me, Et, pr, i-Pr, t-Bu, i-Bu, $CF_3$, $CH_2CF_3$, $CH_2CONH_2$, or cyclopropylmethyl.

In one embodiment, with respect to compounds of formula III, the compound is according to formula XIIa, XIIb, XIIc or XIId:

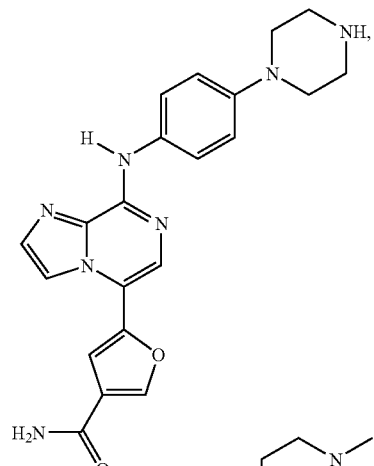

XIIa

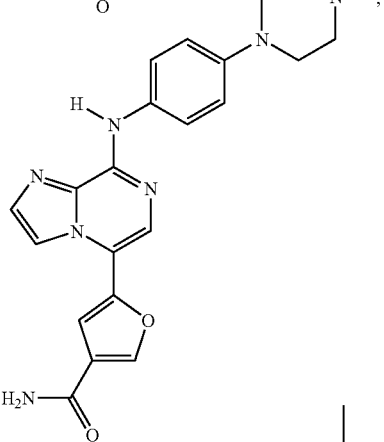

XIIb

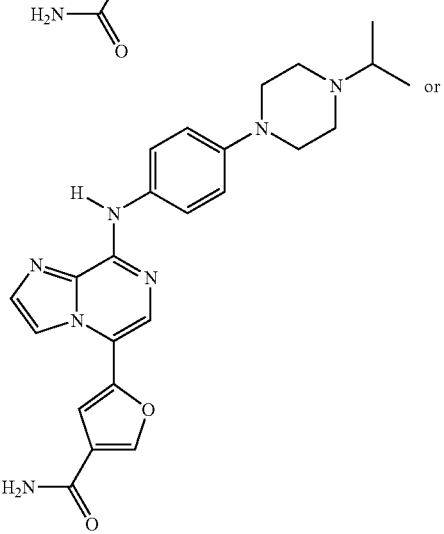

XIIc

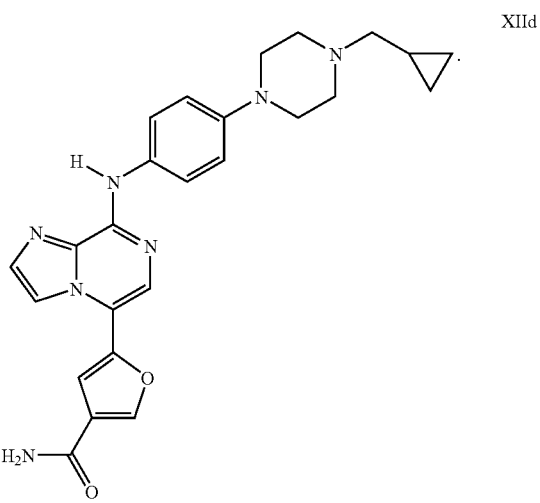

XIId

In one embodiment, with respect to compounds of formula III, the compound is according to formula XIIIa, XIIIb, XIIIc or XIIId:

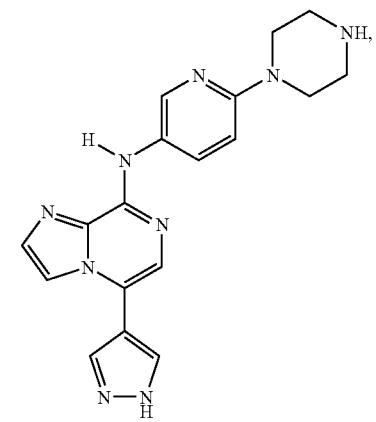

XIIIa

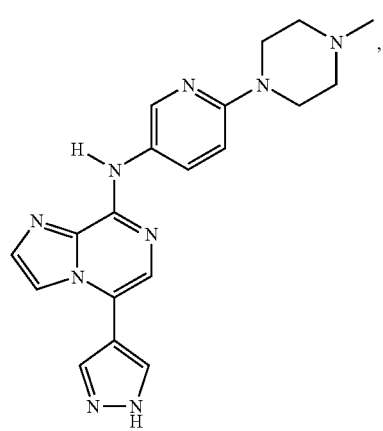

XIIIb

-continued
XIIIc
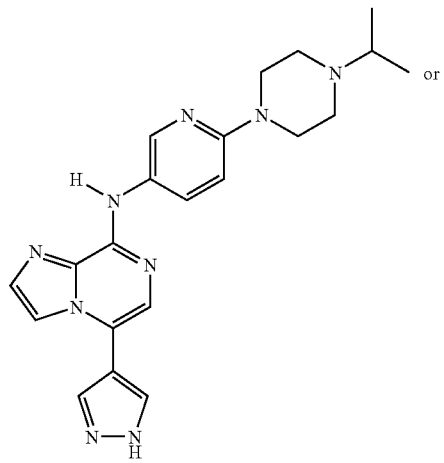
XIIId
In one embodiment, with respect to compounds of formula III, the compound is according to formula XIVa, XIVb, XIVc or XIVd:
XIVa
-continued
XIVb
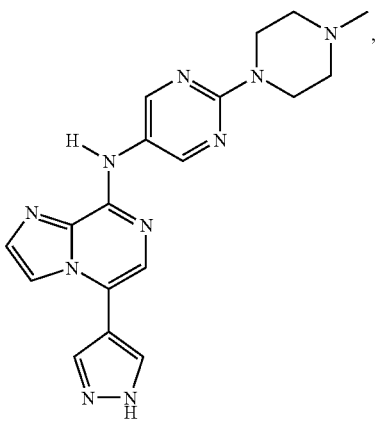
XIVc
XIVd
In one embodiment, with respect to compounds of formula III, the compound is according to formula XVa, XVb, or XIVc:

XVa

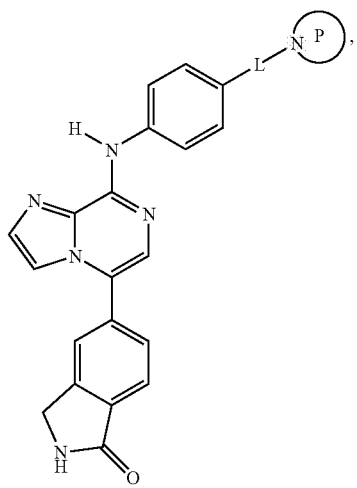

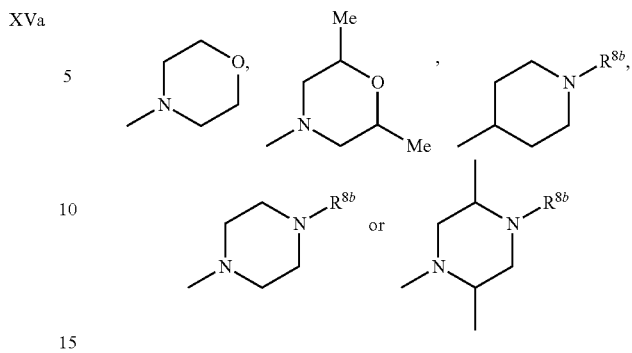

and $R^{8b}$ is H, Me, i-Pr, t-Bu, $CH_2CONH_2$, cyclopropylmethyl, or $CH_2CF_3$.

In one particular embodiment, with respect to compounds of formulae XVa-XVc, L is a bond. In another particular embodiment, L is —O—$CH_2$—$CH_2$—.

In one particular embodiment, with respect to compounds of formulae XVa-XVc, the ring P is XVb

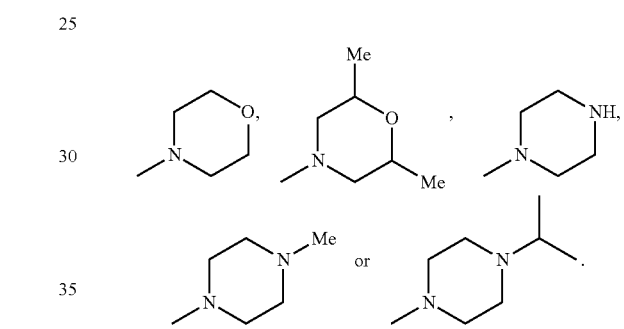

In more particular embodiment, with respect to compounds of formulae XVa-XVc, the ring P is XVc

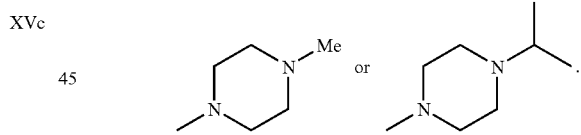

In another embodiment, with respect to compounds of formula III, the compound is selected from Table 1.

In another embodiment, with respect to compounds of formula III, the compound is selected from:
- 4-(8-{4-[Ethyl-(2-hydroxy-ethyl)-amino]-phenylamino}-imidazo[1,2-a]pyrazin-5-yl)-3-methyl-phenol;
- 4-(8-{4-[Ethyl-(2-hydroxy-ethyl)-amino]-phenylamino}-imidazo[1,2-a]pyrazin-5-yl)-benzamide;
- 4-(8-{4-[Ethyl-(2-hydroxy-ethyl)-amino]-phenylamino}-imidazo[1,2-a]pyrazin-5-yl)-phenol;
- 2-({4-[5-(4-Amino-phenyl)-imidazo[1,2-a]pyrazin-8-ylamino]-phenyl}-ethyl-amino)-ethanol;
- 2-({4-[5-(3-Amino-phenyl)-imidazo[1,2-a]pyrazin-8-ylamino]-phenyl}-ethyl-amino)-ethanol;
- 3-[5-(1H-Pyrazol-4-yl)-imidazo[1,2-a]pyrazin-8-ylamino]-benzamide;
- 2-(Ethyl-{3-methyl-4-[5-(1H-pyrazol-4-yl)-imidazo[1,2-a]pyrazin-8-ylamino]-phenyl}-amino)-ethanol;

and L is a bond, —CO—, $SO_2$, —$(CH_2)_{m1}$—, —$O(CH_2)_{m1}$—, —$NH(CH_2)_{m1}$—, —$CON(H)(CH_2)_{m1}$—, or —$SO_2NH(CH_2)_{m1}$—; the subscript m1 is selected from 1-4; the ring P is N-[5-(1H-Pyrazol-4-yl)-imidazo[1,2-a]pyrazin-8-yl]-benzene-1,4-diamine;
4-[3-Methyl-8-(4-morpholin-4-yl-phenylamino)-imidazo[1,2-a]pyrazin-5-yl]-benzamide;
[3-Methyl-5-(1H-pyrazol-4-yl)-imidazo[1,2-a]pyrazin-8-yl]-(4-morpholin-4-yl-phenyl)-amine;
4-[3-Methyl-8-(4-morpholin-4-yl-phenylamino)-imidazo[1,2-a]pyrazin-5-yl]-1H-pyridin-2-one;
4-[8-(4-Morpholin-4-yl-phenylamino)-imidazo[1,2-a]pyrazin-5-yl]-6-trifluoromethyl-1H-pyridin-2-one;
4-[3-Ethyl-8-(4-morpholin-4-yl-phenylamino)-imidazo[1,2-a]pyrazin-5-yl]-benzamide;
6-Methyl-4-[8-(4-morpholin-4-yl-phenylamino)-imidazo[1,2-a]pyrazin-5-yl]-pyridin-2-ol;
4-[3-Ethyl-8-(4-morpholin-4-yl-phenylamino)-imidazo[1,2-a]pyrazin-5-yl]-1H-pyridin-2-one;
[3-Ethyl-5-(1H-pyrazol-4-yl)-imidazo[1,2-a]pyrazin-8-yl]-(4-morpholin-4-yl-phenyl)-amine;
4-(8-{4-[1-(2,2,2-Trifluoro-ethyl)-piperidin-4-yl]-phenylamino}-imidazo[1,2a]pyrazin-5-yl)-thiophene-2-carboxylic acid amide;
[5-(1H-Pyrazol-4-yl)-imidazo[1,2-a]pyrazin-8-yl]-{4-[1-(2,2,2-trifluoro-ethyl)-piperidin-4-yl]-phenyl}-amine;
4-{8-[4-(1-Isopropyl-piperidin-4-yl)-phenylamino]-imidazo[1,2-a]pyrazin-5-yl}-thiophene-2-carboxylic acid amide;
[6-(4-Isopropyl-piperazin-1-yl)-pyridin-3-yl]-[5-(1H-pyrazol-4-yl)-imidazo[1,2-a]pyrazin-8-yl]-amine;
[4-(1-Isopropyl-piperidin-4-yl)-phenyl]-[5-(1H-pyrazol-4-yl)-imidazo[1,2-a]pyrazin-8-yl]-amine;
5-{8-[4-(1-Isopropyl-piperidin-4-yl)-phenylamino]-imidazo[1,2-a]pyrazin-5-yl}-2,3,-dihydro-isoindol-1-one;
5-[8-(6-Morpholin-4-yl-pyridin-3-ylamino)-imidazo[1,2-a]pyrazin-5-yl]-2,3-dihydo-isoindol-1-one;
5-[8-(2-Morpholin-4-yl-pyrimidin-5-ylamino)-imidazo[1,2-a]pyrazin-5-yl]-2,3-dihydro-isoindol-1-one;
2,6-Difluoro-4-{8-[4-(2-morpholin-4-yl-ethoxy)-phenylamino]-imidazo[1,2-a]pyrazin-5-yl}-benzamide;
2-[8-(4-Morpholin-4-yl-phenylamino)-imidazo[1,2-a]pyrazin-5-yl]-5,6-dihydro-furo[2,3-c]pyrrol-4-one;
(3-Dimethylaminomethyl-4-morpholin-4-yl-phenyl)-[5-(1H-pyrazol-4-yl)-imidazo[1,2-a]pyrazin-8-yl]-amine;
5-{8-[2-(4-Isopropyl-piperazin-1-yl)-pyrimidin-5-ylamino]-imidazo[1,2-a]pyrazin-5-yl}-2,3-dihydro-isoindol-1-one;
7-Fluoro-5-{8-[4-(4-isopropyl-piperazin-1-yl)-phenylamino]-imidazo[1,2-a]pyrazin-5-yl}-2,3-dihydro-isoindol-1-one;
2-{8-[4-(4-Isopropyl-piperazin-1-yl)-phenylamino]-imidazo[1,2-a]pyrazin-5-yl}-5,6-dihydro-furo[2,3-c]pyrrol-4-one;
2-(4-{4-[5-(1H-Pyrazol-4-yl)-imidazo[1,2-a]pyrazin-8-ylamino]-phenyl}-piperidin-1yl)-acetamide;
2-(4-{4-[5-(5-Methyl-1H-pyrazol-4-yl)-imidazo[1,2-a]pyrazin-8-ylamino]-phenyl}-piperidin-1-yl)-acetamide;
2-(4-{4-[5-(1-Oxo-2,3-dihydro-1H-isoindol-5-yl)-imidazo[1,2-a]pyrazin-8ylamino]-phenyl}-piperidin-1-yl)-acetamide;
5-{8-[4-(4-Isopropyl-piperazin-1-yl)-phenylamino]-imidazo[1,2-a]pyrazin-5-yl}-3,3-dimethyl-2,3-dihydro-isoindol-1-one; and
2-{8-[4-(4-Isopropyl-piperazin-1-yl)-phenylamino]-imidazo[1,2-a]pyrazin-5-yl}-4,5-dihydro-thieno[2,3-c]pyrrol-6-one.

In another embodiment, with respect to compounds of formula III, the compound is selected from:

(4-Morpholin-4-yl-phenyl)-[5-(1H-pyrazol-4-yl)-imidazo[1,2-a]pyrazin-8-yl]-amine;
N,N-Diethyl-N'-[5-(1H-pyrazol-4-yl)-imidazo[1,2-a]pyrazin-8-yl]-benzene-1,4-diamine;
4-[5-(1H-Pyrazol-4-yl)-imidazo[1,2-a]pyrazin-8-ylamino]-benzamide;
(1H-Indol-5-yl)-[5-(1H-pyrazol-4-yl)-imidazo[1,2-a]pyrazin-8-yl]-amine;
N-{4-[5-(1H-Pyrazol-4-yl)-imidazo[1,2-a]pyrazin-8-ylamino]-phenyl}-methanesulfonamide;
N-{4-[5-(1H-Pyrazol-4-yl)-imidazo[1,2-a]pyrazin-8-ylamino]-phenyl}-acetamide;
N-(2-Diethylamino-ethyl)-4-[5-(1H-pyrazol-4-yl)-imidazo[1,2-a]pyrazin-8-ylamino]-benzamide;
4-[5-(1H-Pyrazol-4-yl)-imidazo[1,2-a]pyrazin-8-ylamino]-N-pyridin-3-ylmethyl-benzamide;
4-[5-(1H-Pyrazol-4-yl)-imidazo[1,2-a]pyrazin-8-ylamino]-benzenesulfonamide;
Morpholin-4-yl-{4-[5-(1H-pyrazol-4-yl)-imidazo[1,2-a]pyrazin-8-ylamino]-phenyl}-methanone;
N-(2-Morpholin-4-yl-ethyl)-4-[5-(1H-pyrazol-4-yl)-imidazo[1,2-a]pyrazin-8-ylamino]-benzamide;
4-[5-(1H-Pyrazol-4-yl)-imidazo[1,2-a]pyrazin-8-ylamino]-N-pyrrolidin-3-yl-benzamide;
N-(2-Ethylamino-ethyl)-4-[5-(1H-pyrazol-4-yl)-imidazo[1,2-a]pyrazin-8-ylamino]-benzamide;
N-(2-Hydroxy-ethyl)-4-[5-(1H-pyrazol-4-yl)-imidazo[1,2-a]pyrazin-8-ylamino]-benzamide;
N-(1-Methyl-pyrrolidin-3-yl)-4-[5-(1H-pyrazol-4-yl)-imidazo[1,2-a]pyrazin-8-ylamino]-benzamide;
N-(2-Diethylamino-ethyl)-4-[5-(1H-pyrazol-4-yl)-imidazo[1,2-a]pyrazin-8-ylamino]-benzenesulfonamide;
[4-(4-Methyl-piperazine-1-sulfonyl)-phenyl]-[5-(1H-pyrazol-4-yl)-imidazo[1,2-a]pyrazin-8-yl]-amine;
[4-(4-Methyl-piperazine-1-sulfonyl)-phenyl]-[5-(1H-pyrazol-4-yl)-imidazo[1,2-a]pyrazin-8-yl]-amine;
N-(2-Diethylamino-ethyl)-2-fluoro-4-[5-(1H-pyrazol-4-yl)-imidazo[1,2-a]pyrazin-8-ylamino]-benzamide;
N-(2-Diethylamino-ethyl)-3-fluoro-4-[5-(1H-pyrazol-4-yl)-imidazo[1,2-a]pyrazin-8-ylamino]-benzamide;
N-(2-Diethylamino-ethyl)-4-[5-(2H-[1,2,3]triazol-4-yl)-imidazo[1,2-a]pyrazin-8-ylamino]-benzamide;
4-[8-(4-Morpholin-4-yl-phenylamino)-imidazo[1,2-a]pyrazin-5-yl]-1H-pyridin-2-one;
N-(4-Hydroxy-benzyl)-4-[5-(1H-pyrazol-4-yl)-imidazo[1,2-a]pyrazin-8-ylamino]-benzamide;
4-[5-(1H-Pyrazol-4-yl)-imidazo[1,2-a]pyrazin-8-ylamino]-N-(2-pyridin-3-yl-ethyl)-benzamide;
N-[2-(1H-Indol-3-yl)-ethyl]-4-[5-(1H-pyrazol-4-yl)-imidazo[1,2-a]pyrazin-8-ylamino]-benzamide;
N-(2-Diethylamino-ethyl)-4-[5-(2-oxo-1,2-dihydro-pyridin-4-yl)-imidazo[1,2-a]pyrazin-8-ylamino]-benzamide;
4-{8-[4-(4-Methyl-piperazin-1-yl)-phenylamino]-imidazo[1,2-a]pyrazin-5-yl}-1H-pyridin-2-one;
5-[5-(1H-Pyrazol-4-yl)-imidazo[1,2-a]pyrazin-8-ylamino]-pyridine-2-carboxylic acid (2-diethylamino-ethyl)-amide;
4-[5-(2-Oxo-1,2-dihydro-pyridin-4-yl)-imidazo[1,2-a]pyrazin-8-ylamino]-N-pyridin-3-ylmethyl-benzamide;
N-(4-Hydroxy-benzyl)-4-[5-(2-oxo-1,2-dihydro-pyridin-4-yl)-imidazo[1,2-a]pyrazin-8-ylamino]-benzamide;
N-(2-Dimethylamino-2-pyridin-3-yl-ethyl)-4-[5-(2-oxo-1,2-dihydro-pyridin-4-yl)-imidazo[1,2-a]pyrazin-8-ylamino]-benzamide;

4-{8-[4-(4-Methyl-piperazin-1-yl)-phenylamino]-imidazo[1,2-a]pyrazin-5-yl}-thiophene-2-carboxylic acid amide;

[4-(4-Methyl-piperazin-1-yl)-phenyl]-[5-(5-methyl-1H-pyrazol-4-yl)-imidazo[1,2-a]pyrazin-8-yl]-amine;

2-Fluoro-4-{8-[4-(4-methyl-piperazin-1-yl)-phenylamino]-imidazo[1,2-a]pyrazin-5-yl}-benzamide;

3-Fluoro-4-{8-[4-(4-methyl-piperazin-1-yl)-phenylamino]-imidazo[1,2-a]pyrazin-5yl}-benzamide;

5-{8-[4-(4-Methyl-piperazin-1-yl)-phenylamino]-imidazo[1,2-a]pyrazin-5-yl}-2-carboxylic acid amide; and 5-{8-[4-(4-Isopropyl-piperazin-1-yl)-3-trifluoromethyl-phenylamino]-imidazo[1,2-a]pyrazin-5-yl}-2,3-dihydro-isoindol-1-one.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. A prodrug may be inactive when administered to a subject but is converted in vivo to an active compound of the invention. "Pharmaceutically acceptable prodrugs" as used herein refers to those prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77,285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound -administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

METHODS OF TREATMENT

The present compounds are used as therapeutic agents for the treatment of conditions in mammals that are causally related or attributable to aberrant activity of MMP1 and/or MAPKAPK5. Accordingly, the compounds and pharmaceutical compositions of this invention find use as therapeutics for preventing and/or treating inflammatory diseases in mammals including humans.

In a method of treatment aspect, this invention provides a method of treating a mammal susceptible to or afflicted with a condition associated with extra-cellular matrix (ECM) degradation, in particular arthritis, and more particularly, rheumatoid arthritis which method comprises administering an effective amount of one or more of the compounds of the invention or a pharmaceutical composition such as just described.

In another method of treatment aspect, the invention provides a method of treating a mammal susceptible to or afflicted with a condition associated with an abnormal cellular expression of MMP1, which comprises administering a therapeutically effective amount of a compound of the invention, or a pharmaceutical composition thereof.

In another method of treatment aspect, the present invention provides a method of treatment or prophylaxis of a condition characterized by abnormal matrix metallo proteinase activity, which comprises administering a therapeutically effective matrix metallo proteinase inhibiting amount of one or more of the compounds of the invention, or pharmaceutical composition thereof.

In yet another method of treatment aspect, this invention provides methods of treating a mammal susceptible to or afflicted with diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; and renal disorders. Such method comprises administering an effective condition-treating or condition-preventing amount of one or more of the compounds of the invention or pharmaceutical compositions just described.

This invention also relates to the use of the present compounds in the manufacture of a medicament for treatment or prophylaxis of a condition prevented, ameliorated or eliminated by administration of an inhibitor of Mitogen-Activated Protein Kinase-Activated Protein Kinase 5, or a condition characterised by abnormal collagenase activity, or a condition associated with ECM degradation or a condition selected from diseases involving inflammation, most preferably in for the treatment of rheumatoid arthritis.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

A preferred regimen of the present method comprises the administration to a subject in suffering from a disease condition characterized as inflammatory, with an effective matrix metallo-protease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as inflammatory and autoimmune conditions, the regimen for treatment usually extends over many months or years, and accordingly oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of an inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

GENERAL SYNTHETIC PROCEDURES

The imidazo[1,2-a]pyridyl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative bicycloheteroaryls that have been listed hereinabove. The compounds of the invention may be prepared from known or commercially available starting materials and reagents by one skilled in the art of organic synthesis.

Synthetic Preparation of Compounds of the Invention

Compounds according to the present invention are produced according to the following scheme.

General Scheme for Synthesising Compounds of Formula (I)

Scheme I

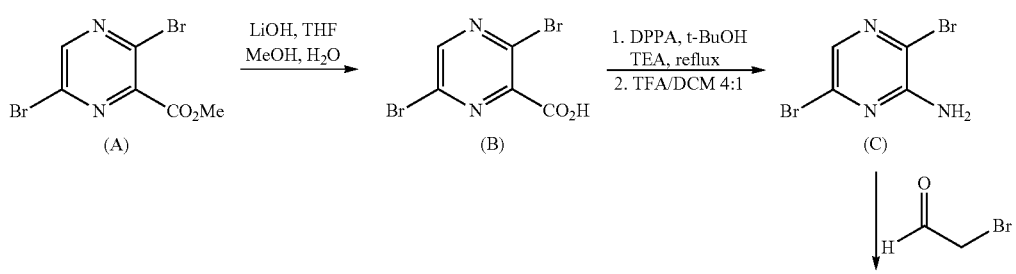

-continued

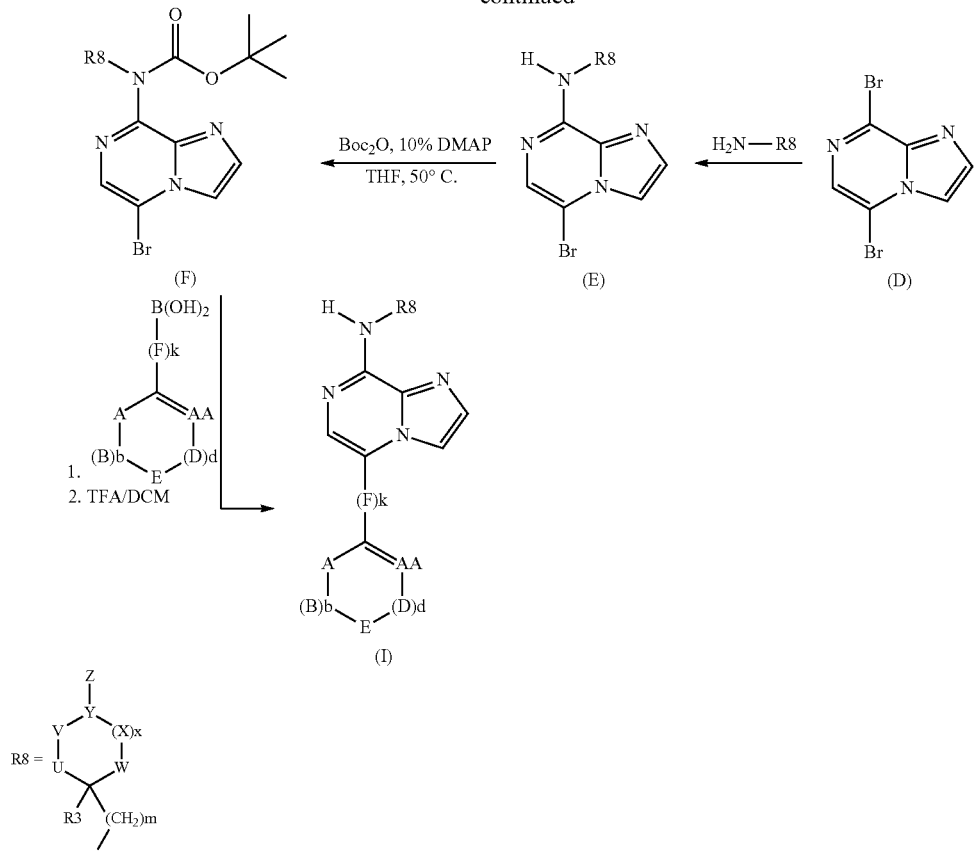

The C8 bromine of 5,8-dibromoimidazo[1,2-a]pyrazine (D) can be selectively displaced with primary and secondary amines or anilines as described in the general reaction scheme. When (D) is displaced by anilines or primary amines ($R^1$=H, $R^8$ for example, 4-chlorophenyl) the product compounds of the general formula (E) are protected as the t-butyl carbamate to give compounds of the general formula (F) which are reacted with the corresponding boronic acids (for example R3=4-pyrazole) to give the desired targets (I) after removal of the protecting group.

General Procedures:

Synthesis of compound (B) as described in the general reaction scheme, 3,6-dibromo-pyrazine-2-carboxylic acid.

LiOH (655 mg, 27 mmol) is added to a solution of methyl-3-amino-2-pyrazine carboxylate (A) (*J. Med. Chem.* 1969, 12, 285-87) (2.7 g, 9 mmol) in THF:water:MeOH (18:4.5:4.5 mL). The reaction is stirred at 5° C. for 30 min, concentrated in vacuo, taken up in DCM and washed with 1N HCl. The organic phase is dried over $MgSO_4$ and concentrated in vacuo to afford compound (B). $^1$H NMR (250 MHz, $CDCl_3$)δ(ppm) 8.70(1H, s).

Synthesis of compound (C) as described in the general reaction scheme, 3,6-Dibromo-pyrazin-2-ylamine.

Diphenylphosphorylazide (2.59 mL, 12 mmol) and triethylamine (1.67 mL, 12 mmol) are added to a solution of 2,5-dibromo-3-pyrazoic acid (3.52 g, 12 mmol) in t-butanol (90 mL). The reaction is heated at reflux for 18 hours. The reaction is quenched with water, then concentrated in vacuo and taken up in DCM. The organic solution is washed with water and 1N NaOH, dried over $MgSO_4$ and concentrated in vacuo. The resultant solid is filtered through a pad of silica using EtOAc, then concentrated and TFA:DCM (4:1, 12 mL) is added to the solid and stirred for 30 min. The solution is concentrated in vacuo then neutralised with 1N NaOH and extracted with DCM. The organic layer is dried over $MgSO_4$ and concentrated in vacuo to give the product. $^1$H NMR (250 MHz, $d_6$-DMSO) δ(ppm) 7.25 (2H, br s), 7.68 (1H, s); m/z (APCI) 254 (M+H)$^+$; m.p 135-139° C.

Synthesis of compound D as described in the general reaction scheme; 5,8-Dibromoimidazo[1,2-a]pyrazine.

Bromoacetaldehyde diethyl acetal (49 mL, 326 mmol) and 48% hydrobromic acid is heated to reflux for 1.5 h, then poured into propan-2-ol (600 mL) and quenched with $NaHCO_3$. After filtering, 2,5-dibromo-3-aminopyrazine (41.34 g, 163 mmol) is added to the solution and heated at reflux overnight. The reaction is cooled and solvents removed in vacuo, followed by addition of aq. $NaHCO_3$ and extraction with EtOAc. The organic phase is dried over $MgSO_4$, filtered, and concentrated in vacuo to afford a brown solid. $^1$H NMR (250 MHz, $CDCl_3$) δ(ppm)7.86 (1H, s), 7.93-7.94 (1H, d), 7.98-7.99 (1H,d); m/z (APCI) 278 (M+H)$^+$; m.p 132-135° C.

Typical Example of Compound of Formula (E).

General procedure for amine displacement

Amine (1.5 eq., 10.8 mmol) and N,N-diisopropylethylamine (1.5 eq, 10.8 mmol) are added to a solution of 5,8-dibromo-imidazo[1,2-a]pyrazine (1.99 g, 7.2 mmol) in ethanol (6 mL), and the reaction stirred at 80° C. for 15 hours. Ethanol is removed in vacuo and the product taken up in DCM and washed with water, dried over MgSO$_4$ and concentrated in vacuo. The resultant oil is passed through a pad of silica using DCM and concentrated in vacuo to yield the desired product.

Typical Example of Compound of Formula (F)

General procedure for Boc protection

Di-tert-butyl-dicarbonate (3 eq, 10.8 mmol) and N,N-dimethylaminopyridine (0.1 eq, 0.36 mmol) are added to a solution of the (5-bromo-imidazo[1,2-a]pyrazin-8-yl)-amine (3.6 mmol) in DCM (4 mL). The solution is then heated at 50° C. overnight, then volatiles removed in vacuo and the product taken up in DCM and washed with 10% citric acid solution. The organic layer is separated, dried over MgSO$_4$ and volatiles removed in vacuo. Recrystallisation from DCM/hexane yields the desired product.

Typical Example of Compound of Formula (I)

General procedure for Suzuki cross coupling reactions and Boc deprotection

A solution of boronic acid in DMF (0.36 mmol, 0.6 mL) and 1.5M Na$_2$CO$_3$(aq.) solution (0.75 mmol, 0.5 mL) are added to a solution of (E) in DMF (0.3 mmol, 0.5 mL). Solutions of palladium acetate (95 mg), triphenylphosphine (335 mg) and catalyst (0.3 mL) in 1,4-dioxane are added and the mixture is then heated at 80° C. for 16 hours. For compounds that require deprotection, the plates are evaporated to dryness and resuspended in a 4:1 mixture of TFA:DCM (1 mL). The plates are agitated overnight and evaporated to dryness. The compounds are resuspended in DMF (2 mL) and purified by preparative reverse phase HPLC.

Synthesis of Intermediates

Intermediate 1: (5-Bromo-imidazo[1,2-a]pyrazin-8-yl)-(4-chloro-phenyl)-amine

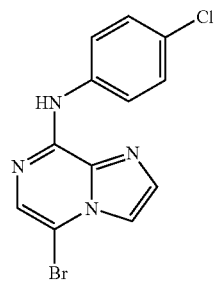

Following the general procedure for amine displacement 5,8-dibromo-imidazo[1,2-a]pyrazine (1.99 g, 7.2 mmol) and 4-chloroaniline (1.37 g, 10.8 mmol) are coupled to give the title compound. Purification on silica gel with dichloromethane, methanol (98:2) gives the final product.

HPLC (254 nm): Rt 3.04 min (100%); m/z (APCI) 323, 325, 327 (M+H)$^+$; $^1$H NMR (250 MHz, CDCl$_3$) δ(ppm) 7.32-7.36 (2H, m), 7.56 (1H, s), 7.64 (1H, m), 7.76-7.80 (3H, m), 7.96 (1H, br s).

Intermediate 2: (5-Bromo-imidazo[1,2-a]pyrazin-8-yl)-(4-methoxy-benzyl)carbamic acid tert-butyl ester

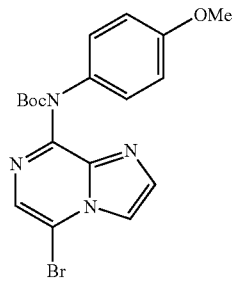

Following the general procedure for Boc protection, (5-bromo-imidazo[1,2-a]pyrazin-8-yl)-(4-methoxybenzyl)-amine (1.18 g, 3.6 mmol) is treated with di-tert-butyldicarbonate (2.34 g, 10.68 mmol) to give the title compound; HPLC (254 nm): R$_t$ 2.84 min (100%); m/z (APCI) 433 (M+H)$^+$, 333 (M+H-BOC); $^1$H NMR (250 MHz, CDCl$_3$) δ(ppm)1.38 (9H, s), 3.74 (3H, s), 6.77 (2H, d), 7.33 (2H, d), 7.80-7.82 (3H, m).

Specific Synthetic Examples of Compounds of the Invention

Compound 1: (4-Morpholin-4-yl-phenyl)-[5-(1H-pyrazol-4-yl)-imidazo[1,2-a]pyrazin-8-yl]-amine

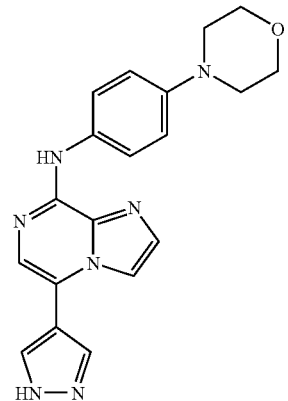

Following the general procedure for Suzuki cross coupling and Boc deprotection (5-bromo-imidazo[1,2-a]pyrazin-8-yl)-(4-morpholin-4-yl-phenyl) carbamic acid tert-butyl ester (142 mg, 0.3 mmol) is coupled with pyrazole-4-boronic acid pinacol ester (70 mg, 0.36 mmol) to give the title compound. The reaction mixture is purified on silica gel using dichloromethane/ methanol (90/10) eluant gave the title compound. HPLC (254 nm): Rt 2.16 min (100%); m/z (APCI) 362 (M+H)$^+$; $^1$H NMR (400 MHz, d$_6$-DMSO) δ(ppm)3.25 (4H, t), 3.94 (4H, t), 7.12 (2H, d), 7.73 (1H, s), 7.88 (1H, d), 8.08 (2H, d), 8.20 (1H, s), 8.27 (1H, d), 8.54 (1H, s), 9.49 (1H, s), 13.55 (1H, br s).

Compound 32: N-(2-Diethylamino-ethyl)-4-[5-(1H-pyrazol-4-yl)-imidazo[1,2-a]pyrazin-8-ylamino]-benzamide Step 1: 4-(5-Bromo-imidazo[1,2-a]pyrazin-8-ylamino)-N-(2-diethylamino-ethyl)-benzamide

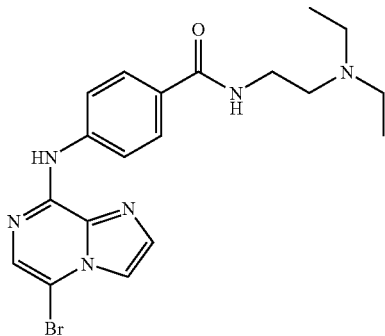

In the same way as described in for Compound 90, step 3, using 4-(5-bromo-imidazo[1,2-a]pyrazin-8-ylamino)-benzoic acid (0.593 g 1.78 mmol), N,N diethylethane-1,2-diamine (0.30 mL, 2.14 mmol), DIPEA (0.48 mL, 2.68 mmol), O-(7-azabenzotriazol-1-yl)-N,N,N',N'-tetramethyluronium hexafluorophosphate (0.68 g, 1.78 mmol) in DMF. The title compound (0.53 g, 69%) is obtained after purification by silica gel column chromatography eluting with DCM followed by 95:5 DCM:NH$_3$ (7M in MeOH). LCMS: Rt 2.21 min (96%).

Step 2: N-(2-Diethylamino-ethyl)-4-[5-(1H-pyrazol-4-yl)-imidazo[1,2-a]pyrazin-8-ylamino]-benzamide

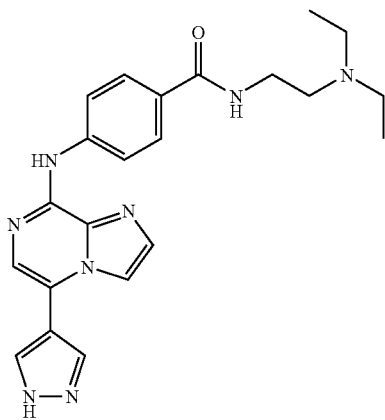

In the same way as described for Compound 85, step 1, using 4-(5-bromo-imidazo[1,2-a]pyrazin-8-ylamino)-N-(2-diethylamino-ethyl)-benzamide (0.12 g, 0.28 mmol), 4-(4,4,5,5-tetramethyl-[1,3,2]dioxaborolan-2-yl)-1H-pyrazole (65 mg, 0.33 mmol), Pd(PPh$_3$)$_4$ (32 mg, 0.028 mmol) and NaO$^t$Bu (0.11 g, 1.11 mmol) in DMF/water. Purification by silica gel column chromatography eluting with 92:8 DCM:NH$_3$ (7M in MeOH) affords the title compound (0.0815 g, 70%). LCMS Rt 1.93 min (99%), m/z (APCI) 419 (M+H)$^+$; $^1$H-NMR (400 MHz, d$_6$-DMSO) δ(ppm) 0.82-0.95 (6H, t), 1.64 (2H, s) 2.37-2.43 (2H, m), 3.17-3.22 (4H, m), 6.55 (1H, br s), 7.20 (1H, br s), 7.55 (1H, s), 7.65-7.69 (3H, m), 7.98-8.09 (4H, m), 9.67 (1H, s), 13.30 (1H, br s).

Compound 69: N-(2-Diethylaminoethyl)-4-[5-(1H-pyrazol-4-yl)imidazo[1,2-a]pyrazin-8-ylamino]benzenesulfonamide Step 1: N-(2-Diethylaminoethyl)-4-nitrobenzenesulfonamide A solution of 2-(N,N-diethyl)ethylamine (0.56 mL, 4.0 mmol) and pyridine (0.7 mL, 8.8 mmol) in DCM is cooled to 0° C. 4-Nitrobenzenesulfonyl chloride (0.98 g, 4.4 mmol) is added and the solution stirred, whilst warming to room temperature, for 18 hours. After this time the solution is cooled to 0° C., and the resultant precipitate filtered, washed with DCM and air-dried. The title sulphonamide is isolated as a cream solid.

Step 2: 4-Amino-N-(2-diethylaminoethyl)benzenesulfonamide

A mixture of N-(2-diethylaminoethyl)-4-nitrobenzenesulfonamide (0.72 g, 2.13 mmol) in cyclohexene (4.8 mL) and EtOH (24 mL) is heated using an oil bath until dissolution had almost been achieved. At this point Pd on C (144 mg, 10% (w/w)) is added, and the mixture heated at reflux for 5 hours. After this time the solution is cooled to room temperature, then filtered through Hy-flo. The filtrate is evaporated in vacuo to afford a yellow gum. The yellow gum is dissolved in the minimum quantity of methanol, then NaHCO$_3$ (1 eq.) dissolved in water, is added. The mixture is stirred at room temperature, then the mixture extracted with EtOAc (2×). The combined organic layers are dried (MgSO$_4$), and evaporated to afford the title aniline.

Step 3: 4-(5-Bromoimidazo[1,2-a]pyrazin-8-ylamino)-N-(2-diethylaminoethyl)benzene stulfonamide A mixture of 5,8-dibromoimidazo[1,2-a]pyrazine (1.0 g, 3.6 mmol), 4-amino-N-(2-diethylaminoethyl)benzenesulfonamide (109 mg, 0.4 mmol), Pd$_2$(dba)$_3$ (7 mg, 0.007 mmol), Xantphos (8.4 mg, 0.015 mmol) and Cs$_2$CO$_3$ (167 mg, 0.52 mmol) in dioxane is heated at 85° C. under nitrogen for 18 hours. The reaction is cooled to room temperature then evaporated to dryness. The residue is chromatographed on silica gel, eluting with DCM then 98:2 DCM:NH$_3$ (7N in MeOH), and the fractions containing the title compound are combined and evaporated to afford a dark oil. This oil contains an impurity, but is used in the subsequent step without further purification.

Step 4: N-(2-Diethylaminoethyl)-4-[5-(1H-pyrazol-4-yl)imidazo[1,2-a]pyrazin-8-ylamino]benzenesulfonamide

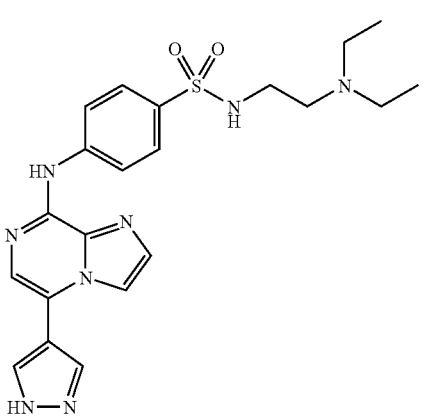

In the same way as described for Compound 85, step 1, using 4-(5-bromoimidazo[1,2-a]pyrazin-8-ylamino)-N-(2-diethylaminoethyl)benzenesulfonamide (100 mg, 0.21 mmol), 4-(4,4,5,5-tetramethyl-[1,3,2]dioxaborolan-2-yl)-1H-pyrazole (17 mg, 0.086 mmol), Pd(PPh₃)₄ (9 mg, 0.007 mmol) and NaO'Bu (27 mg, 0.29 mmol) in DMF:water (3:1, 6 mL). The crude residue is chromatographed on silica gel, eluting with DCM followed by 97:3 DCM:NH₃ (7M in MeOH). The fractions containing the desired product are combined and evaporated, to afford the title compound as a yellow solid. HPLC (254 nm): Rt 2.04 min (97.2%); m/z (APCI) 455 (M+H)⁺

Compound 85: 4-[8-(4-Morpholin-4-yl-phenylamino)imidazo[1,2-a]pyrazin-5-yl]-1H-pyridin-2-one Step 1: [5-(2-Ethoxypyridin-4-yl)imidazo[1,2-a]pyrazin-8-yl]-(4-morpholino-4-ylphenyl)amine

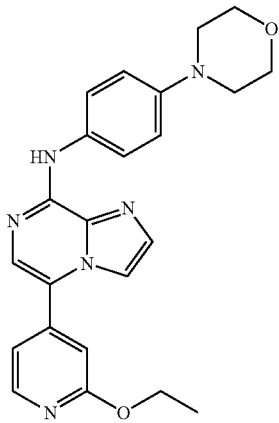

A mixture of 2-ethoxy-4-(4,4,5,5-tetramethyl-[1,3,2]dioxaborolan-2-yl)pyridine (2.84 g, 11.4 mmol), (5-bromoimidazo[1,2-a]pyrazin-8-yl)-4-(4-morpholino-4-ylphenyl) amine (0.85 g, 2.28 mmol), Pd(PPh₃)₄ (263 mg, 0.022 mmol) and NaO'Bu (0.88 g, 9.1 mmol) in DMF (20 mL) and water (7mL) is degassed using nitrogen, then heated at 85° C. for 18 hours. After this time the reaction mixture is cooled to room temperature and the solvents removed in vacuo. The residue is chromatographed on silica gel, eluting with DCM followed by 98:2 DCM:NH₃ (7M in MeOH), and the fractions containing the desired product are combined and evaporated to afford the title ethoxypyridine as a solid. This material is contaminated with some de-brominated compound, and is used without further purification in the next step.

Step 2: (4-Morpholin-4-yl)phenyl)-[5-(2-hydroxypyridin-4-yl)imidazo[1,2-a]pyrazin-8-yl]amine

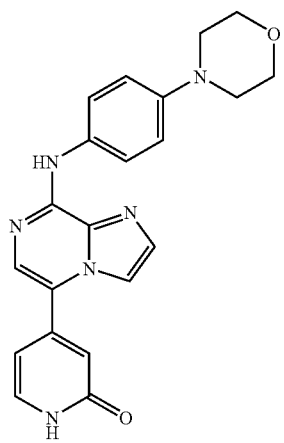

A mixture of [5-(2-ethoxypyridin-4-yl)imidazo[1,2-a]pyrazin-8-yl]-(4-morpholino-4-ylphenyl)amine (1.44 g, 3.46 mmol) and pyridinium hydrochloride (2 g, 17.3 mmol) in water (0.5 mL) is heated at 150° C. for 1 hour in a sealed tube. After this time the solvent is removed in vacuo. The residue is chromatographed on silica gel, eluting with DCM followed by 95:5 DCM:NH₃ (7M in MeOH), and the fractions containing the desired product are combined and evaporated. The residue is triturated with Et₂O to afford the title compound as a solid. HPLC (254 nm): Rt 2.21 min (99.1%); m/z (APCI) 389 (M+H)⁺.

Compound 90 N-(4-Hydroxybenzyl)-4-[5-(1H-pyrazol-4-yl)imidazo[1,2-a]pyrazin-8-ylamino]benzamide Step 1: 4-(5-Bromoimidazo[1,2-a]pyrazin-8-ylamino) benzoic acid methyl ester

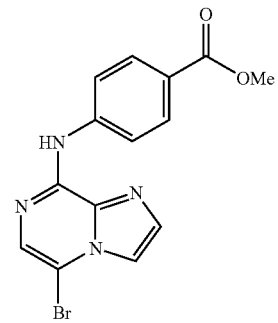

A mixture of 5,8-dibromoimidazo[1,2-a]pyrazine (2 g, 7.3 mmol), 4-amino benzoic acid methyl ester (0.93 g, 6.2 mmol), NaO'Bu (0.98 g, 10.2 mmol), Pd₂(dba)₃ (133 mg, 0.14 mmol), Xantphos (168 mg, 0.29 mmol) and toluene is degassed with nitrogen, then heated at 85° C. for 18 hours. The toluene is removed in vacuo, then MeOH is added to the crude residue. The solid is collected by filtration and dried in the vacuum oven. The solid is identified as the desired title ester. The filtrate is chromatographed with petrol:EtOAc (70:30 followed by 50:50) and the fractions containing the desired product, combined, evaporated and triturated with MeOH. The resultant solid is collected by filtration and is also identified as the desired ester.

Step 2: 4-(5-Bromoimidazo[1,2-a]pyrazin-8-ylamino) benzoic acid

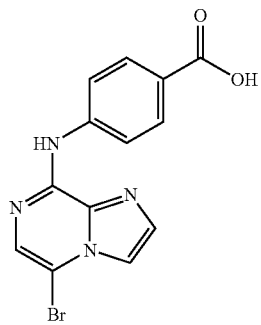

A solution of 4-(5-bromoimidazo[1,2-a]pyrazin-8-ylamino) benzoic acid methyl ester (6.02 g, 17.3 mmol) and LiOH (7.3 g, 174 mmol) in THF (200 mL) and water (200 mL) is stirred at 25° C. for 18 hours. The majority of the solvents are removed in vacuo, then to the remaining aqueous solution is added EtOAc. The aqueous layer is separated, then washed once more EtOAc. The aqueous phase is separated, acidified to pH 5 using concentrated hydrochloric acid and the resultant solid filtered and dried in the vacuum oven. The solid is identified as the desired title acid.

Step 3: 4-(5-Bromoimidazo[1,2-a]pyrazin-8-ylamino)-N-(4-hydroxybenzyl) benzamide

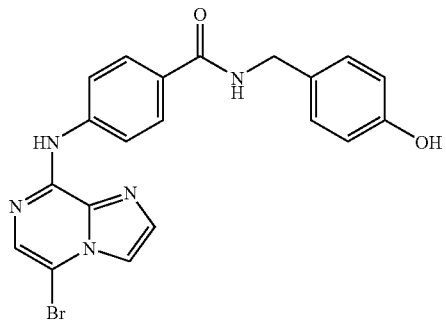

A mixture of 4-(5-bromoimidazo[1,2-a]pyrazin-8-ylamino) benzoic acid (116 mg, 0.35 mmol), 4-aminomethylphenol (43 mg, 0.35 mmol), and N,N-diisopropylethylamine (0.094 mL, 0.525 mmol) in DMF (1 mL) is cooled to 0° C., and O-(7-azabenzotriazol-1-yl)-N,N,N',N'-tetramethyluronium hexafluorophosphate (160 mg, 0.42 mmol) is added. The cooling bath is removed, and the reaction mixture stirred at 25° C. for 18 hours. After this time the solvent is removed in vacuo, and the residue triturated with MeOH. The resultant solid is collected by filtration and identified as the desired phenol.

Step 4: N-(4-Hydroxybenzyl)-4-[5-(1H-pyrazol-4-yl)imidazo[1,2-a]pyrazin-8-ylamino]benzamide

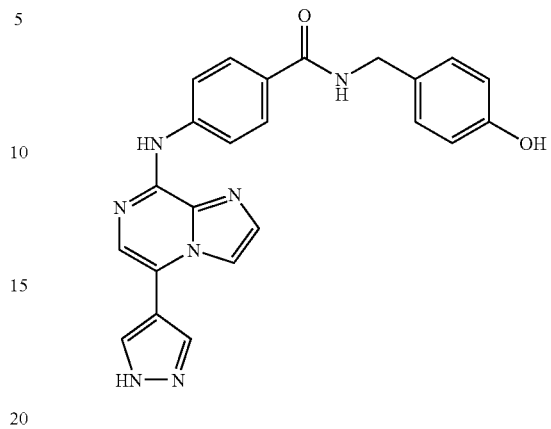

In the same way as described for Compound 85, step 1, using 4-(5-bromoimidazo[1,2-a]pyrazin-8-ylamino)-N-(4-hydroxybenzyl) benzamide (47 mg, 0.11 mmol), 4-(4,4,5,5-tetramethyl-[1,3,2]dioxaborolan-2-yl)-1H-pyrazole (25 mg, 0.13 mmol), Pd(PPh$_3$)$_4$ (12 mg, 0.011 mmol) and NaO$^t$Bu (41 mg, 0.43 mmol) in DMF/water (3:1). The crude residue is chromatographed on silica gel, eluting with petrol:EtOAc (50:50 followed by 0:100) and then EtOAc:MeOH (95:5). The fractions containing the desired product are combined and evaporated, to afford the title compound as a solid. HPLC (254 nm): Rt 2.38 min (90.9%); m/z (APCI) 426 (M+H)$^+$.

Compound 97: 4-[8-(4-Methanesulfonyl-phenylamino)-imidazo[1,2-a]pyrazin-5-yl]-benzamide Step 1: (5-Bromo-imidazo[1,2-a]pyrazin-8-yl)-(4-methanesulfonyl-phenyl)-amine

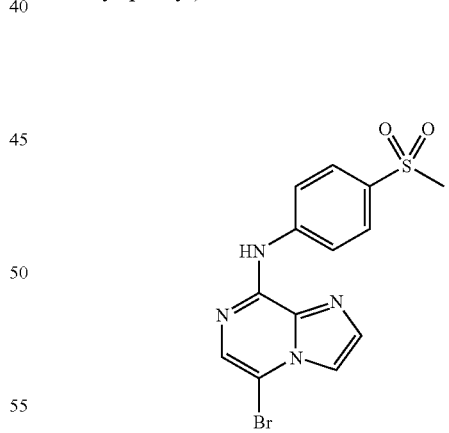

A degassed mixture of 5,8-dibromo-imidazo[1,2-a]pyrazine (2.19 g, 7.916 mmol), 4-methylsulfonylaniline (1.49 g, 8.708 mmol), Pd$_2$dba$_3$ (145 mg, 0.15 mmol) and Xantphos (183 mg, 0.317 mmol), in dry toluene (50 mL) is stirred at 110° C. for 16 hours. After evaporation of the solvent, the residue is purified by silica gel column chromatography eluting with 95:5 DCM:NH$_3$ (7M in MeOH). The title compound (1.496 g, 51%) is isolated containing some starting material (20%) and used in the next step without further purification.

Step 2: 4-[8-(4-Methanesulfonyl-phenylamino)-imidazo[1,2-a]pyrazin-5-yl]-benzamide

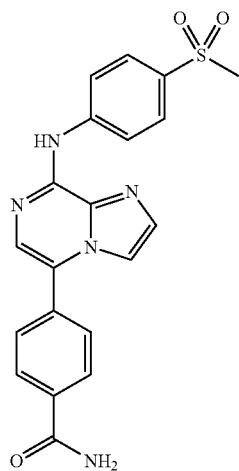

In the same way as described for Compound 85, step 1, using 4-(4,4,5,5-tetramethyl-[1,3,2]dioxaborolan-2-yl)-benzamide (1.0 g, 6.11 mmol), (5-bromo-imidazo[1,2-a]pyrazin-8-yl)-(4-methanesulfonyl-phenyl)-amine (1.49 g, 4.07 mmol), Pd(PPh$_3$)$_4$ (471 mg, 0.41 mmol) and NaO$^t$Bu (1.57 g, 0.82 mmol) in DMF (18 mL) and water (6 mL). The residue is chromatographed on silica gel, eluting with DCM followed by 95:5 DCM:NH$_3$ (7M in MeOH), and the fractions containing the desired product are combined and evaporated to afford a solid, crystallised in ethyl acetate (566 mg, 34%). LCMS: Rt 2.53 min (99%), m/z (APCI) 408 (M+H)$^+$; $^1$H-NMR (400 MHz, d$_6$-DMSO δ(ppm) 3.21 (3H, s), 7.54 (1H, br s), 7.67 (1H, s), 7.81 (1H, s), 7.86-7.92 (4H, m), 8.09-8.17 (3H, m), 8.21 (1H, br s), 8.41 (2H, d), 10.32 (1H, s).

Compound 102: 4-{8-[4-(4-Methylpiperazin-1-yl)-phenylamino]imidazo[1,2-a]pyrazin-5-yl}-1H-pyridin-2-one Step 1: (4-(4-Methylpiperazin-1-yl)phenyl)-[5-(2-ethoxypyridin-4-yl)imidazo[1,2-a]pyrazin-8-yl]amine

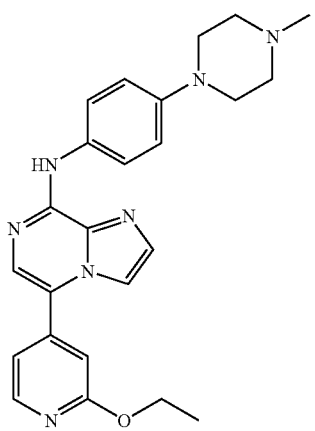

A mixture of 2-ethoxy-4-(4,4,5,5-tetramethyl-[1,3,2]dioxaborolan-2-yl)pyridine (97 mg, 0.31 mmol), (5-bromoimidazo[1,2-a]pyrazin-8-yl)-(4-(4-methylpiperazin-1-yl)phenyl)amine (100 mg, 0.259 mmol), Pd(PPh$_3$)$_4$ (29 mg, 0.026 mmol) and NaO$^t$Bu (99 mg, 1.0 mmol) in DMF (3 mL) and water (1 mL) is heated at 85° C. for 18 hours. After this time the reaction mixture is cooled to room temperature and the solvents removed in vacuo. The residue is chromatographed on silica gel, eluting with DCM followed by 96:4 DCM:NH$_3$ (7M in MeOH), and the fractions containing the desired product are combined and evaporated to afford the title ethoxypyridine as a solid.

Step 2: 4-{8-[4-(4-Methylpiperazin-1-yl)phenylamino]imidazo[1,2-a]pyrazin-5-yl}-1H-pyridin-2-one

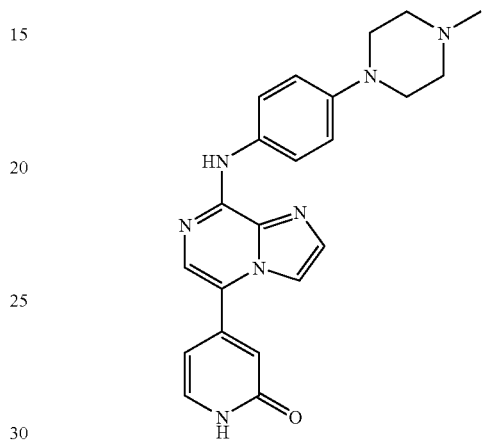

A mixture of (4-(4-methylpiperazin-1-yl)phenyl)-[5-(2-ethoxypyridin-4-yl)-imidazo[1,2-a]pyrazin-8-yl]amine (103 mg, 0.24 mmol) and pyridinium hydrochloride (130 mg, 1.2 mmol) in water (0.2 mL) is heated at 150° C. for 25 minutes in a sealed tube. After this time the solvent is removed in vacuo. The residue is chromatographed on silica gel, eluting with DCM followed by 92:8 DCM:NH$_3$ (7M in MeOH), and the fractions containing the desired product are combined and evaporated to afford the title compound as a solid. HPLC (254 nm): Rt 1.70 min (99.7%); m/z (APCI) 402 (M+H)$^+$.

Compound 103: 5-[5-(1H-Pyrazol-4-yl)-imidazo[1,2-a]pyrazin-8-ylamino]-pyridine-2-carboxylic acid (2-diethylamino-ethyl)-amide Step 1: 5-Amino-pyridine-2-carboxylic acid (2-diethylamino-ethyl)-amide

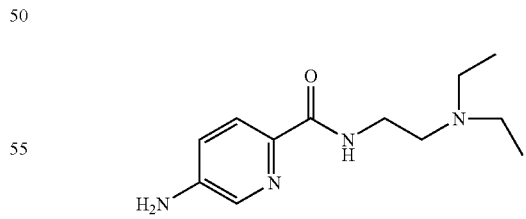

5-Aminopyridine-2-carbonitrile (0.2 g, mmol) is stirred in a mixture of EtOH (1 mL) and 48% aq NaOH (1 mL) at 120°C. overnight. The solvent is removed in vacuo and the water residue is washed with EtOAc. The water layer is acidified to pH 5 and concentrated to afford the crude 5-amino-pyridine-2-carboxylic acid (0.23 g, 0.168 mmol).

The 5-amino-pyridine-2-carboxylic acid is coupled to N,N-diethyl-ethane-1,2-diamine (0.47 mL, 3.32 mmol), in the presence of O-(7-azabenzotriazol-1-yl)-N,N,N',N'-tetramethyluronium hexafluorophosphate (1.26 g, 3.33 mmol), and DIPEA (0.59 mL, 3.33 mmol) in THF (10 mL). The mixture is stirred at room temperature for 48 hours. The solvent is removed in vacuo and the residue partitioned between water-EtOAc. The organic layer is dried over $MgSO_4$, filtered and concentrated to give a residue purified by silica gel column chromatography. 5-Amino-pyridine-2-carboxylic acid (2-diethylamino-ethyl)-amide is isolated (394 mg, 100%) eluting with 96:4 DCM:$NH_3$ (7M in MeOH).

Step 2: 5-(5-Bromo-imidazo[1,2-a]pyrazin-8-ylamino)-pyridine-2-carboxylic acid (2-diethylamino-ethyl)-amide

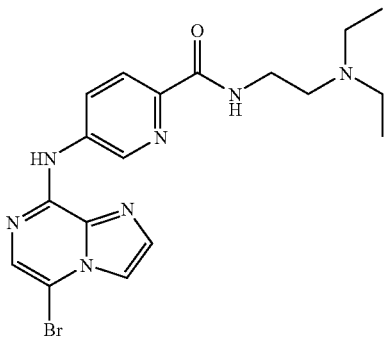

In the same way as described for Compound 90, step 1, using 5,8-dibromoimidazo[1,2-a]pyrazine (0.272 g, 0.982 mmol), 5-amino-pyridine-2-carboxylic acid (2-diethylamino-ethyl)-amide (0.197 g, 0.835 mmol), NaO$^t$Bu (0.132 g, 1.37 mmol), Pd$_2$(dba)$_3$ (18 mg, 0.02 mmol), Xantphos (22 mg, 0.038 mmol) and toluene (3 mL). The crude material is purified by silica gel column chromatography eluting with DCM followed by 94:6 DCM:$NH_3$ (7M in MeOH) to afford the title compound (0.263 g, 72%). HPLC (254 nm) Rt 2.09 min (72%).

Step 3: 5-[5-(1H-Pyrazol-4-yl)-imidazo[1,2-a]pyrazin-8-ylamino]-pyridine-2-carboxylic acid (2-diethylamino-ethyl)-amide

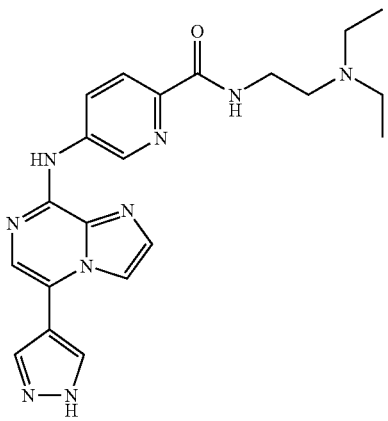

In the same way as described for Compound 85, step 1, using 5-(5-bromo-imidazo[1,2-a]pyrazin-8-ylamino)-pyridine-2-carboxylic acid (2-diethylamino-ethyl)-amide (169 mg, 0.39 mmol), 4-(4,4,5,5-tetramethyl-[1,3,2]dioxaborolan-2-yl)-1H-pyrazole (91 mg, 0.47 mmol), Pd(PPh$_3$)$_4$ (45 mg, 0.039 mmol) and NaO$^t$Bu (150 mg, 1.56 mmol) in DMF: water (3:1, 9 mL). The crude residue is purified by reverse phase preparative HPLC to give the title compound (30 mg, 18%). LCMS: Rt 1.81 min (97.6%); m/z (APCI) 420 (M+H)$^+$; $^1$H-NMR (400 MHz, d$_6$-DMSO) δ (ppm). 1.02 (6H, t), 2.36-2.71 (4H, m), 3.09-3.40 (4H, m), 7.73 (1H, s), 7.84 (1H, s), 8.04 (1H, d), 8.24 (3H, m), 8.56 (1H, m), 8.79 (1H, d), 9.28 (1H, s), 10.24 (1H, s), 13.40 (1H, br s).

Compound 108: 4-[5-(2-Oxo-1,2-dihydropyridin-4-yl)imidazo[1,2-a]pyrazin-8-ylamino]-N-pyridin-3-ylmethyl benzamide Step 1: 4-(5-Bromoimidazo[1,2-a]pyrazin-8-ylamino)-N-pyridin-3-ylmethyl benzamide In the same way as described for Compound 90, step 3, using 4-(5-bromoimidazo[1,2-a]pyrazin-8-ylamino) benzoic acid (365 mg, 1.57 mmol), 3-aminomethylpyridine (0.16 mL, 1.57 mmol), N,N-diisopropylethylamine (0.42 mL, 2.35 mmol), O-(7-azabenzotriazol-1-yl)-N,N,N',N'-tetramethyluronium hexafluorophosphate (HATU) (715 mg, 1.9 mmol) and DMF (6mL). The crude residue is purified using column chromatography, eluting with EtOAc followed by EtOAc: MeOH (95:5) then EtOAc:$NH_3$ (7M in MeOH). The title amide is isolated as a solid.

Step 2: 4-[5-(2-Ethoxypyridin-4-yl)imidazo[1,2-a]pyrazin-8-ylamino]-N-pyridin-3-ylmethyl benzamide A mixture of 2-ethoxy-4-(4,4,5,5-tetramethyl-[1,3,2]dioxaborolan-2-yl)pyridine (85 mg, 0.34 mmol), 4-(5-bromoimidazo[1,2-a]pyrazin-8-ylamino)-N-pyridin-3-ylmethyl benzamide (150 mg, 0.35 mmol), Pd(PPh$_3$)$_4$ (33 mg, 0.028 mmol) and NaO$^t$Bu (109 mg, 1.1 mmol) in DMF:water (3:1, 9 mL) is heated at 85° C. for 18 hours. After this time the reaction mixture is cooled to room temperature and the solvents removed in vacuo. The residue is chromatographed on silica gel, eluting with DCM followed by 95:5 DCM:$NH_3$ (7M in MeOH), and the fractions containing the desired product are combined and evaporated to afford the title ethoxypyridine as a solid.

Step 3: 4-[5-(2-Oxo-1,2-dihydropyridin-4-yl)imidazo[1,2-a]pyrazin-8-ylamino]-N-pyridin-3ylmethyl benzamide

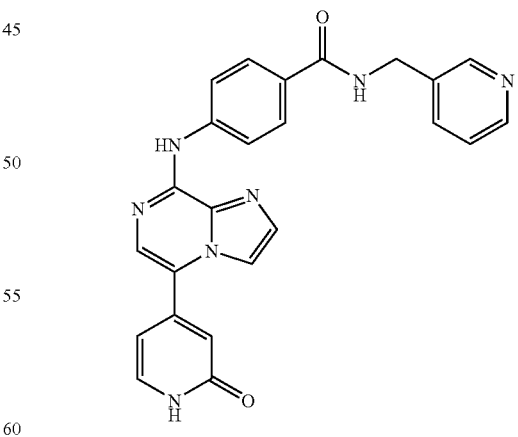

A mixture of 4-[5-(2-ethoxypyridin-4-yl)imidazo[1,2-a]pyrazin-8-ylamino]-N-pyridin-3-ylmethyl benzamide (82 mg, 0.18 mmol) and pyridinium hydrochloride (101 mg, 0.88 mmol) in water (0.5 mL) is heated at 150° C. for 20 minutes in a sealed tube. After this time the solvent is removed in vacuo. The residue is chromatographed on silica gel, eluting with DCM followed by 90:10 DCM:NH₃ (7M in MeOH), and the fractions containing the desired product are combined and evaporated. The title compound is isolated as a solid. HPLC (254 nm): Rt 1.83 min (99.1%); m/z (APCI) 438 (M+H)⁺.

Compound 111: [5-(2-Dimethylamino-pyridin-4-yl)-imidazo[1,2-a]pyrazin-8-yl]-(4-morpholin-4-yl-phenyl)-amine

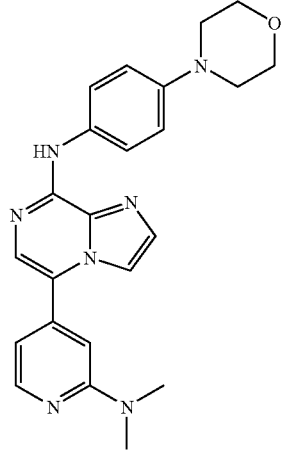

In the same way as described for Compound 85, step 1, using 2-fluoropyridine-4-boronic acid (0.047 g, 0.337 mmol), 5-bromo-imidazo[1,2-a]pyrazin-8-yl)-4-morpholin-4-yl-phenylamine (0.105 g, 0.281 mmol), Pd(PPh₃)₄ (32 mg, 0.0281 mmol) and NaO$^t$Bu (0.108 g, 1.12 mmol) in N,N-dimethylformamide/water (7 mL). The residue is chromatographed on silica gel, eluting with DCM followed by 95:5 DCM:NH₃ (7M in MeOH), and the fractions containing the desired product are combined and evaporated to afford the title compound containing some side products. Additional purification by reverse phase prep HPLC affords the title compound as a yellow solid (18 mg, 16%). LCMS: Rt 1.99 min (98%), m/z (APCI) 416 (M+H)⁺; ¹H-NMR (400 MHz, d₆-DMSO) δ (ppm) 3.09-3.13 (10H, m), 3.78 (4H, m), 6.89 (2H, m), 6.97 (2H, d), 7.59 (1H, s), 7.72 (1H, s), 7.93 (2H, d), 8.09 (1H, s), 8.12 (1H, d), 9.60 (1H, s).

Compound 119: (4-(4-Methylpiperazin-1-yl)phenyl)-[5-(5-methyl-1H-pyrazol-4-yl)imidazo[1,2-a]pyrazin-8-yl]amine

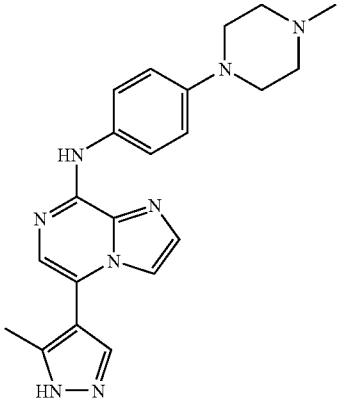

In the same way as described for Compound 127, step 4, using 5-methyl-4-(4,4,5,5-tetramethyl-[1,3,2]dioxaborolan-2-yl)-1H-pyrazole (75 mg, 0.36 mmol), (5-bromoimidazo[1,2-a]pyrazin-8-yl)-(4-(4-methylpiperazin-1-yl)phenyl)amine (70 mg, 0.18 mmol) and Pd(PPh₃)₄ (52 mg, 0.045 mmol) in dioxane (0.6 mL), DMF (1.33 mL) and 1.5M Na₂CO₃ (0.97 mL). The residue is chromatographed on silica gel, eluting with DCM followed by 95:5 DCM:NH₃ (7M in MeOH), and the fractions containing the desired product are combined and evaporated. The title compound is isolated as a solid. HPLC (254 nm): Rt 1.62 min (98.2%); m/z (APCI) 389 (M+H)⁺.

Compound 121: 5-{8-[4-(4-Methyl-piperazin-1-yl)-phenylamino]-imidazo[1,2-a]pyrazin-5-yl}-nicotinamide Step 1: 5-(4,4,5,5-Tetramethyl-[1,3,2]dioxaborolan-2-yl)-nicotinamide

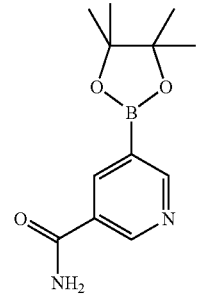

In the same way as described for Compound 209, step 2, using 5-bromo-nicotinamide (0.2 g, 0.99 mmol), bis(pinacolato)diboron (0.27 g, 1.09 mmol), PdCl₂dppf (0.024 g, 0.029 mol) and KOAc (0.29 g, 2.98 mmol) suspended in dioxane (2 mL). The crude compound is used in the next step without further purification.

Step 2: 5-{8-[4-(4-Methyl-piperazin-1-yl)-phenylamino]-imidazo[1,2-a]pyrazin-5-yl}-nicotinamide

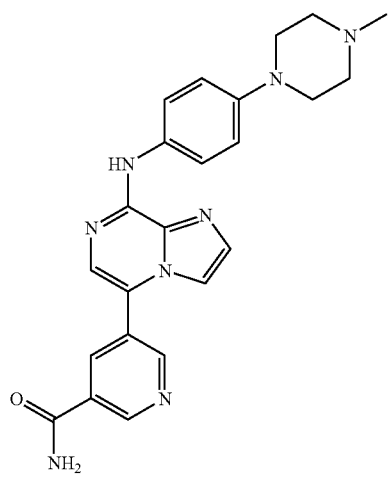

In the same way as described for Compound 127, step 4, using 5-(4,4,5,5-tetramethyl-[1,3,2]dioxaborolan-2-yl)-nicotinamide (51.6 mg, 0.207 mmol), (5-bromoimidazo[1,2-a]pyrazin-8-yl)-(4-(4-methylpiperazin-1-yl)phenyl)amine (40 mg, 0.103 mol), Pd(PPh₃)₄ (30 mg, 0.026 mmol) and 1.5M Na₂CO₃ (0.55 mL), in dioxane (0.46 mL) and DMF (1.01 mL). The residue is chromatographed on silica gel, eluting with DCM followed by 96:4 DCM:NH₃ (7M in MeOH) to afford the title compound (4.8 mg, 11%). LCMS: Rt 1.74 min (97%) m/z (APCI) 429; ¹H-NMR (400 MHz, d₆-DMSO) δ (ppm).2.26 (3H, s), 2.49-2.54 (4H, m), 3.12 (4H, m), 6.97 (2H, d), 7.57 (1H, s), 7.73 (1H, s), 7.75 (1H, br s), 7.91 (2H, d), 8.07 (1H, s), 8.29 (1H, br s), 8.54 (1H, s), 9.03 (1H, s), 9.14 (1H, s), 9.58 (1H, s).

Compound 122: 3-Fluoro-4-{8-[4-(4-methylpiperazin-1-yl)phenylamino]imidazo[1,2-a]pyrazin-5-yl}benzamide

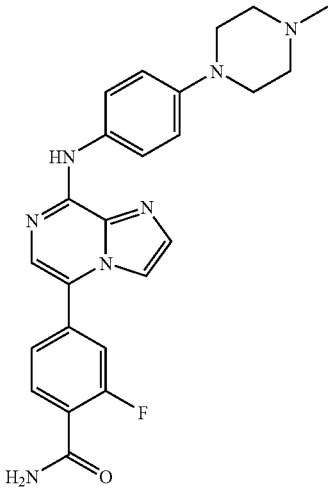

In the same way as described for Compound 127, step 4, using 3-fluoro-4-(4,4,5,5-tetramethyl-[1,3,2]dioxaborolan-2-yl) benzamide (82 mg, 0.31 mmol), (5-bromoimidazo[1,2-a]pyrazin-8-yl)-(4-(4-methylpiperazin-1-yl)phenyl)amine (60 mg, 0.155 mmol) and Pd(PPh₃)₄ (45 mg, 0.038 mmol) in dioxane (0.68 mL), DMF (1.52 mL) and 1.5M Na₂CO₃ (0.83 mL). The residue is chromatographed on silica gel, eluting with DCM followed by 95:5 DCM:NH₃ (7M in MeOH), and the fractions containing the desired product are combined and evaporated. The title compound is isolated as a solid. HPLC (254 nm): Rt 1.92 min (95.0%); m/z (APCI) 446 (M+H)⁺.

Compound 123: 2-Fluoro-4-{8-[4-(4-methylpiperazin-1-yl)phenylamino]imidazo[1,2-a]pyrazin-5-yl}benzamide

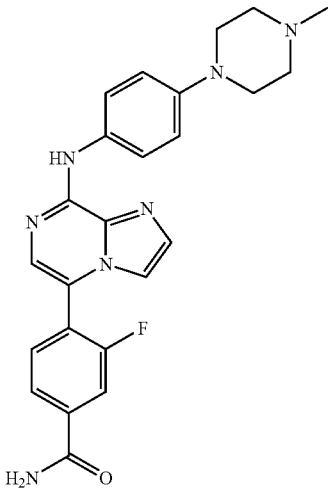

In the same way as described for Compound 127, step 4, using 2-fluoro-4-(4,4,5,5-tetramethyl-[1,3,2]dioxaborolan-2-yl) benzamide (82 mg, 0.31 mmol), (5-bromoimidazo[1,2-a]pyrazin-1-yl)-(4-(4-methylpiperazin-1-yl)phenyl)amine (60 mg, 0.155 mmol) and Pd(PPh₃)₄ (45 mg, 0.038 mol) in dioxane (2.2 mL) and 1.5M Na₂CO₃ (0.83 mL). The residue is chromatographed on silica gel, eluting with DCM followed by 96:4 DCM:NH₃ (7M in MeOH), and the fractions containing the desired product are combined and evaporated. The residue is triturated with Et₂O to afford the title compound as a solid. HPLC (254 nm): Rt 1.94 min (93.5%); m/z (APCI) 446 (M+H)⁺

Compound 125: [5-(2-Fluoro-pyridin-4-yl)-imidazo[1,2-a]pyrazin-8-yl]-[4-(4-methyl-piperazin-1-yl)-phenyl]-amine

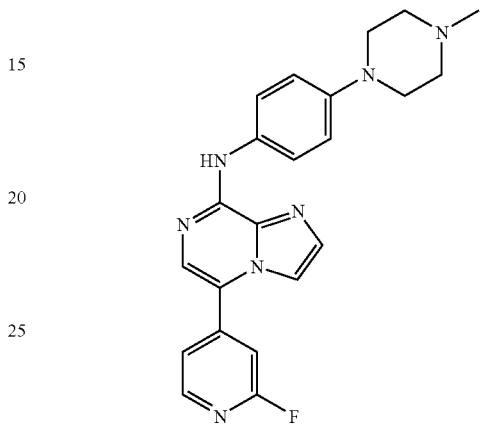

In the same way as described for Compound 127, step 4, using 2-fluoro-pyridine-4-boronic acid (44 mg, 0.310 mmol), (5-bromo-imidazo[1,2-a]pyrazin-8-yl)-(4-(4-methylpiperazin-1-yl)phenyl)amine (60 mg, 0.155 mol), Pd(PPh₃)₄ (45 mg, 0.038 mmol) and 1.5M Na₂CO₃ (0.83 mL) in dioxane (2.2 mL). The residue is chromatographed on silica gel, eluting with DCM followed by 97:3 DCM:NH₃ (7M in MeOH) affording the title compound (37.8 mg, 61%). LCMS: Rt 2.14 min (96%) m/z (APCI) 404 (M+H)⁺; ¹H-NMR (400 MHz, d₆-DMSO) δ (ppm)2.26 (3H, s), 2.49-2.54 (4H, t) 3.13-3.15 (4H, m), 6.97 (2H, d), 7.58 (1H, s), 7.71 (1H, s), 7.75 (2H, m), 7.89 (2H, d), 8.21 (1H, s), 8.43 (1H, d), 9.73 (1H, s).

Compound 126: 2-Dimethylamino-4-{8- [4-(4-methyl-piperazin-1-yl)-phenylamino]-imidazo[1,2-a]pyrazin-5-yl}-benzamide Step 1: 2-Fluoro-4-(4,4,5,5-tetramethyl-[1,3,2]dioxaborolan-2-yl)-benzamide

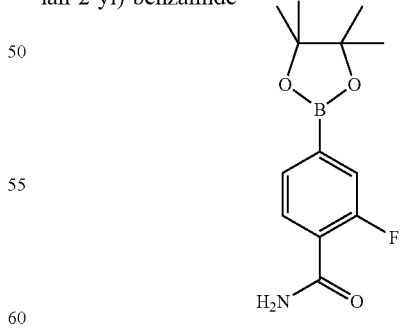

In the same way as described for Compound 209, step 2, using 4-bromo-2-fluoro-benzamide, (0.2 g, 0.94 mmol) bis (pinacolato)diboron (0.26 g, 1.01 mmol), PdCl₂dppf (0.023 g, 0.027 mol) and KOAc (0.29 g, 2.76 mmol) in dioxane (2 mL). The crude compound is used in the next step without further purification.

Step 2: 2-Dimethylamino-4-{8-[4-(4-methyl-piperazin-1-yl)-phenylamino]-imidazo[1,2-a]pyrazin-5-yl}-benzamide

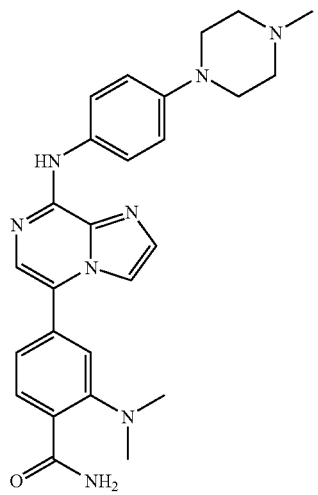

In the same way as described for Compound 127, step 4, using 2-fluoro-4-(4,4,5,5-tetramethyl-[1,3,2]dioxaborolan-2-yl)-benzamide (148 mg, 0.414 mmol), (5-bromoimidazo[1,2-a]pyrazin-8-yl)-(4-(4-methylpiperazin-1-yl)phenyl)amine (80 mg, 0.279 mol) and Pd(PPh$_3$)$_4$ (81 mg, 0.069 mmol) and 1.5M Na$_2$CO$_3$ (1.49 mL), in dioxane (0.93 mL) and N,N-dimethylformamide (2.06 mL). The residue is chromatographed on silica gel, eluting with DCM followed by 96:4 DCM:NH$_3$ (7M in MeOH). The compound, isolated after additional purification by reverse phase prep HPLC is 2-dimethylamino-4-{8-[4-(4-methyl-piperazin-1-yl)-phenylamino]-imidazo[1,2-a]pyrazin-5-yl}-benzamide (3.2 mg). LCMS: Rt 1.67 min (97%) m/z (APCI) 471 (M+H)$^+$; $^1$H-NMR (400 MHz, d$_6$-DMSO) δ (ppm).2.26 (3H, s), 2.48-2.53 (4H, m), 2.85 (6H, s), 3.12-3.14 (4H, m), 6.96 (2H, d), 7.32 (1H, d), 7.36 (1H, d), 7.52 (1H, s), 7.54 (1H, br s), 7.71 (1H, s), 7.74 (1H, d), 7.91 (2H, d), 8.02 (1H, s), 8.28 (1H, br s), 9.48 (1H, s).

Compound 127: (4-(4-Methylpiperazin-1-yl)phenyl)-[5-(2-carboxamido-5-thienyl)imidazo[1,2-a]pyrazin-8-yl]amine Step 1: 5-Bromo-thiophene-2-carboxylic acid amide

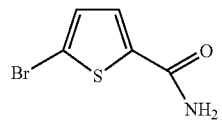

A solution of 5-bromo-thiophene-2-carboxylic acid (4.51 g, 21.78 mmol), 3-hydroxybenzotriazole hydrate (3.24 g, 23.96 mmol), 1-ethyl-3-(3'-dimethylaminopropyl)-carbodiimide (4.6 g, 23.96 mmol) in DMF (70 mL) is stirred at room temperature for 2 hours. The reaction mixture is then cooled to 0° C. and aq. 35% NH$_3$ (2.2 mL) is added. The mixture is stirred at room temperature overnight. The solvent is removed in vacuo and the residue dissolved in EtOAc, washed with 1N NaHCO3, and brine. The organic layers are combined, dried over MgSO$_4$, filtered and concentrated to afford the title compound (3.78 g, 84%). HPLC (254 nm): Rt 2.46 min (96.5%).

Step 2: 5-(4,4,5,5-Tetramethyl-[1,3,2]dioxaborolan-2-yl)-thiophene-2-carboxylic acid amide

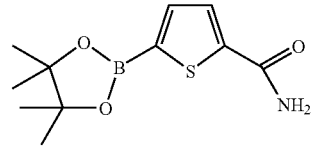

5-Bromo-thiophene-2-carboxylic acid amide (0.5 g, 2.426 mmol), bis(pinacolato)diboron (678 mg, 2.669 mmol), PdCl$_2$dppf (59 mg, 0.072 mmol) and KOAc (0.714 g, 7.28 mmol) are suspended in dioxane (5 mL), purged with nitrogen for 5 minutes and then heated at 85° C. overnight. The solvent is removed in vacuo and the residue partitioned between ethyl acetate and water. The aqueous layer is extracted again with ethyl acetate and the combined organic phases are washed with brine, filtered through MgSO$_4$ and evaporated in vacuo to afford the title compound (417 mg, 68%)

Step 3: (5-Bromoimidazo[1,2-a]pyrazin-8-yl)-(4-(4-methylpiperazin-1-yl)phenylamine

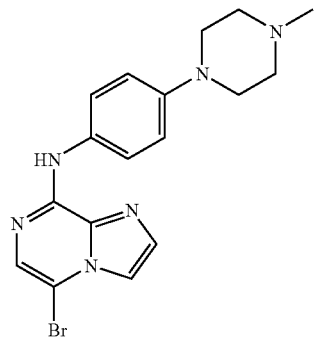

4-(4-Methylpiperazin-1yl)phenylamine (5.08 g, 26.6 mmol) and N,N-diisopropylethylamine (4.6 mL, 26.6 mmol) and 5,8-dibromoimidazo[1,2-a]pyrazine (6.1 g, 22.2 mmol) in iso-propanol (150 mL), is heated at 90° C. for 2 days. The solvent is removed in vacuo, and the crude residue partitioned between DCM and 1N NaOH. The organic phase is separated, then washed with water followed by brine. The organic layer is separated, dried (MgSO$_4$) and evaporated. The crude residue is chromatographed on silica gel, eluting with DCM followed by 96:4 DCM:NH$_3$ (7M in MeOH), and the fractions containing the desired product are combined and evaporated. The residue is triturated with Et$_2$O to afford the title compound as a solid.

Step 4: (4-(4-Methylpiperazin-1-yl)phenyl)-[5-(2-carboxamido-5-thienyl)imidazo[1,2-a]pyrazin-8-yl]amine

81

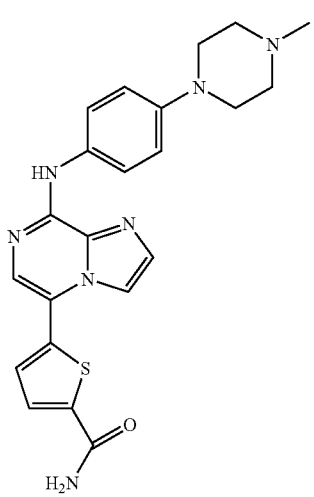

A mixture of 5-(4,4,5,5-tetramethyl-[1,3,2]dioxaborolan-2-yl)thiophene-2-carboxylic acid amide (0.19 g, 0.75 mmol), (5-bromoimidazo[1,2-a]pyrazin-8-yl)-(4-(4-methylpiperazin-1-yl)phenyl)amine (60 mg, 0.155 mmol) and Pd(PPh$_3$)$_4$ (45 mg, 0.038 mmol) in dioxane (2.2 mL) and 1.5M Na$_2$CO$_3$ (0.83 mL) is heated at 85° C. for 18 hours. After this time the reaction mixture is cooled to room temperature and filtered. The filtrate is partitioned between EtOAc and water, and the organic layer separated. The organic phase is washed with water (4×) then separated. The aqueous phase is then washed with EtOAc and the organic layer separated. The combined organic layers are dried (MgSO$_4$) and evaporated. The residue is chromatographed on silica gel, eluting with DCM followed by 95:5 DCM:NH$_3$ (7M in MeOH), and the fractions containing the desired product are combined and evaporated to afford the title compound as a solid. HPLC (254 nm): Rt 1.95 min (98.9%); m/z (APCI) 434 (M+H)$^+$.

Compound 129: 5-{8-[4-(4-Methyl-piperazin-1-yl)-phenylamino]-imidazo[1,2-a]pyrazin-5-yl}-pyridine-2-carboxylic acid amide Step 1: 5-Tributylstannanyl-pyridine-2-carboxylic acid amide

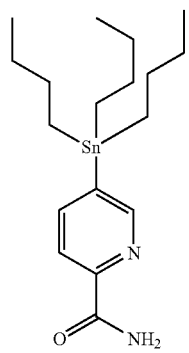

A degassed mixture of 5-bromo-pyridine-2-carboxylic acid (0.2 g, 1 mmol), tributyltin (1.16 g, 2 mmol) and PdCl$_2$(PPh$_3$)$_2$ (0.07 g, 0.1 mmol) in DMF (4 mL) is stirred at 115° C. Additional 20% of PdCl$_2$(PPh$_3$)$_2$ (0.14 g, 0.2 mmol) is added and the reaction stirred for 24 hours. The reaction mixture is partitioned between EtOAc and water, the organic layer is washed with water (4×), dried over MgSO$_4$, filtered and concentrated in vacuo. The crude is purified by silica gel column chromatography eluting with 9:1 petroleum ether-ethyl acetate to afford the title compound (0.132 mg, 32%).

Step 2: 5-{8-[4-(4-Methyl-piperazin-1-yl)-phenylamino]-imidazo[1,2-a]pyrazin-5-yl}-pyridine-2-carboxylic acid amide

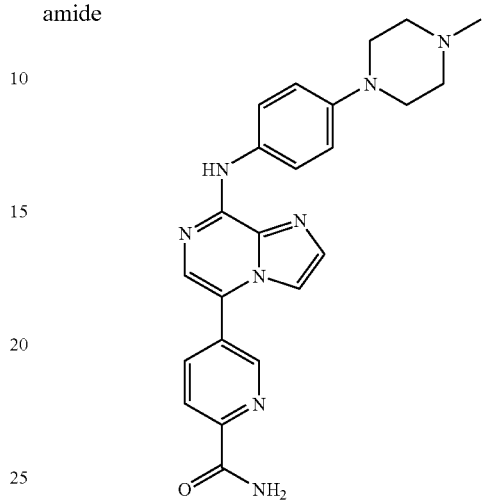

A degassed mixture of (5-bromoimidazo[1,2-a]pyrazin-8-yl)-(4-(4-methylpiperazin-1-yl)phenyl)amine (59 mg, 0.154 mol), 5-tributylstannanyl-pyridine-2-carboxylic acid amide (0.127, 0.309 mmol), PdCl$_2$(PPh$_3$)$_2$ (0.027 g, 0.038 mmol) in DMF (2 mL), is stirred at 85° C. for 20 hours. The reaction mixture is partitioned between EtOAc and water. The organic layer is washed with water (4×), dried over MgSO$_4$, filtered and concentrated in vacuo. The crude is purified by silica gel column chromatography eluting with DCM followed by 97:3 DCM:NH$_3$ (7M in MeOH) affording the title compound (2.0 mg, 3%). LCMS: Rt 1.75 min (92%) m/z (APCI) 429 (M+H)$^+$; $^1$H-NMR (400 MHz, d$_6$-DMSO) δ (ppm) 2.26 (3H, s), 2.49-2.51 (4H, t), 3.12-3.15 (4H, m), 6.97 (2H, d), 7.62 (1H, s), 7.73 (1H, s), 7.77 (1H, br s), 7.91 (2H, d), 8.08 (1H, s), 8.22 (1H, d), 8.24 (1H, br s), 8.37-8.40 (1H, m), 8.96 (1H, s), 9.61 (1H, s).

Compound 130: 4-[3-Methyl-8-(4-morpholin-4-ylphenylamino)imidazo[1,2-a]pyrazin-5-yl]benzamide

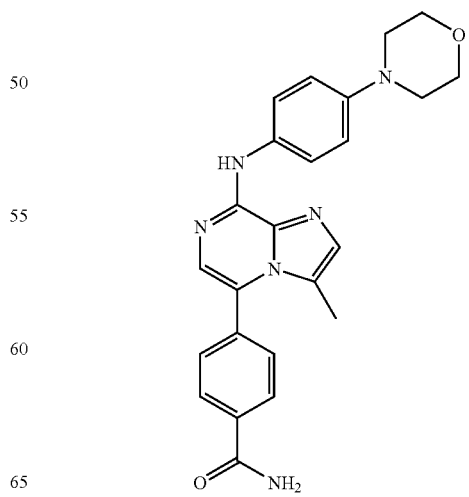

This compound may be prepared using methods as described for Compound 131, using 4-carbamoylbenzene boronic acid in Step 4. LCMS: Rt=1.44 min (100%), m/z (ESI) 429 (M+H)⁺.

Compound 131: [3-Methyl-5-(1H-pyrazol-4-yl)imidazo[1,2-a]pyrazin-8-yl]-(4-morpholin-4yl-phenyl)amine Step 1: 2-Bromo-1,1-dimethoxypropane

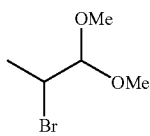

A solution of propanal (12.5 mL, 170 mmol) in MeOH (85 mL) is stirred at rt and molecular sieves (3 Å, powdered, 4.3 g) are added. The mixture is heated at reflux, Br₂ (8.8 mL, 170 mmol) is added dropwise over 30 min and reflux is then continued for 4.5 h. The mixture is stirred overnight at rt and K₂CO₃ (11.9 g, 86 mmol) is then added and the resulting slurry is stirred for 2.5 h. This is filtered and the solid is washed with MeOH (20 mL). Brine (100 mL) is added to the filtrate and the mixture is extracted with pentane (3×75 mL). The extracts are dried over MgSO₄ and evaporated under reduced pressure to afford a pale yellow oil (16.0 g) which is not purified further.

Step 2: 5,8-Dibromo-3-methylimidazo[1,2-a]pyrazine

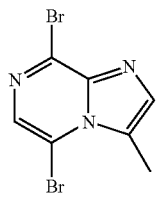

2,5-Dibromo-3-aminopyrazine (2.0 g, 7.9 mmol), 2-bromo-1,1-dimethoxypropane (7.25 g, 40.0 mmol) and pyridinium p-toluenesulfonate (2.0 g, 7.9 mmol) are stirred in acetonitrile (65 mL) at reflux for 3 days. The mixture is cooled and the solvent evaporated under reduced pressure. The residue is partitioned between DCM (150 mL) and water (50 mL) and the layers separated. The organic fraction is washed with NaHCO₃ (sat. aq., 50 mL) and brine (50 mL) and dried over MgSO₄. Evaporation of the solvent under reduced pressure gives a viscous black oil (2.14 g) which is purified by silica chromatography, eluting with 10% -20% EtOAc in cyclohexane to afford the title compound as a red-brown solid (280 mg, 1 mmol).

Step 3: (5-Bromo-3-methylimidazo[1,2-a]pyrazin-8-yl)-(4-morpholin-4-ylphenyl)amine

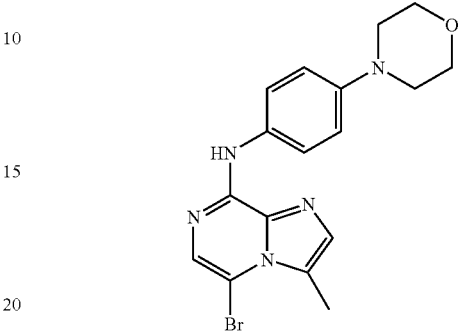

5,8-Dibromo-3-methylimidazo[1,2-a]pyrazine (270 mg, 0.93 mmol) and 4-morpholinoaniline (200 mg, 1.1 mmol) are combined in nBuOH (10 mL) and DIPEA (240 μL, 1.4 mmol) is added. The mixture is heated at reflux for 10 h, cooled and the solvent removed under reduced pressure. The residue is purified by silica chromatography, eluting with 12% -100% EtOAc in cyclohexane, to afford the title compound as a red-brown solid (190 mg).

Step 4: [3-Methyl-5-(1H-pyrazol-4-yl)imidazo[1,2-a]pyrazin-8-yl]-(4-morpholin-4-yl-phenyl)amine

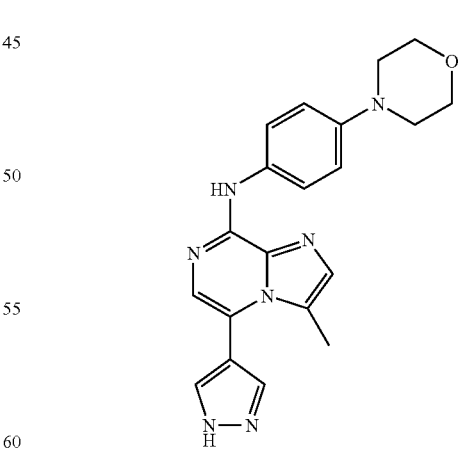

This compound may be prepared using methods as described for Compound 184, step 4. LCMS: Rt=0.81 min (100%), m/z (ESI) 376 (M+H)⁺.

Compound 132: [5-(2-Amino-pyridin-4-yl)-imidazo[1,2-a]pyrazin-8-yl]-[4-(4-methyl-piperazin-1-yl)-phenyl]-amine

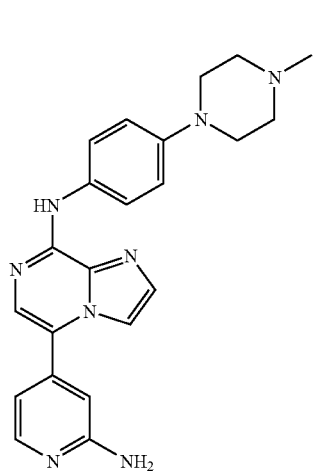

A solution of [5-(2-fluoro-pyridin-4-yl)-imidazo[1,2-a]pyrazin-8-yl]-[4-(4-methyl-piperazin-1-yl)-phenyl]-amine (0.0272, 0.067 mmol) (from Example 125) in a mixture of aq. NH$_3$ (2.5 mL):1M NH$_3$ in MeOH (2.5 mL) is stirred at 100° C. overnight. Additional aq. NE$_3$ (5 mL) and 0.5M NH$_3$ in dioxane (2 mL) are added and the mixture stirred at 120° C. for 4 days. The mixture is concentrated in vacuo and purified by reverse phase HPLC affording the title compound (4.2 mg, 16%). LCMS: Rt 3.76 min (95%) m/z (APCI) 401 (M+H)$^+$; $^1$H-NMR (400 MHz, d$_6$-DMSO) δ (ppm). 2.26 (3H, s), 2.49-2.53 (4H, t), 3.12-3.15 (4H, m), 6.18 (2H, br s) 6.76 (1H, s), 6.81 (1H, d), 6.97 (2H, d), 7.51 (1H, s), 7.72 (1H, s), 7.88 (2H, d), 8.04 (1H, s), 8.09 (1H, d), 9.55 (1H, s).

Compound 136: 4-{8-[3-Chloro-4-(4-methyl-piperazin-1-yl)-phenylamino]-imidazo[1,2-a]pyrazin-5-yl}-benzamide

Step 1: (5-Bromo-imidazo[1,2-a]pyrazin-8-yl)-[3-chloro-4-(4-methyl-piperazin-1-yl)-phenyl]-amine

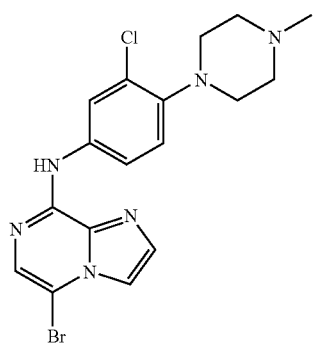

Following the general procedure for amine displacement using 5,8-dibromoimidazo[1,2-a]pyrazine (0.20 g, 0.72 mmol), 3-chloro-4-(4-methyl-piperazin-1-yl)-phenylamine (0.263 g, 1.08 mmol) and DIPEA (0.19 mL, 1.08 mmol) in $^i$PrOH (5 mL). Purification of the crude compound by silica gel column chromatography, eluting with 95:5 DCM:NH$_3$ (7M in MeOH), affords the title compound (60 mg, 20%).

Step 2: 4-{8-[3-Chloro-4-(4-methyl-piperazin-1-yl)-phenylamino]-imidazo[1,2-a]pyrazin-5yl}-benzamide

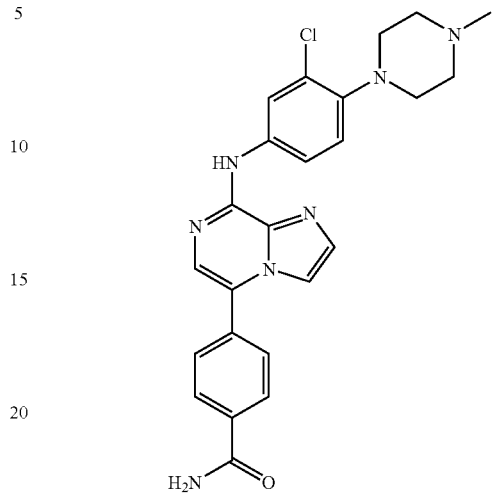

In the same way as described for Compound 178, step 4, using (5-bromo-imidazo[1,2-a]pyrazin-8-yl)-[3-chloro-4-(4-methyl-piperazin-1-yl)-phenyl]-amine (60.0 mg, 0.14 mmol), 4-(4,4,5,5-tetramethyl-[1,3,2]dioxaborolan-2-yl)-benzamide (46.0 mg, 0.28 mmol), Pd(PPh$_3$)$_4$ (40.0 mg, 0.035 mmol) and 1.5 M Na$_2$CO$_3$ (0.75 mL, 1.12 mmol) in 2:1 DMF-dioxane (3 mL). The crude residue is triturated with DCM and then the title compound is crystallised from EtOH (4 mg, 6%). LCMS: Rt 2.01 min (96%) m/z (APCI) 462 (M+H)$^+$; $^1$H-NMR (400 MHz, d$_6$-DMSO) δ (ppm). 2.27 (3H, s), 2.49-2.54 (4H, t), 2.99 (4H, m), 7.19 (1H, d), 7.53 (1H, br s), 7.60 (1H, s), 7.76 (1H, s), 7.84 (2H, d), 7.98 (1H, dd), 8.04 (1H, s), 8.09 (2H, d), 8.13 (1H, br s), 8.35 (1H, s), 9.86 (1H, s).

Compound 139: 5-{8-[4-(4-Methyl-piperazin-1-yl)-phenylamino]-imidazo[1,2-a]pyrazin-5-yl}-furan-2-carboxylic acid amide

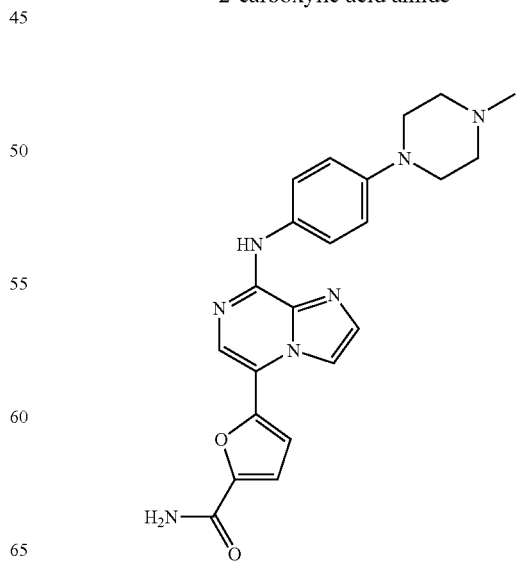

In the same way as described for Compound 145, step 2 using [4-(4-methyl-piperazin-1-yl)-phenyl]-(5-tributylstannanyl-imidazo[1,2-a]pyrazin-8-yl)-carbamic acid tert-butyl ester (0.068 g, 0.162 mmol) in THF (3 mL), 5-bromo-furan-2-carboxylic acid amide (0.061 g, 0.324 mmol) and Pd(PPh$_3$)$_4$ (0.009 g, 0.008 mmol). The crude reaction mixture is stirred in (1:1) TFA:DCM (2 mL) for 2 hours at room temperature. Purification of the crude by silica gel column chromatography, eluting with DCM followed by 97:3 DCM:NH$_3$ (7M in MeOH), affords the title compound (7.4 mg, 11%). LCMS: Rt 1.81 min (99%) m/z (APCI) 418 (M+H)$^+$; $^1$H-NMR (400 MHz, d$_6$-DMSO) δ (ppm).2.26 (3H, s), 2.49-2.53 (4H, m), 3.14 (4H, m), 6.97 (2H, d), 7.28 (1H, d, 7.34 (1H, d), 7.58 (1H, br s), 7.82 (1H, s), 7.90 (2H, d), 8.02 (1H, br s), 8.15 (1H, s), 8.48 (1H, s), 9.62 (1H, s).

Compound 145: 5-{8-[4-(4-Methyl-piperazin-1-yl)-phenylamino]-imidazo[1,2-a]pyrazin-5-yl}-thiophene-3-carboxylic acid amide Step 1: [4-(4-Methyl-piperazin-1-yl)-phenyl]-(5-tributyl-stannanyl-imidazo[1,2-a]pyrazin-8yl)-amine

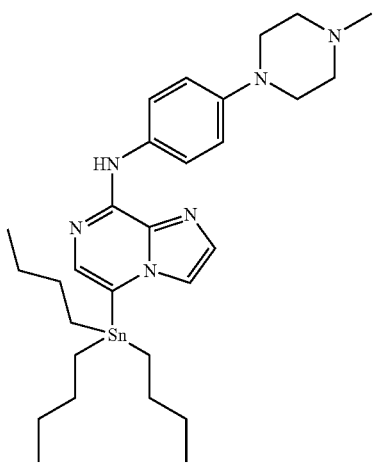

In the same way as described for Compound 212, step 2, using a solution of (5-bromo-imidazo[1,2-a]pyrazin-8-yl)-[4-(4-methyl-piperazin-1-yl)-phenyl]-carbamic acid tert-butyl ester (0.3 g, 0.62 mmol) in THF (5 mL), and isopropylmagnesium chloride (0.46 mL of a 2M solution in THF, 0.67 mmol). After stirring for 5 min, tributyltin chloride (0.28 mL, 1.04 mmol) is added and the reaction is stirred at −78° C. for 10 min before being allowed to warm to room temperature. After stirring at room temperature for 30 min, the mixture is concentrated. The crude mixture is purified by silica gel flash column chromatography using 95:5 DCM:NH$_3$ (7M in MeOH), to give [4-(4-methyl-piperazin-1-yl)-phenyl]-(5-tributylstannanyl-imidazo[1,2-a]pyrazin-8-yl)-carbamic acid tert-butyl ester (0.32 g, 70%) as a yellow oil. LCMS: Rt 7.03 min (92.3%), m/z (ES$^+$) 695, 697, 699.

Step 2: 5-{8-[4-(4-Methyl-piperazin-1-yl)-phenylamino]-imidazo[1,2-a]pyrazin-5-yl}-thiophene-3-carboxylic acid amide

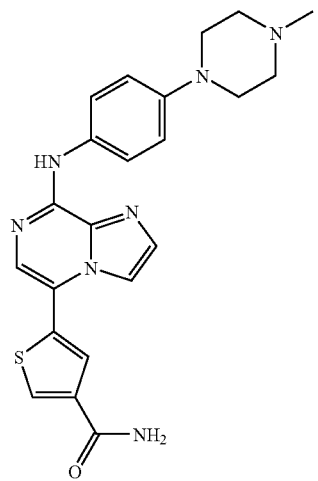

To a solution of [4-(4-methyl-piperazin-1-yl)-phenyl]-(5-tributylstannanyl-imidazo[1,2-a]pyrazin-8-yl)-carbamic acid tert-butyl ester (0.106 g, 0.15 mmol) in DMF (3 mL) is added 5-bromo-thiophene-3-carboxylic acid amide (0.062 g, 0.3 mmol) and tetrakis(triphenylphosphine)palladium(0) (0.018 g, 0.015 mmol). The solution is degassed and heated at 85° C. for 18 hours. The reaction mixture is diluted with ethyl acetate and washed with water (3×) and brine. The aqueous layers are backwashed with ethyl acetate and the organic layers are combined, dried (MgSO$_4$), and concentrated. The crude mixture is then stirred in (1:1) TFA: dichloromethane (3 mL) for 2 hours at room temperature. The resulting solution is diluted with ethyl acetate and washed with water, sat. NaHCO$_3$ and brine. The aqueous layers are backwashed with ethyl acetate and the organic layers are combined, dried (MgSO$_4$), and concentrated. The crude material is purified by flash column chromatography using 99:1 and 95:5 DCM:NH$_3$ (7M in MeOH), to give 5-{8-[4-(4-methyl-piperazin-1-yl)-phenylamino]-imidazo[1,2-a]pyrazin-5-yl}-thiophene-3-carboxylic acid amide (0.013 g, 20%) as a yellow solid. LCMS: Rt 2.79 min, (93.3%), m/z (APCI) 434 (M+H)$^+$; $^1$H-NMR (400 MHz, d$_6$-DMSO) δ (ppm). 2.26 (3H, s), 2.48-2.53 (4H, m), 3.14 (4H, m), 6.96 (2H, d), 7.42 (1H, br s), 7.61 (1H, s), 7.78 (1H, s), 7.82 (2H, d), 7.92 (1H, s), 7.99 (1H, br s), 8.21 (1H, s), 8.31 (1H, s), 9.61 (1H, s).

Compound 150: [4-(2-Morpholin-4-yl-ethoxy)-phenyl]-[5-(1H-pyrazol-4-yl)-imidazo[1,2-a]pyrazin-8-yl]-amine Step 1: 4-(2-Morpholin-4-yl-ethoxy)-phenylamine

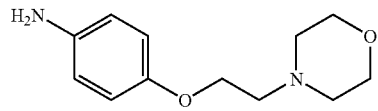

To a solution of 4-[2-(4-nitro-phenoxy)-ethyl]-morpholine (2.25 g, 8.93 mmol) in ethanol (40 mL) is added palladium hydroxide (0.313 g, 0.45 mmol) and the mixture is stirred in a Parr-apparatus under hydrogen pressure (5 bars) for 2 hours.

Filtration over Celite 521 and evaporation gave a red oil purified by silica gel column chromatography. Elution with DCM and a mixture 90:10 DCM:MeOH affords the title compound as a white solid (1.256 g, 63%). $^1$H-NMR (400 MHz, CDCl$_3$) δ (ppm).2.52-2.63 (4H, m), 2.71-2.80 (2H, t), 3.46 (2H, br s), 3.70-3.78 (4H, m), 4.00-4.10 (2H, m), 6.65 (2H, d), 6.77 (2H, d).

Step 2: (5-Bromo-imidazo[1,2-a]pyrazin-8-yl)-[4-(2-morpholin-4-yl-ethoxy)-phenyl]-amine

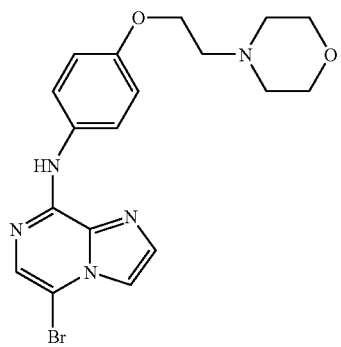

In the same way as described in the general procedure for amine displacement using 4-(2-morpholin-4-yl-ethoxy)-phenylamine (600 mg, 2.7 mmol), N,N-diisopropylethylamine (0.470 mL, 2.7 mmol) and a solution of 5,8-dibromo-imidazo[1,2-a]pyrazine (0.500 g, 1.80 mmol) in isopropanol (6 mL). Purification by silica gel column chromatography eluting with a mixture 97:3 DCM:MeOH affords the title compound as a pale yellow solid (0650 mg, 86%). $^1$H-NMR (400 MHz, CDCl$_3$) δ (ppm) 2.51-2.62 (4H, m), 2.75-2.83 (2H, t), 3.71-3.78 (4H, m), 4.09-4.18 (2H, m), 6.90 (2H, d), 7.51 (1H, s), 7.61 (1H, s), 7.64 (2H, d), 7.70 (1H, s), 7.90 (1H, s). LCMS: Rt 2.09 min (97%).

Step 3: [4-(2-Morpholin-4-yl-ethoxy)-phenyl]-[5-(1H-pyrazol-4-yl)-imidazo[1,2-a]pyrazin-8-yl]amine

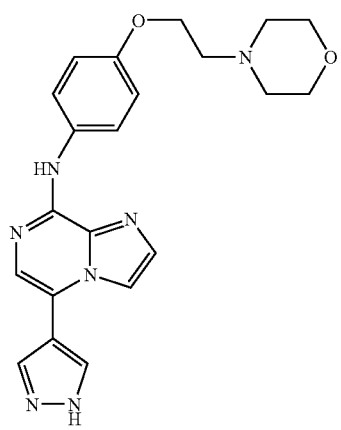

In the same way as described for Compound 178, step 4 using (5-bromo-imidazo[1,2-a]pyrazin-8-yl)-[4-(2-morpholin-4-yl-ethoxy)-phenyl]-amine (113 mg, 0.27 mmol), 4-(4,4,5,5-tetramethyl-1,3,2-dioxaborolan-2-yl)-1H-pyrazole (105 mg, 0.541 mmol), 1.5M Na$_2$CO$_3$ (1.44 mL, 2.14 mmol), and Pd(PPh$_3$)$_4$ (0.78 g, 0.67 mmol) in dioxane (4.3 mL). Purification by silica gel column chromatography eluting with 96:4 DCM:NH$_3$ (7M in MeOH) followed by trituration with diethyl ether, affords the title compound as a free base (0.071 g, 65%). LCMS: Rt 1.59 min (100%), m/z (APCI) 406 (M+H)$^+$; $^1$H-NMR (400 MHz, d$_6$-DMSO) δ (ppm). 2.40-2.60 (4H, m), 2.70-2.73 (2H, t), 3.61-3.63 (4H, m), 4.10 (2H, m), 6.94-6.97 (2H, d), 7.58 (1H, s), 7.74 (1H, s), 7.97 (2H, d), 8.06 (1H, s), 8.13 (1H, s), 8.41 (1H, s), 9.45 (1H, s), 13.41 (1H, br s).

Compound 154: 4-{8-[4-(4-Pyridin-2-yl-[1,2,3]triazol-1-yl)-phenylamino]-imidazo[1,2-a]pyrazin-5-yl}-benzamide Step 1: 2-[1-(4-Nitro-phenyl)-1H-[1,2,3]triazol-4-yl]-pyridine

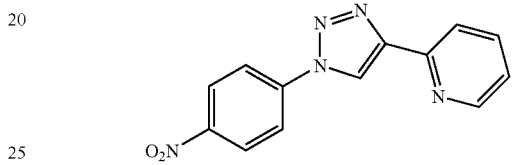

A mixture of 1-iodo-4-nitrobenzene (0.513 g, 2.06 mmol), 2-ethynyl pyridine (0.208 mL, 2.06 mmol), L-proline (47.4 mg, 0.412 mmol), Na$_2$CO$_3$ (43.7 mg, 0.412), NaN$_3$ (0.1607g, 2.47 mmol), (+)-sodium-L-ascorbate (40.8 mg, 0.206 mmol), copper (II) sulphate pentahydrate (16.4 mg, 0.103 mmol) in 9:1 DMSO-water (4 mL) is stirred in a stem-tube at 65° C. for 24 hours. After cooling, the reaction mixture is poured into ice-water (100 mL) and the resulting precipitate is collected by filtration, washed with 7% aq. NH$_3$ and dried in vacuo to give the title compound as a brown solid (0.323 g, 59%). HPLC (254 nm) Rt 2.36 min (89%).

Step 2: 4-(4-Pyridin-2-yl-[1,2,3]triazol-1-yl)-phenylamine

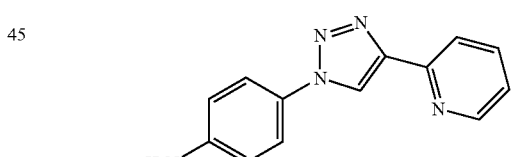

To a stirred solution of 2-[1-(4-nitro-phenyl)-1H-[1,2,3]triazol-4-yl]-pyridine (0.149 g, 0.556 mmol) in 1:1 THF/EtOH (8 mL) is added tin (II) dichloride dihydrate (0.439 g, 1.95 mmol) and the mixture is stirred at room temperature for 22 hours. The solvent is removed in vacuo and 2N NaOH (3 mL) added to the residue. The mixture is stirred for 1 hour, diluted with water and extracted with DCM (3×40 mL). The organic layers are dried over Na$_2$SO$_4$, filtered and evaporated to give a crude product purified by Isolute FlashSilicaII Cartridge chromatography, eluting with 98:2 DCM:MeOH. The fractions containing the title compound are combined and evaporated to afford the desired compound as a yellow solid (41.4 mg, 31%).

Step 3: (5-Bromo-imidazo[1,2-a]pyrazin-8-yl)-[4-(4-pyridin-2-yl-[1,2,3]triazol-1-yl)-phenyl]amine

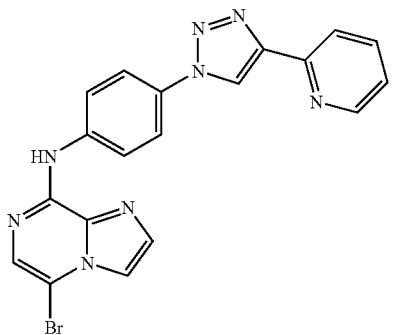

In the same way as described for Compound 90, step 1, using 5,8-dibromoimidazo[1,2-a]pyrazine (80.5 mg, 0.291 mmol), 4-(4-pyridin-2-yl-[1,2,3]triazol-1-yl)-phenylamine (68.3 g, 0.288 mmol), NaO$^t$Bu (38.2 mg, 0.403 mmol), Pd$_2$(dba)$_3$ (10.5 mg, 0.0115 mmol), Xantphos (13.3 mg, 0.023mmol) and toluene (4 mL). The crude material is purified by silica gel column chromatography eluting with 98:2 DCM:MeOH followed by 97:3 DCM:MeOH affording the title compound (52.8 mg, 42%).

Step 4: 4-{8-[4-(4-Pyridin-2-yl-[1,2,3]triazol-1-yl)-phenylamino]-imidazo[1,2-a]pyrazin-5yl}-benzamide

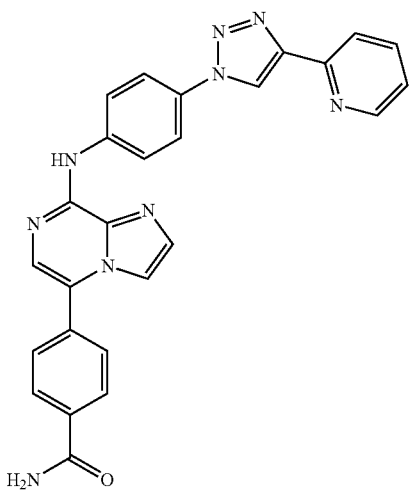

In the same way as described for Compound 178, step 4, using (5-bromo-imidazo[1,2-a]pyrazin-8-yl)-[4-(4-pyridin-2-yl-[1,2,3]triazol-1-yl)-phenyl]-amine (40 mg, 0.0923 mmol), 4-(aminocarbonyl)phenylboronic acid (30.5 mg, 0.185 mmol) 1.5 M Na$_2$CO$_3$ (0.492 mL, 0.738 mmol), and Pd(PPh$_3$)$_4$ (26.7 mg, 0.023 mmol) in (2:1) DMF-dioxane (1.5 mL). The crude material is purified by Isolute FlashSilicaII Cartridge chromatography eluting with 98:2 DCM:NH$_3$ (7M in MeOH) followed by 97:3 DCM:NE$_3$ (7M in MeOH). The title compound is obtained as a white solid (23.5 mg, 54%). LCMS: Rt 2.67 min (95%) m/z (ES$^+$) 474 (M+H)$^+$; $^1$H-NMR (400 MHz, d$_6$-DMSO) δ (ppm) 7.41-7.47 (1H, d), 7.53 (1H, d), 7.66 (1H, br s), 7.81 (1H, s), 7.84-7.90 (2H, d), 7.96-8.07 (3H, m), 8.08-8.20 (5H, m), 8.36-8.44 (2H, d), 8.70 (1H, d), 9.30 (1H, s), 10.15 (1H, s).

Compound 157: [4-(4-Methyl-piperazin-1-yl)-phenyl]-[5-(3-trifluoromethyl-1H-pyrazol-4-yl)-imidazo[1,2-a]pyrazin-8-yl]-amine Step 1: 4-Bromo-5-trifluoromethyl-pyrazole-1-carboxylic acid tert-butyl ester

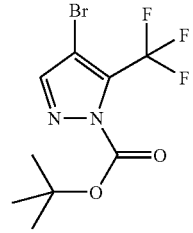

To a solution of 4-bromo-5-trifluoromethyl-1H-pyrazole (0.515 g, 2.4 mmol) in CH$_3$CN at 0° C is added (Boc)$_2$O (0.63 g, 2.89 mmol) followed by DMAP (0.29 g, 2.4 mmol). The reaction mixture is stirred overnight at room temperature. After removing the solvent, the residue is dissolved in DCM and washed with water, 2M HCl, sat. NaHCO$_3$ and brine. The organic layer is dried over MgSO$_4$, filtered and concentrated in vacuo to afford the title compound (0.55 g, 73%).

Step 2: [4-(4-Methyl-piperazin-1-yl)-phenyl]-[5-(3-trifluoromethyl-1H-pyrazol-4-yl)-imidazol[1,2-a]pyrazin-8-yl]-amine

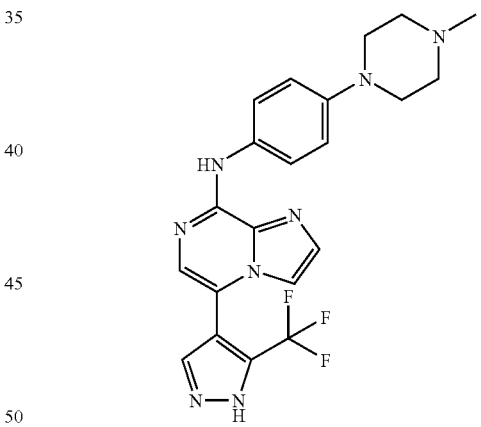

In the same way as described for Compound 145, step 2 using [4-(4-methyl-piperazin-1-yl)-phenyl]-(5-tributylstannanyl-imidazo[1,2-a]pyrazin-8-yl)-carbamic acid tert-butyl ester (0.38 g, 0.78 mmol) in DMF (6mL), 4-bromo-5-trifluoromethyl-pyrazole-1-carboxylic acid tert-butyl ester (0.49 g, 0.15 mmol) and Pd(PPh$_3$)$_4$ (0.09 g, 0.15 mmol). The crude mixture is stirred in (1:1) TFA:DCM (2 mL) at room temperature for 3 hours. Purification by silica gel column chromatography eluting with DCM followed by a mixture of 99:1 and 95:5 DCM:NH$_3$ (7M in MeOH) affords the title compound (2.79 mg, 1%). LCMS: Rt 1.90 min (96%) m/z (ES$^+$) 443 (M+H)$^+$; $^1$H-NMR (400 MHz, d$_6$-DMSO) δ (ppm) 2.26 (3H, s), 2.49-2.54 (4H, m), 3.09-3.14 (4H, m), 6.96 (2H, d), 7.31 (1H, s), 7.63 (2H, d), 7.89 (2H, d), 8.37 (1H, s), 9.44 (1H, s).

Compound 158: 2-[8-(4-Morpholin-4-yl-phenylamino)-imidazo[1,2-a]pyrazin-5-yl]-thiazole-5-carboxylic acid amide Step 1: 2-[8-(4-Morpholin-4-yl-phenylamino)-imidazo[1,2-a]pyrazin-5-yl]-thiazole-5-carboxylic acid methyl ester

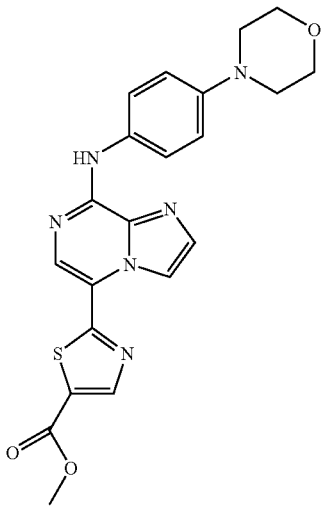

In the same way as described for Compound 212, step 3, using (4-morpholin-4-yl-phenyl)-(5-tributylstannanyl-imidazo[1,2-a]pyrazin-8-yl)-carbamic acid tert-butyl ester (0.25 g, 0.36 mmol), 2-bromo-thiazole-5-carboxylic acid methyl ester (0.159 g, 0.716 mmol), and Pd(PPh$_3$)$_4$ (0.041 g, 0.036 mmol) in DMF (4 mL). The reaction mixture is concentrated, treated with a mixture of (1:1) TFA-DCM and stirred at room temperature for 18 hours. The mixture is diluted with EtOAc and washed with a solution of sat. NaHCO$_3$. The organic layers are dried over MgSO$_4$, filtered and concentrated. Purification by silica gel column chromatography using 75:25 petroleum ether-EtOAc affords the title compound (90 mg, 57%). HPLC (254 nm): Rt 3.89 min (73%)

Step 2: 2-[8-(4-Morpholin-4-yl-phenylamino)-imidazo[1,2-a]pyrazin-5-yl]-thiazole-5-carboxyl acid amide

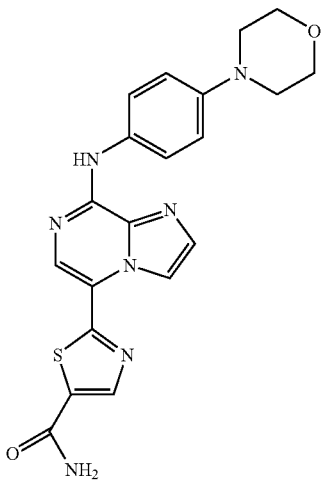

A solution of 2-[8-(4-morpholin-4-yl-phenylamino)-imidazo[1,2-a]pyrazin-5-yl]-thiazole-5-carboxylic acid methyl ester (90 mg, 0.21 mmol), 35% NH$_4$OH (2.5 mL), and NH$_4$Cl (0.2 g), in MeOH (12 mL) is heated at 85° C. in a stem tube for 48 hours. The mixture is concentrated in vacuo and purified by silica gel column chromatography eluting with 99:1 and 97:3 DCM:NH$_3$ (7M in MeOH). Trituration with diethyl ether-MeOH gives the title compound (4.9 mg, 6%). LCMS: Rt 2.52 min (90%), m/z (ES$^+$) 422 (M+H)$^+$; $^1$H-NMR (400 MHz, d$_6$-DMSO.) δ (ppm) 3.13 (4H, m), 3.79 (4H, m), 7.00 (2H, d), 7.75 (1H, br s), 7.81 (1H, s), 7.91 (2H, d), 8.25 (1H, s), 8.28 (1H, br s), 8.55 (1H, s), 9.08 (1H, s), 10.05 (1H, s).

Compound 159: 2-Fluoro-4-{8-[4-(1-methyl-piperidin-4-ylmethoxy)-phenylamino]-imidazo[1,2-a]pyrazin-5-yl}-benzamide Step 1: 4-(1-Methyl-piperidin-4-ylmethoxy)-phenyl amine

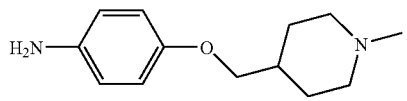

In the same way as described for Compound 150, step 1, using 1-methyl-4-(4-nitro-phenoxymethyl)-piperidine (0.65 g, 2.6 mmol) in ethanol (40 mL) and palladium hydroxide (0.182 g, 0.26 mmol). Filtration over Celite 521 and evaporation gave a red oil that was purified by silica gel column chromatography eluting with DCM and a 80:20 mixture DCM:MeOH. The title compound was obtained as a white solid (0.402 g, 70%). $^1$H-NMR (400 MHz, CDCl$_3$) δ (ppm) 1.30-1.51 (2H, m), 1.65-1.88 (3H, m), 1.89-2.09 (2H, t), 2.29 (3H, s), 2.90 (2H, d,), 3.45 (2H, br s), 3.73 (2H, d), 6.67 (2H, d), 6.75 (2H, d).

Step 2: (5-Bromo-imidazo[1,2-a]pyrazin-8-yl)-[4-(1-methyl-piperidin-4-ylmethoxy)-phenyl]-amine

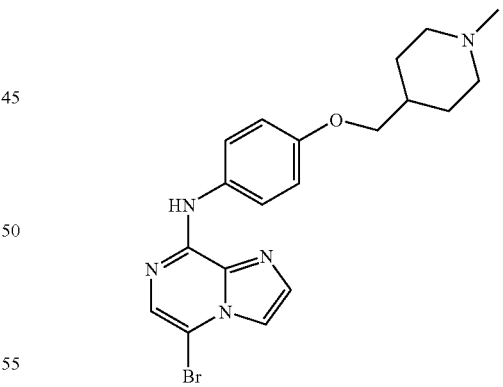

To a solution of 5,8-dibromo-imidazo[1,2-a]pyrazine (0.100 g, 0.36 mmol) in isopropanol (5 mL) are added 1,4-diazabicyclo[2,2,2]octane (DABCO) (0.036 mL, 0.36 mmol) and 4-(1-methyl-piperidin-4-ylmethoxy)-phenylamine (79.6 mg, 0.36 mmol). The reaction mixture is stirred at 90° C. overnight. The solvent is evaporated and the residue chromatographed on silica gel column eluting with 97:3 followed by 94:6 and 90:10 DCM:MeOH. The title compound is obtained as a solid (20 mg, 13%). LCMS: Rt 2.30min (94%), m/z (APCI) 417.

Step 3: 2-Fluoro-4-{8-[4-(1-methyl-piperidin-4-ylmethoxy)-phenylamino]-imidazo[1,2-a]pyrazin-5-yl}-benzamide

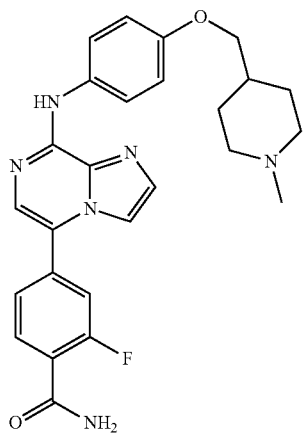

In the same way as described for Compound 178, step 4, using (5-bromo-imidazo[1,2-a]pyrazin-8-yl)-[4-(1-methyl-piperidin-4-ylmethoxy)-phenyl]-amine (20 mg, 0.048 mmol), 2-fluoro-4-(4,4,5,5-tetramethyl-[1,3,2]dioxaborolan-2-yl)-benzamide (25.5 mg, 0.10 mmol), Pd(PPh₃)₄ (13.9 mg, 0.001 mmol) and 1M Na₂CO₃ (0.8 mL) in dioxane (2 mL). Purification by silica gel column chromatography eluting with a mixture 95:5 followed by 90:10 DCM:MeOH affords a solid that was triturated with ethyl acetate to give the title compound (19.4 mg, 85%). LCMS: Rt 1.96min (94%), m/z (APCI) 475 (M+H)⁺; ¹H-NMR (400 MHz, d₆-DMSO) δ (ppm) 1.48-1.61 (2H, m), 1.98-2.02 (3H, m), 2.51-2.58 (4H, m), 2.70 (3H, br s), 3.91 (2H, d), 6.98 (2H, d), 7.55 (1H, s), 7.65-7.87 (6H, m), 7.98 (2H, d), 8.06 (1H, s), 9.68 (1H, s).

Compound 160: [5-(5-Cyclopropyl-1H-pyrazol-4-yl)-imidazo[1,2-a]pyrazin-8-yl]-(4-morpholin-4-yl-phenyl)-amine Step 1: 4-Bromo-5-cyclopropyl-1H-pyrazole

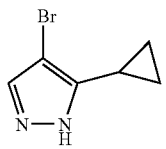

To a solution of 2-cyclopropyl-1H-pyrazole (0.716 g, 6.62 mmol) in AcOH (10 mL) is added dropwise bromine (0.339 mL, 6.62 mmol). The reaction mixture is stirred vigorously for 10 min. The solvent is removed and the residue partitioned between DCM and sat. Na₂CO₃. The aqueous phase (pH 11) is extracted with DCM (3×). The organic layers are combined, dried over MgSO₄, filtered and concentrated to give a yellow solid (1.19 g, 96%). The compound is used in the next step without further purification.

Step 2: 5-Cyclopropyl-4-(4,4,5,5-tetramethyl-[1,3,2]dioxaborolan-2-yl)-1H-pyrazole

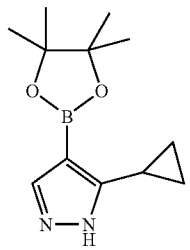

In the same way as described for Compound 209, step 2, using 4-bromo-5-cyclopropyl-1H-pyrazole (0.477 g, 2.55 mmol), bis(pinacolato)diboron (1.29 g, 5.1 mmol), PdCl₂dppf (0.417 g, 0.51 mmol) and KOAc (0.751 g, 7.65 mmol) suspended in DMSO (10 mL). Purification by silica gel column chromatography eluting with a 1:1 mixture petroleum ether:EtOAc affords 5-cyclopropyl-4-(4,4,5,5-tetramethyl-[1,3,2]dioxaborolan-2-yl)-1H-pyrazole (214 mg, 14%). ¹H-NMR (400 MHz, CDCl₃) δ (ppm).0.83-1.05 (4H, m), 1.25-1.42 (12H, m), 1.81 (1H, m), 7.78 (1H, s).

Step 3: 5-(5-Cyclopropyl-1H-pyrazol-4-yl)-imidazo[1,2-a]pyrazin-8-yl]-(4-morpholin-4-yl-phenyl)-amine In the same way as described for Compound 178, step 4, using 5-bromo-imidazo[1,2-a]pyrazin-8-yl)-4-morpholin-4-yl-phenylamine (80 mg, 0.214 mmol), 5-cyclopropyl-4-(4,4,5,5-tetramethyl-[1,3,2]dioxaborolan-2-yl)-1H-pyrazole (219 mg, 0.37 mmol), Pd(PPh₃)₄ (49.4 mg, 0.04 mmol) and 0.5M Na₂CO₃ (0.036 mL) in dioxane (2 mL). Purification by silica gel column chromatography eluting with 97:3 DCM:MeOH, followed by crystallization in DCM (drops of hexane) affords the title compound (13.3 mg, 15%). LCMS: Rt 2.12 min (98%) m/z (ES⁺) 402 (M+H)⁺; ¹H-NMR (400 MHz, d₆-DMSO) δ (ppm) 0.80-0.98 (4H, m), 1.70-1.98 (1H, m), 3.10 (4H, m), 3.79 (4H, m), 6.97 (2H, d), 7.40 (1H, s), 7.68 (1H, s), 7.77 (1H, s), 7.92-7.95 (3H, m), 9.36 (1H, s), 12.65 (1H, d).

Compound 161: 6Trifluoromethyl-4-[8-(4-morpholin-4-ylphenylamino)imidazo[1,2-a]pyrazin-5-yl]-1H-pyridin-2-one Step 1: 2-Fluoro-3-iodo-6-(trifluoromethyl)pyridine

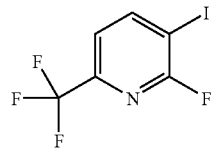

A solution of N,N-diisopropylamine (1.4 mL, 10.0 mmol) in anhydrous THF (15 mL) is cooled under $N_2$ to −78° C. and ″BuLi (2.5 M in hexanes, 4.0 mL, 10.0 mmol) is added dropwise at a rate to maintain the temperature below −65° C. A solution of 2-fluoro-6-(trifluoromethyl)pyridine (1.65 g, 10.0 mmol) in anhydrous THF (15 mL) is added dropwise over 10 min and the resulting orange solution is stirred for 2 h at −78° C. Iodine (2.54 g, 10.0 mmol) in anhydrous THF (12.5 mL) is then added dropwise over 15 min (keeping the temperature under −65° C.), causing the colour of the solution to change to red-brown and a precipitate to form. After 30 min the mixture is allowed to warm to 10° C. and the solvent is evaporated under reduced pressure. The residue is diluted with diethyl ether (25 mL) and washed with $Na_2S_2O_3$ (2 M aq., 10 mL), HCl (2 M aq., 2×12.5 mL), $NaHCO_3$ (sat. aq., 12.5 mL) and brine (12.5 mL). The organic solvents are dried over $Na_2SO_4$ and evaporated under reduced pressure to afford a yellow oil. The product is purified by silica chromatography, eluting with cyclohexane, to afford the title compound as a white solid (1.36 g). Alternatively, this compound may be used directly in the next step without further purification.

Step 2: 2-Fluoro-4-iodo-6-(trifluoromethyl)pyridine

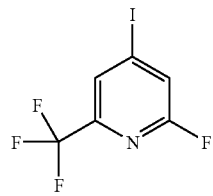

N,N-Diisopropylamine (3.0 mL, 21.0 mmol) is diluted with anhydrous THF (19 mL) and cooled to −30° C. ″BuLi (2.5 M in hexanes, 8.4 mL, 21.0 mmol) is added over 10 min, keeping the temperature under −20° C., and the resulting solution is cooled to −78° C. A solution of 2-fluoro-3-iodo-6-(trifluoromethyl)-pyridine (crude from previous step, 2.82 g, theoretical 9.7 mmol) in anhydrous THF (4 mL) is added over 10 min, keeping the temperature under −65° C., and the solution is stirred for 5 min before HCl (2 M aq., 20 mL) is added and the mixture allowed to warm to rt. This is extracted with diethyl ether (3×35 mL) and the combined solvents are dried over $Na_2SO_4$ and evaporated under reduced pressure to afford a brown oil. This is purified by silica chromatography, eluting with cyclohexane, to afford the title compound as a pale yellow oil (2.33 g).

Step 3: 2-Fluoro-4-(4,4,5,5-tetramethyl-[1,3,2]dioxaborolan-2-yl)-6-(trifluoromethyl)pyridine

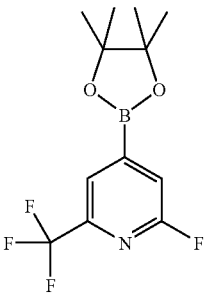

2-Fluoro-4-iodo-6-(trifluoromethyl)pyridine (145 mg, 0.50 mmol), bis(pinacolato)diboron (254 mg, 1.00 mmol), KOAc (147 mg, 1.50 mmol) and Pd(dppf)$Cl_2$DCM (20 mg, 0.025 mmol) are stirred under $N_2$ in dioxane (0.5 mL) and heated at 80° C. overnight. The mixture is cooled, diluted with $NaHCO_3$ (5% aq., 5 mL) and EtOAc (15 mL) and filtered through celite. The layers are separated and the aqueous phase extracted with further EtOAc (2×10 mL). The combined organic extracts are dried over $Na_2SO_4$ and evaporated under reduced pressure to afford the title compound as a brown oil which is used without further purification.

Step 4: [5-(2-Fluoro-6-trifluoromethyl-pyridin-4-yl)imidazo[1,2-a]pyrazin-8-yl]-(4-morpholin-4yl-phenyl)carbamic acid tert-butyl ester

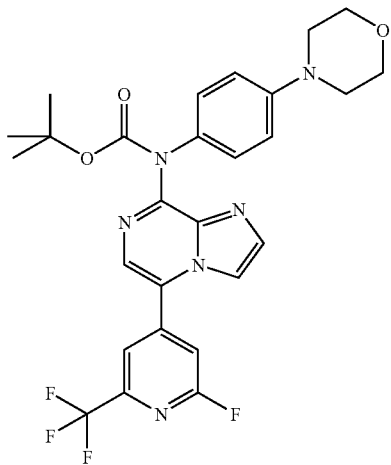

(5-Bromoimidazo[1,2-a]pyrazin-8-yl)-(4-morpholin-4-ylphenyl)carbamic acid tert-butyl ester (50 mg, 0.11 mmol), 2-fluoro-4-(4,4,5,5-tetramethyl-[1,3,2]dioxaborolan-2-yl)-6-(trifluoromethyl)pyridine (126 mg, 0.21 mmol), KOAc (31 mg, 0.32 mmol) and Pd(dppf)Cl2DCM (4.3 mg, 0.0053 mmol) are stirred under $N_2$ in dioxane (0.3 mL) and heated at 85° C. for 2.5 h. The mixture is cooled and partitioned between $NaHCO_3$ (5% aq., 5 mL) and EtOAc (15 mL). The layers are separated and the aqueous phase extracted with further EtOAc (2×10 mL). The combined organic extracts are washed with brine (10 mL), dried over $Na_2SO_4$ and evaporated under reduced pressure to afford the title compound as a brown oil (93 mg) which was used without further purification.

Step 5: 6-Trifluoromethyl-4-[8-(4-morpholin-4-ylphenylamino)imidazo[1,2-a]pyrazin-5-yl]-1H-pyridin-2-one

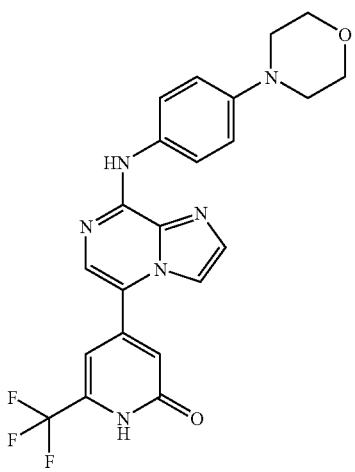

To a solution of [5-(2-fluoro-6-trifluoromethyl-pyridin-4-yl)imidazo[1,2-a]pyrazin-8-yl]-(4-morpholin-4-yl-phenyl)carbamic acid tert-butyl ester (92 mg, 0.12 mmol) in THF (0.5 mL) is added KOtBu (26 mg, 0.23 mmol) and the mixture is stirred at rt for 20 min. HCl (12 M aq., 0.1 mL) is added and the mixture is diluted with water (10 mL) and concentrated under reduced pressure. The residue is dissolved in THF (5 mL) and HCl (12 M aq., 0.5 mL) is added and the mixture is stirred at rt for 5 h. NaHCO$_3$ (sat. aq.) is added until the pH is 7 and the mixture is extracted with DCM (3×10 mL). The extracts are dried over Na$_2$SO$_4$ and evaporated under reduced pressure to afford a pale orange solid. This is purified by preparative HPLC to afford the title compound as a yellow solid (9.5 mg). LCMS: Rt=1.04 min (100%), m/z (ESI) 457 (M+H)$^+$.

Compound 162: 4-[3-Ethyl-8-(4-morpholin-4-ylphenylamino)-imidazo[1,2-a]pyrazin-5-yl]benzamide

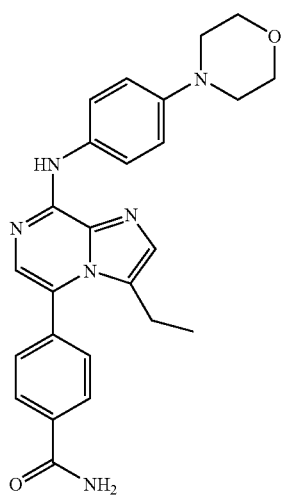

This compound may be prepared using the methods as described for Compound 189, using 4-carbamoylbenzene boronic acid in Step 4. LCMS: Rt=1.03 min (100%), m/z (ESI) 443 (M+H)$^+$.

Compound 166: 4-{8-[4-(4-Dimethylaminomethyl-[1,2,3]triazol-1-yl)-phenylamino]-imidazo[1,2-a]pyrazin-5-yl}-benzamide Step 1: Dimethyl-[1-(4-nitro-phenyl)-1H-[1,2,3]triazol-4-ylmethyl]-amine

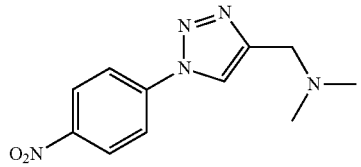

In the same way as described for Compound 154, step 1 using 1-iodo-4-nitrobenzene (0.498 g, 2.0 mmol), 1-dimethylamino-2-propyne (0.216 mL, 2.00 mmol), L-proline (46.1 mg, 0.40 mmol), Na$_2$CO$_3$ (42.4 mg, 0.40), NaN$_3$ (0.156 g, 2.40 mmol), (+)-sodium-L-ascorbate (39.7 mg, 0.20 mmol), copper(II) sulphate pentahydrate (16.0 mg, 0.10 mmol) in 9:1 DMSO-water (4 mL). The residue is purified on Isolute FlashSilicaII cartridge eluting with 97:3 DCM:NH$_3$ (7M in MeOH), to afford the title compound as a brown solid (0.179 g, 36%).

Step 2: 4-(4-Dimethylaminomethyl-[1,2,3]triazol-1-yl)-phenylamine

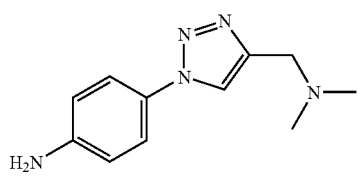

In the same way as described for Compound 154, step 2 using dimethyl-[1-(4-nitro-phenyl)-1H-[1,2,3]triazol-4-ylmethyl]-amine (0.178 g, 0.722 mmol), tin(II) chloride dehydrate (0.578 g, 2.54 mmol) in (1:1) THF/EtOH (4 mL). The residue is purified on Isolute FlashSilicaII cartridge eluting with 95:5 DCM:NH$_3$ (7M in MeOH), to afford the desired compound as a yellow solid (93.2 mg, 59%).

Step 3: (5-Bromo-imidazo[1,2-a]pyrazin-8-yl)-[4-(4-dimethylaminomethyl-[1,2,3]triazol-1-yl)-phenyl]-amine

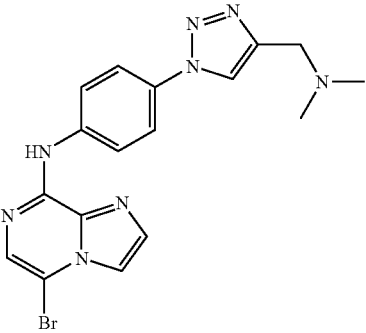

In the same way as described for Compound 90, step 1, using 5,8-dibromoimidazo[1,2-a]pyrazine (116.9 mg, 0.422 mmol), 4-(4-dimethylaminomethyl-[1,2,3]triazol-1-yl)-phenylamine (91.7 g, 0.422 mmol), NaO$^t$Bu (56.8 mg, 0.591 mmol), Pd$_2$(dba)$_3$ (15.5 mg, 0.0169 mmol), Xantphos (19.5 mg, 0.0337 mmol) and toluene (5 mL). The crude product is purified by Isolute FlashSilicaII cartridge chromatography eluting with 99:1 DCM/NH$_3$ (7M in MeOH), followed by 97:3 DCM:NH₃ (7M in MeOH). The title compound (63 mg, 36%) is isolated after a second column chromatography purification eluting with 97:3 DCM:NH₃ (7M in MeOH).

Step 4: 4-{8-[4-(4-Dimethylaminomethyl-[1,2,3]triazol-1-yl)-phenylamino]-imidazo[1,2-a]pyrazin-5-yl}-benzamide

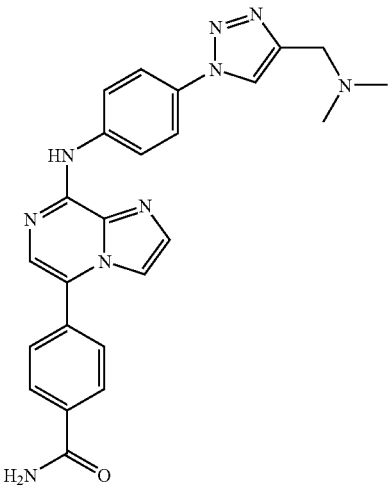

In the same way as described for Compound 178, step 4, using (5-bromo-imidazo[1,2-a]pyrazin-8-yl)-[4-(4-dimethylaminomethyl-[1,2,3]triazol-1-yl)-phenyl]-amine (63 mg, 0.152 mmol), 4-(aminocarbonyl)phenylboronic acid (50.3 mg, 0.305 mmol) 1.5 M Na₂CO₃ (0.813 mL, 1.22 mmol) and Pd(PPh₃)₄ (44.0 mg, 0.0381 mmol) in (2:1) DMF-dioxane (1.8 m1L). Purification of the crude material by Isolute Flash-SilicaII Cartridge chromatography eluting with 95:5 DCM:NH₃ (7M in MeOH) followed by reverse phase preparative HPLC, affords the title compound as a white solid (4.7 mg, 7%). LCMS: Rt 1.92 min (96%) m/z (APCI) 455 (M+H)⁺; ¹H-NMR (400 MHz, d₆-DMSO) δ (ppm) 2.24 (6H, s), 3.61 (2H, s), 7.51 (1H, br s), 7.64 (1H, s), 7.80 (1H, s), 7.85-7.91 (4H, m), 8.08-8.12 (3H), m), 8.16 (1H, br s), 8.36 (2H, d), 8.66 (1H, s), 10.09 (1H, s).

Compound 168: (4-Imidazol-1-yl-phenyl)-[5-(1H-pyrazol-4-yl)-imidazo[1,2-a]pyrazin-8-yl]-amine Step 1: (5-Bromo-imidazo[1,2-a]pyrazin-8-yl)-(4-imidazol-1-yl-phenyl)-amine

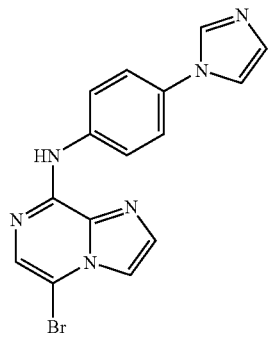

In the same way as described for Compound 90, step 1, using 5,8-dibromoimidazo[1,2-a]pyrazine (203.8 mg, 0.736 mmol), 4-imidazol-1-yl-phenylamine (117.7 g, 0.739 mmol), NaOᵗBu (99 mg, 1.03 mmol), Pd₂(dba)₃ (27.0 mg, 0.0295 mmol), Xantphos (34.1 mg, 0.0589 mmol) and toluene (10 mL). The crude material is purified by Isolute FlashSilicaII cartridge chromatography eluting with 99:1 DCM:NH₃ (7M in MeOH), followed by 97:3 DCM/NH₃ (7M in MeOH). The title compound is isolated, after a second column chromatography purification using a 5:5:1 mixture EtOAc-petroleum ether-MeOH, as a yellow solid (104 mg, 40%).

Step 2: (4-Imidazol-1-yl-phenyl)-[5-(1H-pyrazol-4-yl)-imidazo[1,2-a]pyrazin-8-yl]-amine

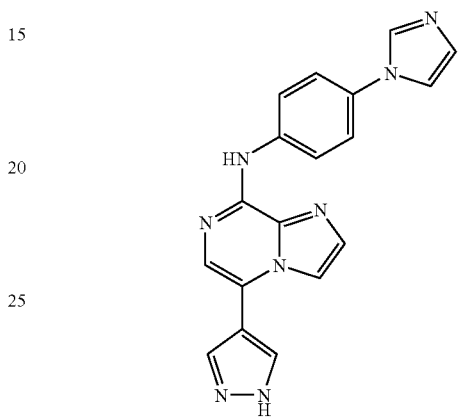

In the same way as described for Compound 178, step 4, using (5-bromo-imidazo[1,2-a]pyrazin-8-yl)-(4-imidazol-1-yl-phenyl)-amine (49.8 mg, 0.14 mmol), 4-(4,4,5,5-tetramethyl-[1,3,2]dioxaborolan-2-yl)-1H-pyrazole (54.4 mg, 0.280 mmol), Pd(PPh₃)₄ (39.1 mg, 0.0338 mmol) and 1.5 M Na₂CO₃ (0.748 mL, 1.12 mmol) in 2:1 DMF-dioxane (1.5 mL). Purification by Isolute Flash SiII cartridge chromatography eluting with 98:2 DCM:NH₃ (7M in MeOH), followed by 97:3 DCM:NH₃ (7M in MeOH) and 95:5 DCM:NH₃ (7M in MeOH) affords the title compound as a white solid (26.5 mg, 55%). LCMS: Rt 1.75 min (96%), m/z (APCI) 343 (M+H)⁺; ¹H-NMR (400 MHz, d₆-DMSO) δ (ppm) 7.13 (1H, s), 7.63 (2H, d), 7.67 (1H, s), 7.73 (1H, s), 7.79 (1H, s), 8.09 (1H, br s), 8.18 (1H, s), 8.22 (1H, s), 8.27 (2H, d), 8.43 (1H, br s), 9.82 (1H, s), 13.39 (1H, br s).

Compound 169: [4-(2-Methyl-2H-tetrazol-5-yl)-phenyl]-[5-(1H-pyrazol-4-yl)-imidazol[1,2-a]pyrazin-8-yl]-amine Step 1: 2-Methyl-5-(4-nitro-phenyl)-2H-tetrazole

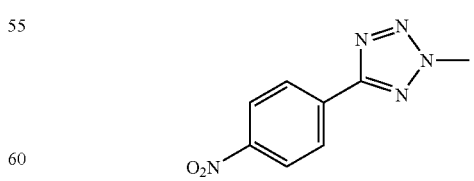

To a stirred solution of 60% NaH (0.116 g, 2.89 mmol) and MeI (0.196 mL, 3.15 mmol) in DMF (2 mL) (cooled to 0° C., under N₂) is added dropwise, a solution of 5-(4-nitrophenyl)-1H-tetrazole (0.502, 2.63 mmol) in DMF (7 mL). The reaction mixture is stirred under N₂ for 1 hour and 30 min at 5° C.

and then quenched with water and extracted with EtOAc. The organic layers are combined and washed with sat. NaCl, dried over MgSO$_4$, filtered and evaporated to give a residue purified by silica gel column chromatography. Elution with 80:20 followed by 60:40 petroleum ether-EtOAc affords 2-methyl-5-(4-nitro-phenyl)-2H-tetrazole (0.265 g, 49%) as a white solid and 1-methyl-5-(4-nitro-phenyl)-1H-tetrazole (37.7 mg, 7%) as a yellow solid. The isomers are identified by NOE experiments.

2-Methyl-5-(4-nitro-phenyl)-2H-tetrazole: $^1$H-NMR (400 MHz, d$_6$-DMSO), δ (ppm) 4.47 (3H, s) 8.34-8.40 (4H, m).

1-Methyl-5-(4-nitro-phenyl)-1H-tetrazole: $^1$H-NMR (400 MHz, d$_6$-DMSO) δ (ppm) 4.25 (3H, s), 7.98-8.01 (2H, d), 8.44-8.47 (2H, d).

Step 2: 4-(2-Methyl-2H-tetrazol-5-yl)-phenylamine

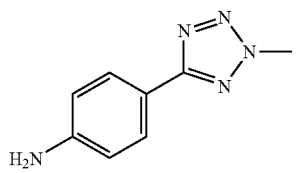

A mixture of 2-methyl-5-(4-nitro-phenyl)-2H-tetrazole (0.260 g, 1.27 mmol) and palladium on charcoal (53.6 mg) in ethanol (50 mL) is stirred in high pressure reactor under H2 at 4 bars for 17 hours. The catalyst is removed by filtration through Celite 521, washing with EtOH. The filtrates are combined and concentrated in vacuo to afford the title compound as a white solid (0.213 g, 96%). HPLC (254 nm) 1.50 min (89%)

Step 3: (5-Bromo-imidazo[1,2-a]pyrazin-8-yl)-[4-(2-methyl-2H-tetrazol-5-yl)-phenyl]-amine

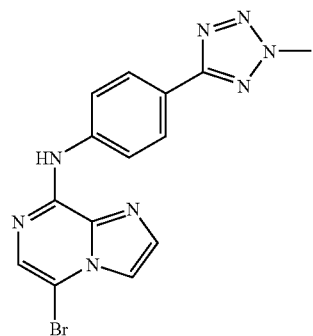

In the same way as described for Compound 90, step 1, using 5,8-dibromoimidazo[1,2-a]pyrazine (334 mg, 1.21 mmol), 4-(2-methyl-2H-tetrazol-5-yl)-phenylamine (211.1 g, 1.21 mmol), NaO$^t$Bu (162 mg, 1.69 mmol), Pd$_2$(dba)$_3$ (44.1 mg, 0.0482 mmol), Xantphos (55.8 mg, 0.0964 mmol) and toluene (16 mL). The crude product is purified by silica gel column chromatography eluting with a 8:2:1 mixture petroleum ether:EtOAc:MeOH to afford the title compound as a yellow solid (198 mg, 44%).

Step 4: [4-(2-Methyl-2H-tetrazol-5-yl)-phenyl]-[5-(1H-pyrazol-4-yl)-imidazo[1,2-a]pyrazin-8yl]-amine

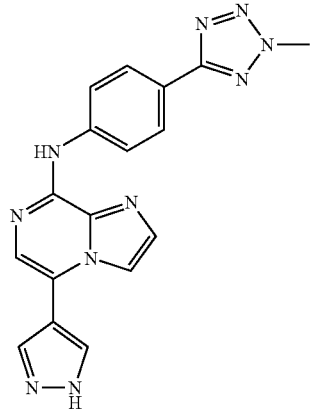

In the same way as described for Compound 178, step 4, using (5-bromo-imidazo[1,2-a]pyrazin-8-yl)-[4-(2-methyl-2H-tetrazol-5-yl)-phenyl]-amine (49.4 mg, 0.1333 mmol), 4-(4,4,5,5-tetramethyl-[1,3,2]dioxaborolan-2-yl)-1H-pyrazole (51.6 mg, 0.266 mmol), Pd(PPh$_3$)$_4$ (39.3 mg, 0.034 mmol), 1.5 M Na$_2$CO$_3$ (0.710 mL, 1.07 mmol) in (2:1) DMF-dioxane (1.5 mL). Purification by Isolute FlashSilicaII cartridge chromatography eluting with 97:3 DCM:NH$_3$ (7M in MeOH) affords the title compound as a white solid (17.3 mg, 36%). LCMS: Rt 2.60 min (96%), m/z 359 (M+H)$^+$; $^1$H-NMR (400 MHz, d$_6$-DMSO) δ (ppm) 4.45 (3H, s), 7.72 (1H, s), 7.81 (1H, s), 8.05 (2H, d), 8.10 (1H, s), 8.21 (1H, s), 8.33 (2H, d), 8.48 (1H, s), 9.91 (1H, s), 13.42 (1H, br s).

Compound 171: 4-{8-[3-Fluoro-4-(4-methyl-piperazin-1-yl)-phenylamino]-imidazo[1,2-a]pyrazin-5-yl}-benzamide Step 1: (5-Bromo-imidazo[1,2-a]pyrazin-8-yl)-[3-fluoro-4-(4-methyl-piperazin-1-yl)-phenyl]-amine

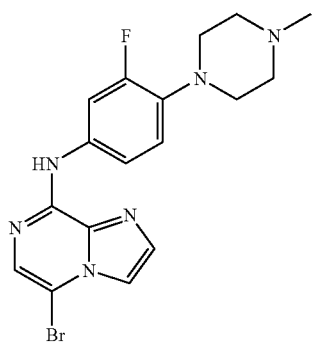

Following the general procedure for amine displacement using 5,8-dibromoimidazo[1,2-a]pyrazine (0.50 g, 1.81 mmol), 3-fluoro-4-(4-methyl-piperazin-1-yl)-phenylamine (0.45 g, 2.17 mmol) and DIPEA (0.47 mL, 2.72 mmol) in $^i$PrOH (5 mL). The crude material is purified by silica gel column chromatography eluting with 90:10 DCM:MeOH to give the title compound (35 mg, 5%).

Step 2: 4-{8-[3-Fluoro-4-(4-methyl-piperazin-1-yl)-phenylamino]-imidazo[1,2-a]pyrazin-5-yl}-benzamide

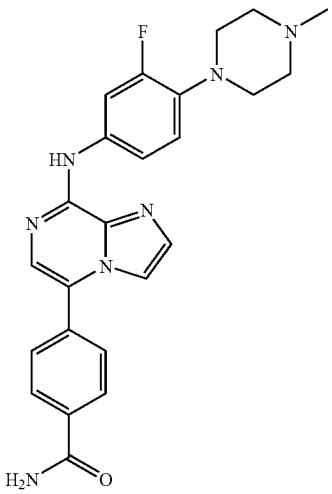

In the same way as described for Compound 178, step 4, using (5-bromo-imidazo[1,2-a]pyrazin-8-yl)-[3-fluoro-4-(4-methyl-piperazin-1-yl)-phenyl]-amine (60.0 mg, 0.15 mmol), 4-(4,4,5,5-tetramethyl-[1,3,2]dioxaborolan-2-yl)-benzamide (49.5 mg, 0.30 mmol), Pd(PPh$_3$)$_4$ (43.0 mg, 0.038 mmol) and 1.5 M Na$_2$CO$_3$ (0.80 mL, 1.20 mmol) in dioxane (3 mL). The crude material is purified by silica gel column chromatography eluting with 95:5 and 90:10 DCM:MeOH to afford the title compound (11 mg, 16%). LCMS: Rt 1.86 min (96%), m/z (ES$^+$) 446 (M+H)$^+$; $^1$H-NMR (400 MHz, d$_6$-DMSO) δ (ppm) 2.26 (3H, s), 2.52 (4H, m), 3.01 (4H, m), 7.05 (1H, t), 7.52 (1H, br s), 7.59 (1H, s), 7.75 (1H, s), 7.79-7.85 (3H, m), 8.04 (1H, s), 8.09-8.11 (3H, m), 8.15 (1H, br s), 9.86 (1H, s).

Compound 173: 5-[8-(4-Morpholin-4-yl-phenylamino)-imidazo[1,2-a]pyrazin-5-yl]-thiazole-2-carboxylic acid amide Step 1: 5-Bromo-thiazole-2-carboxylic acid amide

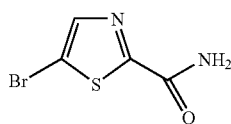

To 5-bromo-thiazole-2-carboxylic acid (0.267 g, 0.128 mmol) suspended in dry dichloromethane (30 mL) are added oxalyl chloride (0.22 mL, 0.257 mmol) and a drop of DMF. The reaction is stirred for 1 hour at room temperature. The solvent is evaporated and the resultant crude is dissolved in 7M NE$_3$ in MeOH. The reaction mixture is stirred overnight at room temperature. After evaporation of the solvent, the residue is dissolved in dichloromethane and washed with 1M NaOH. The organic phase is dried over MgSO$_4$, filtered and evaporated. The residue is purified by silica gel column chromatography eluting with 95:5 DCM:MeOH to give the title compound (33.8 mg, 25%).

Step 2: 5-[8-(4-Morpholin-4-yl-phenylamino)-imidazo[1,2-a]pyrazin-5-yl]-thiazole-2-carboxylic acid amide

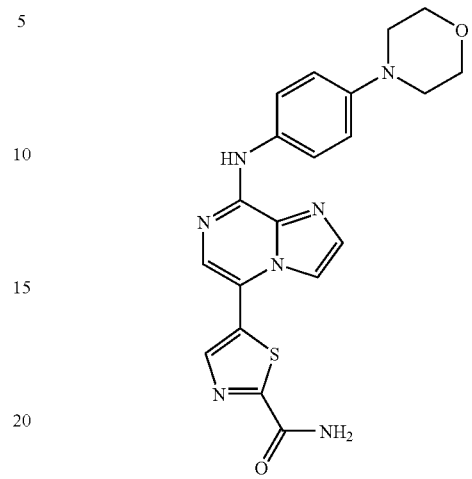

In the same way as described for Compound 212, step 3, using (4-morpholin-4-yl-phenyl)-(5-tributylstannanyl-imidazo[1,2-a]pyrazin-8-yl)-carbamic acid tert-butyl ester (0.25 g, 0.365 mmol), 5-bromo-thiazole-2-carboxylic acid amide (60.5 mg, 0.29 mmol) and Pd(PPh$_3$)$_4$ (63.3 mg, 0.055 mmol) in DMF. Purification by silica gel column chromatography eluting with 99:1 and 95:5 DCM:MeOH affords the title compound as a free base (27.4 mg, 49%).

Conversion into the mesylate salt following the usual procedure, using 1M methanesulfonic acid (0.650 mL) affords the target compound (13.9 mg, 41%). LCMS: Rt 2.57 min (97%), m/z (APCI) 422 (M+H)$^+$; $^1$H-NMR (400 MHz, d$_6$-DMSO) δ (ppm) 2.34 (3H, s, MsOH), 3.20 (4H, m), 3.82 (4H, t), 6.99-7.09 (2H, m), 7.76 (1H, br s), 7.84 (1H, s), 7.94 (2H, d), 8.24 (1H, s), 8.30 (1H, br s), 8.56 (1H, s), 9.09 (1H, s), 10.17 (1H, br s).

Compound 174: 6-Methyl-4-[8-(4-morpholin-4-ylphenylamino)-imidazol[1,2-a]pyrazin-5-yl]-1H-pyridin-2-one Step 1: 4-Bromo-6-methylpyridin-2-ol

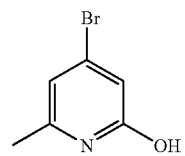

A solution of 6-methylpyridine-2,4-diol (1.75 g, 14.0 mmol) in dry DMF (6.0 mL) is stirred under N$_2$ and phosphorus oxybromide (3.05 g, 10.6 mmol) is added in one portion. The mixture is heated at 110° C. for 45 min and then cooled and diluted with water (7 mL). Na$_2$CO$_3$ (s) is added to bring the pH to 7 and the resulting suspension is cooled to 0° C. The product is collected by suction filtration, rinsing with cold water and diethyl ether, and dried overnight in a vacuum desiccator to afford the title compound as a light brown solid (920 mg).

Step 2: 4-Bromo-2-(tert-butyldimethylsilyloxy)-6-methylpyridine

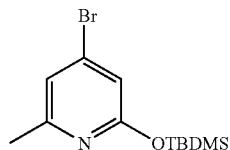

A solution of 4-bromo-6-methylpyridin-2-ol (376 mg, 2 mmol) in dry DMF (20 mL) is stirred under $N_2$. TBDMS-Cl (600 mg, 4 mmol) is added, followed by triethylamine (0.97 mL, 7.00 mmol), and the mixture is stirred at rt for 1 h. The solution is poured into ice-water (170 mL) and extracted with diethyl ether (5×50 mL). The combined extracts are dried over $Na_2SO_4$ and the solvent is evaporated under reduced pressure. The residue is taken up in pentane (50 mL), dried over $Na_2SO_4$ and the solvent evaporated again, to afford the crude title compound as a yellow oil. This is used without further purification.

Step 3: (4-Morpholin-4-ylphenyl)-[5-(4,4,5,5-tetramethyl-[1,3,2]dioxaborolan-2-yl)imidazo[1,2-a]pyrazin-8-yl]carbamic acid tert-butyl ester

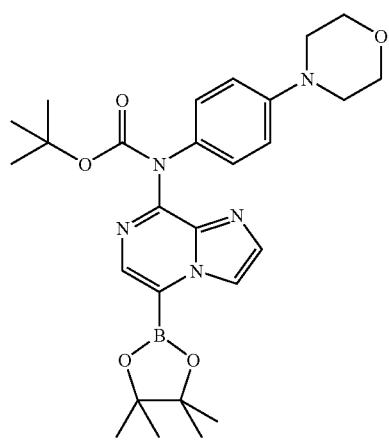

(5-Bromoimidazo[1,2-a]pyrazin-8-yl)-(4-morpholin-4-ylphenyl)carbamic acid tert-butyl ester (47 mg, 0.10 mmol), bis(pinacolato)diboron (51 mg, 0.20 mmol), KOAc (29 mg, 0.30 mmol) and Pd(dppf)Cl$_2$-DCM (4 mg, 0.0050 mmol) are stirred under $N_2$ in dioxane (0.3 mL) and heated at 80° C. for 1.5 h. The resulting solution is cooled and used for the following step.

Step 4: 6-Methyl-4-[8-(4-morpholin-4-ylphenylamino)-imidazo[1,2-a]pyrazin-5-yl]-1H-pyridin-2-one

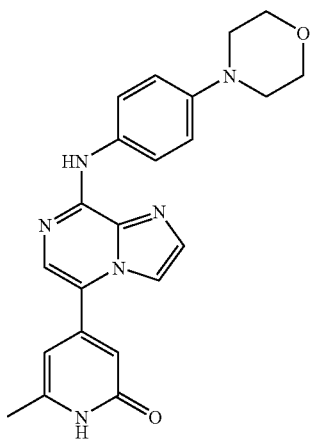

Half of the solution prepared in Step 3 and 4-bromo-2-(tert-butyldimethylsilyloxy)-6-methylpyridine (30 mg, 0.10 mmol) are mixed and diluted with dioxane (0.15 mL). KOAc (15 mg, 0.15 mmol) and Pd(dppf)Cl$_2$DCM (2 mg, 0.0025 mmol) are added and the system is flushed with $N_2$ and heated at 80° C. for 2.5 h. The mixture is cooled to rt, diluted with DCM (5 mL) and MeOH (1 mL) and filtered through celite. The solvents are evaporated, the residue is suspended in DCM (2 mL) and TFA (0.5 mL) is added, causing the solid to dissolve. The solution is stirred at rt overnight and the solvents are then evaporated. The residue is purified by preparative HPLC to afford the title compound as a yellow solid. LCMS: Rt=0.84 min (100%), m/z (ESI) 403 (M+H)$^+$.

Compound 175: 4-[8-(3-Carbamoyl-4-morpholin-4-yl-phenylamino)-imidazo[1,2-a]pyrazin-5-yl]-2,6-difluoro-benzamide

Step 1: 5-(5-Bromo-imidazo[1,2-a]pyrazin-8-ylamino)-2-morpholin-4-yl-benzamide

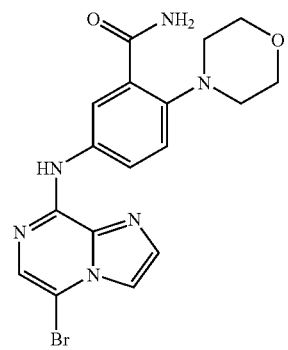

In the same way as described in the general procedure for amine displacement using 5,8-dibromo-imidazo[1,2-a]pyrazine (0.131 g, 0.47 mmol), 5-amino-2-morpholin-4-yl benzamide (157 mg, 0.71 mmol), N,N-diisopropylethylamine (0.120 mL, 0.71 mmol) in iso-propanol (3.7 mL). Trituration with $^i$PrOH and Et$_2$O affords the title compound (127 mg, 67%).

Step 2: 4-Bromo-2,6-difluoro-benzamide

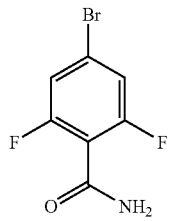

To a solution of 4-bromo-2,6-difluoro-benzoic acid (2.77 g, 11.7 mmol) and 1-hydroxybenzotriazole (1.74 g, 12.8 mmol) is added 1-ethyl-3-(3'-dimethylaminopropyl)carbodiimide (2.46 g, 12.9 mmol) and the solution is stirred at room temperature for 2 hours. After cooling at 0° C. is added aq. NH3 (1.74 mL) and the reaction mixture is stirred for an additional 20 hours. The solvent is evaporated in vacuo and the residue partitioned between diethyl ether and water. The aqueous phase is extracted several times with $Et_2O$, the organic layers are then combined, washed with 1M HCl, sat. $NaHCO_3$, dried over $MgSO_4$, filtered and concentrated in vacuo to afford the benzamide as a white solid (2.56 g, 93%).

Step 3: 2, 6-Difluoro-4-(4,4,5,5-tetramethyl-[1,3,2]dioxaborolan-2-yl)-benzamide

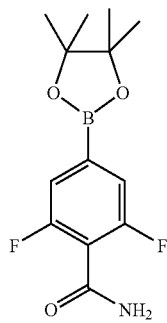

In the same way as described for Compound 209, step 2 using 4-bromo-2,6-difluoro-benzamide (2.50 g, 10.6 mmol), bis(pinacolato)diboron (2.96 g, 11.7 mmol), $PdCl_2dppf$ (0.260 g, 0.32 mmol) and KOAc (3.12 g, 31.6 mmol) suspended in dioxane (30 mL). The reaction mixture is filtered through silica and washed with DCM. After evaporation of the solvent, the residue is dissolved in EtOAc and washed with water and brine. The organic layer is dried over $MgSO_4$, filtered and concentrated in vacuo to afford the boronic ester as a brown solid (2.95 g, 98%).

Step 4: 4-[8-(3-Carbamoyl-4-morpholin-4-yl-phenylamino)-imidazo[1,2-a]pyrazin-5-yl]-2,6-difluoro-benzamide

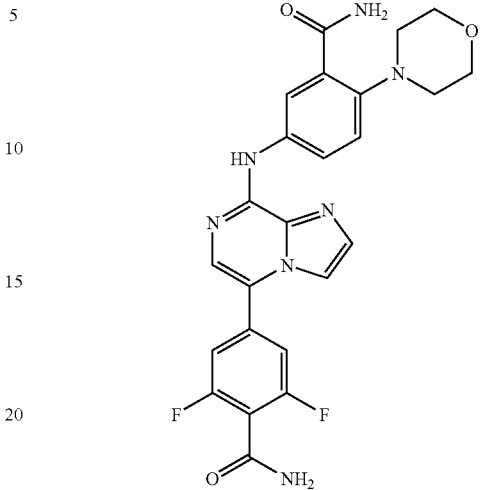

In the same way as described for Compound 178, step 4, using 5-(5-bromo-imidazo[1,2-a]pyrazin-8-ylamino)-2-morpholin-4-yl-benzamide (120 mg, 0.29 mmol), 2,6-difluoro-4-(4,4,5,5-tetramethyl-[1,3,2]dioxaborolan-2-yl)-benzamide (163 mg, 0.58 mmol) 1.5M $K_2CO_3$ (1.7 mL, 2.55 mmol), and $Pd(PPh_3)_4$ (84 mg, 0.073 mmol) in dioxane (3 mL). Purification by silica gel column chromatography eluting with 98:8 DCM:$NH_3$ (7M in MeOH) affords the title compound as a pale yellow solid (30 mg, 21%). Following the usual procedure, using methanesulfonic acid (0.593 mL), the free base (29.3 mg, 0.060 mmol) is converted into the mesylate salt (27 mg, 99%). LCMS: Rt 2.47 min (98%), m/z (ES$^+$) 494 (M+H)$^+$, $^1$H-NMR (400 MHz, d$_6$-DMSO) δ (ppm.) 2.35 (3H, s, MsOH), 2.97-3.05 (4H, m), 3.74-3.83 (4H, t), 7.35 (1H, d), 7.60-7.65 (4H, m), 7.80 (1H, s), 7.98 (1H, br s), 8.05-8.08 (1H, m), 8.13 (1H, s), 8.26 (1H, br s), 8.50 (1H, d), 8.68 (1H, br s), 10.00 (1H, s).

Compound 177: 4-[8-(4-Morpholin-4-yl-phenylamino)-imidazo[1,2-a]pyrazin-5-yl]-thiophene-2-carboxylic acid amide Step 1: 4-Bromo-thiophene-2-carboxylic acid amide

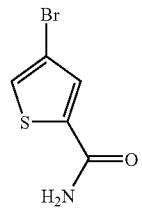

In the same way as described for Compound 179, step 2, using 4 bromo-thiophene-2-carboxylic acid (2.0 g, 9.66 mmol), 1-ethyl-3-(3'-dimethylaminopropyl)carbodiimide hydrochloride (2.04 g, 10.63 mmol), 1-hydroxybenzotriazole hydrate (1.44 g, 10.63 mmol) and aq. $NH_3$ (1 ml, 17.3 mmol) in DMF (20 ml). Water is added to the reaction mixture and the resultant precipitate is collected by filtration and washed with 1M NaOH, H₂O and petrol. The title compound is isolated as a white solid (1.56 g, 78%).

Step 2: 4-(4,4,5,5-Tetramethyl-[1,3,2]dioxaborolan-2-yl)-thiophene-2-carboxylic acid amide

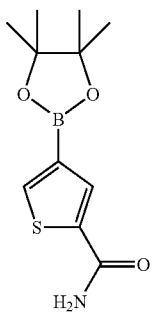

In the same way as described for Compound 209, step 2 using 4-bromo-thiophene-2-carboxylic acid amide (1.3 g, 6.34 mmol), bis(pinacolato)diboron (3.22 g, 12.68 mmol), PdCl₂dppf (0.26 g, 0.318 mol) and KOAc (1.87 g, 19.10 mmol) in dioxane (20 mL). The title product is crystallised from EtOAc-petroleum ether (2.135 g, 77% pure by LCMS).

Step 3: 4-[8-(4-Morpholin-4-yl-phenylamino)-imidazo[1,2-a]pyrazin-5-yl]-thiophene-2-carboxylic acid amide

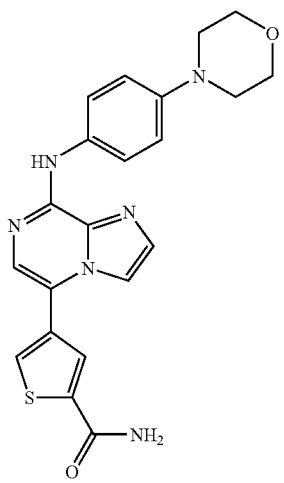

In the same way as described for Compound 178, step 4, using 5-bromo-imidazo[1,2-a]pyrazin-8-yl)-4-morpholin-4-yl-phenylamine (100 mg, 0.268 mmol), 4-(4,4,5,5-tetramethyl-[1,3,2]dioxaborolan-2-yl)-thiophene-2-carboxylic acid amide (136 mg, 0.536 mmol), Na₂CO₃ (85.3 mg, 0.804 mmol), and Pd(PPh₃)₄ (77.5 mg, 0.067 mmol) in dioxane: water (2.5 mL). The crude compound is precipitated from THF, filtered, dissolved in MeOH and converted into the mesylate salt using the procedure described previously employing methanesulfonic acid (1.08 mL, 0.108 mmol). Trituration with diethyl ether gives the mesylate salt as a yellow solid (48.8 mg, 43%). LCMS: Rt 2.19 min (96%), m/z (APCI) 421 (M+H)⁺; ¹H-NMR (400 MHz, d₆-DMSO) δ (ppm) 2.35 (3H, s, MsOH), 3.10-3.19 (4H, m), 3.79 (4H, t), 7.05 (2H, d), 7.51 (1H, s), 7.59 (1H, br s), 7.82-7.84 (3H, m), 8.16 (3H, m), 8.21 (1H, s), 9.93 (1H, br s).

Compound 178: 5-[8-(4-Morpholin-4-yl-phenylamino)-imidazo[1,2-a]pyrazin-5-yl]-2,3-dihydro-isoindol-1-one Step 1: 4-Bromo-2-bromomethyl-benzoic acid methyl ester

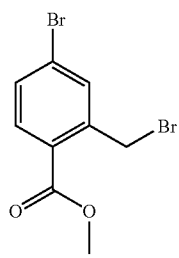

4-Bromo-2-methyl-benzoic acid (4.6 g, 21.39 mmol) is dissolved in 2M HCl in MeOH and refluxed for 3 hours. The solvent is evaporated to give the 4-bromo-2-methyl-benzoic acid methyl ester (4.24 g, 86%). This intermediate (18.51 mmol) is dissolved in carbon tetrachloride (100 mL) and N-bromosuccinimide (NBS) (5.57 g, 24.06 mmol) is added. AIBN (122 mg, 740 □mol) is then added and the mixture purged with nitrogen for 5 min. The reaction mixture is then refluxed for 4 hours. After cooling to room temperature the reaction mixture is filtered and the filtrate is evaporated. The residue is purified by flash chromatography (silica gel, 2:1 petroleum ether/ethyl acetate) to give the title compound (3.42 g, 60%).

Step 2: 5-Bromo-2,3-dihydro-isoindol-1-one

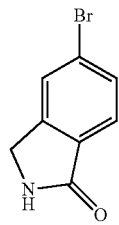

4-Bromo-2-bromomethyl-benzoic acid methyl ester (0.5 g, 16.2 mmol) is treated with methanolic ammonia (10 mL, 7 N NH₃ in MeOH) for 5 minutes at 90° C. After cooling to room temperature a precipitate is formed, collected by filtration and washed with a small amount of methanol to afford the title compound as a colourless solid (224 mg, 65%). ¹H-NMR (400 MHz, d₆-DMSO) δ (ppm) 4.41 (2H, s), 7.64 (1H, d), 7.70 (1H, d), 7.87 (1H, s), 8.67 (1H, br s). LCMS: Rt 2.49 min, (99.6%), m/z (APCI) 212 (M+H⁺).

Step 3: 5-(4,4,5,5-Tetramethyl-[1,3,2]dioxaborolan-2-yl)-2,3-dihydro-isoindol-1-one

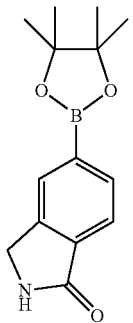

5-Bromo-2,3-dihydro-isoindol-1-one (230 mg, 1.08 mmol), bis(pinacolato)diboron (300 mg, 1.18 mmol), PdCl₂dppf (25 mg, 31☐mol) and KOAc (320 mg, 3.26 mmol) are suspended in dioxane (4 mL), purged with nitrogen for 5 minutes and then heated at 85° C. overnight. The solvent is removed in vacuo and the residue partitioned between ethyl acetate and water. The aqueous layer is extracted with ethyl acetate (3×) and the combined organic phases are washed once with brine, filtered through MgSO₄ and evaporated. The solid residue is triturated with hexane and dried in vacuo to yield the title compound (185 mg, 66%) as a grey solid. ¹H-NMR (400 MHz, CDCl₃) δ (ppm) 1.37 (12H, s), 4.45 (2H, s), 6.38 (1H, br s), 7.87 (1H, d), 7.93 (2H, m).

Step 4: 5-[8-(4-Morpholin-4-yl-phenylamino)-imidazo[1,2-a]pyrazin-5-yl]-2,3-dihydro-isoindol-1-one

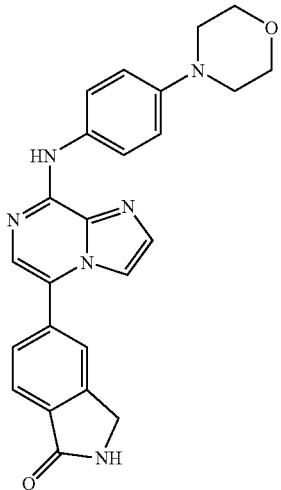

A degassed solution of 5-bromo-imidazo[1,2-a]pyrazin-8-yl)-4-morpholin-4-yl-phenylamine (1.0 g, 2.06 mmol), 5-(4,4,5,5-tetramethyl-[1,3,2]dioxaborolan-2-yl)-2,3-dihydro-isoindol-1-one (1.04 g, 4.02 mmol), 1.5 M Na₂CO₃ (14.3 mL, 21.44 mmol) and Pd(PPh₃)₄ (0.77 g, 0.67 mmol) in dioxane (40 mL) is stirred overnight at 90° C. The solvent is removed in vacuo and the residue partitioned between ethyl acetate and water. A solid is formed and collected by filtration. The aqueous layer is extracted with ethyl acetate (2×) and the combined organic phases and the solid are dissolved using MeOH/DCM and then evaporated to dryness. The residue is purified by silica gel column chromatography eluting with DCM followed by 95:5 DCM:NH₃ (7M in MeOH). The fractions containing the desired product are combined and evaporated to afford the title compound as a solid.

After trituration with diethyl ether, the compound (0.93 g, 2.18 mmol, 83%) is converted into the mesylate salt. The solid is dissolved in the minimum amount of MeOH/DCM, (refluxed to dissolve) and 1M methane sulfonic acid in MeOH (2.18 mL, 2.18 mmol) is added. The mixture is cooled and concentrated to afford a solid that is triturated several times with a mixture of 1:1 ethyl acetate-diethyl ether and DCM-diethyl ether, filtered and dried in vacuo to afford the desired compound as a yellow solid (0.954 g, 84%). LCMS: Rt 2.32 min (98.4%); m/z (APCI) 427 (M+H)⁺; ¹H-NMR (400 MHz, d₆-DMSO) δ (ppm) 2.39 (3H, s, MsOH), 3.29 (4H, m), 3.85 (4H, m), 4.52 (2H, s), 7.22 (2H, d), 7.45 (1H, s), 7.68-7.82 (3H, m), 7.89-7.93 (3H, m), 8.14 (1H, s), 8.77 (1H, s), 10.77 (1H, br s).

Compound 179: 5-[8-(4-Morpholin-4-yl-phenylamino)-imidazo[1,2-a]pyrazin-5-yl]-furan-3-carboxylic acid amide Step 1: 5-Bromo-furan-3-carboxylic acid

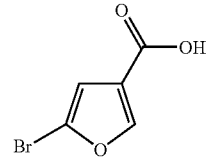

Furan-3-carboxylic acid (1 g, 8.93 mmol) is added to a solution of pyridinium hydrobromide perbromide (3.02 g, 9.46 mmol) in acetic acid (5 mL). The reaction mixture is stirred at 50° C. for 5 hours, then at room temperature overnight. After removing the solvent in vacuo, water is added and a precipitate is formed. The solid is collected by filtration and dried to yield the title compound (0.364 g, 21%). HPLC (254 nm): Rt 2.65 min (88%).

Step 2: 5-Bromo-furan-3-carboxylic acid amide

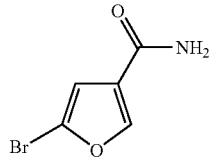

A solution of 5-bromo-furan-3-carboxylic acid (0.364 g, 1.92 mmol), 3-hydroxybenzotriazole hydrate (0.28 g, 2.11 mmol), 1-ethyl-3-(3'-dimethylaminopropyl)carbodiimide (0.40 g, 2.11 mmol) in DMF (11 mL) is stirred at room temperature for 2 hours. The reaction mixture is then cooled to 0° C. and aq. NH₃ (0.22 mL) is added. The mixture is stirred at room temperature for an additional 5 hours, then the solvent is removed in vacuo and the residue dissolved in EtOAc, washed with 1N NaOH, and 1N HCl. The organic layers are combined, dried over MgSO₄ and concentrated to afford the title compound (0.288 g, 79%). HPLC (254 nm): Rt 2.17 min (85.3%).

Step 3: 5-[8-(4-Morpholin-4-yl-phenylamino)-imidazo[1,2-a]pyrazin-5-yl]-furan-3-carboxylic acid amide

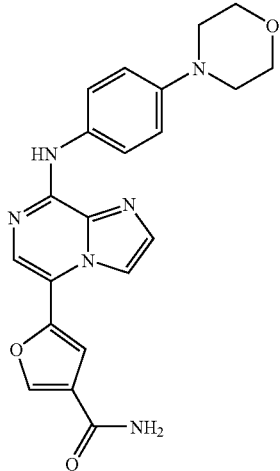

In the same way as described for Compound 212, step 3, using (4-morpholin-4-yl-phenyl)-(5-tributylstannanyl-imidazo[1,2-a]pyrazin-8-yl)-carbamic acid tert-butyl ester (0.25 g, 0.365 mmol), 5-bromo-furan-3-carboxamide (0.139 g, 0.66 mmol) and Pd(PPh$_3$)$_4$ (63.3 mg, 0.05 mmol) in DMF (10 mL). Purification by silica gel column chromatography eluting with DCM followed by 97:3 and 94:6 DCM:MeOH gives (4-morpholin-4-yl-phenyl)-(5-tributylstannanyl-imidazo[1,2-a]pyrazin-8-yl)-carbamic acid tert-butyl ester as a yellow solid (153 mg, 83%). HPLC (254 nm): Rt 2.72 min (93.7%), m/z 505 (M+H)$^+$ The solid is dissolved in dioxane:4M HCl (4 mL). A few drops of methanol are added to achieve complete dissolution. The yellow solution is stirred at room temperature for 20 min. A precipitate is formed and collected by filtration, washed with diethyl ether and dried in vacuo to afford 5-[8-(4-morpholin-4-yl-phenylamino)-imidazo[1,2-a]pyrazin-5-yl]-furan-3-carboxylic acid amide as the hydrochloride salt (111.6 mg, 91%). HPLC (254 nm) (HCl salt): Rt 2.31 min (98.2%), m/z 405 (M+H)$^+$. The hydrochloride salt is converted into the free base suspending in ethyl acetate and washing with 1M Na$_2$CO$_3$.

Formation of the mesylate salt, following the procedure described previously, using 5-[8-(4-morpholin-4-yl-phenylamino)-imidazo[1,2-a]pyrazin-5-yl]-furan-3-carboxylic acid amide (83 mg, 0.205 mmol) and methanesulfonic acid (2.06 mL) affords the title compound as a solid (95.4 mg, 93%). LCMS: Rt 2.34 min (96.2%), m/z (APCI) 405 (M+H)$^+$; $^1$H-NMR (400 MHz, d$_6$-DMSO) δ (ppm) 2.35 (3H, s, MsOH), 3.28 (4H, m), 3.86 (4H, m), 7.21 (2H, br d), 7.42 (1H, br s), 7.50 (1H, s), 7.80-8.07 (5H, m), 8.40 (1H, s), 8.49 (1H, s), 10.34 (1H, br s).

Compound 183: N-{5-[5-(1H-Pyrazol-4-yl)imidazo[1,2-a]pyrazin-8-ylamino]pyridin-2-yl}benzamide

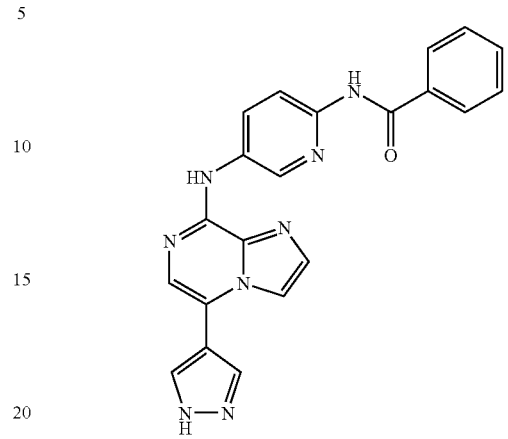

This compound may be prepared using the same methods as described for compound 200, using benzoyl chloride in Step 1. LCMS: Rt=1.13 min (100%), m/z (ESI) 397 (M+H)$^+$.

Compound 184: 2-Methoxy-N-(6-methylpyridin-3-ylmethyl)-4-[5-(1H-pyrazol-4-yl)imidazo[1,2-a]pyrazin-8-ylamino]benzamide Step 1: 2-Methoxy-N-(6-methylpyridin-3-yl)methyl-4-nitrobenzamide

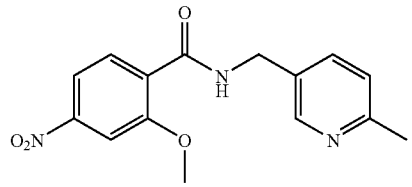

2-Methoxy-4-nitrobenzoic acid (293 mg, 1.49 mmol) is dissolved in DMF (2 mL) and 4-methylmorpholine (220 µL, 3.0 mmol) and TBTU (1.79 g, 1.7 mmol) are added. The mixture is stirred at rt for 30 min and C-(6-methylpyridin-3-yl)methylamine (400 mg, 3.27 mmol) is added. Stirring is continued at rt for 12 h. DCM (10 mL) is added and the organic phase is washed with Na$_2$CO$_3$ (5% aq.), HCl (3% aq.) and water, and then dried over Na$_2$SO$_4$. After evaporation of the solvents, the residue is triturated with ether-hexane to afford the title compound as a white solid.

Step 2: 4-Amino-2-methoxy-N-[(6-methylpyridin-3-yl)methyl]benzamide

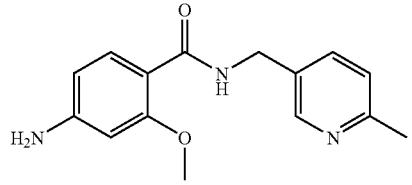

A solution of 2-methoxy-N-(6-methylpyridin-3-yl)methyl-4-nitrobenzamide (448 mg, 1.49 mmol) in EtOH and EtOAc (8 mL each) is stirred and ammonium formate (375 mg, 6 mmol) and 10% Pd/C (100 mg) are added. The mixture is heated at reflux for 20 min, cooled, filtered through celite, the solid is washed with EtOH and the combined solvents are evaporated to afford the title compound.

Step 3: 4-(5-Bromo-imidazo[1,2-a]pyrazin-8-ylamino)-2-methoxy-N-(6-methylpyridin-3-ylmethyl) benzamide

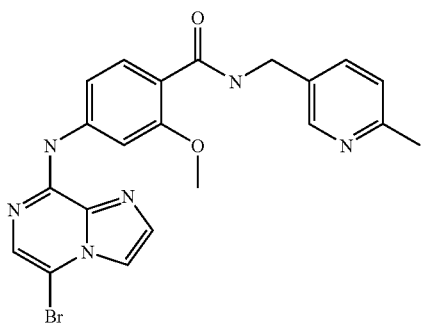

5,8-dibromoimidazo[1,2-a]pyrazine (285 mg, 1.03 mmol) and 4-amino-2-methoxy-N-[(6-methylpyridin-3-yl)methyl]benzamide (280 mg, 1.03 mmol) are stirred in $^i$PrOH (5 mL) and HBr (48% aq., 380 µL) is added. The mixture is heated at reflux for 24 hours. The cooled suspension is poured into NaHCO$_3$ (sat. aq., 25 mL) and water (25 mL) and extracted with CDCl$_3$ (3×40 mL). The extracts are dried over MgSO$_4$ and evaporated. The residue is purified by column chromatography, eluting with 10% -20% DCM/MeOH to afford the title compound as a pale yellow solid (200 mg, 0.43 mmol).

Step 4: 2-Methoxy-N-(6-methylpyridin-3-ylmethyl)-4-[5-(1H-pyrazol-4-yl)-imidazo[1,2-a]pyrazin-8-ylamino-benzamide

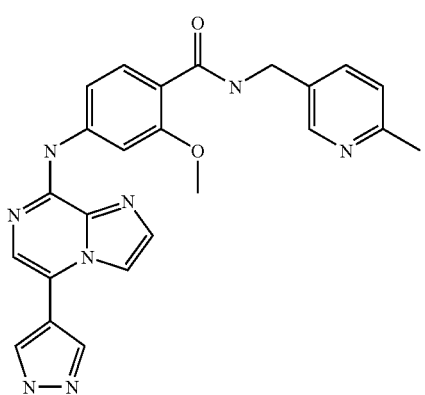

Pyrazole-4-boronic acid (19 mg, 0.17 mmol), 4-(5-bromo-imidazo[1,2-a]pyrazin-8-ylamino)-2-methoxy-N-(6-methylpyridin-3-ylmethyl)benzamide (40 mg, 0.085 mmol), K$_2$CO$_3$ (24 mg, 0.17 mmol) and Pd(dppf)Cl$_2$-CH$_2$Cl$_2$ (4 mg, 0.005 mmol) are weighed into a sealable tube. The tube is flushed with nitrogen and dioxane-water (4:1, 4 mL) is added. The tube is sealed, placed in an ultrasonic bath under a flow of nitrogen gas for 30 seconds and then placed into an oil bath at 85° C. The reaction is stirred for 28 hours, adding additional portions of boronic acid (10 mg) and catalyst (2 mg) after 2 h and 18 h. The crude mixture is absorbed onto SiO$_2$ and purified by column chromatography, eluting with 5% MeOH in DCM and then 5% 2 M NH$_3$/MeOH in DCM to afford the title compound as a brown powdery solid (27.8 mg). $^1$H NMR (400 MHz, DMSO-d$_6$): δ=13.40 (1H, br s); 9.83 (1H, s); 8.62 (1H, t, J=5 Hz); 8.44-8.42 (2H, m); 8.18 (1H, s); 8.08 (1H, br s); 8.02 (1H, d, J=2 Hz); 7.91 (1H, dd, J=8 Hz, 2 Hz); 7.81 (1H, d, J=9 Hz); 7.78 (1H, s); 7.69 (1H, s); 7.62 (1H, dd, J=8 Hz, 2 Hz); 7.21 (1H, d, J=8 Hz); 4.48 (2H, d, J=6 Hz); 3.93 (3H, s); 2.44 (3H, s). LCMS: Rt 0.83 min (100%) m/z (ESI) 455 (M+H)$^+$.

Compound 189: [3-Ethyl-5-(1H-pyrazol-4-yl)imidazo[1,2-a]pyrazin-8-yl]-(4-morpholin-4-yl-phenyl)amine

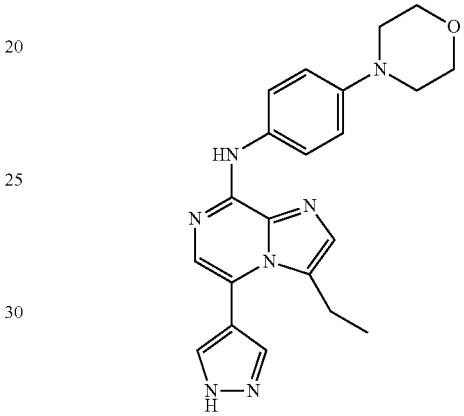

This compound may be prepared using the methods described for Compound 131, using butanal in step 1. LCMS: Rt=0.94 min (100%), m/z (ESI) 390 (M+H)$^+$.

Compound 190: 4-(8-{3-Methoxy-4-[(6-methylpyridin-3-ylmethyl)carbamoyl]phenylamino}imidazo[1,2-a]pyrazin-5-yl)thiophene-2-carboxylic acid amide

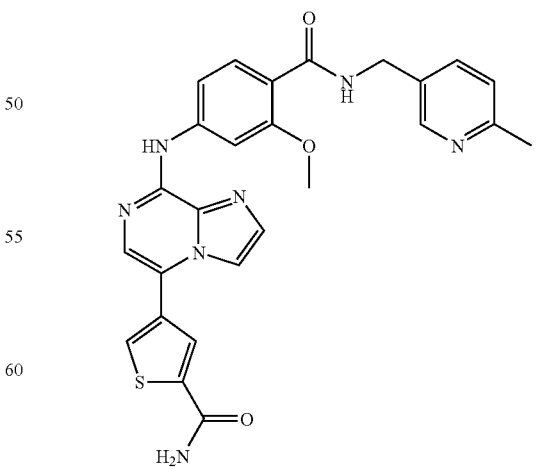

This compound may be prepared using the method described for compound 184, using 2-(aminocarbonyl)

thiophene-4-boronic acid in Step 4. LCMS: Rt=0.95 min (100%), m/z (ESI) 514 (M+H)⁺.

Compound 192: 4-(8-{4-[1-(2,2,2-Trifluoroethyl)piperidin-4-yl]phenylamino}imidazo[1,2-a]pyrazin-5-yl)thiophene-2-carboxylic acid amide Step 1: 1-Trifluoroacetyl-4-(4-nitrophenyl)piperidine

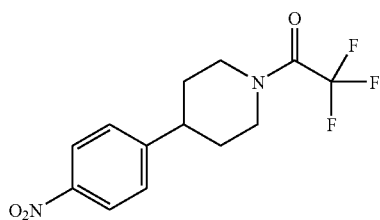

Triethylamine (1.0 mL, 7.3 mmol) and 4-(4-nitrophenyl)piperidine (1.0 g, 4.8 mmol) are stirred in DCM (25 mL) at 0° C. under $N_2$ and trifluoroacetic anhydride (0.81 mL, 5.8 mmol) is added. The mixture is stirred for three days, allowing the temperature to warm to rt. The solution is then diluted with DCM (50 mL) and washed with water (2×15 mL), NaHCO₃ (50% sat. aq., 2×15 mL) and brine (15 The solvent is dried over MgSO₄ and evaporated to afford the desired compound (1.46 g, 4.66 mmol).

Step 2: 1-(2, 2, 2-Trifluoroethyl)-4-(4-nitrophenyl)piperidine

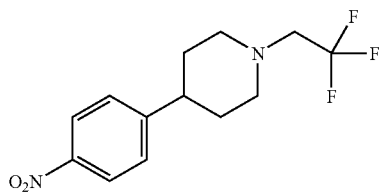

A solution of 1-trifluoroacetyl-4-(4-nitrophenyl)piperidine (1.42 g, 4.7 mmol) in THF (15 mL) is stirred in 25 mL 2-necked flask fitted with a condenser and pressure-equalising addition funnel. The system is flushed with $N_2$, NaBH₄ (210 mg, 5.6 mmol) is added and the flask is cooled to 0° C. A solution of iodine (600 mg, 2.3 mmol) in THF (5 mL) is then added dropwise over 20 minutes, after which the addition funnel is removed and the mixture heated at reflux overnight. The resulting pale yellow suspension is cooled to rt and MeOH (1.5 mL) is added cautiously, causing vigorous evolution of a gas. Evaporation of the solvents affords the title compound, which is used without further purification.

Step 3: 4-[1-(2,2,2-Trifluoroethyl)piperidin-4-yl]phenylamine

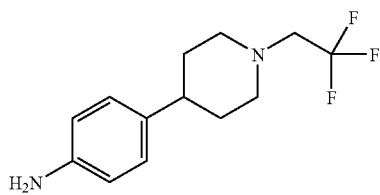

Ammonium formate (1.38 g, 22 mmol) and 10% Pd/C (230 mg, 0.2 mmol) are added to a solution of 1-(2,2,2-trifluoroethyl)-4-(4-nitrophenyl)piperidine (1.26 g, 4.4 mmol) in EtOH (10 mL) and EtOAc (10 mL). The suspension is heated at reflux for 24 hours, adding further portions of ammonium formate (2 g) after 4 h and 8 h. The mixture is filtered through celite and evaporated to afford an orange solid. This is partitioned between DCM (40 mL) and water (20 mL) and the layers separated. The aqueous phase is extracted with DCM (2×20 mL) and the combined organic layers are dried over MgSO4 and evaporated under reduced pressure to afford N-{4-[1-(2,2,2-trifluoroethyl)piperidin-4-yl]phenyl}formamide as a pale orange solid (980 mg).

A solution of the formamide in MeOH (20 mL) is stirred at rt and HCl (conc., 1 mL) is added. The deep purple solution is heated at reflux for 1 h, cooled and the MeOH is evaporated. The residue is stirred with water (20 mL) and NaHCO₃ (sat. aq.) is added until bubbling ceases. The mixture is extracted with DCM (20 mL, 2×10 mL) and the combined extracts are dried over MgSO₄ and evaporated under reduced pressure to afford the title compound as an orange solid (870 mg).

Steps 4 and 5: 4-(8-{4-[1-(2,2,2-Trifluoroethyl)piperidin-4-yl]phenylamino}imidazo[1,2-a]pyrazin-5-yl)thiophene-2-carboxylic acid amide

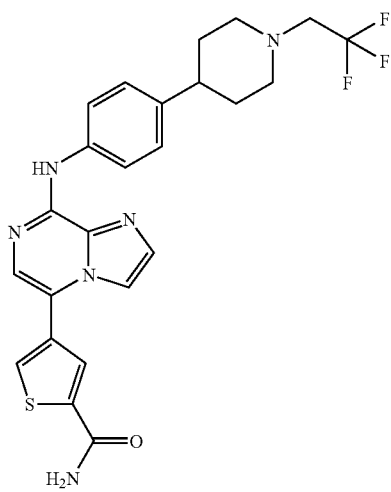

These steps may be performed using the methods as described for Compound 202, step 3 and for Compound 200, Step 4. LCMS: Rt=2.10 min (100%), m/z (ESI) 501 (M+H)⁺.

Compound 198: 2-[8-(4-Morpholin-4-yl-phenylamino)-imidazo[1,2-a]pyrazin-5-yl]-4,5-dihydro-thieno[2,3-c]pyrrol-6-one Step 1: 3-Bromomethyl-thiophene-2-carboxylic acid methyl ester

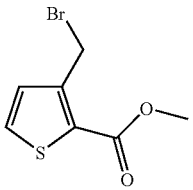

3-Methyl-thiophene-2-carboxylic acid methyl ester (1 g, 6.4 mmol) is dissolved in CCl₄ (15 mL), and NBS (1.19 g, 6.7 mmol) and benzoyl peroxide (15 mg) are added. The reaction mixture is refluxed for 6 hours, then water is added and the mixture is extracted with EtOAc (3×). The organic layers are dried over MgSO₄, filtered and concentrated. The crude product is purified by silica gel column chromatography eluting with 98:2 petroleum ether-EtOAc to give the title compound (1.34 g, 27%).

Step 2: 3-Aminomethyl-thiophene-2-carboxylic acid methyl ester

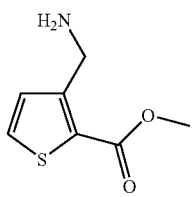

3-Bromomethyl-thiophene-2-carboxylic acid methyl ester (1.297 g, 5.54 mmol) is dissolved in DMF (30 mL) and MeOH/NH₃ is added (30 mL). The reaction mixture is stirred at room temperature for 1 hour, and concentrated in vacuo. Purification of the residue by silica gel column chromatography eluting with 95:5 and 93:7 DCM:MeOH affords the title compound (0.82 g, 86%).

Step 3: 4,5-Dihydro-thieno[2,3-c]pyrrol-6-one

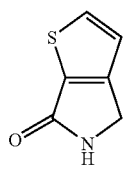

To a solution of 3-aminomethyl-thiophene-2-carboxylic acid methyl ester (0.82 g, 4.79 mmol) in 1:1 MeOH-EtOH (125 mL), is added K₂CO₃ (0.66 g, 4.79 mmol) and the mixture is stirred at 90° C. for 5 hours. The solvent is removed in vacuo and the residue purified by silica gel column chromatography eluting with 97:3 DCM:MeOH. The title compound is isolated (0.365 g, 55%).

Step 4: 2-Bromo-4,5-dihydro-thieno[2,3-c]pyrrol-6-one

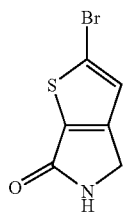

4,5-Dihydro-thieno[2,3-c]pyrrol-6-one (0.365 g, 2.63 mmol) is dissolved in acetonitrile (10 mL), and NBS (0.47 g, 2.63 mmol) is slowly added at −10° C. The reaction mixture is stirred at room temperature overnight. The solvent is removed in vacuo and the residue taken-up in EtOAc and washed with 1M NaOH. The organic phase is dried over MgSO₄, filtered and concentrated in vacuo. The crude is purified by silica gel column chromatography eluting with a 50:50 mixture and then 50:70 petroleum ether-EtOAc. The title compound is isolated (91.1 mg, 16%). HPLC (254 nm): Rt 2.55 min (70.3%), m/z 218/220 (M+H)⁺.

Step 5: 2-[8-(4-Morpholin-4-yl-phenylamino)-imidazo[1,2,-a]pyrazin-5-yl]-4,5-dihydro-thieno[2,3-c]pyrrol-6-one

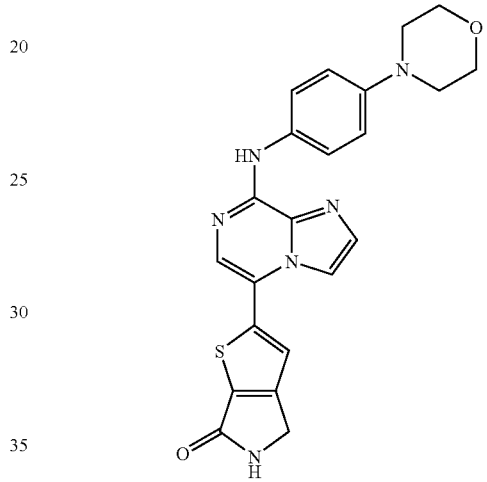

In the same way as described for Compound 212, step 3, using (4-morpholin-4-yl-phenyl)-(5-tributylstannanyl-imidazo[1,2-a]pyrazin-8-yl)-carbamic acid tert-butyl ester (0.28 g, 0.41 mmol), 2-bromo-4,5-dihydro-thieno[2,3-c]pyrrol-6-one (0.06 g, 0.276 mmol), and Pd(PPh₃)₄ (0.032 g, 0.0276 mmol) in DMF (3 mL). The reaction mixture is concentrated, treated with a mixture of (1:1) DCM-TFA and stirred at room temperature for 6 hours. The mixture is diluted with DCM and washed with a solution of sat. NaHCO₃. The organic layers are combined, dried over MgSO₄, filtered and concentrated to afford a solid, which is purified by silica gel column chromatography using 98:2 DCM:NH₃ (7M in MeOH). The residue is triturated with diethyl ether affording the title compound as a free base (70.5 mg, 59%). HPLC (254 nm): Rt 2.53 min (95%), m/z 433 (M+H)⁺.

Conversion into the mesylate salt, using 2-[8-(4-morpholin-4-yl-phenylamino)-imidazo[1,2-a]pyrazin-5-yl]-4,5-dihydro-thieno[2,3-c]pyrrol-6-one (69.2 mg, 016 mmol) and 0.1M methanesulfonic acid (1.598 mL), affords the title compound (76.2 mg, 90%). LCMS: Rt 2.50 min (96.4%), m/z (APCI) 433 (M+H)⁺; ¹H-NMR (400 MHz, d₆-DMSO) δ (ppm) 2.34 (3H, s, MsOH), 3.21-3.26 (4H, m), 3.83-3.86 (4H, m), 4.45 (2H, s), 7.17 (2H, d), 7.68 (1H, br s), 7.74 (1H, s), 7.87-7.90 (3H, m), 8.30 (1H, s), 8.63 (1H, s), 10.25 (1H, s).

Compound 199: 4-{8-[4-(1-Isopropylpiperidin-4-yl)phenyl-amino]imidazo[1,2-a]pyrazin-5-yl}thiophene-2-carboxylic acid amide

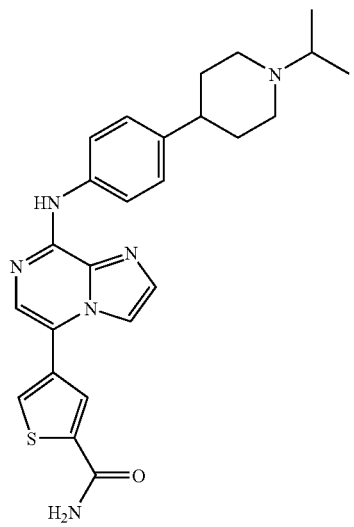

This compound may be prepared using the same methods as described for Compound 202 using 2-(aminocarbonyl) thiophene-4-boronic acid in Step 4.

LCMS: Rt 0.88 min (100%) m/z (ESI) 461 (M+H)+.

Compound 200: 2-Phenyl-N-{5-[5-(1H-pyrazol-4-yl)imidazo[1,2-a]pyrazin-8-ylamino]pyridin-2-yl}acetamide Step 1: N-(5-Nitropyridin-2-yl)-2-phenylacetamide

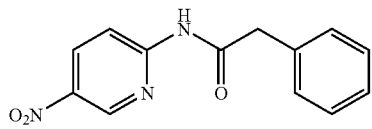

A solution of 2-amino-5-nitropyridine (4.17 g, 30 mmol) in pyridine (30 mL) is stirred at rt and a solution of phenylacetyl chloride (4.64 g, 30 mmol) in THF (30 mL) is added dropwise. The mixture is stirred for 24 h and then poured into ice-water (250 mL) to afford a brown solid, which is used without further purification.

Step 2: N-(5-Amino-pyridin-2-yl)-2-phenylacetamide

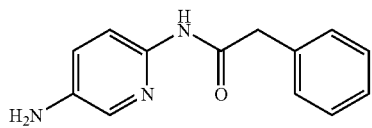

A solution of N-(5-nitropyridin-2-yl)-2-phenylacetamide (4.35 g, 16.9 mmol) in EtOH (75 mL) and EtOAc (75 mL) is stirred at rt and ammonium formate (4.27 g) and 10% Pd/C (500 mg) are added. The mixture is heated at reflux for 30 min, cooled, filtered through celite and evaporated to afford the title compound as an off-white solid which was used without further purification.

Steps 3 and 4: 2-Phenyl-N-{5-[5-(1H-pyrazol-4-yl)imidazo[1,2-a]pyrazin-8-ylamino]pyridin-2-yl}acetamide

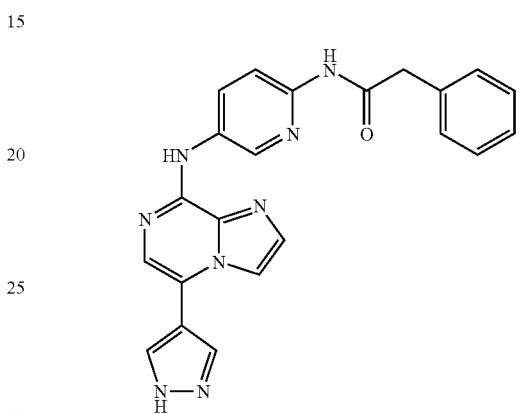

This compound may be prepared using the same methods as described for compound 184, steps 3 and 4. LCMS: Rt=0.99 min (100%), m/z (ESI) 411 (M+H)+.

Compound 201: [6(4-Isopropylpiperazin-1-yl)pyridin-3-yl]-[5-(1H-pyrazol-4-yl)-imidazo[1,2-a]pyrazin-8-yl]amine

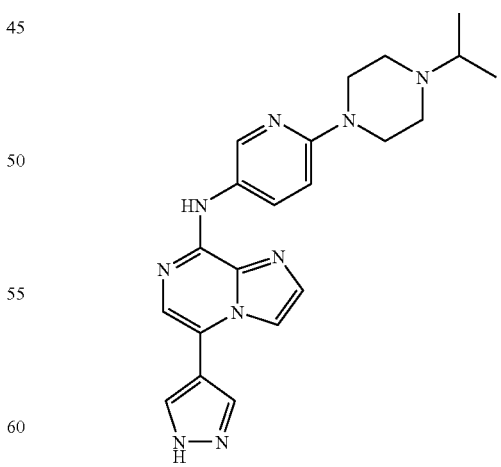

This compound may be prepared using the same methods as described for Compound 184, using 6(4-isopropylpiperazin-1-yl)pyridin-3-ylamine in Step 3. LCMS: Rt=0.72 min (95%), m/z (ESI) 404 (M+H)+.

Compound 202: [4-(1-Isopropylpiperidin-4-yl)phenyl]-[5-(1H-pyrazol-4-yl)imidazo[1,2-a]pyrazin-8-yl]amine Step 1: 1-Isopropyl-4-(4-nitrophenyl)piperidine

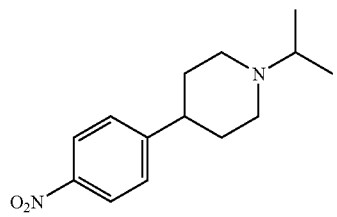

4-(4-Nitrophenyl)piperidine (250 mg, 1.21 mmol), $K_2CO_3$ (170 mg, 1.21 mmol) and 2-iodopropane (240 μL, 2.4 mmol) are stirred in acetonitrile (3 mL) in a sealed tube at 120° C. for 45 min. The mixture is cooled and the solvent removed under reduced pressure. The residue is partitioned between DCM (20 mL) and water (5 mL), the layers are separated and the DCM is washed with water (5 mL) and brine (5 mL) and dried over $MgSO_4$. Evaporation of the solvent affords the title compound (300 mg) which is used without further purification.

Step 2: 4-(1-Isopropylpiperidin-4-yl)phenylamine

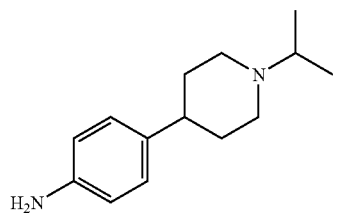

Hydrazine (35% by weight in water, 0.67 mL, 7.2 nnol) and 10% Pd/C (38 mg, 0.03 mmol) are added to a solution of 1-isopropyl-4-(4-nitrophenyl)piperidine (180 mg, 0.72 mmol) in EtOH (10 mL) and the mixture is heated at reflux for 3 h. After cooling, the mixture is filtered through celite and the solvent evaporated. The residue is redissolved in DCM (25 mL), dried over $MgSO_4$ and the solvent evaporated to afford the desired compound as a pale yellow solid (113 mg, 0.52 mmol) which was used without further purification.

Step 3: (5-Bromo-imidazo[1,2-a]pyrazin-8-yl)-[4-(1-Isopropylpiperidin-4-yl)-phenyl]amine

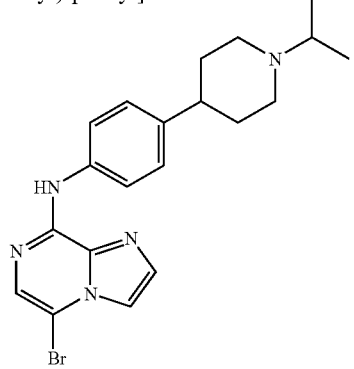

N,N-Diisopropylethylamine (360 μL, 2.2 mmol) is added to a mixture of 4-(1-isopropylpiperidin-4-yl)phenylamine (220 mg, 1.0 mmol) and 5,8-dibromoimidazo[1,2-a]pyrazine (280 mg, 1.0 mmol) in $^i$PrOH (5 mL) and heated at reflux for 48 h. The mixture is cooled and the solvent evaporated under reduced pressure to afford an orange-brown solid. This is partitioned between DCM (50 mL) and water (20 mL) and the layers are separated. The organic phase is washed with citric acid (10% aq., 3×25 mL). The combined washings are extracted with DCM (25 mL) and then made basic by addition of $NaHCO_3$ (s). The mixture is extracted with DCM (3×25 mL) and the combined extracts dried over $MgSO_4$ and evaporated. The material is used without further purification.

Step 4: [4-(1-Isopropylpiperidin-4-yl)phenyl]-[5-(1H-pyrazol-4-yl)imidazo[2-a]pyrazin-8-yl]amine

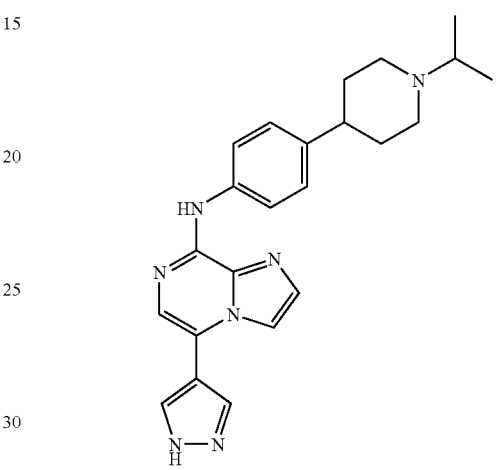

This step may be performed using the same methods as described for Compound 184, step 4, using (5-bromo-imidazo[1,2-a]pyrazin-8-yl)-[4-(1-isopropylpiperidin-4-yl)-phenyl]amine. LCMS: Rt 0.78 min (100%) m/z (ESI) 402 $(M+H)^+$.

Compound 204: 4-{8-[4-(4-Isopropyl-piperazin-1-yl)-phenylamino]-imidazo[1,2-a]pyrazin-5-yl}-furan-2-carboxylic acid amide

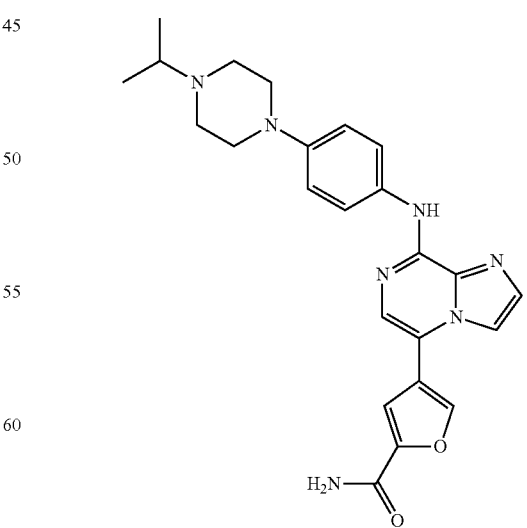

In the same way as described for Compound 178, step 4, using, 5-bromo-imidazo[1,2-a]pyrazin-8-yl-[4-(4-isopropylpiperazin-1-yl)-phenyl]-amine (0.08 g, 0.19 mmol), 4-(4,4,5,5-tetramethyl-[1,3,2]dioxaborolan-2-yl)-furan-2-carboxylic acid amide (0.092 g, 0.39 mmol), 1.5M $Na_2CO_3$ (1.02 mL, 1.53 mmol) and $Pd(PPh_3)_4$ (0.055 g, 0.47 mmol) in dioxane (4 mL). Purification using silica gel column chromatography, eluting with DCM followed by 97:3 DCM:$NH_3$ (7M in MeOH), affords the title compound (30.2 mg, 36%).

Conversion into the mesylate salt as described in for Compound 178, step 4, using 1M methanesulfonic acid (0.068 mL), affords the title compound as a yellow solid (31.6 mg, 86%). LCMS: Rt 1.84 min (90.3%); m/z (APCI) 446 $(M+H)^+$; $^1$H-NMR (400 MHz, $d_6$-DMSO) δ (ppm) 1.35 (6H, d), 2.34 (3H, s, MsOH), 2.97-3.03 (2H, t), 3.22-3.36 (2H, m), 3.55-3.63 (3H, m), 3.86 (2H, d) 7.06 (2H, d), 7.60 (1H, br s), 7.67 (2H, s), 7.79 (1H, s), 7.98 (3H, br d), 8.17 (1H, s), 8.51 (1H, s), 9.28 (1H, br s), 9.60 (1H, s).

Compound 205: 5-{8-[4-(4-Isopropyl-piperazin-1-yl)-phenylamino]-imidazo[1,2-a]pyrazin-5-yl}-2,3-dihydro-isoindol-1-one Step 1: 1-Isopropyl-4-(4-nitro-phenyl)-piperazine

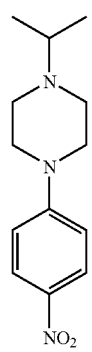

To a solution of 4-fluoronitrobenzene (5 g, 35.4 mmol) in THF (50 mL), 1-isopropylpiperazine (4.54 g, 35.4 mmol) and $K_2CO_3$ (7.35 g, 53.2 mmol) are added. The reaction mixture is stirred at room temperature overnight. The solvent is removed in vacuo and the residue is partitioned between EtOAc and water. The organic layer is washed with brine, dried over $MgSO_4$, filtered and concentrated. The crude compound is purified by silica gel column chromatography using 99:1 and 98:2 DCM:$NH_3$ (7M in MeOH) to give the title compound (8.2 g, 94%).

Step 2: 4-(4-Isopropyl-piperazin-1-yl)-phenylamine

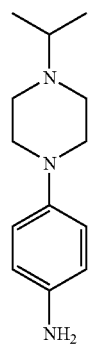

1-Isopropyl-4-(4-nitro-phenyl)-piperazine (8.3 g, 33.2 mmol) is dissolved in MeOH (120 mL) and tin (II) dichloride dihydrate (37.4 g, 0.165 mol) is added. The mixture is cooled using a water bath and conc. HCl is added (36 mL). The reaction is stirred at room temperature overnight. After removing the methanol, the resultant solution is basified using conc. NaOH (pH 11). The water phase is extracted with diethyl ether (3×) and the organic layers combined, dried over $MgSO_4$, filtered, concentrated in vacuo to afford the title compound (6.4 g, 88%).

Step 3: (5-Bromo-imidazo[1,2-a]pyrazin-8-yl)-[4-(4-isopropyl-piperazin-1-yl)-phenyl]-amine

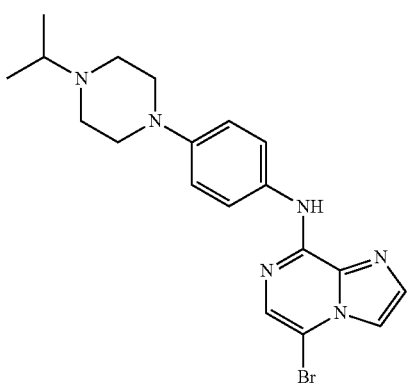

A solution of 5,8-dibromo-imidazo[1,2-a]pyrazine (0.134 g, 0.48 mmol), 4-(4-isopropyl-piperazin-1-yl)-phenylamine (0.118 g, 0.54 mmol) and diisopropylethylamine (0.093 mL, 0.54 mmol) is stirred at 90° C. for 18 hours. The reaction mixture is concentrated in vacuo and partitioned between DCM and sat. $NaHCO_3$. The organic layer is washed with brine, dried over $MgSO_4$, filtered and concentrated. The residue is purified by silica gel column chromatography eluting with 98:2 DCM:MeOH to afford the title compound (0.086 g,. 43%).

Step 4: 5-{8-[4-(4-Isopropyl-piperazin-1-yl)-phenylamino]-imidazo[1,2-a]pyrazin-5-yl}-2,3-dihydro-isoindol-1-one

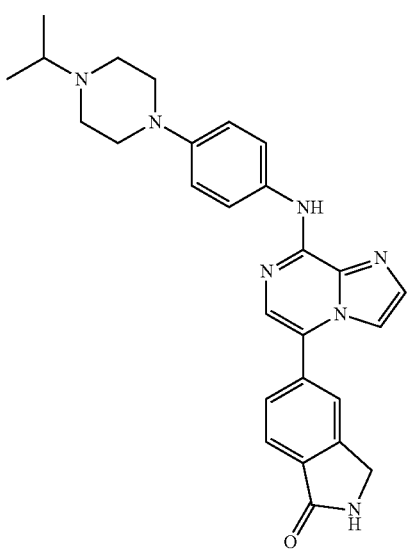

In the same way as described for Compound 178, step 4, using, (5-bromo-imidazo[1,2-a]pyrazin-8-yl)-[4-(4-isopropyl-piperazin-1-yl)-phenyl]-amine (0.08 g, 0.19 mmol), 5-(4,4,5,5-tetramethyl-[1,3,2]dioxaborolan-2-yl)-2,3-dihydro-isoindol-1-one (0.075 g, 0.29 mmol), 1.5M Na₂CO₃ (1.03 mL), and Pd(PPh₃)₄ (0.055 g, 0.047 mmol) in dioxane. The reaction mixture is purified by silica gel column chromatography eluting with DCM followed by 96:4 DCM:NH₃ (7M in MeOH). The residue is triturated using diethyl ether to afford the title compound (49.2 mg, 55%). Conversion into the mesylate salt, as described in step 4, Example 178, using 1M methanesulfonic acid (0.1 mL), gives the title compound (40.8 mg, 69%). LCMS: Rt 1.93 min (94.2%); m/z (APCI) 468 (M+H)$^+$; $^1$H-NMR (400 MHz, d₆-DMSO) δ (ppm) 1.34 (6H, d), 2.34 (3H, s, MsOH), 3.04 (2H, t), 3.22 (2H, m), 3.57-3.63 (3H, m), 3.91 (2H, d), 4.52 (2H, s), 7.13 (2H, d), 7.49 (1H, s), 7.81-7.94 (6H, m), 8.11 (1H, s), 8.76 (1H, br s), 9.32 (1H, br s).

Compound 206: 5-{8-[4-(1-Isopropylpiperidin-4-yl)phenylamino]-imidazo[1,2-a]pyrazin-5-yl}-2,3-dihydroisoindol-1-one

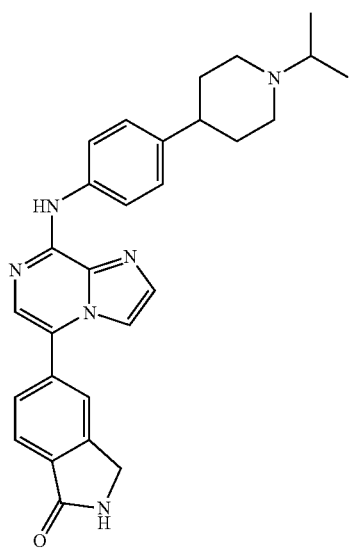

This compound may be prepared using the same methods as described for compound 202, using 5-(4,4,5,5-tetramethyl-[1,3,2]dioxaborolan-2-yl)-2,3-dihydroisoindol-1-one in Step 4.

LCMS: Rt 0.86 min (100%) m/z (ESI) 467 (M+H)$^+$.

Compound 208: N-(5-Morpholinopyridin-2-yl)-5-(1H-pyrazol-4-yl)imidazo[1,2-a]pyrazin-8-amine Step 1: 4-(6-Nitro-pyridin-3-yl)-morpholine

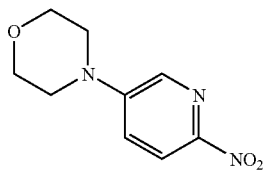

A mixture of 5-bromo-2-nitro-pyridine (5 g, 24.75 mmol), tetrabutyl ammonium iodide (0.46 g, 1.24 mmol), K₂CO₃ (3.76 g, 27.22 mmol) and morpholine (2.34 g, 27.22 mmol) in DMSO (50 mL) is stirred at 80° C. in a stem tube for 20 hours. The reaction mixture is diluted with ethyl acetate and filtered. The organic solution is washed with water, dried over MgSO₄ and concentrated in vacuo. The residue is triturated with dichloromethane and hexane to afford the title compound as a solid (2.39 g, 46%).

Step 2: 5-Morpholin-4-yl-pyridin-2-ylamine

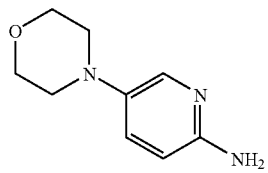

In the same way as described in for Compound 154, step 2 using 4-(6-nitro-pyridin-3-yl)-morpholine (2.39 g, 11.43 mmol), tin(II) chloride dihydrate (12.9 g, 57.17 mmol) in MeOH (40 mL) and conc. HCl (12.4 mL). The reaction mixture is concentrated in vacuo cooled to 0° C. and dissolved in water. The aqueous solution is basified using conc. NaOH and extracted with ethyl acetate (3×). The organic layers are combined, dried over MgSO₄, filtered and concentrated to afford the title compound (1.77 g, 87%) which is used in the next step without further purification.

Step 3: (5-Bromo-imidazo[1,2-a]pyrazin-8-yl)-(5-morpholin-4-yl-pyridin-2-yl)-amine

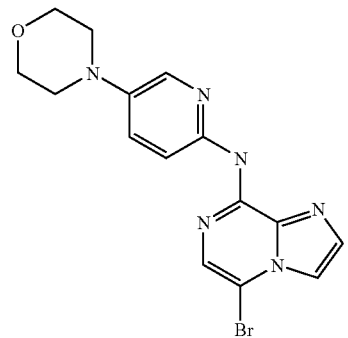

In the same way as described for compound 90, step 1, using 5,8-dibromo-imidazo[1,2-a]pyrazine (0.4 g, 1.45 mmol), 5-morpholin-4-yl-pyridin-2-ylamine (0.258 g, 1.23 mmol), NaO$^t$Bu (0.19 g, 2.04 mmol), Pd₂dba₃ (0.053 g, 0.058 mmol) and Xantphos (0.067 g, 0.116 mmol) in toluene (6 mL). After removing the solvent in vacuo, the mixture is purified by silica gel column chromatography eluting with 1:4 petroleum ether:ethyl acetate followed by 99:1 DCM:NH₃ (7M in MeOH). The title compound is isolated (216.4 mg, 47%). LCMS: Rt 2.16 min (93.2%).

Step 4: N-(5-Morpholinopyridin-2-yl)-5-(1H-pyrazol-4-yl)imidazo[1,2-a]pyrazin-8-amine

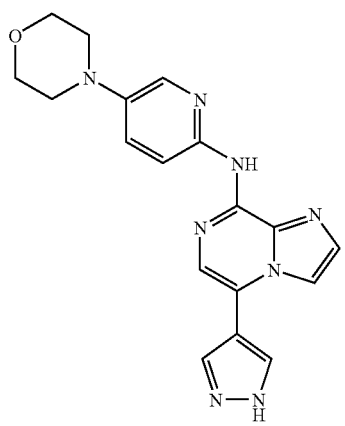

In the same way as described for compound 127, step 4 using (5-bromo-imidazo[1,2-a]pyrazin-8-yl)-(5-morpholin-4-yl-pyridin-2-yl)-amine (100 mg, 0.266 mmol), 4-(4,4,5,5-tetramethyl-[1,3,2]dioxaborolan-2-yl)-1H-pyrazole (77.6 mg, 0.4 mmol), Pd(PPh$_3$)$_4$ (77 mg, 0.066 mmol) and 1.5M Na$_2$CO$_3$ (1.42 mL, 2.13 mmol) in dioxane (4 mL). The crude compound is purified by silica gel column chromatography eluting with 96:4 DCM:NH$_3$ (7M in MeOH) to afford the title compound which is triturated with diethyl ether (12.9 mg, 8%) and converted into the mesylate salt (6.1 mg, 38%) LCMS: Rt 1.95 min (96%), m/z (APCI) 363 (M+H)$^+$, $^1$H-NMR (400 MHz, d$_6$-DMSO) δ (ppm) 2.34 (3H, s, MsOH), 3.20 (4H, m), 3.83 (4H, m), 7.38 (1H, br s), 7.64 (1H, br s), 7.71 (1H, s), 7.86 (1H, d), 7.98 (1H, d), 8.04 (2H, m), 8.35 (2H, br s), 8.43 (1H, s).

Compound 209: 4-{8-[6-(4-Isopropyl-piperazin-1-yl)-pyridin-3-ylamino]-imidazo[1,2-a]pyrazin-5-yl}-furan-2-carboxylic acid amide Step 1: 4-Bromo-furan-2-carboxylic acid amide

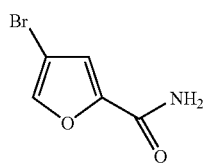

To a solution of 4,5-dibromo-furan-2-carboxylic acid (7.79 g, 28.85 mmol) in NH$_4$OH (100 ml) is added zinc dust (2.29 g, 34.62 mmol) in small portions. The reaction mixture is stirred at room temperature for 7 minutes then filtered over celite and washed with water and 2M HCl. The filtrate is acidified to pH 1 using collc. HCl and extracted with ethyl acetate (3×). The organic phase is washed with brine, dried over MgSO$_4$, filtrated and concentrated in vacuo to give an oil (4.96 g) which solidifies on standing to give a white solid, used in the amide formation step, without further purification.

The solid (4.93 g, 25.81 mmol) is dissolved in thionyl chloride (44.2 mL) and refluxed for 1 hour. After removing the solvent in vacuo the residue is dissolved in dichloromethane (75 mL) and a solution of 0.5 M NH3 in dioxane (52 mL) is added. The reaction mixture is stirred at room temperature for 1 hour, then 33% aq. NH$_3$ (5 mL) is added and the reaction stirred for additional 2 hours. The solvent is removed in vacuo and the residue taken-up with a solution of sat. NaHCO$_3$. The basic solution is extracted using ethyl acetate (3×), the combined organic layers are dried over MgSO$_4$ and concentrated in vacuo. Purification by silica gel column chromatography eluting with a mixture of (50:49:1) ethyl acetate:petroleum ether:acetic acid, affords the title compound (1.2 g, 22%).

Step 2: 4-(4,4,5,5-Tetramethyl-[1,3,2]dioxaborolan-2-yl)-furan-2-carboxylic acid amide

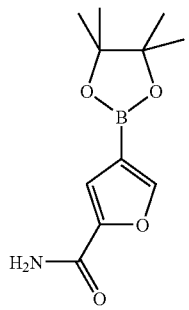

4-Bromo-furan-2-carboxylic acid amide (1.2 g, 6.32 mmol), bis(pinacolato)diboron (1.76 g, 6.94 mmol), PdCl$_2$dppf (0.154 g, 189 mol) and KOAc (1.85 g, 18.94 mmol) are suspended in dioxane (20 mL), purged with nitrogen for 5 minutes and then heated at 90° C. overnight. The solvent is removed in vacuo and the residue partitioned between ethyl acetate and water. The aqueous layer is extracted three times with ethyl acetate and the combined organic phases are washed with brine, filtered through MgSO$_4$ and evaporated. The solid residue is triturated with hexane and dried in vacuo to afford the title compound as a solid (0.984 g, 66%).

Step 3: 4-{8-[6-(4-Isopropyl-piperazin-1-yl-pyridin-3-ylamino]-imidazo[1,2-a]pyrazin-5-yl}-furan-2-carboxylic acid amide

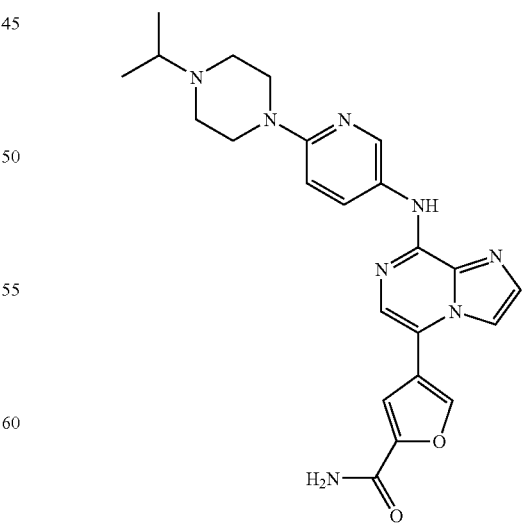

In the same way as described for Compound 178, step 4, using (5-bromo-imidazo[1,2-a]pyrazin-8-yl)-[6-(4-isopropyl-piperazin-1-yl)-pyridin-3-yl]-amine (0.05 g, 0.12 mmol), 4-(4,4,5,5-tetramethyl-[1,3,2]dioxaborolan-2-yl)-furan-2-carboxylic acid amide (0.050 g, 0.22 mmol), 1.5M Na$_2$CO$_3$ (0.64 mL, 0.96 mmol) and Pd(PPh$_3$)$_4$ (0.042 g, 0.36 mmol) in dioxane (2 mL). Purification using silica gel column chromatography, eluting with DCM followed by 99:1 and 97:3 DCM:NH$_3$ (7M in MeOH), affords the title compound (38 mg, 70%).

Conversion into the mesylate salt as described for Compound 178, step 4, affords the title compound as a yellow solid (28 mg, 52%). LCMS: Rt 2.58 min (95%); m/z (ES$^+$) 447 (M+H)$^+$; $^1$H-NMR (400 MHz, d$_6$-DMSO) δ (ppm) 1.34 (6H, d), 2.36 (6H, s, 2×MsOH), 3.06-3.20 (4H, m), 3.52-3.59 (3H, m), 4.42-4.46 (2H, d), 7.12 (1H, d), 7.63 (1H, br s), 7.68 (2H, d), 7.84 (1H, s), 8.01 (1H, br sH), 8.21 (1H, s), 8.27 (1H, m), 8.53 (1H, s), 8.82 (1H, br s), 9.37 (1H, br s), 9.94 (1H, br s).

Compound 210: 5-{8-[6-(4-Isopropyl-piperazin-1-yl)-pyridin-3-ylamino]-imidazo[1,2-a]pyrazin-5-yl}-2,3-dihydro-isoindol-1-one Step 1: 1-Isopropyl-4-(5-nitro-pyridin-2-yl)-piperazine

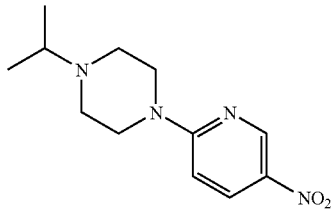

To a solution of 2-chloro-5-nitropyridine (2.5 g, 15.7 mmol) in THF (25 mL), are added 1-isopropylpiperazine (2.01 g, 15.7 mmol) and K$_2$CO$_3$ (3.25 g, 23.6 mmol). The reaction mixture is stirred 50° C. for 4 hours and then at 70° C. overnight. The solvent is removed in vacuo and the resultant orange solid is triturated using 10:1 petroleum ether-diethyl ether. The isolated compound (3.7 g, 94%) is used in the next step without further purification.

Step 2: 6-(4-Isopropyl-piperazin-1-yl)-pyridin-3-yl-amine

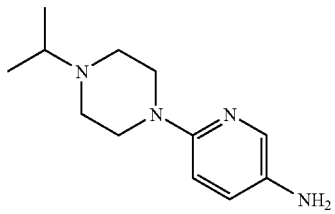

1-Isopropyl-4-(5-nitro-pyridin-2-yl)-piperazine (0.9 g, 3.6 mmol) is dissolved in MeOH (20 mL) and tin (II) dichloride dihydrate (4 g, 18 mmol) is added. The mixture is cooled using a water bath and conc. HCl is added (4 mL). The reaction is stirred at room temperature overnight. After removing the methanol, the resultant light yellow solution is basified using conc. NaOH (pH 11) and a white precipitate is formed. The solid is collected by filtration and the water is extracted with diethyl ether (5×). The organic layers are combined, dried over MgSO$_4$, filtered, concentrated under vacuum to afford an orange oil which crystallizes on standing to afford an orange solid (0.68 g, 86%).

Step 3: (5-Bromo-imidazo[1,2-a]pyrazin-8-yl)-[6-(4-isopropyl-piperazin-1-yl)-pyridin-3-yl]-amine

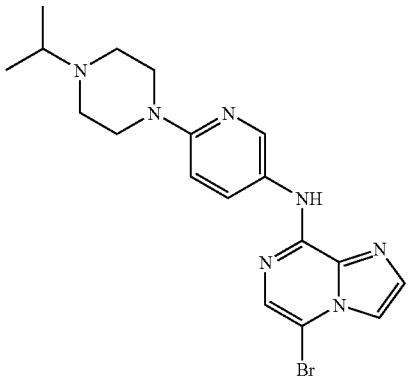

To a solution of 5,8-dibromo-imidazo[1,2-a]pyrazine (0.85 g, 3.1 mmol) in isopropanol are added 6-(4-isopropyl-piperazin-1-yl)-pyridin-3-yl-amine (0.68 g, 3.1 mmol) and diisopropylethylamine (0.6 mL, 4.6 mmol) and the mixture is stirred at 90° C. for 48 hours. The solvent is removed in vacuo and the product taken up in DCM-10% citric acid. The organic layer is discarded and the aqueous solution basified with sat. NaHCO$_3$ (pH 7-8) and extracted using DCM. The organic layer is dried over MgSO$_4$, filtered and concentrated in vacuo to afford the title compound as a purple solid (0.92 g, 71%). HPLC (254 nm): Rt 3.30 min (95.8%); m/z 416/418 (M+H)$^+$.

Step 4: 5-{8-[6-(4-Isopropyl-piperazin-1-yl)-pyridin-3-ylamino]-imidazo[1,2-a]pyrazin-5-yl}-2,3-dihydro-isoindol-1-one

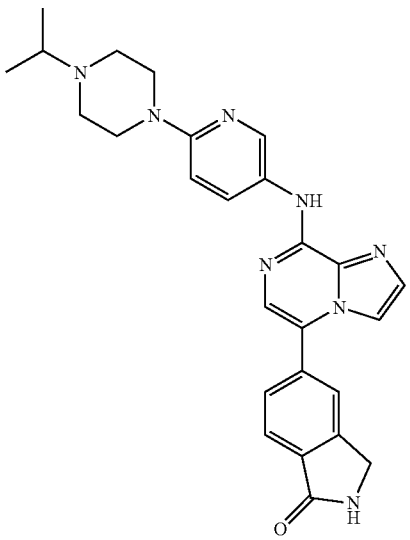

In the same way as described for Compound 178, step 4, using (5-bromo-imidazo[1,2-a]pyrazin-8-yl)-[6-(4-isopropyl-piperazin-1-yl)-pyridin-3-yl]-amine (0.05 g, 0.12 mmol), 5-(4,4,5,5-tetramethyl-[1,3,2]dioxaborolan-2-yl)-2,3-dihydro-isoindol-1-one (0.056 g, 0.22 mmol), 1.5M Na$_2$CO$_3$ (0.64 mL, 0.96 mmol) and Pd(PPh$_3$)$_4$ (0.042 g, 0.36 mmol) in dioxane (2 mL). Purification using silica gel column chromatography, eluting with DCM followed by 99:1 and 97:3

DCM:NH₃ (7M in MeOH), affords the title compound as a yellow solid (28 mg, 50%). Conversion into the mesylate salt, as described for Compound 178, step 4, affords the title compound as a yellow solid (32 mg, 95%). LCMS: Rt 2.70 min (92%); m/z (APCI) 469 (M+H)⁺; ¹H-NMR (400 MHz, d₆-DMSO) δ (ppm) 1.34 (6H, d), 2.34 (3H, s, MsOH), 3.10-3.21 (4H, m), 3.57-3.59 (3H, m), 4.43 (2H, d), 4.52 (2H, s), 7.08 (1H, d), 7.52 (1H, s), 7.77-7.94 (4H, m), 8.07 (1H, s), 8.30 (1H, d), 8.75 (1H, s), 8.83 (1H, br s), 9.34 (1H, br s), 9.88 (1H, br s).

Compound 212: 4-[8-(4-Morpholin-4-yl-phenylamino)-imidazol[1,2-a]pyrazin-5-yl]-2H-pyrazole-3-carbonitrile Step 1: 4-Bromo-2-(tetrahydro-pyran-2-yl)-2H-pyrazole-3-carbonitrile

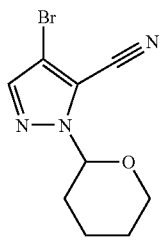

4-Bromo-1H-pyrazole-3-carbonitrile (150 mg, 0.87 mmol) is dissolved in 3,4-dihydro-2H-pyran (25 mL, 2.6 mmol) in the presence of a catalytic amount of TFA (1 mg, 0.009 mmol). The reaction mixture is stirred at 95° C. for 1 hour, cooled and then quenched using NaH (1.2 mg, 0.052 mmol). After removing the solvent, the residue is purified by silica gel column chromatography eluting with a mixture of 3:1 petroleum ether-dichloromethane, followed by 10:1 petroleum ether-ethyl acetate. The fractions containing the desired compounds are collected and concentrated in vacuo to afford the title compound as a colorless oil (90 mg, 40%).

Step 2: (4-Morpholin-4-yl-phenyl)-(5-tributylstannanyl-imidazo[1,2-a]pyrazin-8-yl)-carbamic acid tert-butyl ester

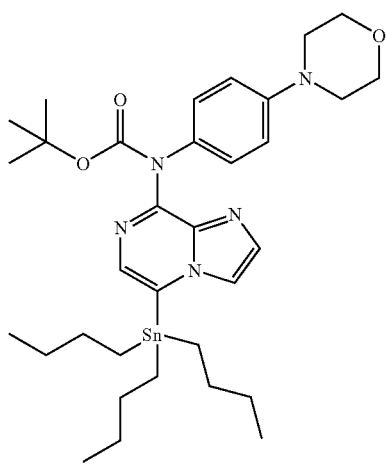

To a cooled (−78° C.) solution of (5-bromo-imidazo[1,2-a]pyrazin-8-yl)-(4-morpholin-4-yl-phenyl)-carbamic acid tert-butyl ester (2.55 g, 5.38 mmol) in tetrahydrofuran (20 mL) is added isopropylmagnesium chloride (0.829 g, 8.06 mmol). After stirring for 5 min tributyltin chloride (2.97 g, 9.14 mmol) is added and the reaction is stirred at −78 ° C. for 10 min before being allowed to warm to room temperature. After stirring at room temperature for 30 min, the mixture is concentrated. The residue is purified by silica gel flash column chromatography eluting with 5:1 petroleum ether-ethyl acetate followed by 1:1 petroleum ether-ethyl acetate to afford the product as yellow solid (2.35 g, 64%).

Step 3: 4-[8-(4-Morpholin-4-yl-phenylamino)-imidazo[1,2-a]pyrazin-5-yl]-2H-pyrazole-3-carbonitrile

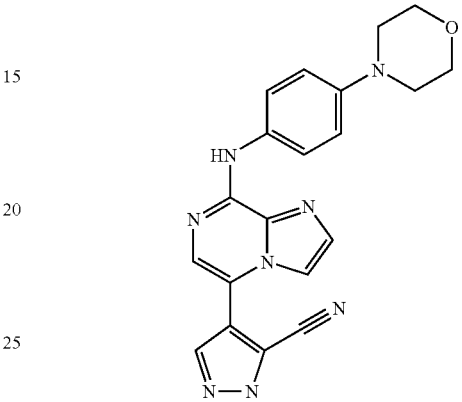

(4-Morpholin-4-yl-phenyl)-(5-tributylstannanyl-imidazo[1,2-a]pyrazin-8-yl)-carbamic acid tert-butyl ester (385 mg, 0.56 mmol), 4-bromo-2-(tetrahydro-pyran-2-yl)-2H-pyrazole-3-carbonitrile (90 mg, 0.35 mmol) and Pd(PPh₃)₄ (41 mg, 0.035 mmol) are suspended in DMF and, after purging with nitrogen, the reaction mixture is stirred at 90° C. overnight. The solvent is evaporated in vacuo and the resulting yellow oil (590 mg) is dissolved in a mixture 1:1 TFA-DCM (2 mL) (2 drops H₂O) and stirred at room temperature overnight. The mixture is diluted with DCM and washed with a solution of sat. NaHCO₃. The organic layer is dried over MgSO₄, filtered and concentrated to afford a yellow solid. Purification by silica gel column chromatography using DCM followed by 98:2 and 96:4 DCM:NH₃ (7M in MeOH) affords an oil, which is purified by reverse phase preparative HPLC to give the title compound (5 mg, 2%). LCMS: Rt 2.81 min (92%); m/z (ES⁺) 387 (M+H)⁺; ¹H-NMR (400 MHz, d₆-DMSO) δ (ppm) 3.10 (4H, m), 3.79 (4H, m), 6.98 (2H, d), 7.52 (1H, s), 7.73 (1H, s), 7.93 (3H, d), 7.99 (1H, s), 8.55 (1H, s), 9.58 (1H, s).

Compound 217: 2-[8-(4-Morpholin-4-yl-phenylamino)-imidazol[1,2-a]pyrazin5-yl]-5,6-dihydro-furo[2,3-c]pyrrol-4-one Step 1: 5-Bromo-2-bromomethyl-furan-3-carboxylic acid methyl ester

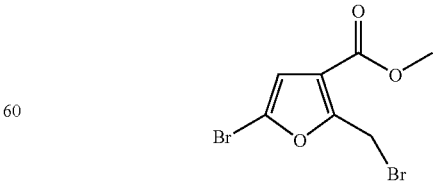

To a cooled solution (0° C.) of 2-methyl-furan-3-carboxylic acid methyl ester (3 g, 21.43 mmol) in DMF (60 mL) is added NBS (8.77 g, 49.28 mmol) in portions. The reaction mixture is stirred at 0° C. for 1 hour and at room temperature overnight. The reaction mixture is then diluted with water and extracted with diethyl ether (3×). The organic layers are combined and washed with brine and water, dried over MgSO$_4$, filtered and concentrated in vacuo. The crude compound is purified by silica gel column chromatography eluting with 95:5 petroleum ether:diethyl ether to afford the title compound (0.626 g, 10%).

Step 2: 5-Bromo-2-[(4-methoxy-benzylamino)-methyl]-furan-3-carboxylic acid methyl ester

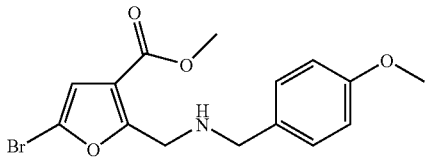

A solution of 5-bromo-2-bromomethyl-furan-3-carboxylic acid methyl ester (1.74, 5.88 mmol) and p-methoxy benzylamine (0.76 mL, 5.88 mmol) in MeOH (30 mL) is stirred at 85° C. for 1.5 hours. The reaction mixture is concentrated in vacuo and the residue purified by silica gel column chromatography eluting with 4:1 petroleum ether:ethyl acetate followed by 1:1 petroleum ether:ethylacetate. The title compound is isolated (643.8 mg).

Step 3: 5-Bromo-2-[(4-methoxy-benzylamino)-methyl]-furan-3-carboxylic acid

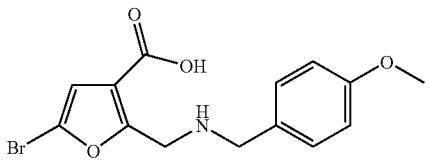

A solution of 5-bromo-2-[(4-methoxy-benzylamino)-methyl]-furan-3-carboxylic acid methyl ester (643.8 mg, 1.82 mmol) and LiOH (115 mg, 2.74 mmol) in 1:1 THF:H$_2$O (30 mL) is refluxed for 3 hours. The solvent is evaporated in vacuo to afford the title compound (620 mg, 99%) which is used in the next step without further purification.

Step 4: 2-Bromo-5-(4-methoxy-benzyl)-3a, 5,6, 6a-tetrahydro-furo[2, 3-c]pyrrol-4-one

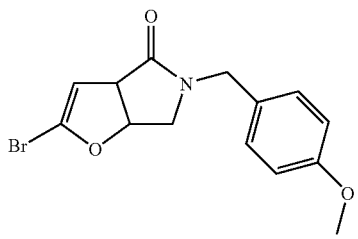

A solution of 5-bromo-2-[(4-methoxy-benzylamino)-methyl]-furan-3-carboxylic acid (618 mg, 1.82 mmol) and SOCl$_2$ (0.136 mL) in DCM (2 mL) is stirred at 85° C. for 18 hours. The mixture is concentrated in vacuo and purified by silica gel column chromatography eluting with 7:3 petroleum ether:ethyl acetate to afford the title compound (0.169 g, 28%).

Step 5: 2-Bromo-3a, 5,6,6a-tetrahydro-furo[2,3-c]pyrrol-4-one

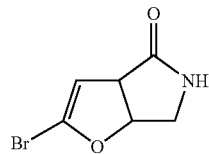

A solution of 2-bromo-5-(4-methoxy-benzyl)-3a,5,6,6a-tetrahydro-furo[2,3-c]pyrrol-4-one (0.16 g, 0.498 mmol) in TFA (1.8 mL) and anisole (0.2 mL) is stirred at 80° C. for 2.5 hours. The reaction mixture is then diluted with ethyl acetate and neutralised with sat. NaHCO$_3$. The aqueous layer is extracted with ethyl acetate (3×) and the combined organic layers are dried over MgSO$_4$, filtered and concentrated in vacuo. The crude compound is purified by silica gel column chromatography eluting with 1:1 petroleum ether:ethyl acetate followed by 1:4 petroleum ether:ethyl acetate, to afford the title compound (79 mg, 78%).

Step 6: 2-[8-(4-Morpholin-4-yl-phenylamino)-imidazo[1,2-a]pyrazin5-yl]-5,6-dihydro-furo[2,3-c]pyrrol-4one

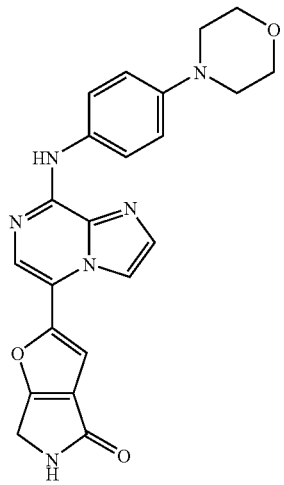

In the same way as described for Compound 212, step 3 using (4-morpholin-4-yl-phenyl)-(5-tributylstannanyl-imidazo[1,2-a]pyrazin-8-yl)-carbamic acid tert-butyl ester (255 mg, 0.373 mmol), 2-bromo-3a,5,6,6a-tetrahydro-furo[2,3-c]pyrrol-4-one (50 mg, 0.249 mmol) and Pd(PPh$_3$)$_4$ (29 mg, 0.0249 mmol) in DMF (3 mL). The reaction mixture is concentrated in vacuo and the residue dissolved in 1:1 DCM:TFA (drop of H$_2$O) and stirred at room temperature for 3 hours. The mixture is partitioned between ethyl acetate and sat. NaHCO$_3$ and the aqueous layer is extracted with ethyl acetate (3×). The organic layers are combined, dried over MgSO$_4$, filtered and concentrated in vacuo. The residue is purified by silica gel column chromatography eluting with DCM followed by a 97:3 mixture DCM:NH$_3$ (7M in MeOH). The fractions containing the desired compound are concentrated in vacuo to give a solid which is triturated with diethyl ether to afford the title compound (66.3 mg, 64%). Conversion of the compound into the mesylate salt using 1M MsOH (0.16 mL) affords the title product as a solid (69.3 mg, 87%). LCMS: Rt 2.52 min (99%), m/z (APCI) 417 (M+H)$^+$, 1H-NMR (400 MHz, d6-DMSO) δ (ppm). 2.36 (3H, s, MsOH), 3.25 (4H, m), 3.84 (4H, m), 4.52 (2H, s), 7.18 (2H, br s), 7.40 (1H, s), 7.83 (1H, s), 7.90 (3H, m), 8.21 (1H, br s), 8.44 (1H, s), 10.25 (1H, br s).

Compound 218: (3-Dimethylaminomethyl-4-morpholin-4-yl-phenyl)-[5-(1H-pyrazol-4-yl)-imidazol[1,2-a]pyrazin-8-yl]-amine Step 1: (2-Morpholin-4-yl-5-nitro-phenyl)-methanol

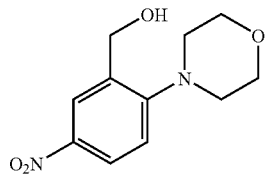

To a cooled (0° C.) solution of 2-morpholin-4-yl-5-nitro-benzaldehyde (0.8 g, 3.39 mmol) in MeOH (5 mL) is added NaBH4 (0.125 g, 3.39 mmol) and the reaction mixture is stirred at room temperature for 3 hours. After quenching the reaction with water, the solvent is removed in vacuo and the residue dissolved in ethyl acetate and washed with brine. The organic layer is dried over MgSO4, filtered and concentrated to afford the title compound (870 mg), which is used in the next step without further purification.

Step 2: (5-Amino-2-morpholin-4-yl-phenyl)-methanol

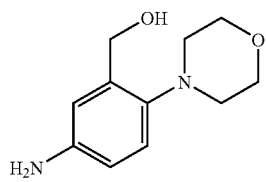

To a solution of (2-morpholin-4-yl-5-nitro-phenyl)-methanol (870 mg) in ethanol (40 mL), palladium hydroxide (87 mg) is added and the mixture is stirred in a Parr-apparatus under hydrogen pressure (10 bars) for 4 hours. The reaction mixture is filtrated over Celite 521, washed with ethanol and concentrated in vacuo to give the title compound (640 mg, 83%).

Step 3: 3-(tert-Butyl-dimethyl-silanyloxymethyl)-4-morpholin-4-yl-phenylamine

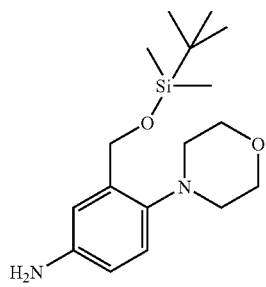

A solution of (5-amino-2-morpholin-4-yl-phenyl)-methanol (640 mg, 3.07 mmol), tert-butyldimethylsilyl chloride (509 mg, 3.38 mmol) and imidazole (250 mg, 3.68 mmol) in dimethylformamide (20 mL) is stirred at room temperature overnight. The solvent is removed in vacuo and the residue partitioned between water and ethyl acetate. The organic layer is washed with brine, dried over MgSO4, filtered and concentrated to afford a crude product. Purification, using silica gel column chromatography, eluting with DCM followed by a 95:5 mixture DCM:MeOH, affords the title compound as a pink solid (390 mg, 27%).

Step 4: (5-Bromo-imidazo[1,2-a]pyrazin-8-yl)-[3-(tert-butyl-dimethyl-silanyloxymethyl)-4-morpholin-4-yl-phenyl]-amine

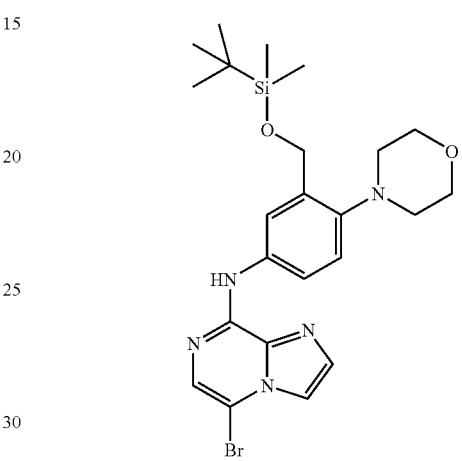

In the same way as described in the general procedure for amine displacement using 5,8-dibromo-imidazo[1,2-a]pyrazine (0.534 g, 1.94 mmol), 3-(tert-butyl-dimethyl-silanyloxymethyl)-4-morpholin-4-yl-phenylamine (0.751 g, 2.33 mmol), N,N-diisopropyethylamine (0.31 mL, 1.8 mmol) and iso-propanol (10 mL). Purification by silica gel column chromatography eluting with 7:3 petroleum ether:ethyl acetate followed by trituration with diethyl ether affords the title compound (0.216 g, 17%).

Step 5. (5-Bromo-imidazo[1,2-a]pyrazin-8-yl)-[3-(tert-butyl-dimethyl-silanyloxymethyl)-4-morpholin-4-yl-phenyl]-carbamic acid tert-butyl ester

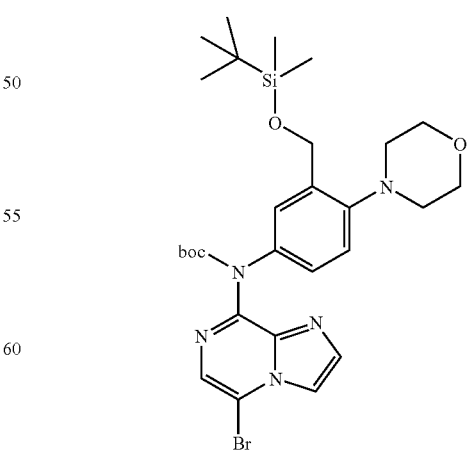

In the same way as described in the general procedure for Boc protection using (5-bromo-imidazo[1,2-a]pyrazin-8- yl)-[3-(tert-butyl-dimethyl-silanyloxymethyl)-4-morpholin-4-yl-phenyl]-amine (0.216 g, 0.41 mmol), di-tert-butyl-dicarbonate (0.266 g, 1.21 mmol) and N,N-dimethylaminopyridine (4 mg, 0.04 mmol) in DCM (5 mL). The title compound (0.164 g, 54%) is isolated after purification by silica gel column chromatography eluting with 4:1 petroleum ether:ethyl acetate followed by 7:3 petroleum ether:ethyl acetate.

Step 6: (5-Bromo-imidazo[1,2-a]pyrazin-8-yl)-(3-hydroxymethyl-4-morpholin-4-yl-phenyl)-carbamic acid tert-butyl ester

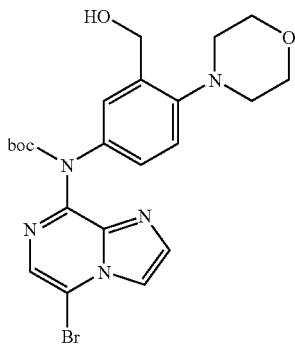

A solution of (5-bromo-imidazo[1,2-a]pyrazin-8-yl)-[3-(tert-butyl-dimethyl-silanyloxymethyl)-4-morpholin-4-yl-phenyl]-carbamic acid tert-butyl ester (0.164 g, 0.265 mmol) in 1M tetrabutylammonium fluoride in THF (0.29 mL, 0.29 mmol) is stirred at room temperature overnight. The solvent is removed under vacuum and the residue is purified by silica gel column chromatography eluting with ethyl acetate. The title compound is isolated (0.126 g, 94%).

Step 7: Methanesulfonic acid 5-[(5-bromo-imidazo[1,2-a]pyrazin-8-yl)-tert-butoxycarbonyl-amino]-2-morpholin-4-yl-benzyl ester

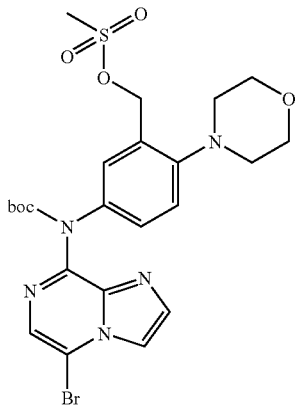

To a cooled solution (0° C.) of (5-bromo-imidazo[1,2-a]pyrazin-8-yl)-(3-hydroxymethyl-4-morpholin-4-yl-phenyl)-carbamic acid tert-butyl ester (0.17 g, 0.34 mmol) in DCM (0.5 mL), is added triethylamine (0.104 mL, 0.74 mmol) followed by methanesulfonyl chloride (0.046 mL, 0.6 mmol). The reaction mixture is stirred at 0° C. for 1 hour and an additional hour at room temperature. The reaction mixture is diluted with ethyl acetate and washed with water. The organic layer is dried over MgSO$_4$, filtered and concentrated in vacuo to give the title compound (0.224 g) used in the next step without further purification.

Step 8: (5-Bromo-imidazo[1,2-a]pyrazin-8-yl)-(3-dimethylaminomethyl-4-morpholin-4-yl-phenyl)-carbamic acid tert-butyl ester

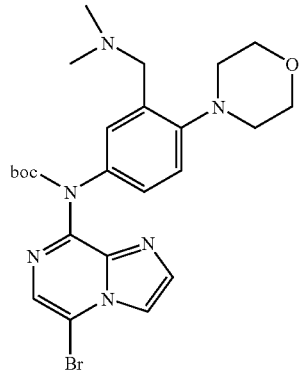

To a solution of methanesulfonic acid 5-[(5-bromo-imidazo[1,2-a]pyrazin-8-yl)-tert-butoxycarbonyl-amino]-2-morpholin-4-yl-benzyl ester (0.098 g, 0.169 mmol) in THF (0.5 mL) is added 2M N,N-dimethylamine solution in THF (0.50 mL, 1.1 mmol) followed by K$_2$CO$_3$ (0.028 g, 0.202 mmol). The reaction mixture is stirred at room temperature for 1.5 hours and at 75° C. for an additional 3 hours. The solvent is removed under vacuum and the residue is partitioned between ethyl acetate and water. The organic layer is dried over MgSO$_4$, filtered and concentrated in vacuo to give the crude compound which is purified by silica gel column chromatography. Elution using 97:3 DCM:NH$_3$ (7M in MeOH) affords the title compound (0.0543 g, 61%). LCMS: Rt 2.37 min (95%), m/z (ES$^+$) 531/533 (M+H)$^+$.

Step 9: (3-Dimethylaminomethyl-4-morpholin-4-yl-phenyl)-[5-(1H-pyrazol-4-yl)-imidazo[1,2-a]pyrazin-8-yl]-amine

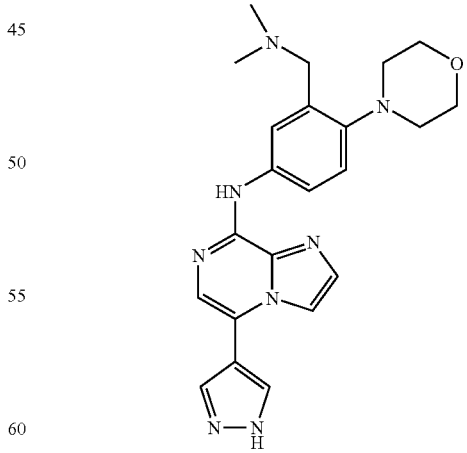

In the same way as described for Compound 85, step 1, using (5-bromo-imidazo[1,2-a]pyrazin-8-yl)-(3-dimethylaminomethyl-4-morpholin-4-yl-phenyl)-carbamic acid tert-butyl ester (54 mg, 0.1024 mmol), 4-(4,4,5,5-tetramethyl-[1,3,2]dioxaborolan-2-yl)-1H-pyrazole (29.8 mg, 0.153 mmol), Pd(PPh₃)₄ (12 mg, 0.0102 mmol) and NaO^tBu (39 mg, 0.41 mmol) in 3:1 DMF/water (4 mL). The reaction mixture is concentrated under reduced pressure and the residue is dissolved in a mixture 1:1 DCM:TFA (drop of water). After stirring the solution at room temperature for 4 hours, ethyl acetate is added and the mixture is basified using sat. NaHCO₃. The organic layer is separated, dried over MgSO₄, filtered and concentrated in vacuo to afford a crude compound. Purification by silica gel column chromatography eluting with DCM followed by 95:5 DCM:NH₃ (7M in MeOH), affords the title compound (28.1 mg, 66%). Conversion into the mesylate salt using 0.1M MsOH (0.67 mL) yields the title compound (26.9 mg, 78%). LCMS: Rt 1.97 min (97%), m/z (APCI) 419 (M+H)⁺, ¹H-NMR (400 MHz, d₆-DMSO) δ (ppm) 2.35 (3H, s, MsOH), 2.74-2.89 (10H, m), 3.82 (4H, m), 4.39 (2H, d), 7.42 (1H, d), 7.61 (1H, s), 7.81 (1H, s), 8.08 (1H, d), 8.14-8.26 (4H, m), 9.19 (1H, br s), 9.75 (1H, br s).

Compound 220: 7-Fluoro-5-{8-[4-(4-isopropyl-piperazin-1-yl)phenylamino]imidazo[1,2-a]pyrazin-5-yl}-2,3-dihydroisoindol-1-one Step 1: 4-Bromo-2,6-difluorobenzoic acid methyl ester

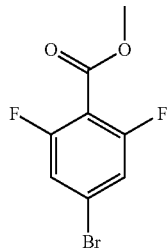

To a suspension of 4-Bromo-2,6-difluoro-benzoic acid (5 g, 21 mmol) in DCM (10 mL) is added thionyl chloride (15 mL) and DMF (0.5 mL). The mixture is stirred at room temperature for 2.5 h. It is then cooled to 0° C. and MeOH (20 mL) is added carefully causing vigorous HCl evolution. After stirring for an additional 0.5 h, the clear solution is partitioned between DCM (50 mL) and water (50 mL). The organic layer is washed with saturated NaHCO₃, brine, dried over MgSO₄ and the solvent is removed under vacuum to afford the title compound as a pale yellow oil which is used without further purification.

Step 2: 4-Bromo-2-fluoro-6-(nitromethyl)benzoic acid methyl ester

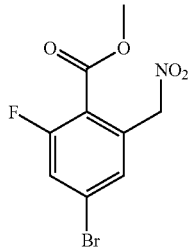

Nitromethane (10 mL, 169 mmol, 8 equiv.) is added cautiously to a suspension of sodium hydride (4.05 g, 169 mmol, 8 equiv.) and MgSO₄ (40 g) in DMSO (100 mL) at rt and the resulting slurry is stirred for 0.25 h. To the resulting yellow slurry is added 4-bromo-2,6-difluorobenzoic acid methyl ester (5.3 g, 21 mmol) and the mixture is stirred at rt for 3 days at which point all the starting material has been consumed. Water (200 mL) and 6M HCl (50 mL) is added followed by DCM (200 mL). More water (500 mL) is added to yield a clear biphasic system. The aqueous layer is extracted with DCM (3×100 mL), the DCM layers are then combined, washed with saturated NaHCO₃ and brine, and dried over MgSO₄. Evaporation of the solvent affords an orange solid containing 64% of the desired material, used without further purification. LCMS; Rt=1.27 min (64%).

Step 3: 5-Bromo-7-fluoro-2,3-dihydro-isoindol-1-one

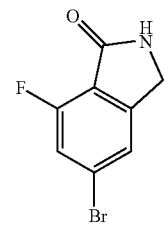

Crude 4-bromo-2-fluoro-6-(nitromethyl)benzoic acid methyl ester from the previous step is dissolved in MeOH (100 mL). To this clear orange solution is added Zinc dust (3.35 g, 51.3 mmol, 3 equiv.) followed by ammonium formate (3.23 g, 51.3 mmol, 3 equiv.) which results in an exothermic reaction. After 0.3 h, 7M NH₃ in MeOH (50 mL) is added and the mixture is stirred overnight at room temperature. The resulting mixture is filtered through celite, and the yellow filtrate is adsorbed on silica and roughly cleaned by LC using 94/6 DCM/ MeOH 7M NH₃. Removal of the solvent affords a tan solid that is redissolved in DCM, washed with 10% NaOH, and concentrated under reduced pressure to leave a white solid, which is triturated further with small amounts of DCM to afford the title compound. LCMS: Rt 0.96 min (100%) m/z 230/232 (M+H)⁺.

Step 4: 7-Fluoro-5-(4,4,5,5-tetramethyl-[1,3,2]dioxaborolan-2-yl)-2,3-dihydroisoindol-1one

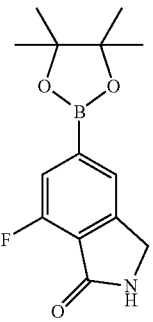

A solution of 5-bromo-7-fluoro-2,3-dihydroisoindol-1-one (531 mg, 2.31 mmol) in dioxane (5 mL) is stirred under nitrogen. Pd(dppf)Cl₂ (94 mg, 5 mol %), potassium acetate (453 mg, 4.62 mmol, 2.0 equiv.) and bispinacolatodiboron (1.17 g, 4.62 mmol, 2 equiv.) are added, and the reaction is heated at 80° C. for 3 h. The resulting orange suspension is diluted with DCM, filtered through celite and concentrated under vacuum to afford an oil that is redissolved in a minimum of DCM. Diethyl ether is slowly added to afford the title compound as a tan solid. LCMS: Rt 1.18 min (100%) m/z 277/279 (M+H)⁺.

Step 5: 7-Fluoro-5-{8-[4-(4-isopropyl-piperazin-1-yl)phenylamino]imidazo[1,2-a]pyrazin-5-yl}-2,3-dihydroisoindol-1-one

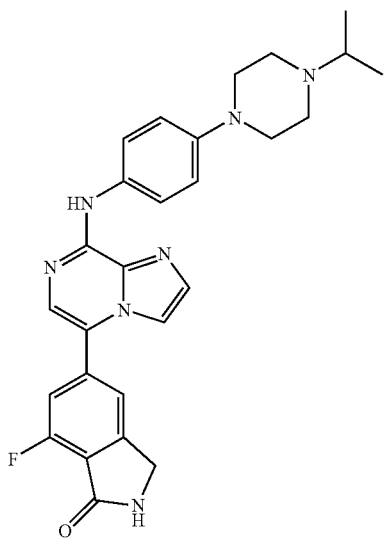

This compound may be prepared using the methods as described for Compound 184, step 4, using (5-bromo-imidazo[1,2-a]pyrazin-8-yl)-[4-(4-isopropylpiperazin-1-yl)phenyl]amine and the above boronate. LCMS: Rt=0.82 min (95%), m/z 486 (M+H)⁺.

Compound 224: 2-(4-{4-[5-(1H-Pyrazol-4-yl)imidazo[1,2-a]pyrazin-8-ylamino]phenyl}piperidin-1-yl)acetamide

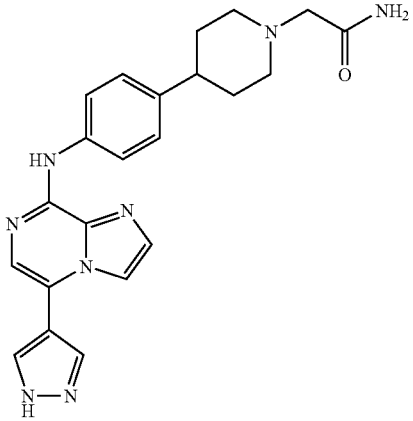

This compound may be prepared using the methods described for Compound 202, using 2-bromoacetamide in Step 1. LCMS: Rt=0.73 min (100%), m/z (ESI) 417 (M+H)⁺.

Compound 225: 2-(4-{4-[5-(3-Methyl-1H-pyrazol-4-yl)imidazo[1,2-a]pyrazin-8-ylamino]phenyl}piperidin-1-yl)acetamide

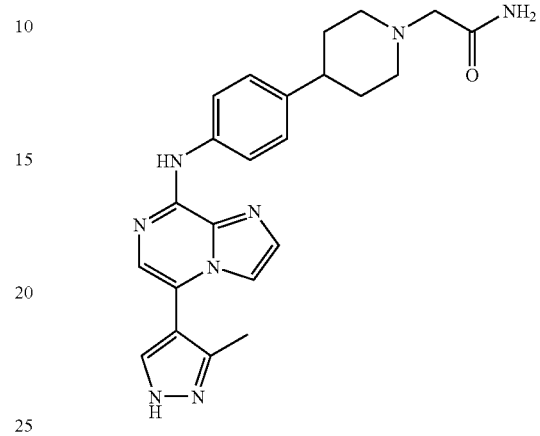

This compound may be prepared using the methods as described for Compound 224, using 3-methyl-4-(4,4,5,5-tetramethyl-[1,3,2]dioxaborolan-2-yl)-1H-pyrazole in Step 4. LCMS: Rt=0.75 min (100%), m/z (ESI) 431 (M+H)⁺.

Compound 226: 2-(4-{4-[5-(1-Oxo-2,3-dihydro-1H-isoindol-5-yl)-imidazo[1,2-a]pyrazin-8-ylamino]-phenyl}piperidin-1-yl)acetamide

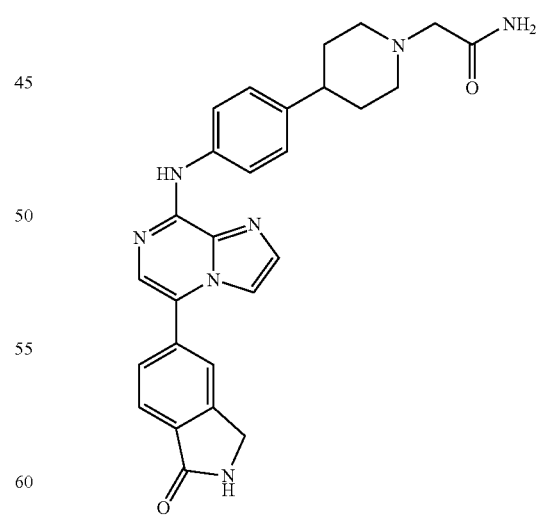

This compound may be prepared using the methods as described for Compound 224, using 5-(4,4,5,5-tetramethyl-[1,3,2]dioxaborolan-2-yl)-2,3-dihydroisoindol-1-one in Step 4. LCMS: Rt=0.79 min (100%), m/z (ESI) 483 (M+H)⁺.

Compound 229: 5-{8-[4-(4-Isopropylpiperazin-1-yl)-3-trifluoromethylphenylamino]imidazo[1,2-a]pyrazin-5-yl}-2,3-dihydroisoindol-1-one

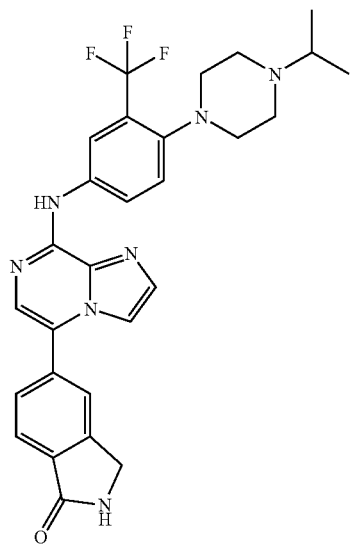

This compound may be prepared using the methods as described for Compound 206, using 4-(4-isopropylpiperazin-1-yl)-3-(trifluoromethyl)phenylamine in Step 3. LCMS: Rt=0.98 min (95%), m/z 536 (M+H)+.

Purifications Conditions and Characterization

Routinely, post-synthesis all compounds may be purified using reverse phase HPLC using a Gilson preparative HPLC system (322 pump, 155 UV/VIS detector, 215 liquid handler). The Gilson 215 acts as both auto-sampler and fraction collector. Compounds can also be purified by flash chromatography on silica gel.

Compounds are characterised by mass spectrometry using single quadrupole instrumentation with an electrospray source.

Biological Assays Demonstrating the Usefulness of the Compounds

EXAMPLE 1

MAPKAP-K5 Assay

MAPKAP-K5 reactions are performed in FlashPlate format using 0.1 or 0.2 μCi 33P-ATP; 0.6 μM ATP; 1mU MAPKAP-K5; 3 μM MAPKAP-K5 peptide substrate, incubated at room temperature for 30 minutes.

Flashplate Assay:

The MAPKAP-K5 kinase reaction is performed in a 384 well polypropylene plate (Matrix Technologies) and then transferred to a streptavidin-coated 384 well flashplate (Perkin-Elmer).

To wells containing 2 μL test compound or standard inhibitor, 13 μL Enzyme mix or diluent are added using a Hydra (Robbins Scientific).

Reactions are started by addition of 10 μL of [2.5×]substrate cocktail using a Multidrop (Thermo-Labsystems), to give final concentrations in the assay of:

1 mU MAPKAP-K5

3 μM MAPKAP-K5 peptide substrate

~0.6 μM ATP 0.004 μCi [33P]-γ-ATP/μL

1× reaction buffer

Plates are incubated at room temperature for 30 minutes.

Reactions are terminated by the addition of 25 μL EDTA (50 mM) to each well using a Micro-fill (Biotek).

Reactions are transferred to a streptavidin-coated flashplate using a Zymark robotic system. Plates are incubated for 60 minutes at room temperature.

All wells are washed 3 times with 100 μL phosphate buffered saline using a Tecan plate washer.

Radioactivity is determined by scintillation counting of the flashplate (empty wells) on a Packard TopCount.

Enzyme Mix:
  Enzyme
  50 mM Tris HCl (pH 7.5)
  0.1 mM EGTA
  2 mM DTT
  1 mg/ml BSA Reaction Buffer:
  50 mM Tris HCl (pH 7.5)
  0.1 mM EGTA
  10 mM Magnesium acetate
  2 mM DTT Exemplary Compounds of the Invention The following compounds have been or can be prepared according to the synthetic methods described above. For the purpose of Table 1 below, activity of each compound, which can be determined using the MAPKAPK5 assay method described in Example 1, is expressed as follows:

TABLE 1

Structure and activity of of Exemplary Compounds

| Compound ID | STRUCTURE | MW | MAPKAPK5 IC$_{50}$ (nM) |
|---|---|---|---|
| 1 | 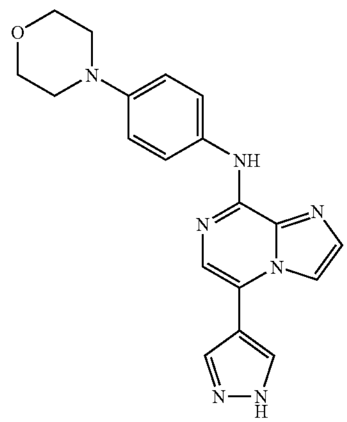 | 361.41 | ++ |
| 2 | 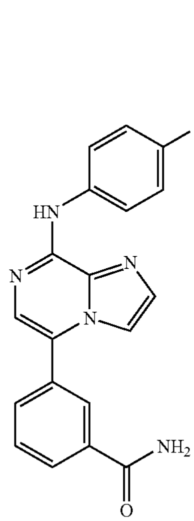 | 416.49 | + |
| 3 | 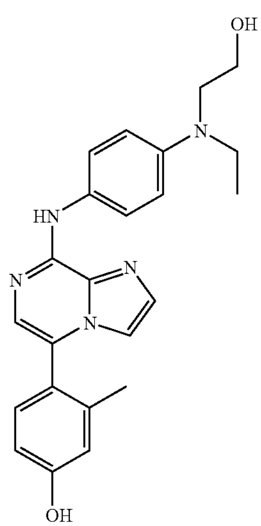 | 403.49 | + |

TABLE 1-continued

Structure and activity of of Exemplary Compounds

| Compound ID | STRUCTURE | MW | MAPKAPK5 IC$_{50}$ (nM) |
|---|---|---|---|
| 4 | 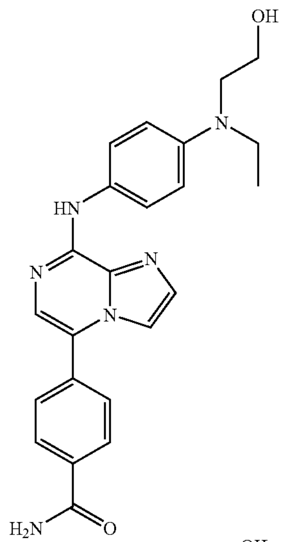 | 416.49 | + |
| 5 | 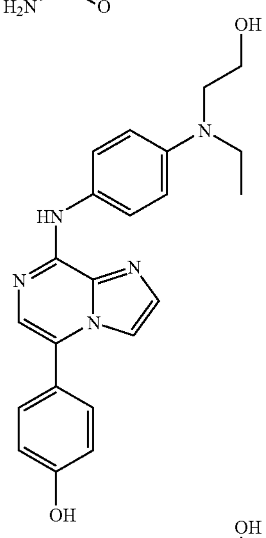 | 389.46 | + |
| 6 | 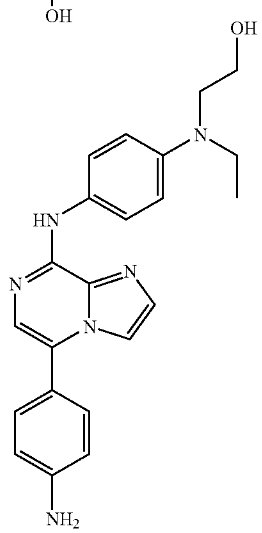 | 388.48 | + |

TABLE 1-continued
Structure and activity of of Exemplary Compounds
| Compound ID | STRUCTURE | MW | MAPKAPK5 IC$_{50}$ (nM) |
|---|---|---|---|
| 7 | 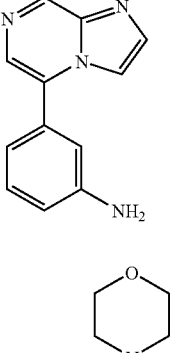 | 388.48 | + |
| 8 | 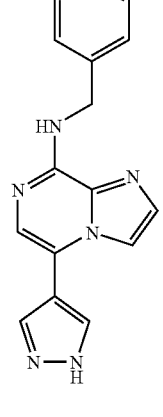 | 375.44 | + |
| 9 | 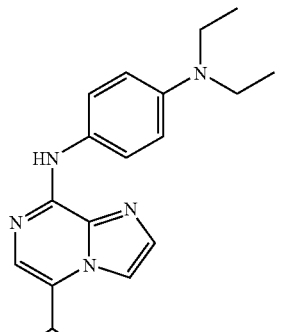 | 347.43 | ++ |

TABLE 1-continued
| Compound ID | STRUCTURE | MW | MAPKAPK5 IC$_{50}$ (nM) |
|---|---|---|---|
| 10 | 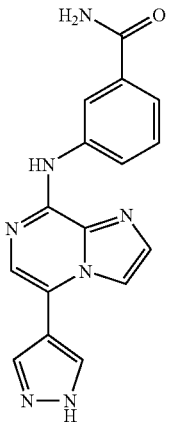 | 319.33 | + |
| 11 | 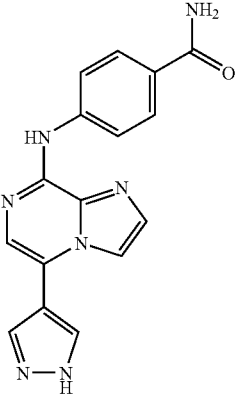 | 319.33 | +++ |
| 12 | 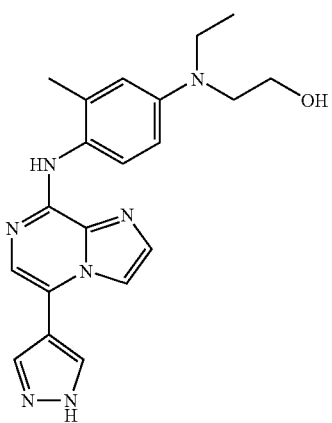 | 377.45 | + |

TABLE 1-continued

Structure and activity of of Exemplary Compounds

| Compound ID | STRUCTURE | MW | MAPKAPK5 IC$_{50}$ (nM) |
|---|---|---|---|
| 13 | 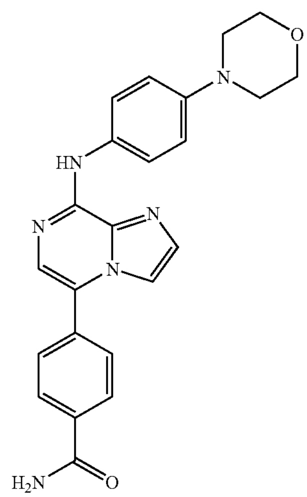 | 414.47 | + |
| 14 | 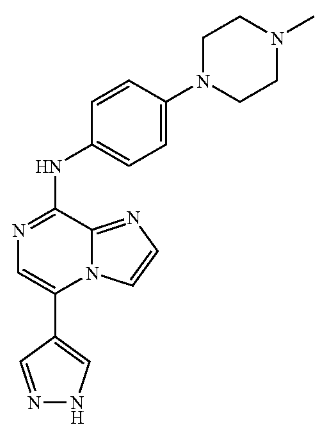 | 374.45 | + |
| 15 | 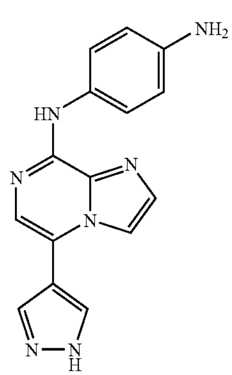 | 291.32 | + |

TABLE 1-continued
Structure and activity of of Exemplary Compounds
| Compound ID | STRUCTURE | MW | MAPKAPK5 IC$_{50}$ (nM) |
|---|---|---|---|
| 16 | 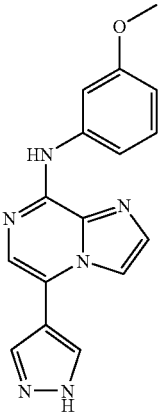 | 306.33 | + |
| 17 | 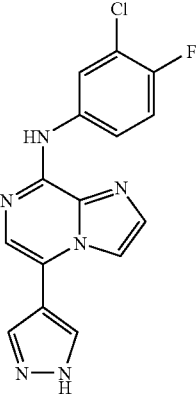 | 328.74 | + |
| 18 | 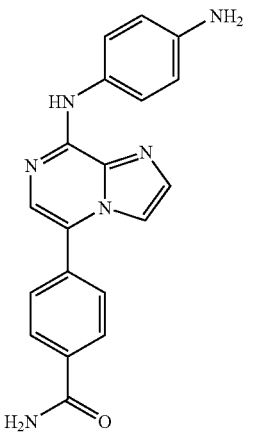 | 344.38 | + |

TABLE 1-continued

Structure and activity of Exemplary Compounds

| Compound ID | STRUCTURE | MW | MAPKAPK5 IC$_{50}$ (nM) |
|---|---|---|---|
| 19 | 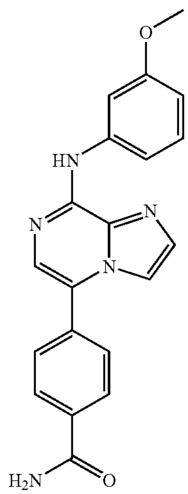 | 359.39 | + |
| 20 | 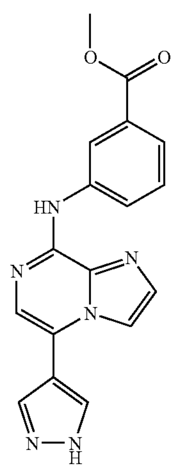 | 334.34 | + |
| 21 | 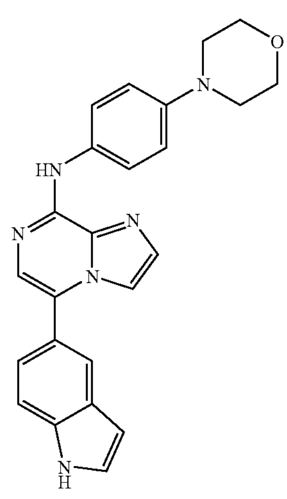 | 410.48 | + |

TABLE 1-continued

Structure and activity of of Exemplary Compounds

| Compound ID | STRUCTURE | MW | MAPKAPK5 IC$_{50}$ (nM) |
|---|---|---|---|
| 22 | 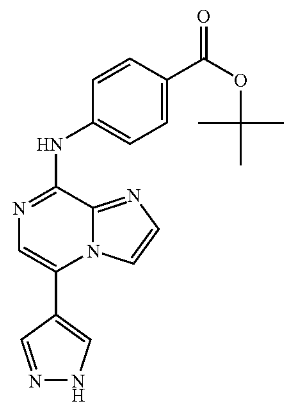 | 376.42 | + |
| 23 | 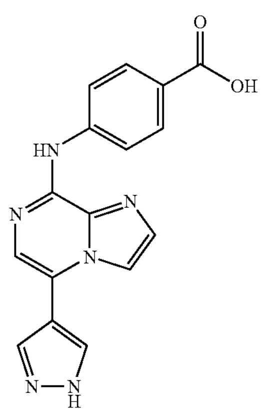 | 320.31 | + |
| 24 | 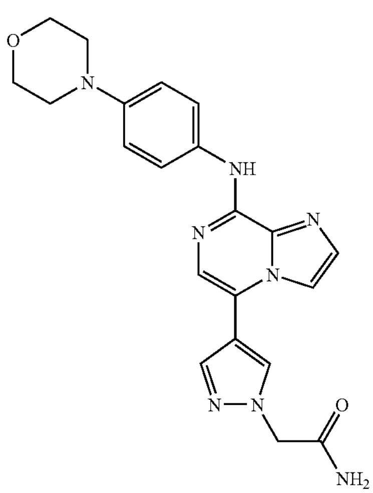 | 418.46 | + |

TABLE 1-continued

Structure and activity of of Exemplary Compounds

| Compound ID | STRUCTURE | MW | MAPKAPK5 IC$_{50}$ (nM) |
|---|---|---|---|
| 25 | 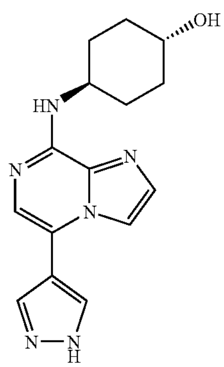 | 298.35 | + |
| 26 | 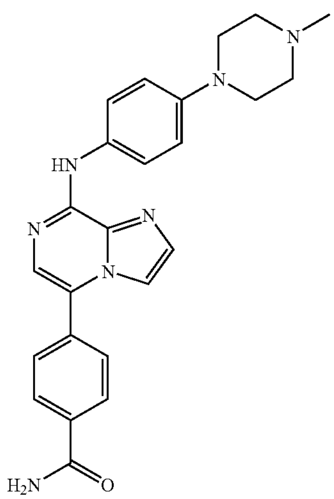 | 427.51 | ++ |
| 27 | 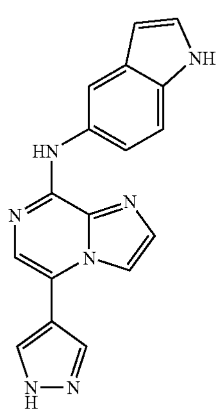 | 315.34 | ++ |

TABLE 1-continued

Structure and activity of of Exemplary Compounds

| Compound ID | STRUCTURE | MW | MAPKAPK5 IC$_{50}$ (nM) |
|---|---|---|---|
| 28 | 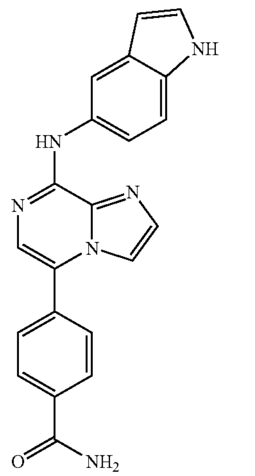 | 368.40 | + |
| 29 | 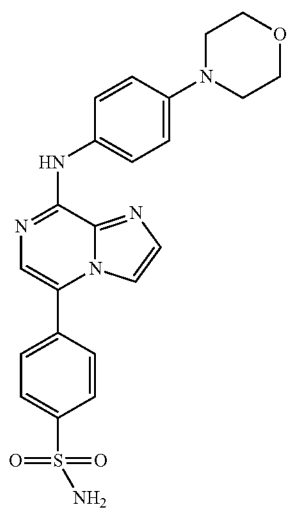 | 450.52 | + |
| 30 | 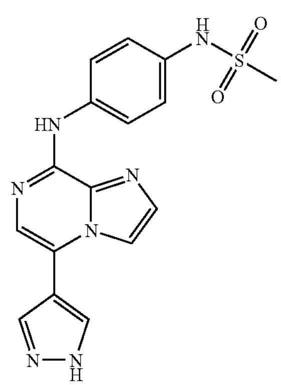 | 369.41 | ++ |

TABLE 1-continued

Structure and activity of of Exemplary Compounds

| Compound ID | STRUCTURE | MW | MAPKAPK5 IC$_{50}$ (nM) |
|---|---|---|---|
| 31 | 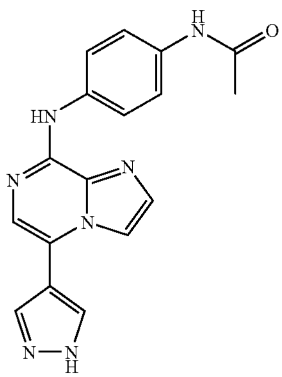 | 333.36 | ++ |
| 32 | 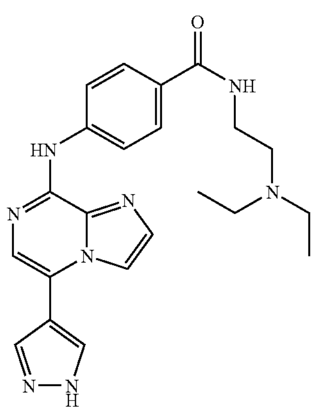 | 418.51 | +++ |
| 33 | 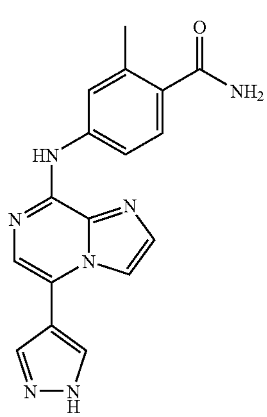 | 333.36 | + |

TABLE 1-continued

Structure and activity of of Exemplary Compounds

| Compound ID | STRUCTURE | MW | MAPKAPK5 IC$_{50}$ (nM) |
|---|---|---|---|
| 34 | 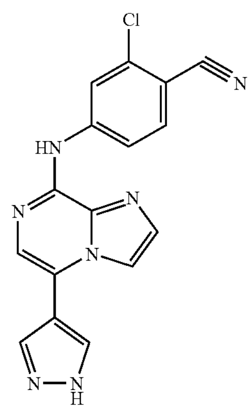 | 335.76 | + |
| 35 | 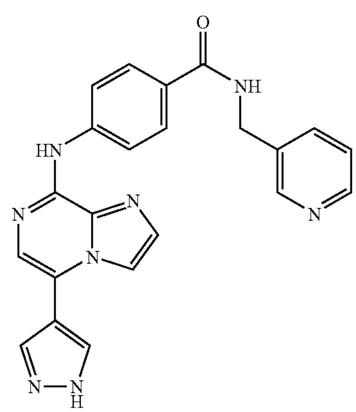 | 410.44 | ++ |
| 36 | 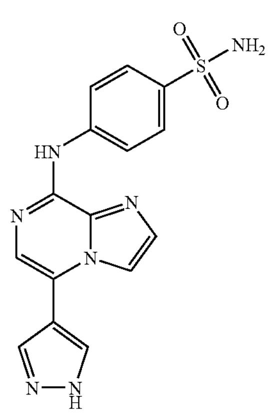 | 355.38 | +++ |

TABLE 1-continued

Structure and activity of of Exemplary Compounds

| Compound ID | STRUCTURE | MW | MAPKAPK5 IC$_{50}$ (nM) |
|---|---|---|---|
| 37 | 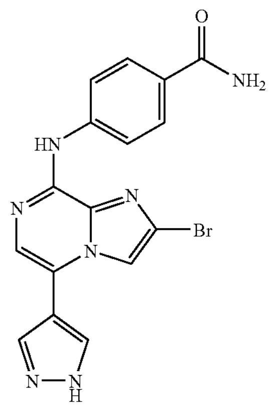 | 398.22 | + |
| 38 | 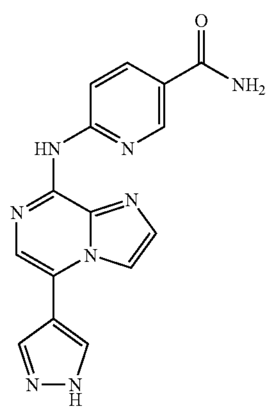 | 320.32 | + |
| 39 | 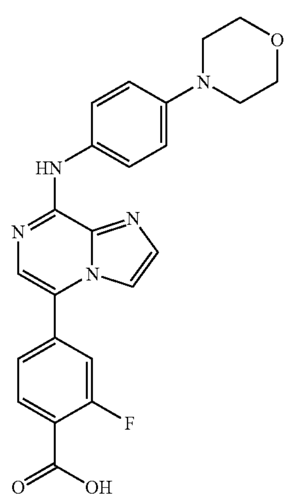 | 433.45 | + |

TABLE 1-continued

Structure and activity of of Exemplary Compounds

| Compound ID | STRUCTURE | MW | MAPKAPK5 IC$_{50}$ (nM) |
|---|---|---|---|
| 40 | 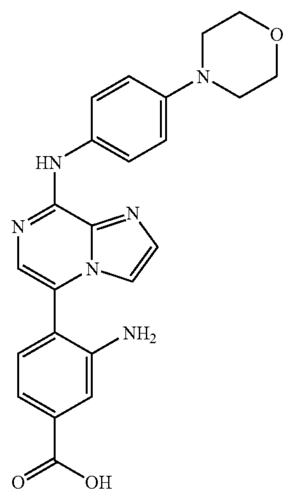 | 430.47 | + |
| 41 | 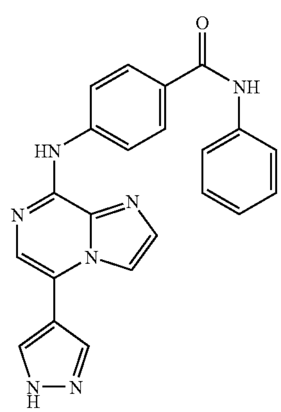 | 395.43 | + |
| 42 | 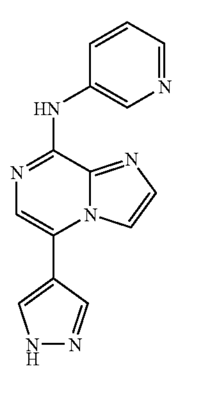 | 277.29 | + |

TABLE 1-continued
Structure and activity of of Exemplary Compounds
| Compound ID | STRUCTURE | MW | MAPKAPK5 IC$_{50}$ (nM) |
|---|---|---|---|
| 43 | 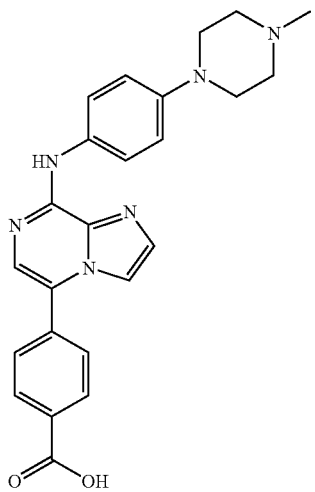 | 428.50 | + |
| 44 | 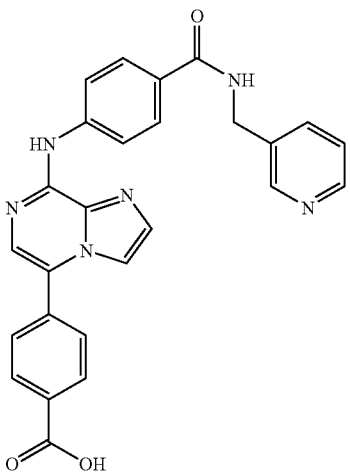 | 464.49 | + |
| 45 | 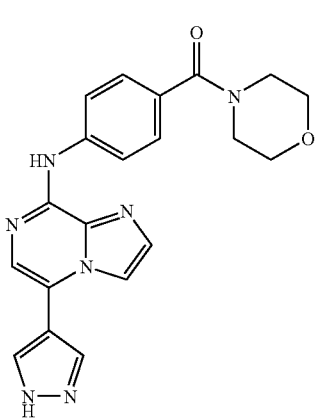 | 389.42 | ++ |

TABLE 1-continued

Structure and activity of of Exemplary Compounds

| Compound ID | STRUCTURE | MW | MAPKAPK5 IC$_{50}$ (nM) |
|---|---|---|---|
| 46 | 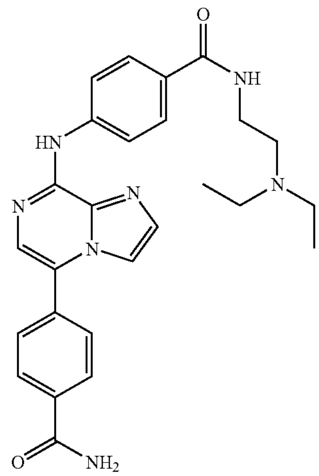 | 471.57 | + |
| 47 | 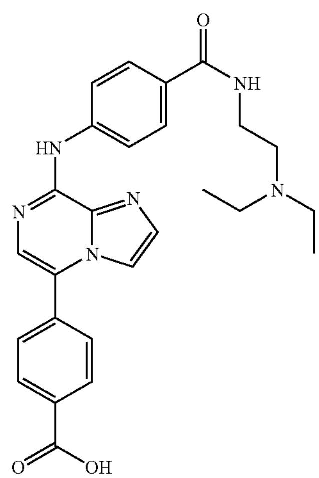 | 472.55 | + |
| 48 | 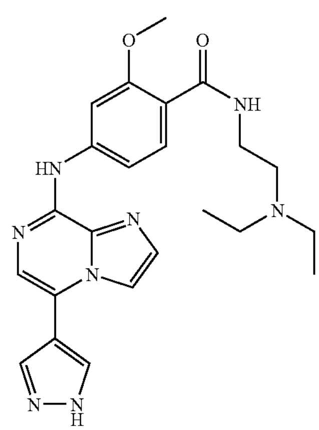 | 448.53 | + |

TABLE 1-continued

Structure and activity of of Exemplary Compounds

| Compound ID | STRUCTURE | MW | MAPKAPK5 IC$_{50}$ (nM) |
|---|---|---|---|
| 49 | 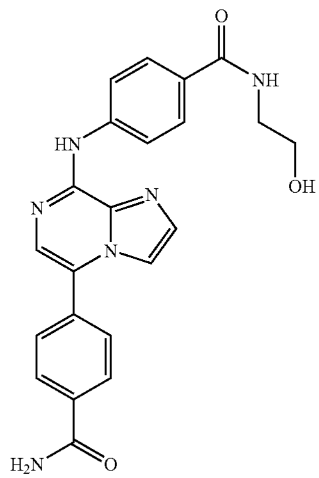 | 416.44 | + |
| 50 | 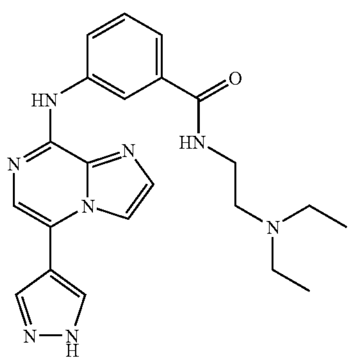 | 418.51 | + |
| 51 | 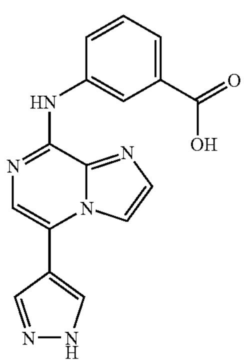 | 320.31 | + |

TABLE 1-continued

Structure and activity of of Exemplary Compounds

| Compound ID | STRUCTURE | MW | MAPKAPK5 IC$_{50}$ (nM) |
|---|---|---|---|
| 52 | 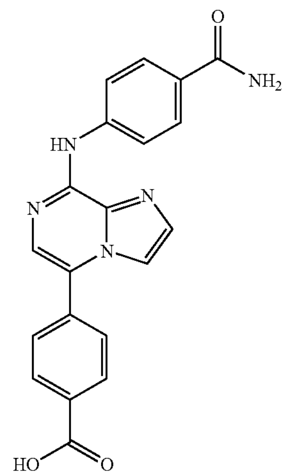 | 373.37 | + |
| 53 | 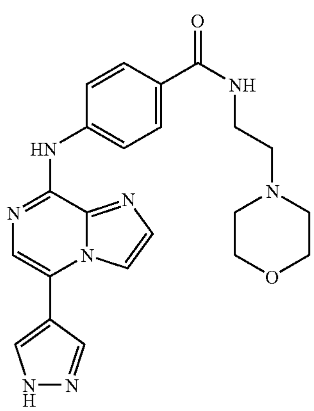 | 432.49 | +++ |
| 54 | 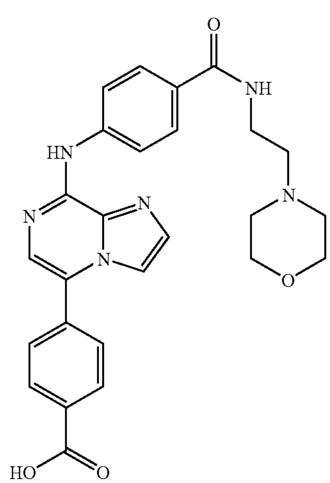 | 486.53 | + |

TABLE 1-continued

Structure and activity of of Exemplary Compounds

| Compound ID | STRUCTURE | MW | MAPKAPK5 IC$_{50}$ (nM) |
|---|---|---|---|
| 55 | 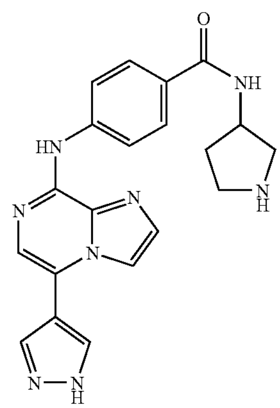 | 388.44 | +++ |
| 56 | 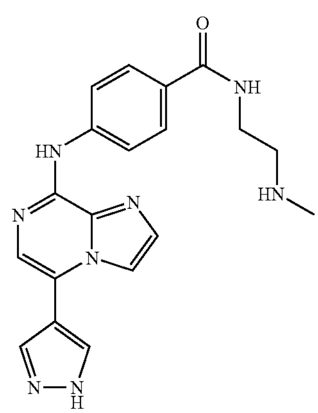 | 390.45 | +++ |
| 57 | 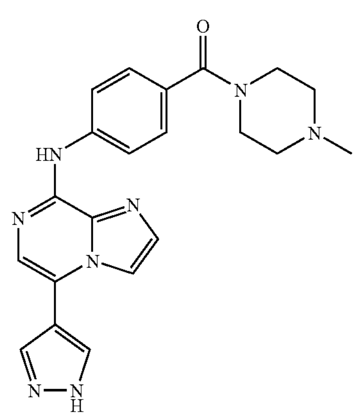 | 402.46 | +++ |

TABLE 1-continued

Structure and activity of of Exemplary Compounds

| Compound ID | STRUCTURE | MW | MAPKAPK5 IC$_{50}$ (nM) |
|---|---|---|---|
| 58 | 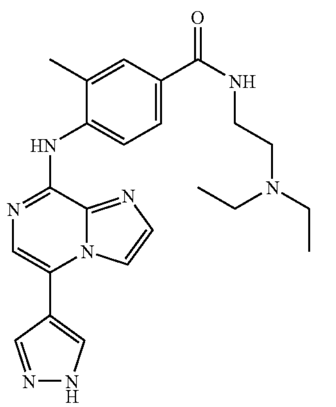 | 432.53 | + |
| 59 | 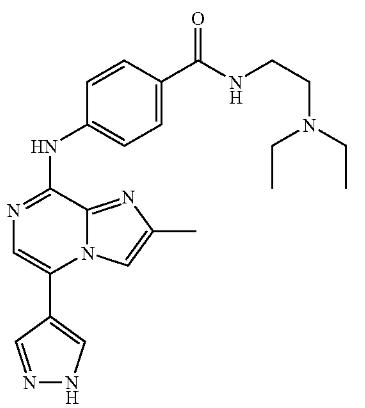 | 432.53 | + |
| 60 | 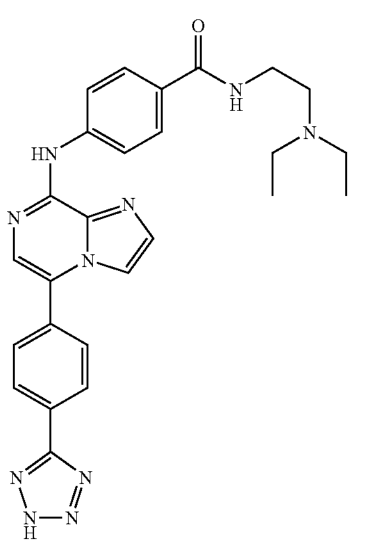 | 496.58 | + |

TABLE 1-continued

Structure and activity of of Exemplary Compounds

| Compound ID | STRUCTURE | MW | MAPKAPK5 IC$_{50}$ (nM) |
|---|---|---|---|
| 61 | 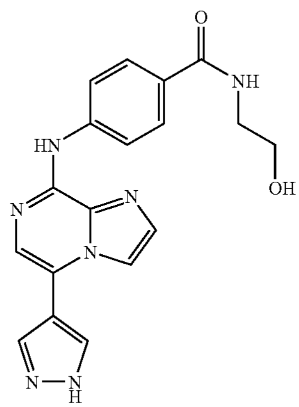 | 363.38 | ++ |
| 62 | 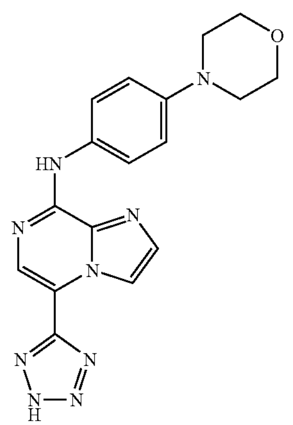 | 363.38 | + |
| 63 | 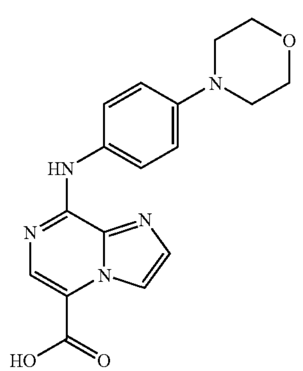 | 339.36 | + |

TABLE 1-continued
Structure and activity of of Exemplary Compounds
| Compound ID | STRUCTURE | MW | MAPKAPK5 IC$_{50}$ (nM) |
|---|---|---|---|
| 64 | 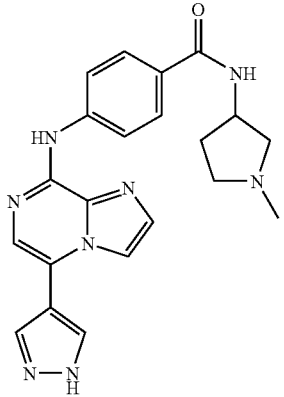 | 402.46 | +++ |
| 65 | 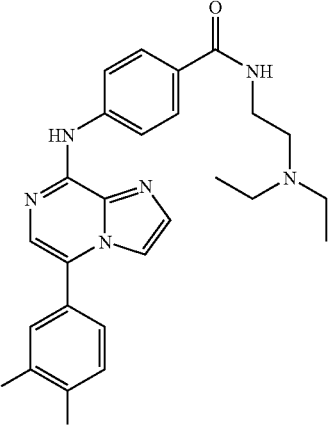 | 474.57 | + |
| 66 | 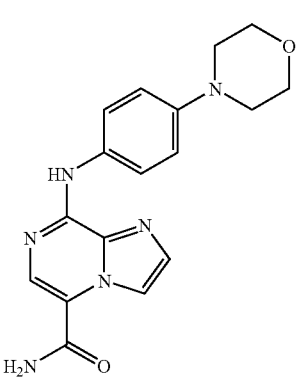 | 338.37 | + |

TABLE 1-continued

Structure and activity of of Exemplary Compounds

| Compound ID | STRUCTURE | MW | MAPKAPK5 IC$_{50}$ (nM) |
|---|---|---|---|
| 67 | 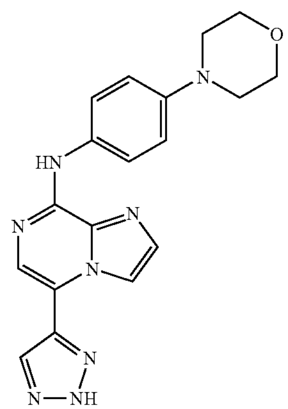 | 362.40 | + |
| 68 | 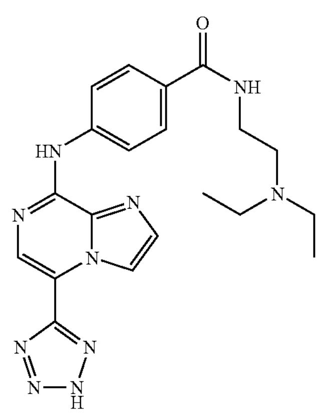 | 420.48 | + |
| 69 | 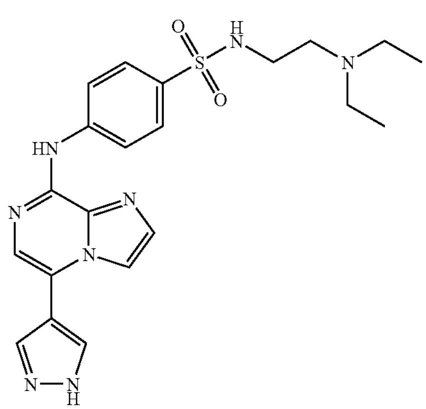 | 454.56 | +++ |

TABLE 1-continued

Structure and activity of of Exemplary Compounds

| Compound ID | STRUCTURE | MW | MAPKAPK5 IC$_{50}$ (nM) |
|---|---|---|---|
| 70 | 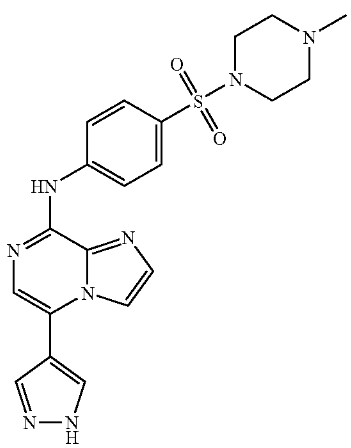 | 438.51 | + |
| 71 | 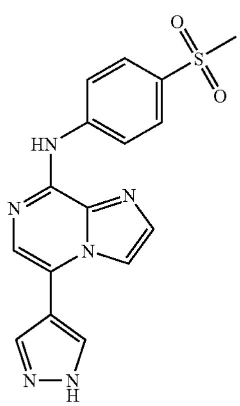 | 354.39 | +++ |
| 72 | 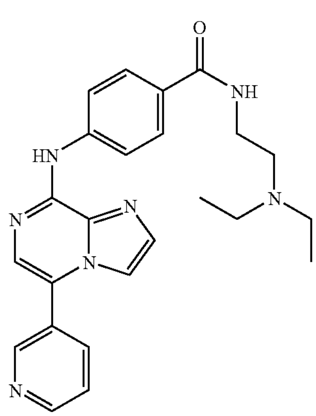 | 429.53 | + |

TABLE 1-continued

Structure and activity of of Exemplary Compounds

| Compound ID | STRUCTURE | MW | MAPKAPK5 IC$_{50}$ (nM) |
|---|---|---|---|
| 73 | 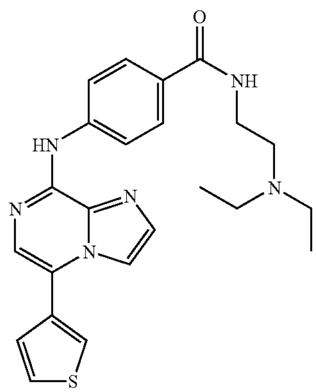 | 434.57 | + |
| 74 | 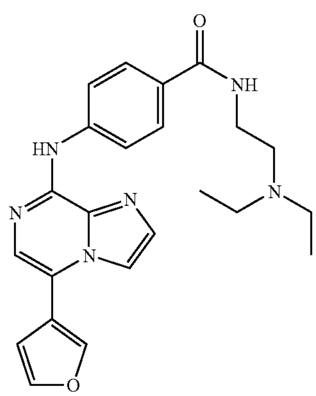 | 418.50 | + |
| 75 | 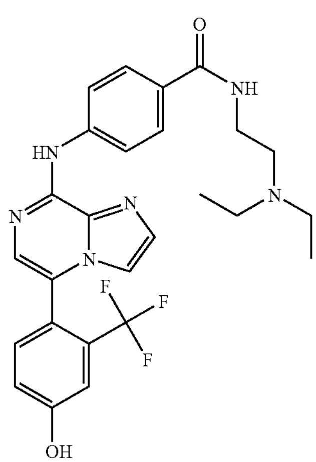 | 512.54 | + |

TABLE 1-continued

Structure and activity of of Exemplary Compounds

| Compound ID | STRUCTURE | MW | MAPKAPK5 IC$_{50}$ (nM) |
|---|---|---|---|
| 76 | 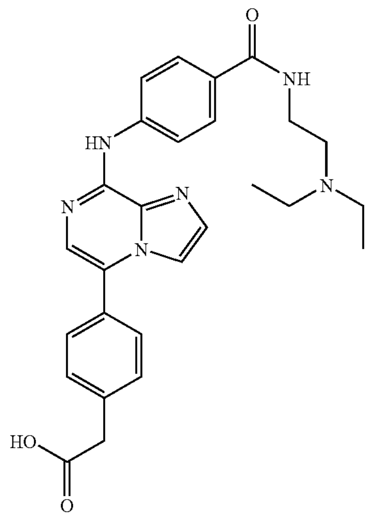 | 486.58 | + |
| 77 | 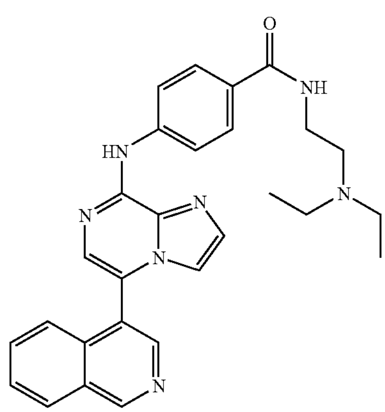 | 479.59 | + |
| 78 | 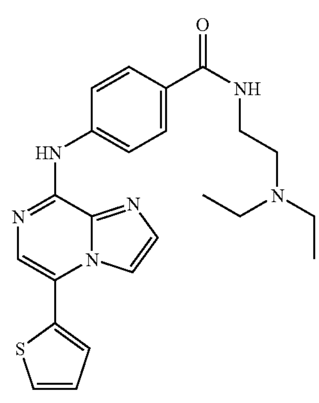 | 434.57 | + |

TABLE 1-continued

Structure and activity of of Exemplary Compounds

| Compound ID | STRUCTURE | MW | MAPKAPK5 IC$_{50}$ (nM) |
|---|---|---|---|
| 79 | 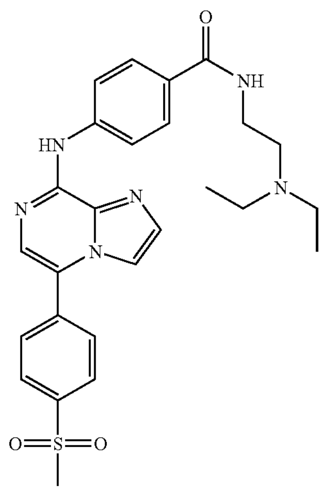 | 506.63 | + |
| 80 | 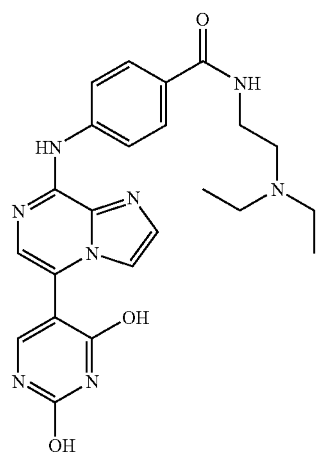 | 462.52 | + |
| 81 | 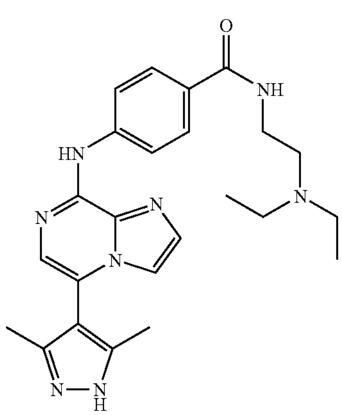 | 446.56 | + |

TABLE 1-continued

Structure and activity of of Exemplary Compounds

| Compound ID | STRUCTURE | MW | MAPKAPK5 IC$_{50}$ (nM) |
|---|---|---|---|
| 82 | 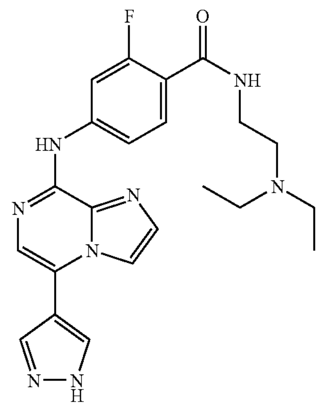 | 436.50 | ++ |
| 83 | 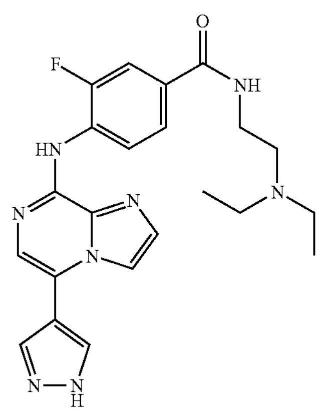 | 436.50 | +++ |
| 84 | 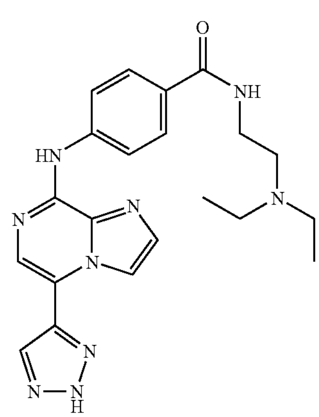 | 419.49 | ++ |

TABLE 1-continued
Structure and activity of of Exemplary Compounds
| Compound ID | STRUCTURE | MW | MAPKAPK5 IC$_{50}$ (nM) |
|---|---|---|---|
| 85 | 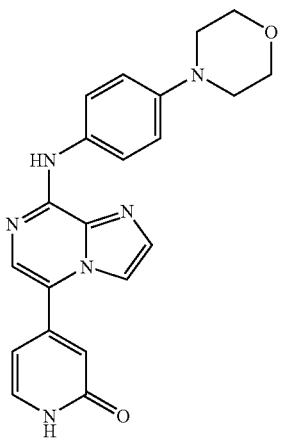 | 388.43 | +++ |
| 86 | 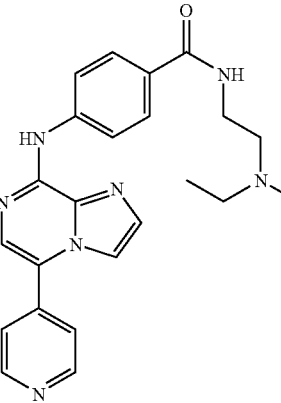 | 429.53 | + |
| 87 | 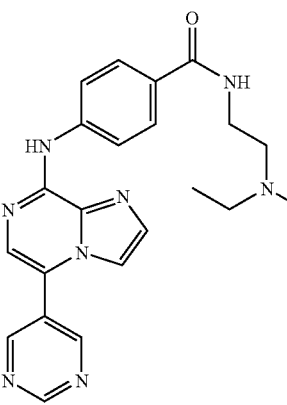 | 430.52 | + |

TABLE 1-continued

Structure and activity of of Exemplary Compounds

| Compound ID | STRUCTURE | MW | MAPKAPK5 IC$_{50}$ (nM) |
|---|---|---|---|
| 88 | 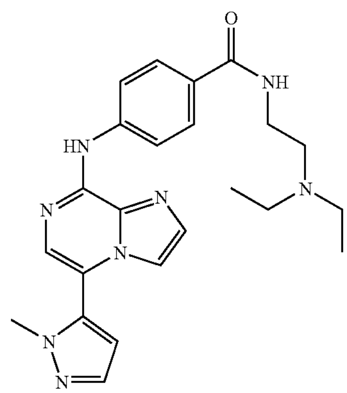 | 432.53 | + |
| 89 | 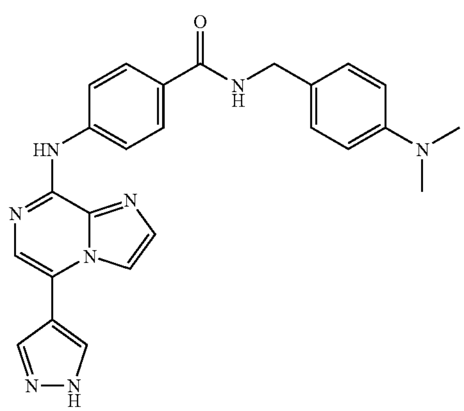 | 452.52 | + |
| 90 | 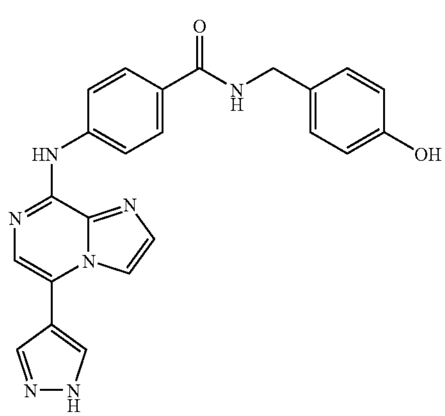 | 425.45 | ++ |

TABLE 1-continued
Structure and activity of of Exemplary Compounds
| Compound ID | STRUCTURE | MW | MAPKAPK5 IC$_{50}$ (nM) |
|---|---|---|---|
| 91 | 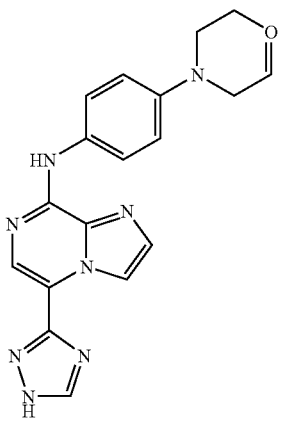 | 362.40 | + |
| 92 | 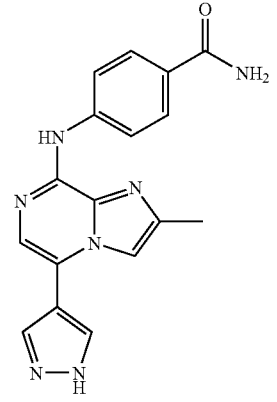 | 333.36 | + |
| 93 | 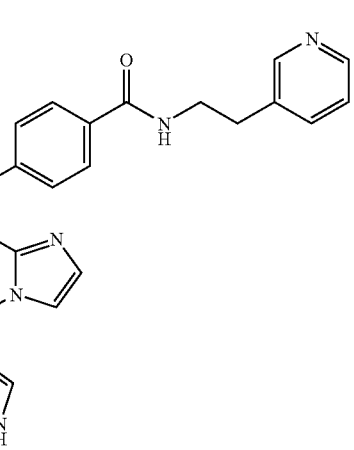 | 424.47 | +++ |

TABLE 1-continued

Structure and activity of of Exemplary Compounds

| Compound ID | STRUCTURE | MW | MAPKAPK5 IC$_{50}$ (nM) |
|---|---|---|---|
| 94 | 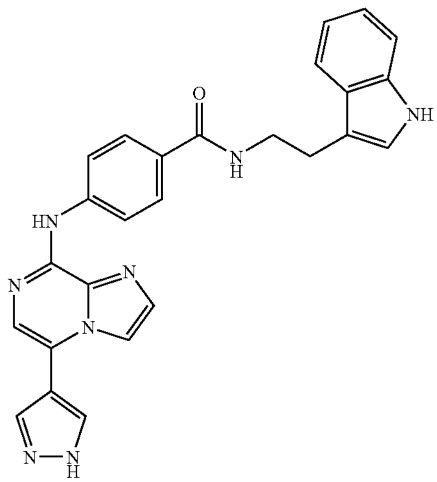 | 462.52 | ++ |
| 95 | 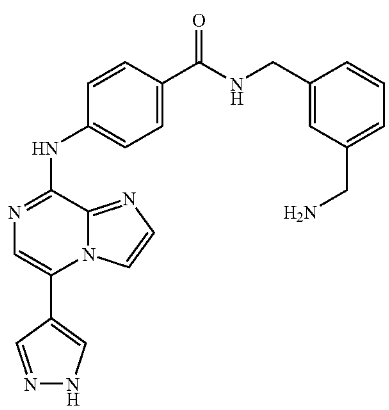 | 438.50 | + |
| 96 | 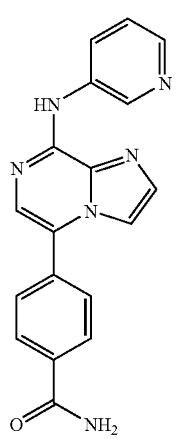 | 330.35 | + |

TABLE 1-continued

Structure and activity of of Exemplary Compounds

| Compound ID | STRUCTURE | MW | MAPKAPK5 IC$_{50}$ (nM) |
|---|---|---|---|
| 97 | 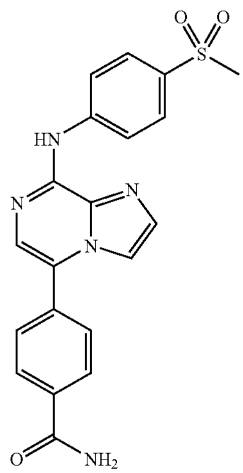 | 407.45 | + |
| 98 | 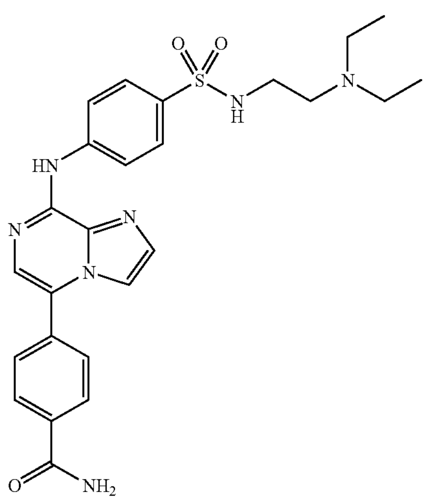 | 507.62 | + |
| 99 | 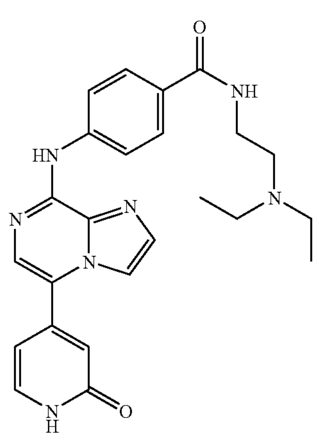 | 445.53 | +++ |

TABLE 1-continued

Structure and activity of of Exemplary Compounds

| Compound ID | STRUCTURE | MW | MAPKAPK5 IC$_{50}$ (nM) |
|---|---|---|---|
| 100 | 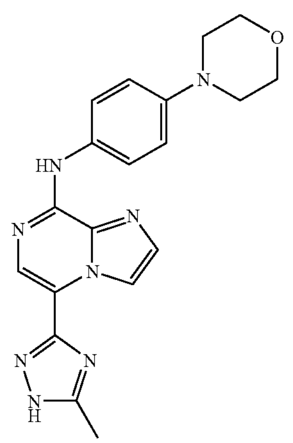 | 376.42 | + |
| 101 | 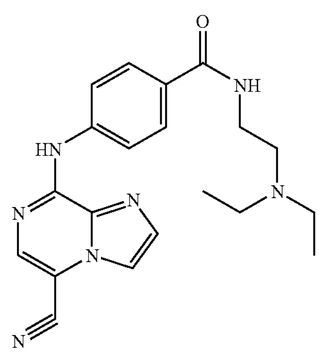 | 377.45 | + |
| 102 | 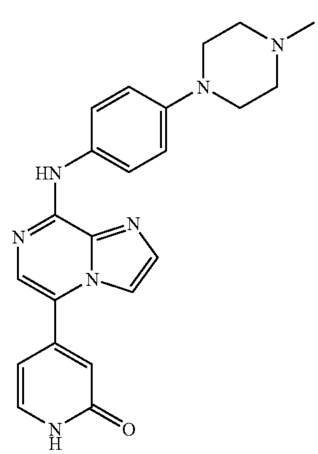 | 401.47 | +++ |

TABLE 1-continued

Structure and activity of of Exemplary Compounds

| Compound ID | STRUCTURE | MW | MAPKAPK5 IC$_{50}$ (nM) |
|---|---|---|---|
| 103 | 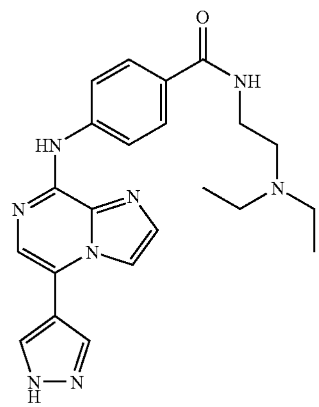 | 419.49 | ++ |
| 104 | 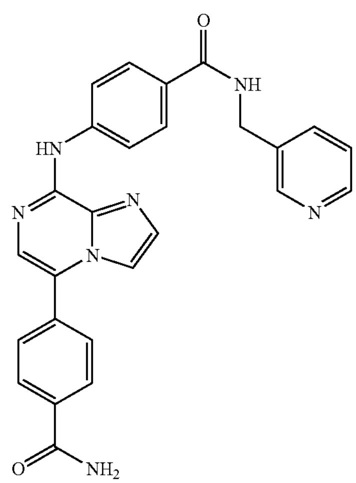 | 463.50 | + |
| 105 | 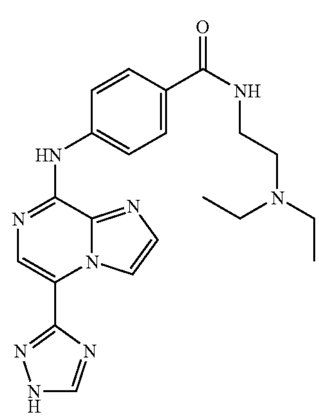 | 419.49 | + |

TABLE 1-continued

Structure and activity of of Exemplary Compounds

| Compound ID | STRUCTURE | MW | MAPKAPK5 IC$_{50}$ (nM) |
|---|---|---|---|
| 106 | 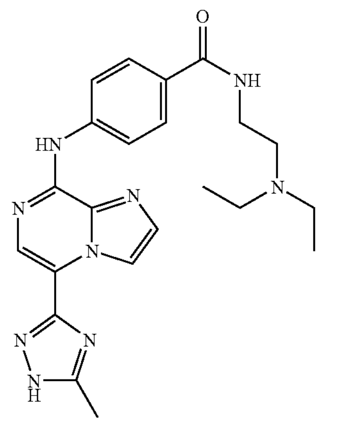 | 433.52 | + |
| 107 | 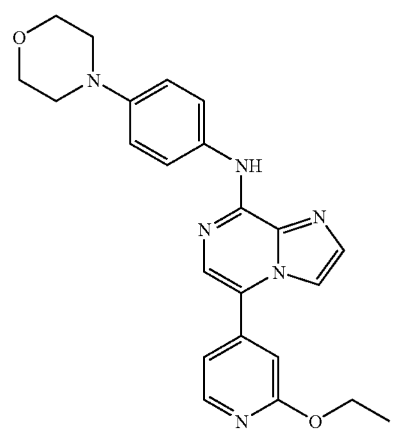 | 416.49 | + |
| 108 | 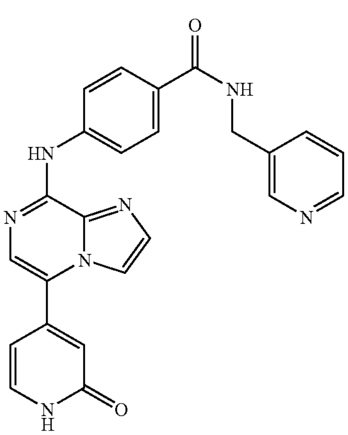 | 437.46 | ++ |

TABLE 1-continued

Structure and activity of of Exemplary Compounds

| Compound ID | STRUCTURE | MW | MAPKAPK5 IC$_{50}$ (nM) |
|---|---|---|---|
| 109 | 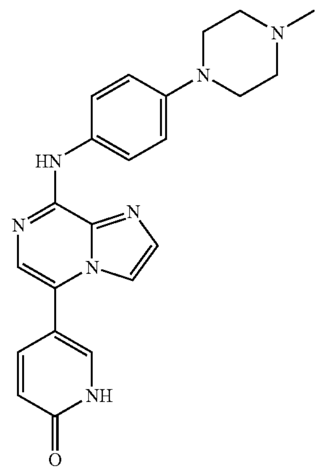 | 401.47 | + |
| 111 | 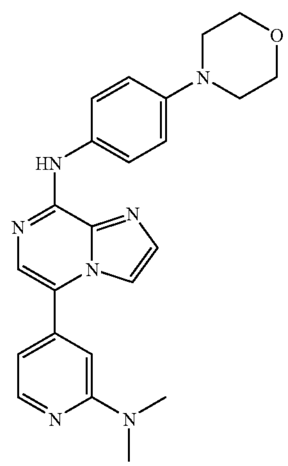 | 415.50 | + |
| 112 | 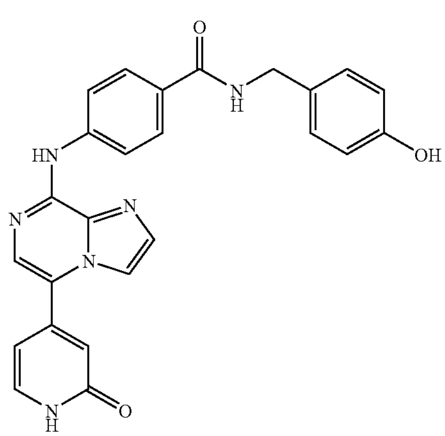 | 452.48 | +++ |

TABLE 1-continued

Structure and activity of Exemplary Compounds

| Compound ID | STRUCTURE | MW | MAPKAPK5 IC$_{50}$ (nM) |
|---|---|---|---|
| 114 | 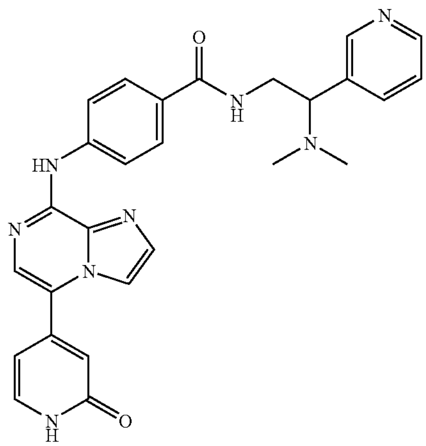 | 494.56 | +++ |
| 115 | 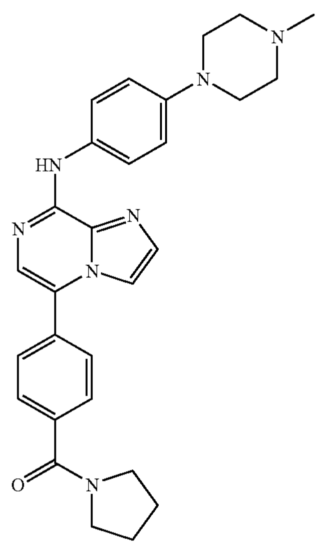 | 481.61 | + |
| 116 | 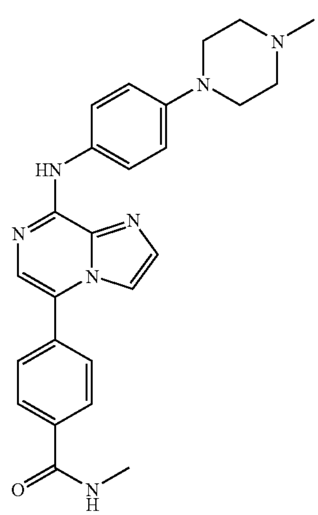 | 441.54 | + |

TABLE 1-continued

Structure and activity of of Exemplary Compounds

| Compound ID | STRUCTURE | MW | MAPKAPK5 IC$_{50}$ (nM) |
|---|---|---|---|
| 117 | 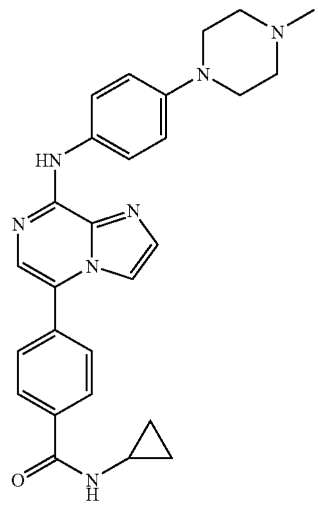 | 467.58 | + |
| 118 | 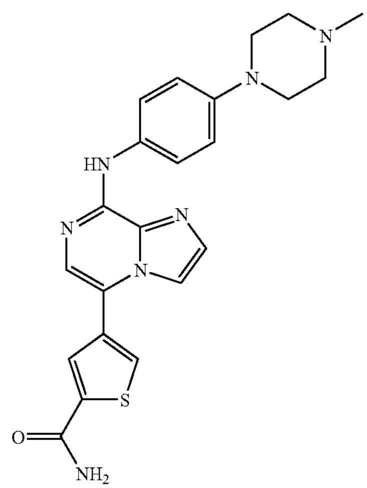 | 433.54 | +++ |
| 119 | 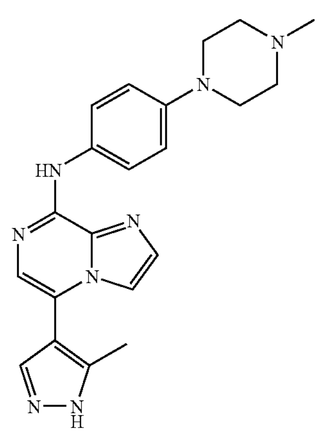 | 388.48 | +++ |

TABLE 1-continued

Structure and activity of of Exemplary Compounds

| Compound ID | STRUCTURE | MW | MAPKAPK5 IC$_{50}$ (nM) |
|---|---|---|---|
| 120 | 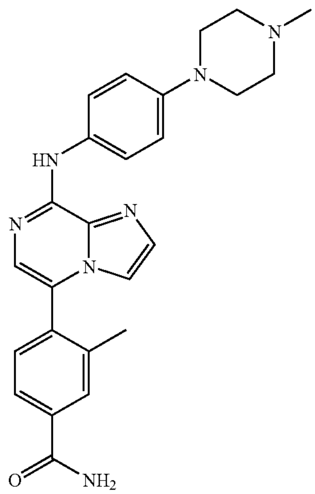 | 441.54 | + |
| 121 | 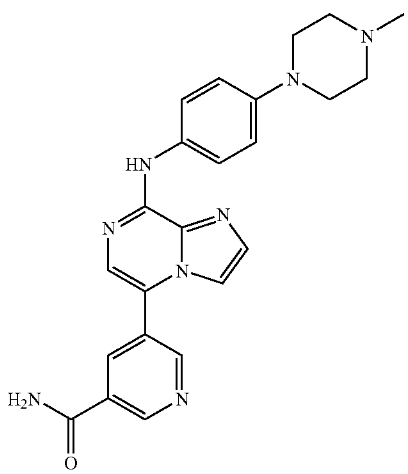 | 428.50 | + |
| 122 | 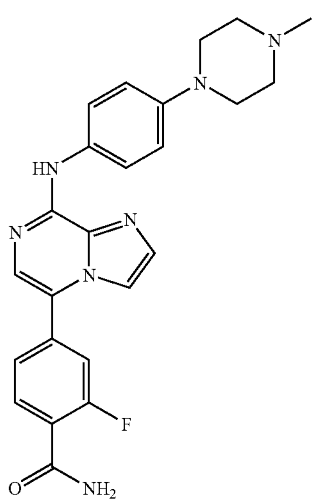 | 445.50 | ++ |

TABLE 1-continued

Structure and activity of of Exemplary Compounds

| Compound ID | STRUCTURE | MW | MAPKAPK5 IC$_{50}$ (nM) |
|---|---|---|---|
| 123 | 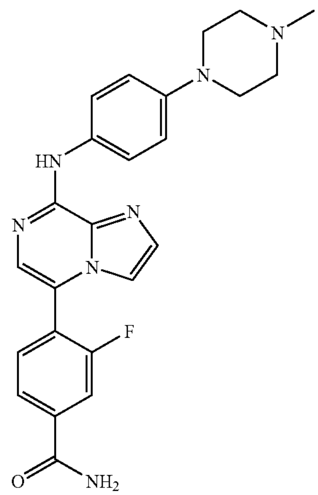 | 445.50 | ++ |
| 124 | 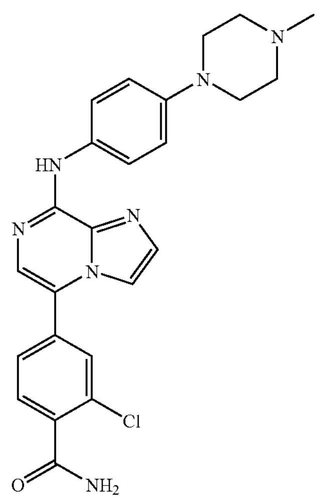 | 461.96 | + |
| 125 | 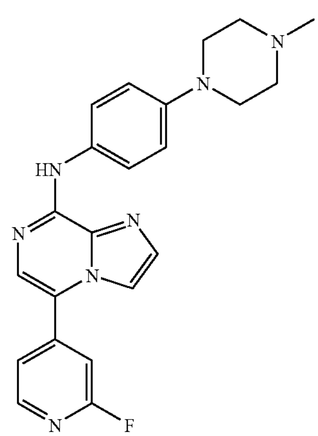 | 403.47 | + |

TABLE 1-continued

Structure and activity of of Exemplary Compounds

| Compound ID | STRUCTURE | MW | MAPKAPK5 IC$_{50}$ (nM) |
|---|---|---|---|
| 126 | 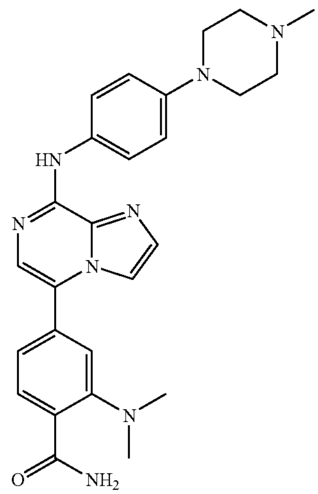 | 470.58 | + |
| 127 | 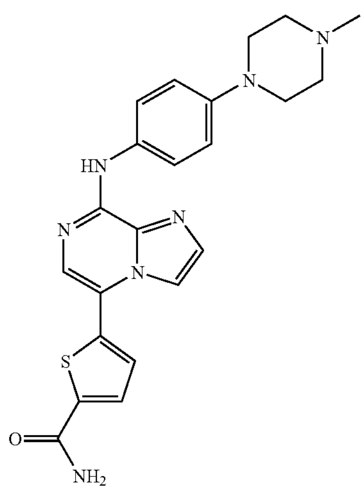 | 433.54 | +++ |
| 128 | 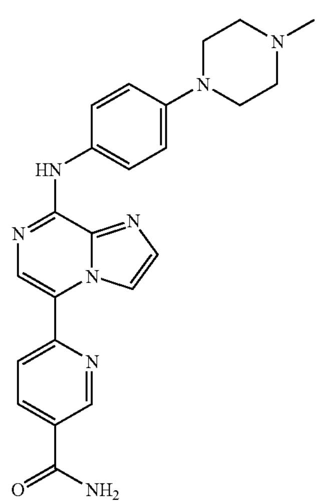 | 428.50 | + |

TABLE 1-continued

Structure and activity of of Exemplary Compounds

| Compound ID | STRUCTURE | MW | MAPKAPK5 IC$_{50}$ (nM) |
|---|---|---|---|
| 129 | 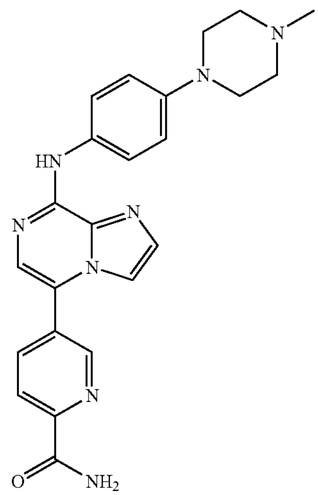 | 428.50 | + |
| 130 | 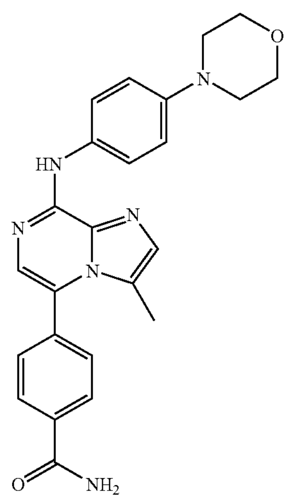 | 428.50 | + |
| 131 | 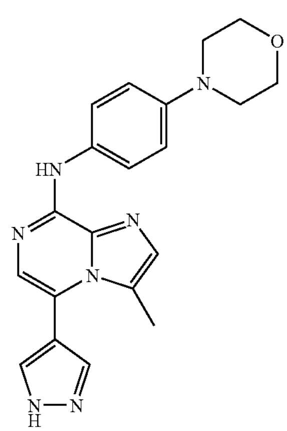 | 375.44 | + |

TABLE 1-continued

Structure and activity of of Exemplary Compounds

| Compound ID | STRUCTURE | MW | MAPKAPK5 IC$_{50}$ (nM) |
|---|---|---|---|
| 132 | 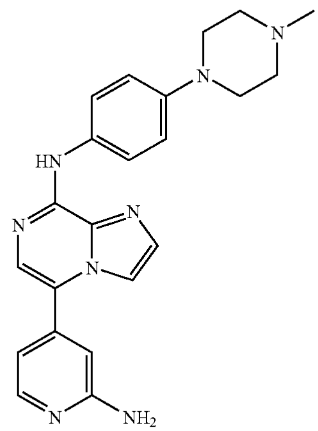 | 400.49 | + |
| 133 | 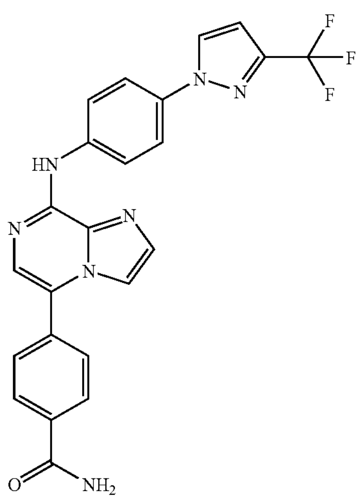 | 463.43 | + |
| 134 | 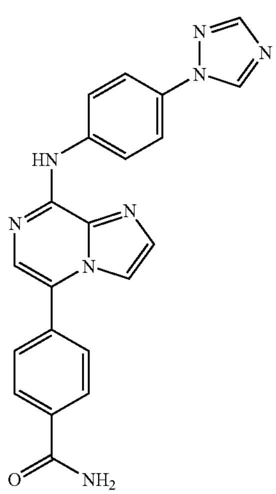 | 396.41 | + |

TABLE 1-continued
Structure and activity of of Exemplary Compounds
| Compound ID | STRUCTURE | MW | MAPKAPK5 IC$_{50}$ (nM) |
|---|---|---|---|
| 135 | 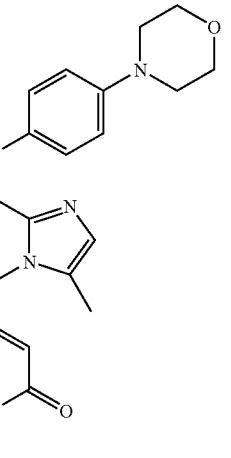 | 402.46 | + |
| 136 | 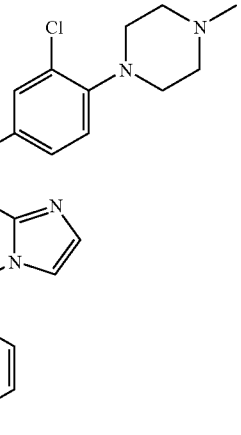 | 461.96 | +++ |
| 137 | 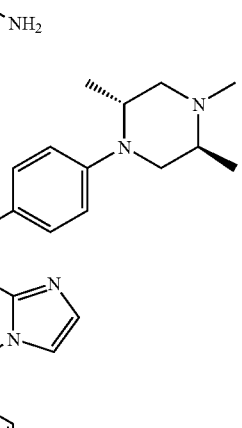 | 455.57 | +++ |

TABLE 1-continued

Structure and activity of of Exemplary Compounds

| Compound ID | STRUCTURE | MW | MAPKAPK5 IC$_{50}$ (nM) |
|---|---|---|---|
| 138 | 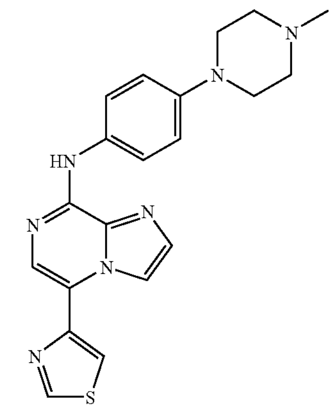 | 391.50 | + |
| 139 | 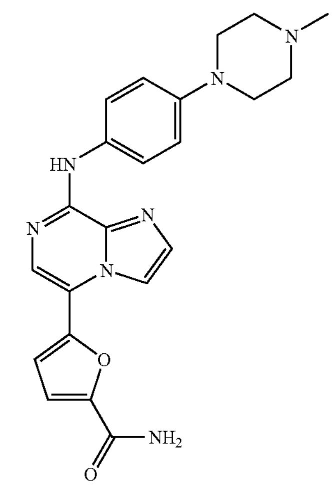 | 417.47 | + |
| 140 | 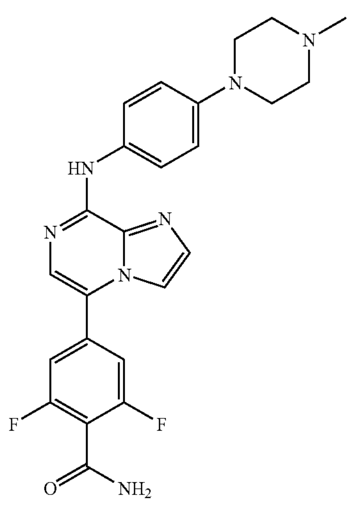 | 463.49 | +++ |

TABLE 1-continued

Structure and activity of of Exemplary Compounds

| Compound ID | STRUCTURE | MW | MAPKAPK5 IC$_{50}$ (nM) |
|---|---|---|---|
| 141 | 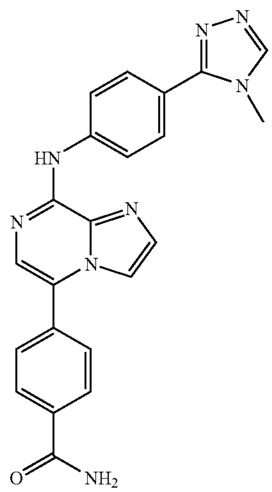 | 410.44 | + |
| 142 | 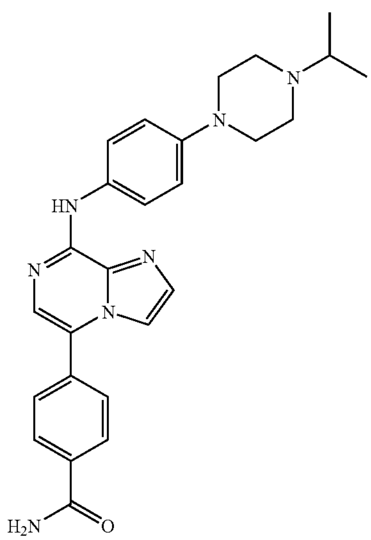 | 455.57 | + |
| 143 | 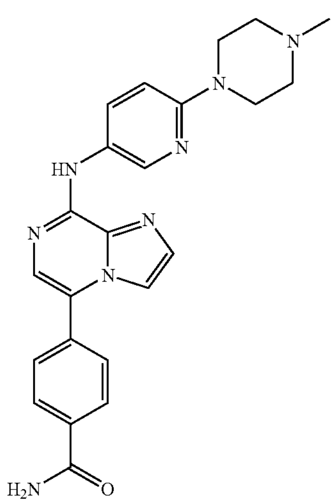 | 428.50 | + |

TABLE 1-continued

Structure and activity of of Exemplary Compounds

| Compound ID | STRUCTURE | MW | MAPKAPK5 IC$_{50}$ (nM) |
|---|---|---|---|
| 144 | 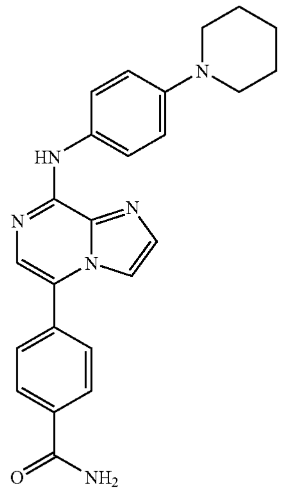 | 412.50 | + |
| 145 | 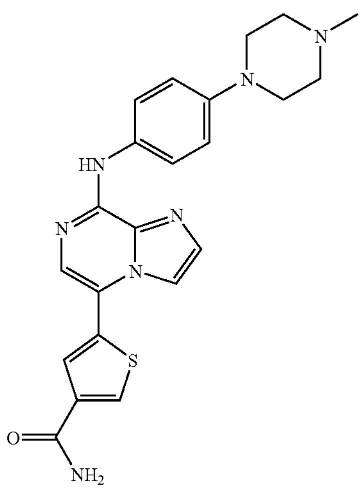 | 433.54 | + |
| 146 | 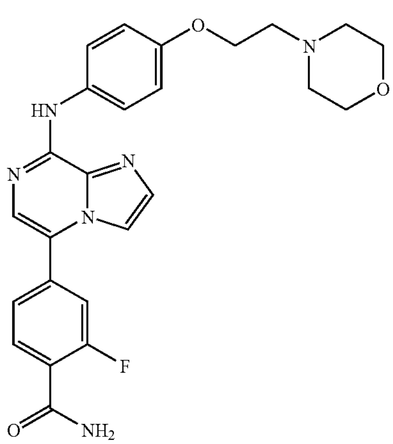 | 476.51 | + |

TABLE 1-continued

Structure and activity of of Exemplary Compounds

| Compound ID | STRUCTURE | MW | MAPKAPK5 IC$_{50}$ (nM) |
|---|---|---|---|
| 147 | 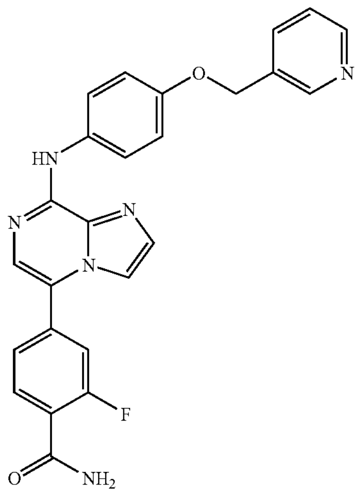 | 454.47 | + |
| 148 | 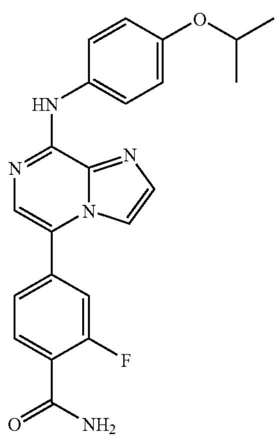 | 405.44 | + |
| 149 | 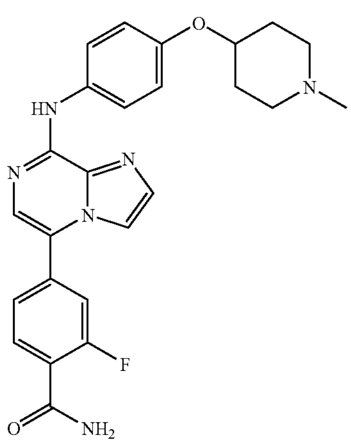 | 460.52 | + |

TABLE 1-continued

Structure and activity of of Exemplary Compounds

| Compound ID | STRUCTURE | MW | MAPKAPK5 IC$_{50}$ (nM) |
|---|---|---|---|
| 150 | 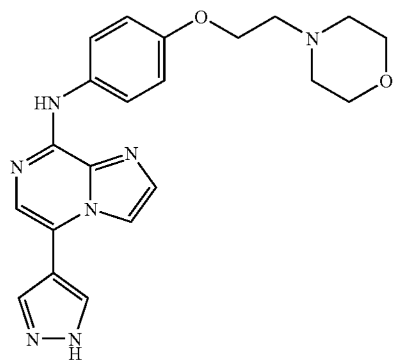 | 405.46 | ++ |
| 151 | 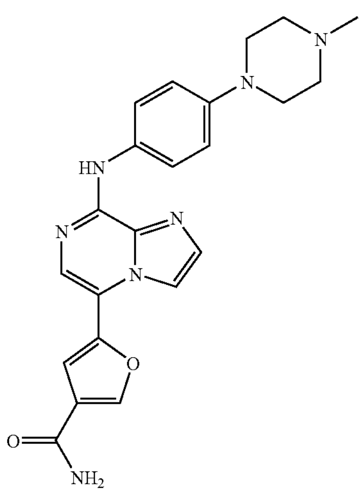 | 417.47 | ++++ |
| 152 | 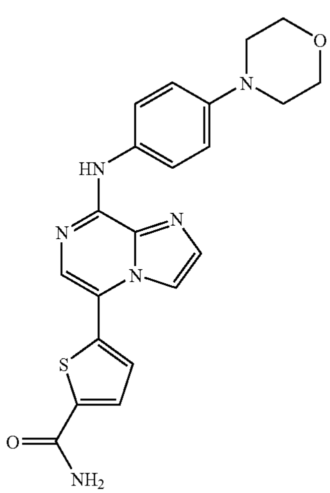 | 420.50 | + |

TABLE 1-continued
Structure and activity of of Exemplary Compounds
| Compound ID | STRUCTURE | MW | MAPKAPK5 IC$_{50}$ (nM) |
|---|---|---|---|
| 153 | 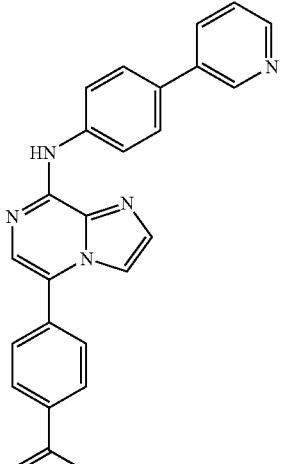 | 406.45 | + |
| 154 | 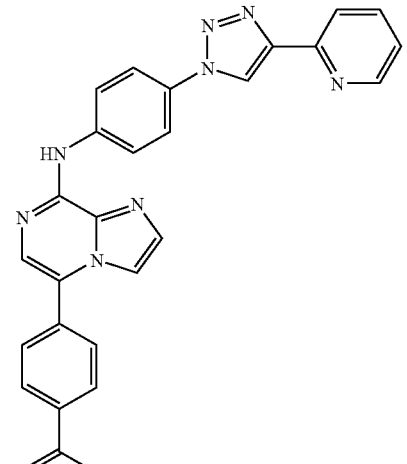 | 473.50 | + |
| 155 | 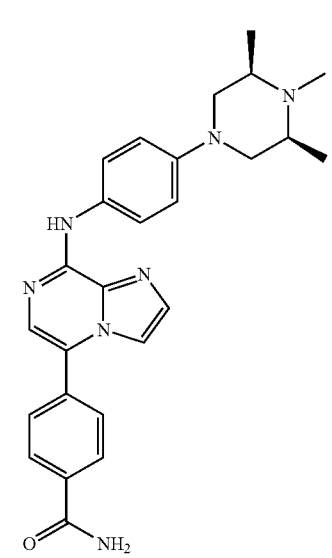 | 455.57 | + |

TABLE 1-continued

Structure and activity of of Exemplary Compounds

| Compound ID | STRUCTURE | MW | MAPKAPK5 IC$_{50}$ (nM) |
|---|---|---|---|
| 156 | 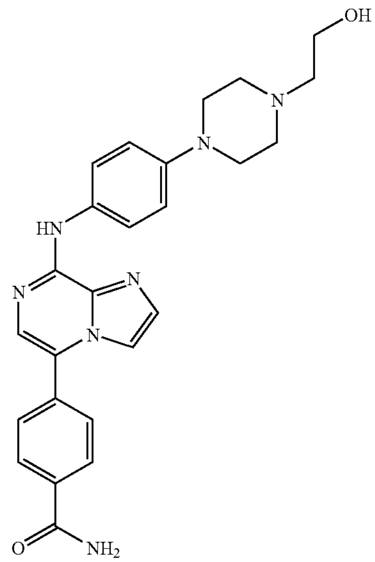 | 457.54 | ++ |
| 157 | 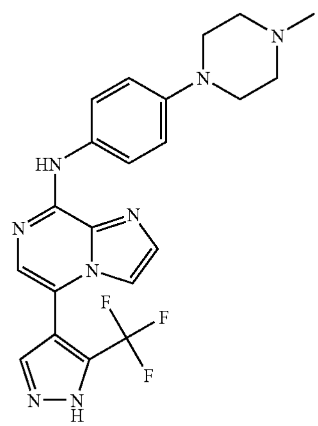 | 442.45 | + |
| 158 | 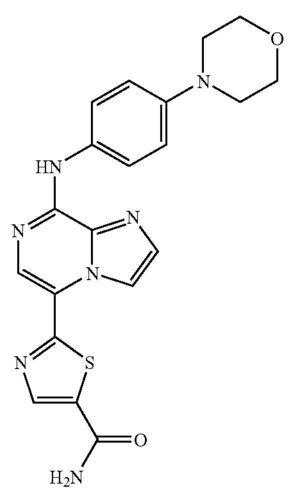 | 421.48 | + |

TABLE 1-continued

Structure and activity of of Exemplary Compounds

| Compound ID | STRUCTURE | MW | MAPKAPK5 IC$_{50}$ (nM) |
|---|---|---|---|
| 159 | 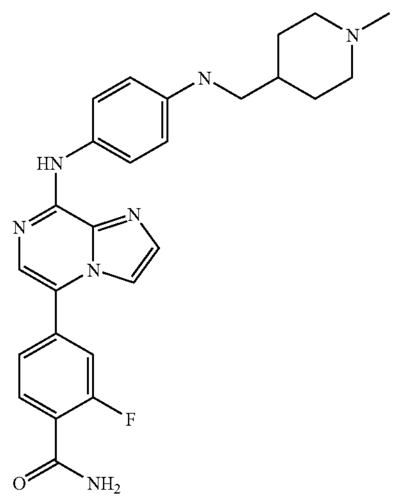 | 474.54 | + |
| 160 | 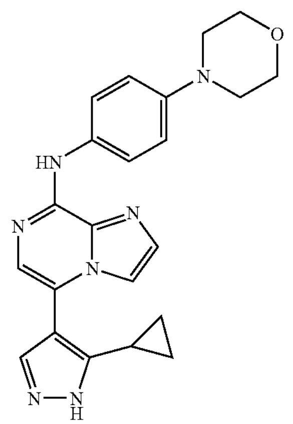 | 401.47 | +++ |
| 161 | 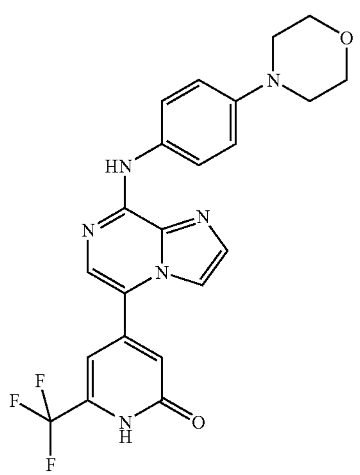 | 456.43 | + |

TABLE 1-continued

Structure and activity of of Exemplary Compounds

| Compound ID | STRUCTURE | MW | MAPKAPK5 IC$_{50}$ (nM) |
|---|---|---|---|
| 162 | 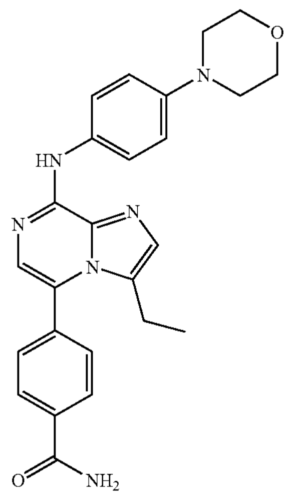 | 442.52 | + |
| 163 | 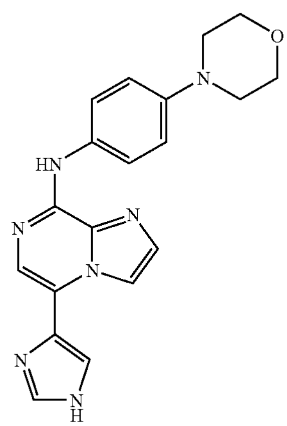 | 361.41 | + |
| 164 | 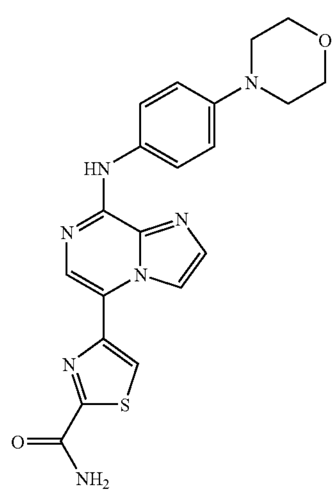 | 421.48 | + |

TABLE 1-continued

Structure and activity of of Exemplary Compounds

| Compound ID | STRUCTURE | MW | MAPKAPK5 IC$_{50}$ (nM) |
|---|---|---|---|
| 165 | 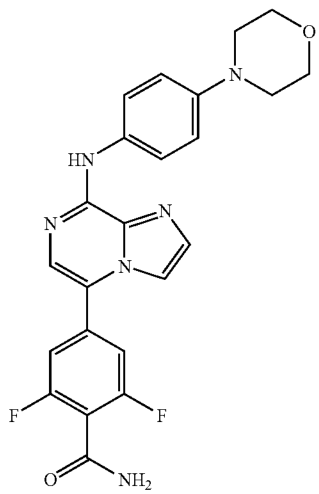 | 450.45 | + |
| 166 | 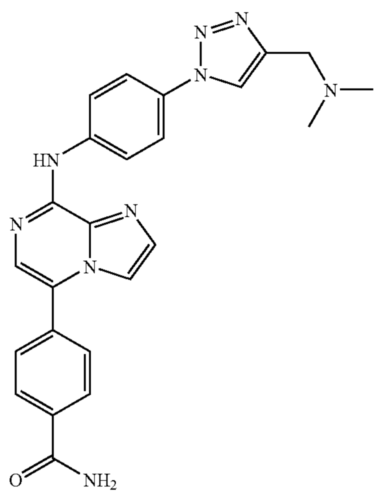 | 453.51 | + |
| 167 | 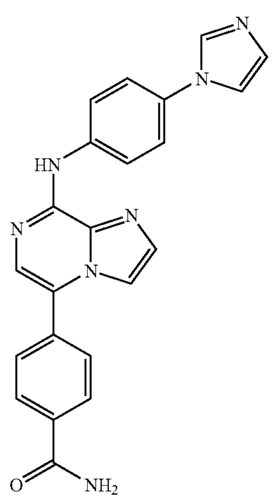 | 395.43 | + |

TABLE 1-continued

Structure and activity of of Exemplary Compounds

| Compound ID | STRUCTURE | MW | MAPKAPK5 IC$_{50}$ (nM) |
|---|---|---|---|
| 168 | 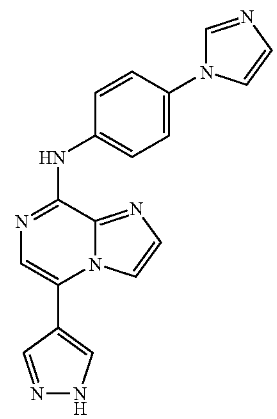 | 342.37 | + |
| 169 | 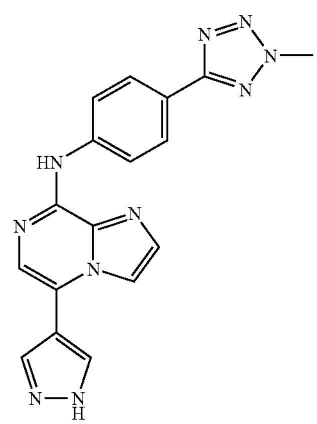 | 358.37 | + |
| 170 | 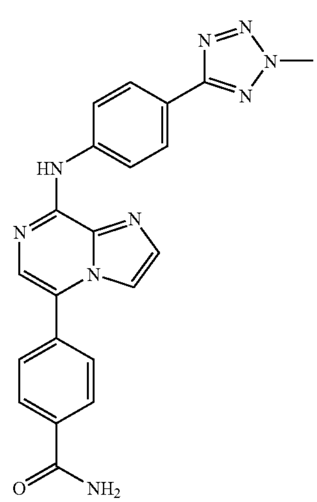 | 411.43 | + |

TABLE 1-continued

Structure and activity of of Exemplary Compounds

| Compound ID | STRUCTURE | MW | MAPKAPK5 IC$_{50}$ (nM) |
|---|---|---|---|
| 171 | 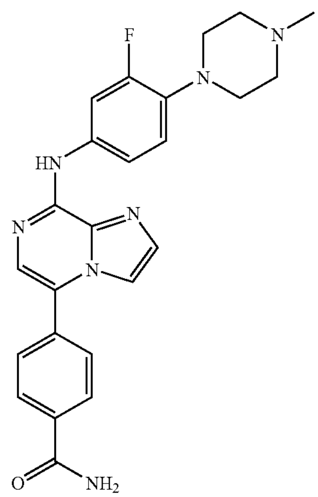 | 445.50 | + |
| 172 | 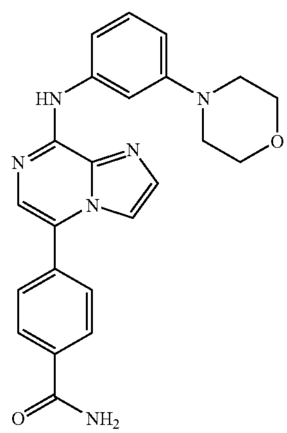 | 414.47 | + |
| 173 | 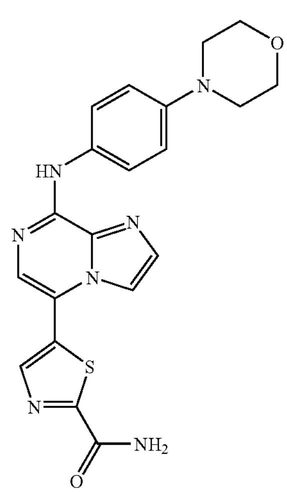 | 421.48 | + |

TABLE 1-continued

Structure and activity of of Exemplary Compounds

| Compound ID | STRUCTURE | MW | MAPKAPK5 IC$_{50}$ (nM) |
|---|---|---|---|
| 174 | 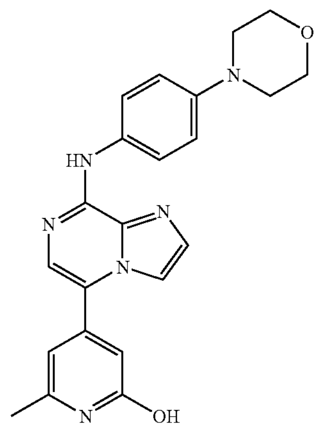 | 402.46 | + |
| 175 | 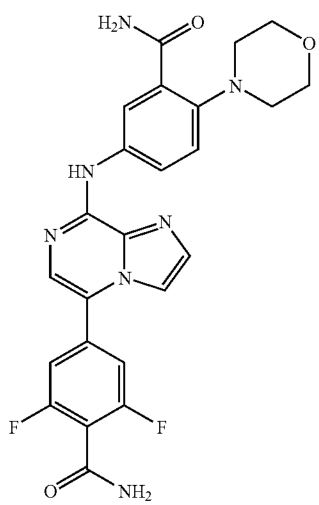 | 493.48 | +++ |
| 176 | 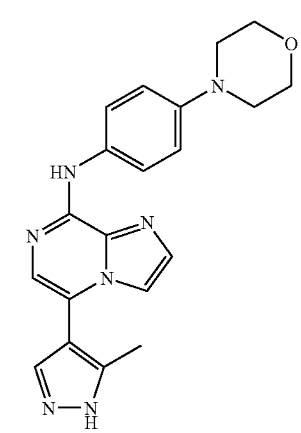 | 375.44 | ++ |

TABLE 1-continued

Structure and activity of of Exemplary Compounds

| Compound ID | STRUCTURE | MW | MAPKAPK5 IC$_{50}$ (nM) |
|---|---|---|---|
| 177 | 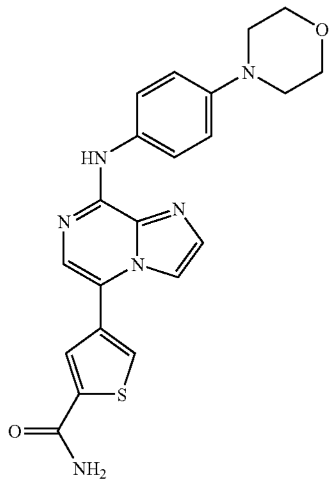 | 420.50 | +++ |
| 178 | 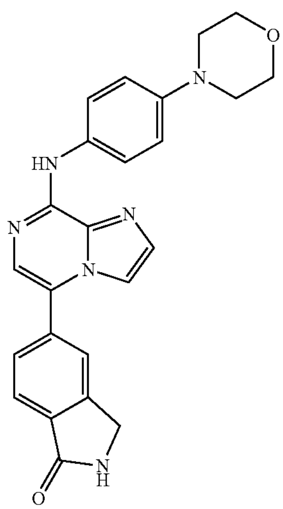 | 426.48 | +++ |
| 179 | 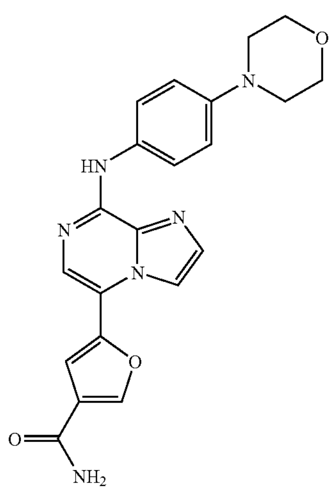 | 404.43 | +++ |

TABLE 1-continued

Structure and activity of of Exemplary Compounds

| Compound ID | STRUCTURE | MW | MAPKAPK5 IC$_{50}$ (nM) |
|---|---|---|---|
| 180 | 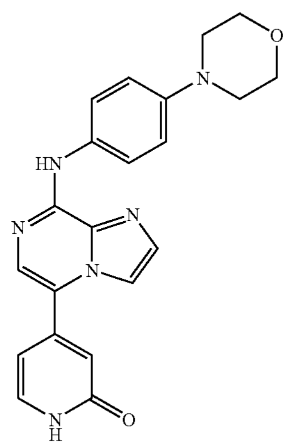 | 416.49 | + |
| 181 | 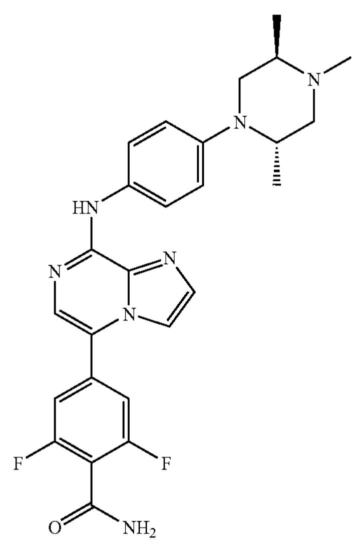 | 491.55 | +++ |
| 182 | 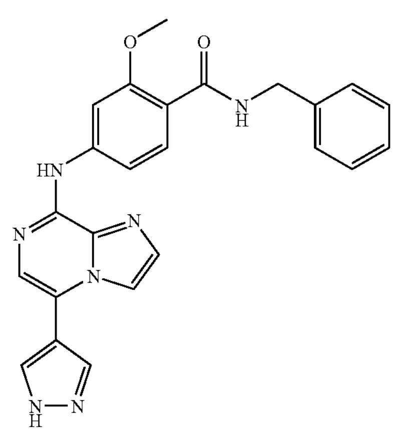 | 439.48 | + |

TABLE 1-continued
Structure and activity of of Exemplary Compounds
| Compound ID | STRUCTURE | MW | MAPKAPK5 IC$_{50}$ (nM) |
|---|---|---|---|
| 183 | 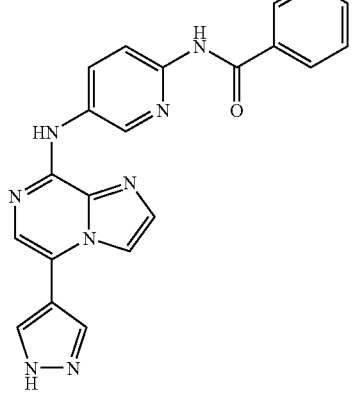 | 396.41 | + |
| 184 | 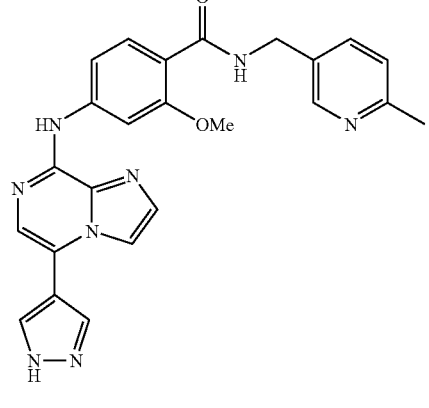 | 454.50 | |
| 185 | 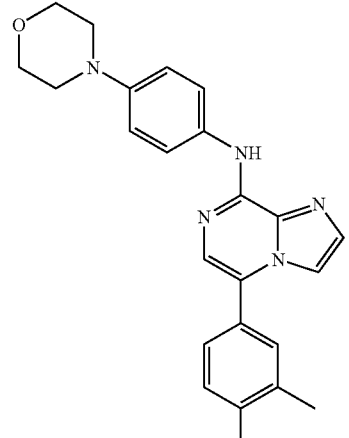 | 428.50 | + |

TABLE 1-continued

Structure and activity of of Exemplary Compounds

| Compound ID | STRUCTURE | MW | MAPKAPK5 IC$_{50}$ (nM) |
|---|---|---|---|
| 186 | 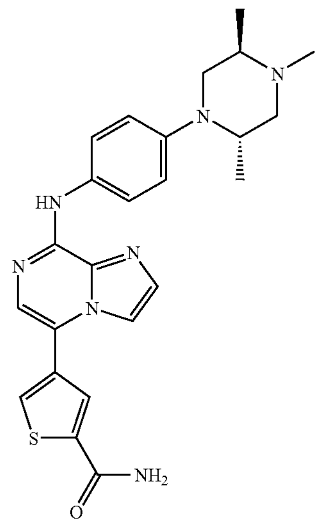 | 461.59 | +++ |
| 187 | 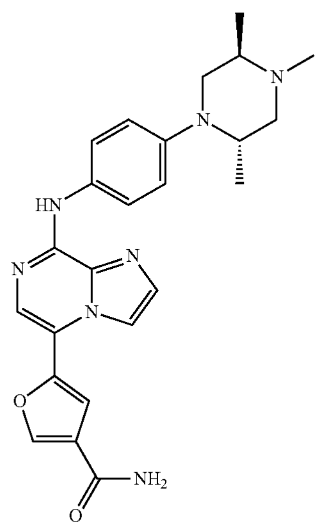 | 445.53 | ++++ |
| 188 | 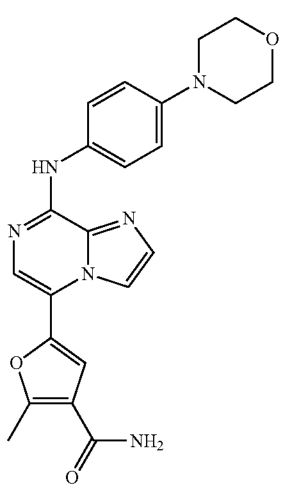 | 418.46 | + |

TABLE 1-continued

Structure and activity of of Exemplary Compounds

| Compound ID | STRUCTURE | MW | MAPKAPK5 IC$_{50}$ (nM) |
|---|---|---|---|
| 189 | 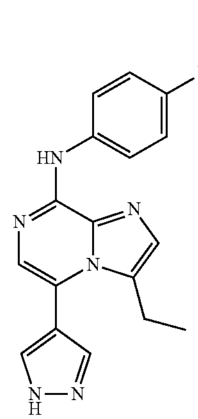 | 389.46 | + |
| 190 | 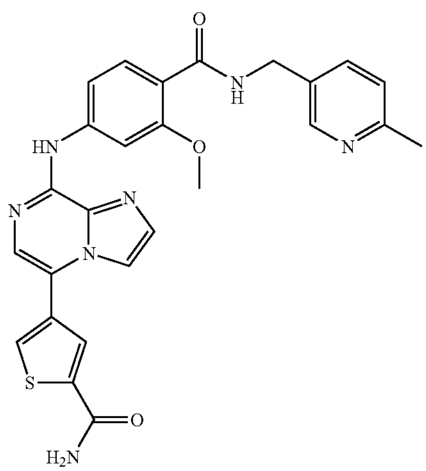 | 513.58 | + |
| 191 | 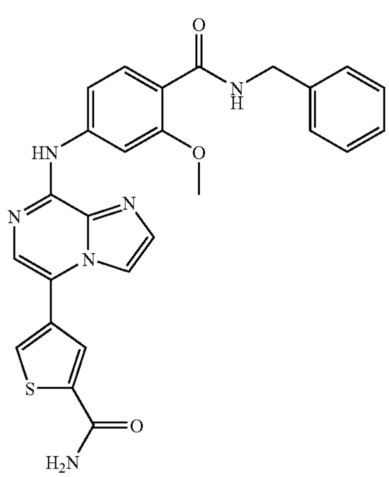 | 498.57 | + |

TABLE 1-continued
Structure and activity of of Exemplary Compounds
| Compound ID | STRUCTURE | MW | MAPKAPK5 IC$_{50}$ (nM) |
|---|---|---|---|
| 192 | 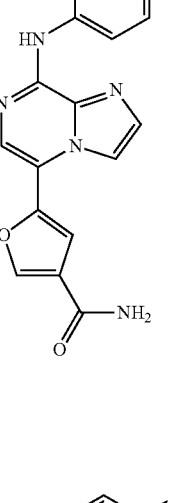 | 403.45 | ++++ |
| 193 | 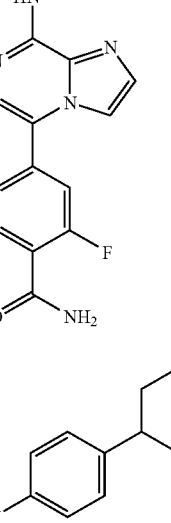 | 491.55 | ++ |
| 194 | 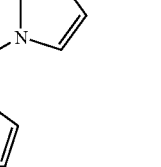 | 500.55 | + |

277
278
TABLE 1-continued
Structure and activity of of Exemplary Compounds
| Compound ID | STRUCTURE | MW | MAPKAPK5 IC$_{50}$ (nM) |
|---|---|---|---|
| 195 | 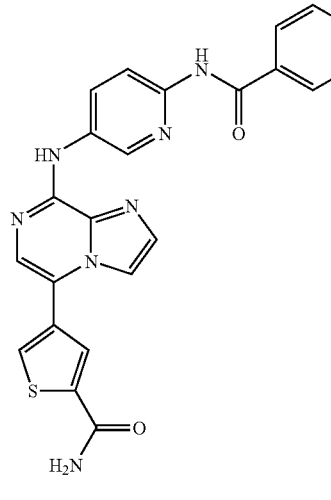 | 455.50 | + |
| 196 | 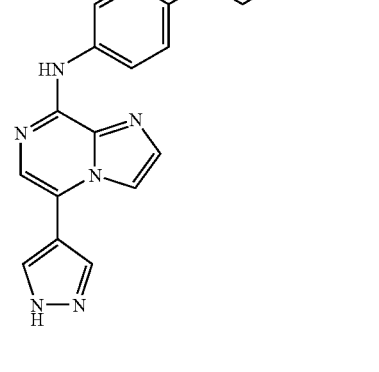 | 441.46 | + |
| 197 | 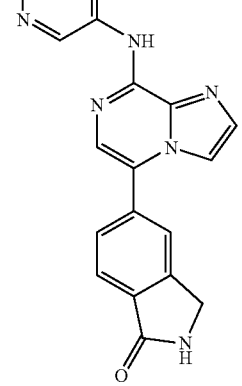 | 342.36 | +++ |

TABLE 1-continued
Structure and activity of of Exemplary Compounds
| Compound ID | STRUCTURE | MW | MAPKAPK5 IC$_{50}$ (nM) |
|---|---|---|---|
| 198 | 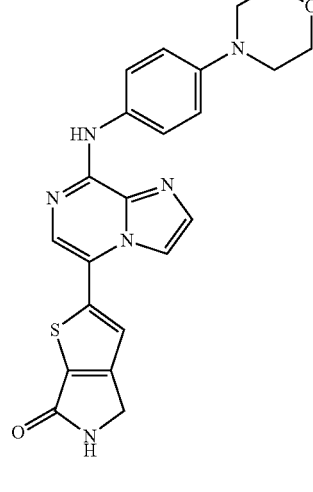 | 432.51 | +++ |
| 199 | 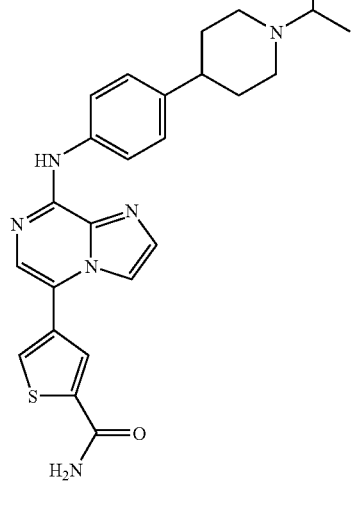 | 460.61 | +++ |
| 200 | 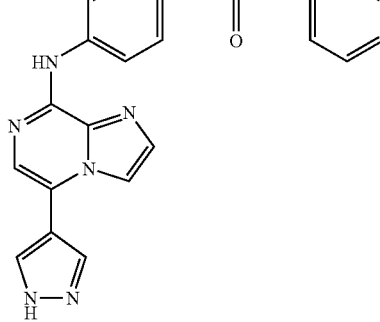 | 410.44 | + |

TABLE 1-continued

Structure and activity of of Exemplary Compounds

| Compound ID | STRUCTURE | MW | MAPKAPK5 IC$_{50}$ (nM) |
|---|---|---|---|
| 201 | 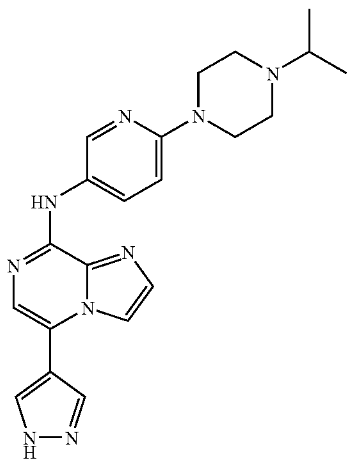 | 403.49 | ++ |
| 202 | 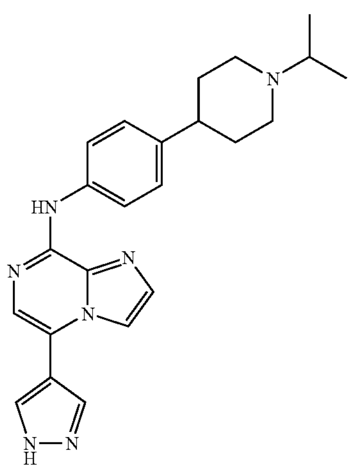 | 401.52 | +++ |
| 203 | 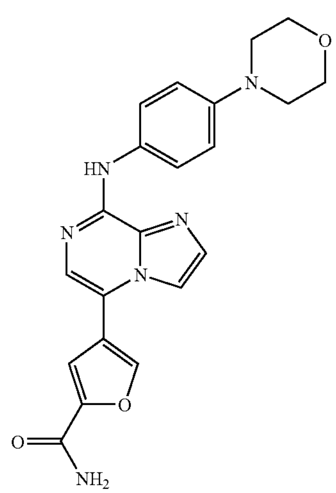 | 404.43 | ++++ |

TABLE 1-continued
Structure and activity of of Exemplary Compounds
| Compound ID | STRUCTURE | MW | MAPKAPK5 IC$_{50}$ (nM) |
|---|---|---|---|
| 204 | 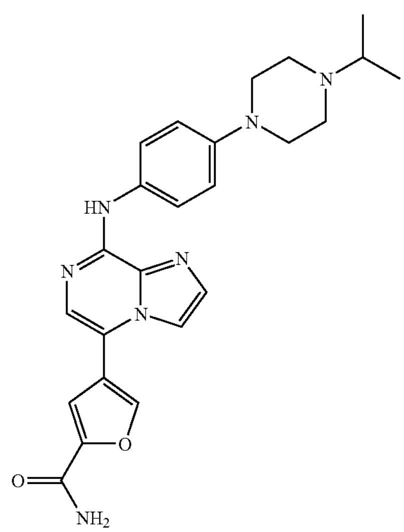 | 445.53 | +++ |
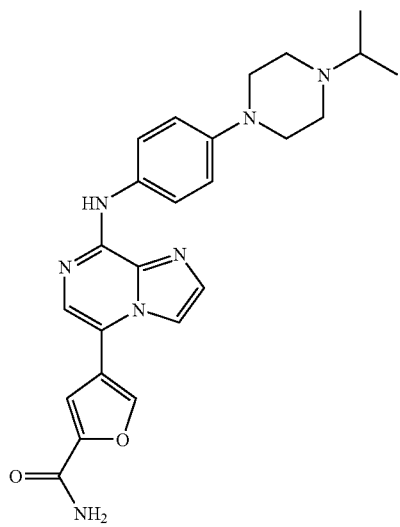
| 205 | | 467.58 | ++++ |
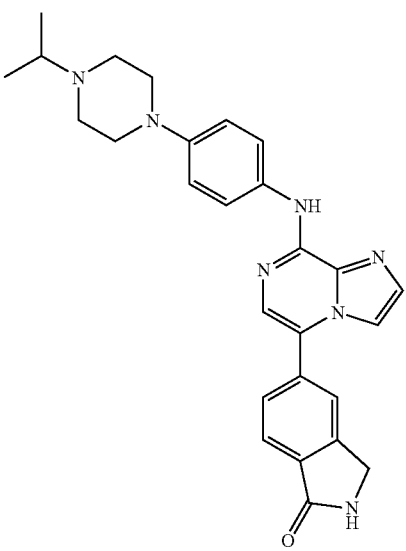

TABLE 1-continued

Structure and activity of of Exemplary Compounds

| Compound ID | STRUCTURE | MW | MAPKAPK5 IC$_{50}$ (nM) |
|---|---|---|---|
| 206 | 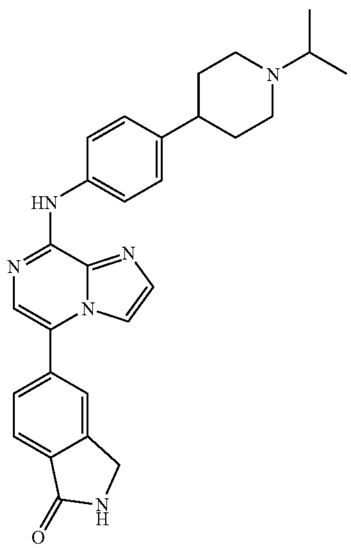 | 466.59 | ++++ |
| 207 | 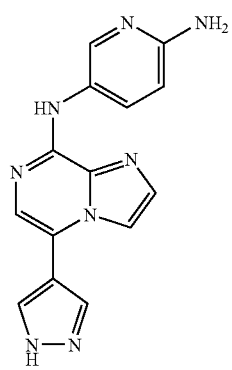 | 292.31 | ++ |
| 208 | 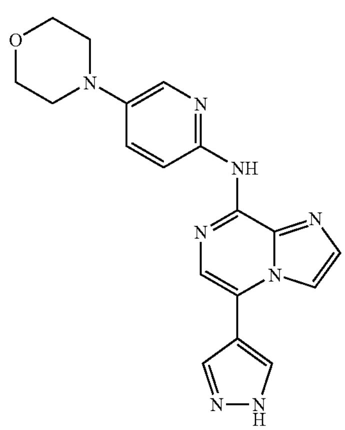 | 362.40 | + |

TABLE 1-continued
Structure and activity of of Exemplary Compounds
| Compound ID | STRUCTURE | MW | MAPKAPK5 IC$_{50}$ (nM) |
|---|---|---|---|
| 209 | 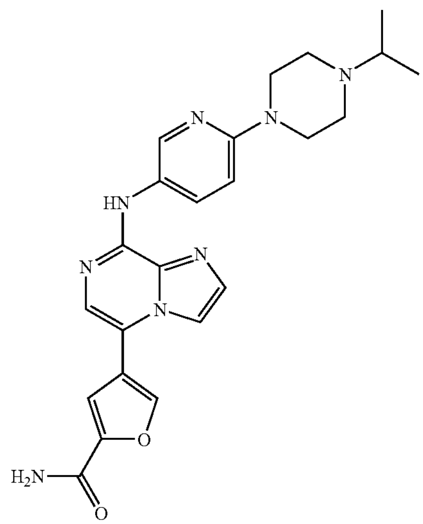 | 446.52 | +++ |
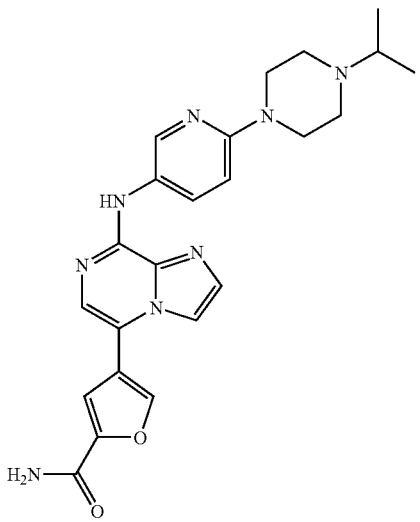
| 210 | | 468.57 | ++++ |
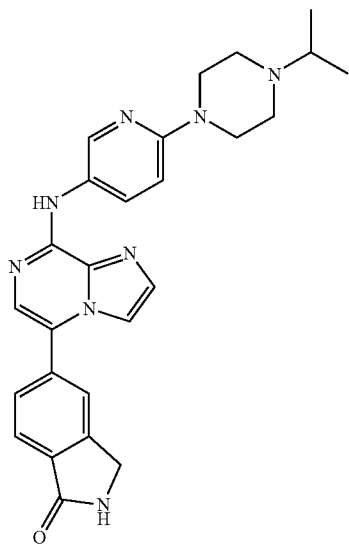

TABLE 1-continued
Structure and activity of of Exemplary Compounds
| Compound ID | STRUCTURE | MW | MAPKAPK5 IC$_{50}$ (nM) |
|---|---|---|---|
| 211 | 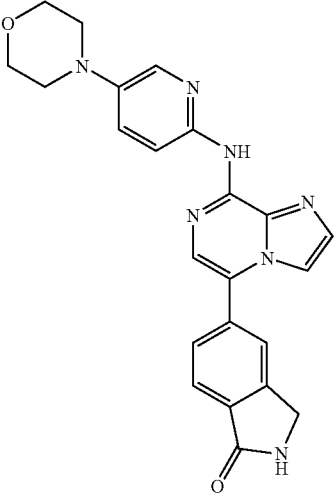 | 427.47 | +++ |
| 212 | 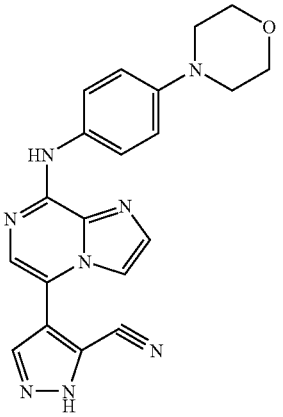 | 386.42 | +++ |
| 213 | 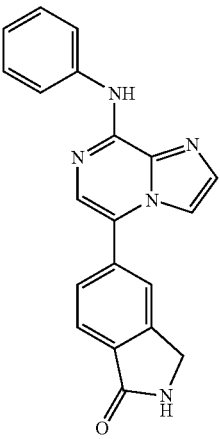 | 341.38 | +++ |

TABLE 1-continued
Structure and activity of of Exemplary Compounds
| Compound ID | STRUCTURE | MW | MAPKAPK5 IC$_{50}$ (nM) |
|---|---|---|---|
| 214 | 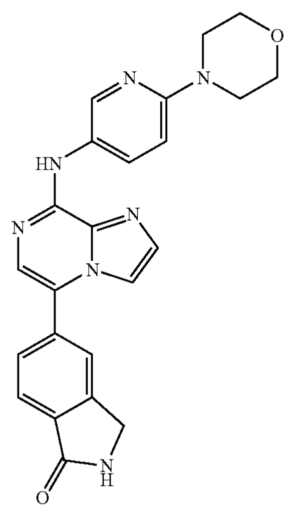 | 427.47 | ++++ |
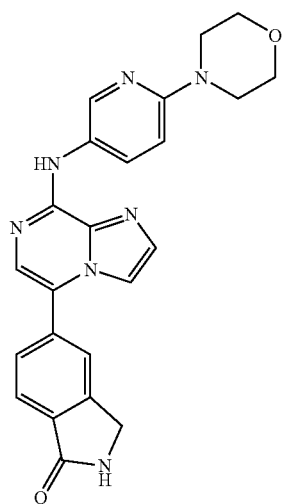
| 215 | | 428.46 | +++ |
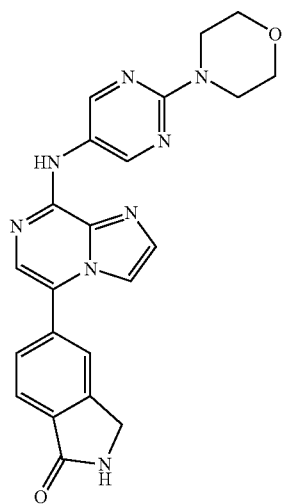

TABLE 1-continued
Structure and activity of of Exemplary Compounds
| Compound ID | STRUCTURE | MW | MAPKAPK5 IC$_{50}$ (nM) |
|---|---|---|---|
| 216 | 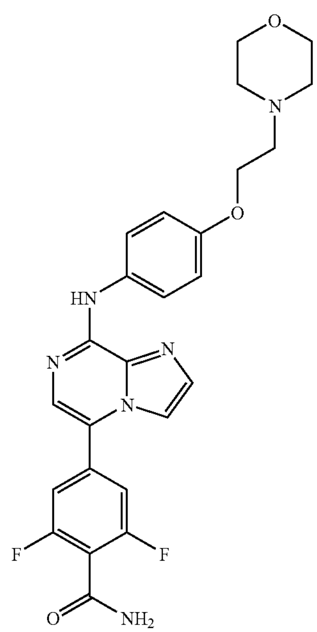 | 494.51 | ++ |
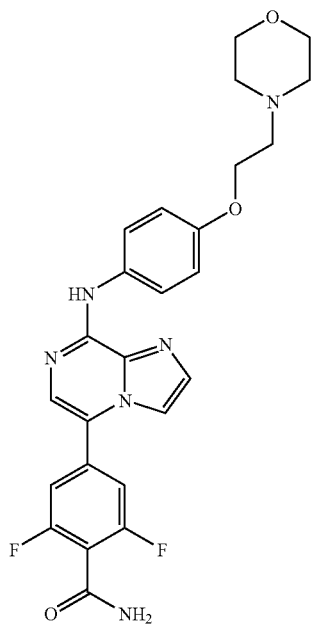
| 217 | | 416.44 | +++ |
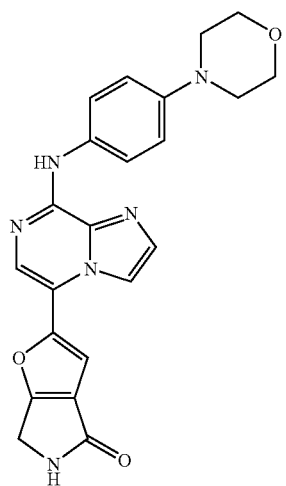

TABLE 1-continued
Structure and activity of of Exemplary Compounds
| Compound ID | STRUCTURE | MW | MAPKAPK5 IC$_{50}$ (nM) |
|---|---|---|---|
| 218 | 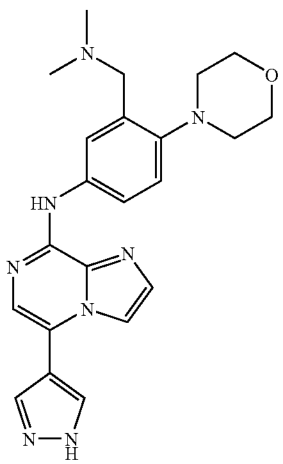 | 418.51 | + |
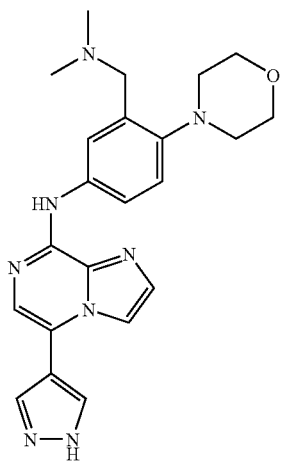
| | | | |
|---|---|---|---|
| 219 | | 469.55 | +++ |
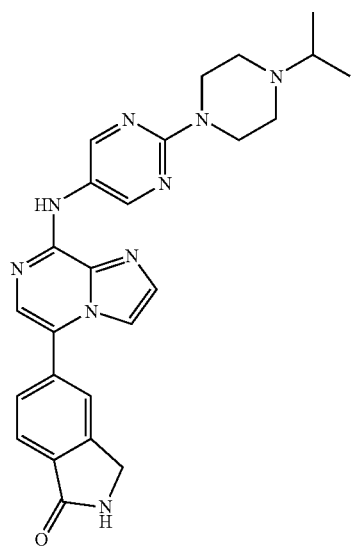

TABLE 1-continued

Structure and activity of of Exemplary Compounds

| Compound ID | STRUCTURE | MW | MAPKAPK5 IC$_{50}$ (nM) |
|---|---|---|---|
| 220 | 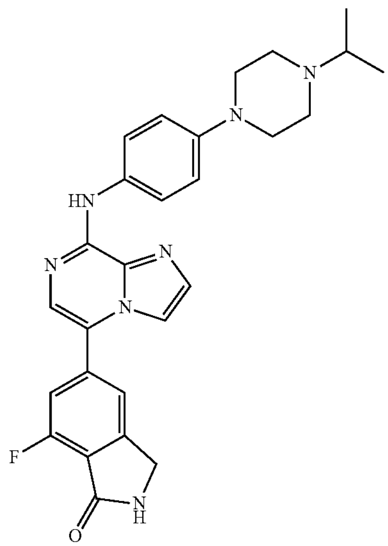 | 485.57 | ++++ |
| 222 | 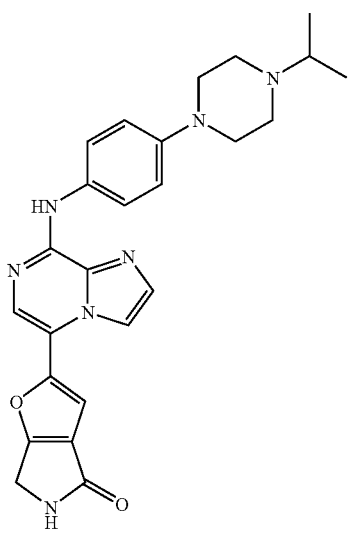 | 457.54 | +++ |
| 224 | 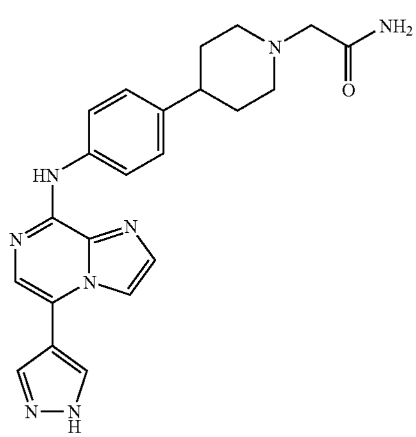 | 416.49 | ++ |

TABLE 1-continued
Structure and activity of of Exemplary Compounds
| Compound ID | STRUCTURE | MW | MAPKAPK5 IC$_{50}$ (nM) |
|---|---|---|---|
| 225 | 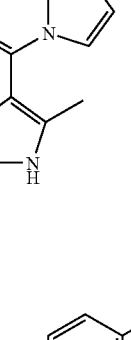 | 430.52 | ++ |
| 226 | 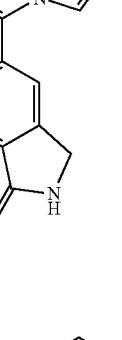 | 481.56 | +++ |
| 227 | 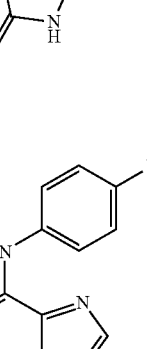 | 495.63 | + |

TABLE 1-continued

Structure and activity of of Exemplary Compounds

| Compound ID | STRUCTURE | MW | MAPKAPK5 IC$_{50}$ (nM) |
|---|---|---|---|
| 228 | 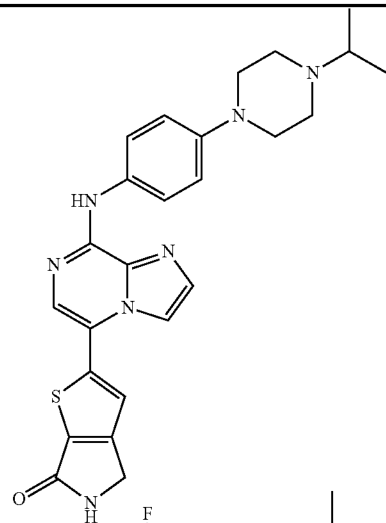 | 473.60 | +++ |
| 229 | 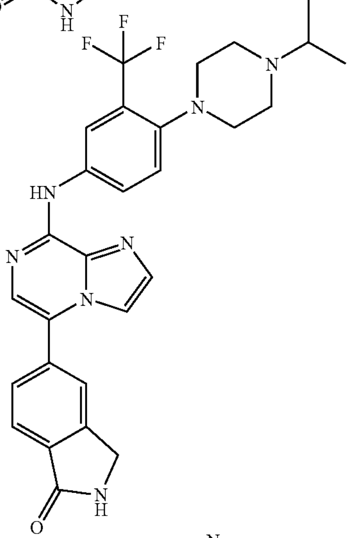 | 535.58 | |
| 230 | 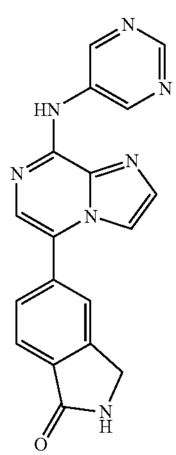 | 343.35 | +++ |

++++ compound exhibited MAPKAPK5 IC$_{50}$ 1-100 nM
+++ compound exhibited MAPKAPK5 IC$_{50}$ 101-500 nM
++ compound exhibited MAPKAPK5 IC$_{50}$ 501-1000 nM
+ compound exhibited MAPKAPK5 IC$_{50}$ >1000 nM

EXAMPLE 2

Development of an Assay for the Identification of Regulators of the Expression of MMP1 by Activated Primary Synovial Fibroblasts To identify compounds that decrease the ECM-degrading activity of cells, the ECM-degrading activity of cells may be induced to allow proper detection of this activity, and to achieve a clearer read-out. In the context of RA, the cells of choice are mammalian synovial fibroblasts and the triggers that may be used to induce the ECM-degrading activity are cytokines relevant in the field of arthritis: for instance TNF-α, IL1β, IL6, OSM, IL17, and MIF1-α. This list is not comprehensive due to the plethora of cytokines potentially involved in the RA pathogenesis (Smolen and Steiner, 2003). To set up an in vitro assay that is as close as possible to the complexity of the pathology, the trigger applied should be a mixture of factors generated by contacting cytokine-producing cells relevant in the field of arthritis, such as monocytes, macrophages, T-cells, and B-cells, with a trigger. The cytokine-producing cells will respond to the contact by producing a complex and unbiased mixture of factors. If the cytokine-producing cell used is also found in a pannus, and the cytokine applied to produce this trigger is found in the synovial fluid of rheumatoid arthritis patients, the mixture of factors ultimately produced will contain part of the factors that are present in the joints of arthritis patients.

Principle of the 'MMP Assay'

Matrix Metallo Proteases (MMPs) possess various physiological roles, as e.g. the maturation of other proteases, growth factors, and the degradation of extra-cellular matrix components. MMP1 is one of the members of the MMP family that is able to degrade native collagen, the main component of bone and cartilage. An increased expression of MMP1 by synovial fibroblasts (SFs) is diagnostic for the progression of the arthritic disease and is predictive for erosive processes in the joint (Cunnane et al., 2001). The expression of MMP1 by SFs: can be increased by the activation of SFs with triggers relevant for rheumatoid arthritis, as cytokines like TNF-α or IL1β (Andreakos et al., 2003). Taken together, measurement of the levels of MMP1 produced by activated SFs is a readout that is highly relevant in the context of RA as this event reflects the level of activation of SFs towards an erosive phenotype as it is seen in the pannus. If a reduced expression of a candidate drug target in activated SFs leads to the reduction of MMP1 expression by these cells, the drug target is then proven to be involved in the regulation of MMP1 expression and thus considered relevant for the development of therapeutic strategies for the treatment of RA.

In the following examples, the development of an assay, further referred to as 'MMP assay', monitors the MMP1 production by synovial fibroblasts (SFs) in response to diverse activating triggers (Example 2.1). The use of this assay is then described for the validation of gene products that are considered drug targets for the development of RA therapies (Example 2.2). The validation of drug targets is performed using recombinant adenoviruses, further referred to as knock-down viruses or Ad-siRNAs, that mediate the expression in cells of shRNA's which reduce the expression levels of targeted genes by a RNAi (RNA interference)-based mechanism, (see WO 03/020931). The identification of compounds modulating the activity of the validated drug targets is then described in Table B. The use of the 'MMP assay' for the testing of compounds that modulate the activity of the drug targets identified is described further below.

Control Viruses Used:

The control viruses used in these studies are listed below. dE1/dE2A adenoviruses are generated from these adapter plasmids by co-transfection of the helper plasmid pWEAd5AflII-rITR.dE2A in PER.E2A packaging cells, as described in WO99/64582.

Negative Control Viruses.
Ad5-eGFP_KD: Target sequence: GCTGACCCTGAAGT-TCATC (SEQ ID NO: 1). Cloned using Sap1-sites into vector and virus generated as described in WO03/02093 1.
Ad5-Luc_v13_KD: Target sequence GGTTACCTAAGGGT-GTGGC (SEQ ID NO: 2). Cloned using Sap1-sites into vector and virus generated as described in WO03/02093 1.
Ad5-M6PR_v1_KD: Target sequence CTCTGAGTGCAGT-GAAATC (SEQ ID NO: 3). Cloned using Sap1-sites into vector and virus generated as described in WO03/02093 1.

Positive Control Viruses:
Ad5-MMP1_v10_KD: Target sequence ACAAGAGCAA-GATGTGGAC (SEQ ID NO: 4). Cloned using Sap1-sites into vector and virus generated as described in WO03/02093 1.

Viruses Used for Target Validation:
Ad5-MAPKAPK5_v13_KD: Target sequence CGGCACTT-TACAGAGAAGC (SEQ ID NO: 5). Cloned using Sap1-sites into vector and virus generated as described in WO03/020931.
Ad5-MAPKAPK5_v12_KD: Target sequence ATGATGT-GTGCCACACACC (SEQ ID NO: 6). Cloned using Sap1-sites into vector and virus generated as described in WO03/02093 1.

EXAMPLE 2.1

Development of the MMP Assay

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 μg/mL anti-MMP1 antibody MAB1346 (Chemicon). The antibody is diluted in buffer 40 (1.21 g Tris base (Sigma), 0.58 g NaCl (Calbiochem) and 5 ml 10% $NaN_3$ (Sigma) in 1 L milliQ water and adjusted to pH 8.5). After overnight incubation at 4° C., plates are washed with PBS (80 g NaCl, 2g KCl (Sigma), 11.5 g $Na_2HPO_4.7H_2O$ and 2 g $KH_2PO_4$ in 10 L milliQ; pH 7.4) and blocked with 100 μL/well Casein buffer (2% Casein (VWR International) in PBS). Next day, casein buffer is removed from ELISA plates and replaced by 50 μL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 mL 0.5 M EDTA pH 8 (Invitrogen), 5 mL 10% $NaN_3$ in 1 L milliQ and adjusted to pH 7.0). 0.25 mM DTT (Sigma) is added to the thawed samples plates. After removal of the EC buffer, 20 μL of sample is transferred to the ELISA plates. After overnight incubation at 4° C. plates are washed twice with PBS and once with PBST (PBS with 0.05% Tween-20 (Sigma)) and incubated with 35 μL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0.5M EDTA pH 8 in 2 L milliQ and adjusted to pH 7.0) at a concentration of 5 µg/mL. After 2 h of incubation at RT, plates are washed as described above and incubated with 50 µL/well streptavidin-HRP conjugate (Biosource). Streptavidin-HRP conjugate is diluted in buffer C at a concentration of 0.25 µg/mL. After 45 min, plates are washed as described above and incubated for 5 min with 50 µL/well BM Chem ELISA Substrate (Roche). Readout is performed on the Luminoscan Ascent Luminometer (Labsystems) with an integration time of 200 msec or with an Envision reader (Perkin Elmer).

Figure 2:
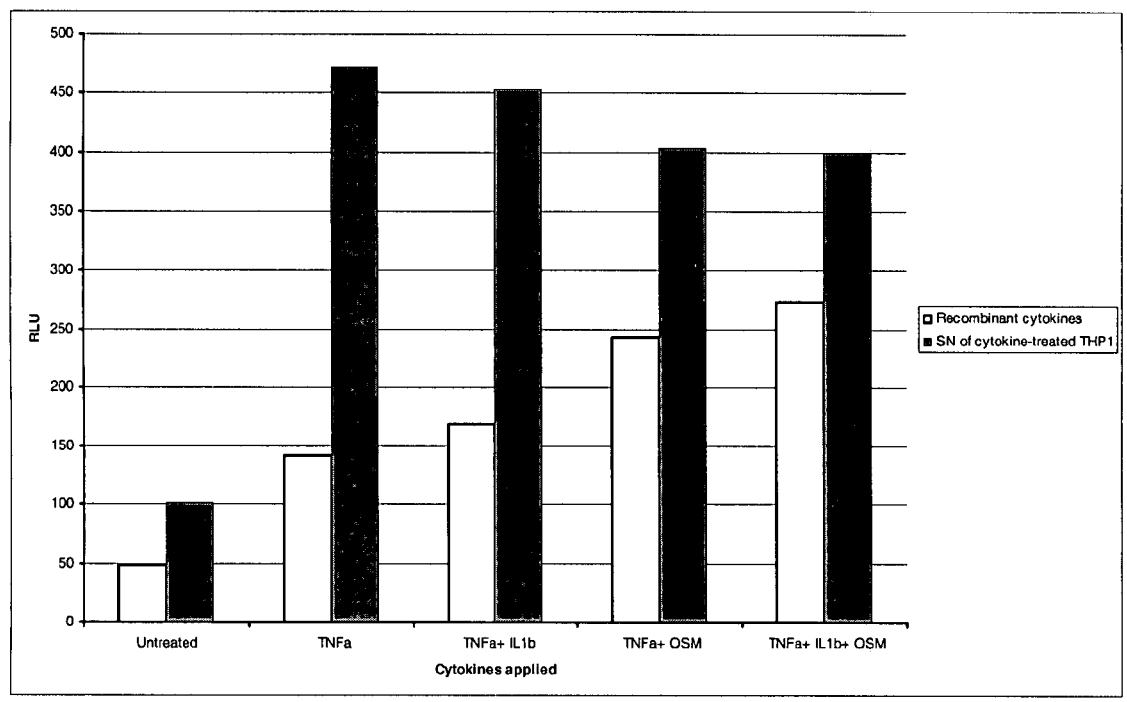
FIG. 2. This chart shows the increased expression of MMP1 in synovial fibroblasts triggered with cytokines involved in rheumatoid arthritis pathology.

The increase of MMP1 expression by SFs upon treatment with cytokines relevant in the field of RA (TNF-α, IL1β and OSM) or a combination thereof is shown in FIG. 2 as white bars. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/mL. 72 h after cytokine addition, the supernatant is collected and processed in the MMP1 ELISA as described in the protocol given above. In parallel with this experiment, SFs are triggered, using the same protocol, with the supernatant of THP1 cells (2-fold diluted in M199+1% FBS) treated with the same cytokines or combinations of cytokines for 48 h in M199 medium+1% FBS. MMP1 levels for these samples are shown in FIG. 2 as grey bars. The induction of the MMP1 expression by SFs triggered with the supernatants of TNF-α-treated THP1 cells is stronger (>4.5 fold induction) as compared to the SFs triggered with recombinant TNF-α alone (3-fold induction) and almost equals the 5-fold induction obtained by a mixture of 3 purified cytokines (TNF-α, IL1βb, OSM). This result indicates that the supernatant of TNF-α-induced THP1 cells contains, besides TNF-α, additional pro-inflammatory factors that activate SFs towards MMP1 expression. As the role of TNF-α in the RA pathogenesis is validated (TNF-α-blockers such as Infliximab and Etanercept show some efficacy in the treatment of RA patients) and the THP-1 cells are representative for monocytes/macrophages present in the joint of RA patients, the TNF-α-based trigger mixture prepared by contacting THP-1 cells with TNF-α will contain factors present in the joints of RA patients and subsequently is relevant to RA. This TNF-α-based complex trigger, further referred to as the 'complex trigger', will further be used as basis for the 'MMP assay'.

Figure 3:
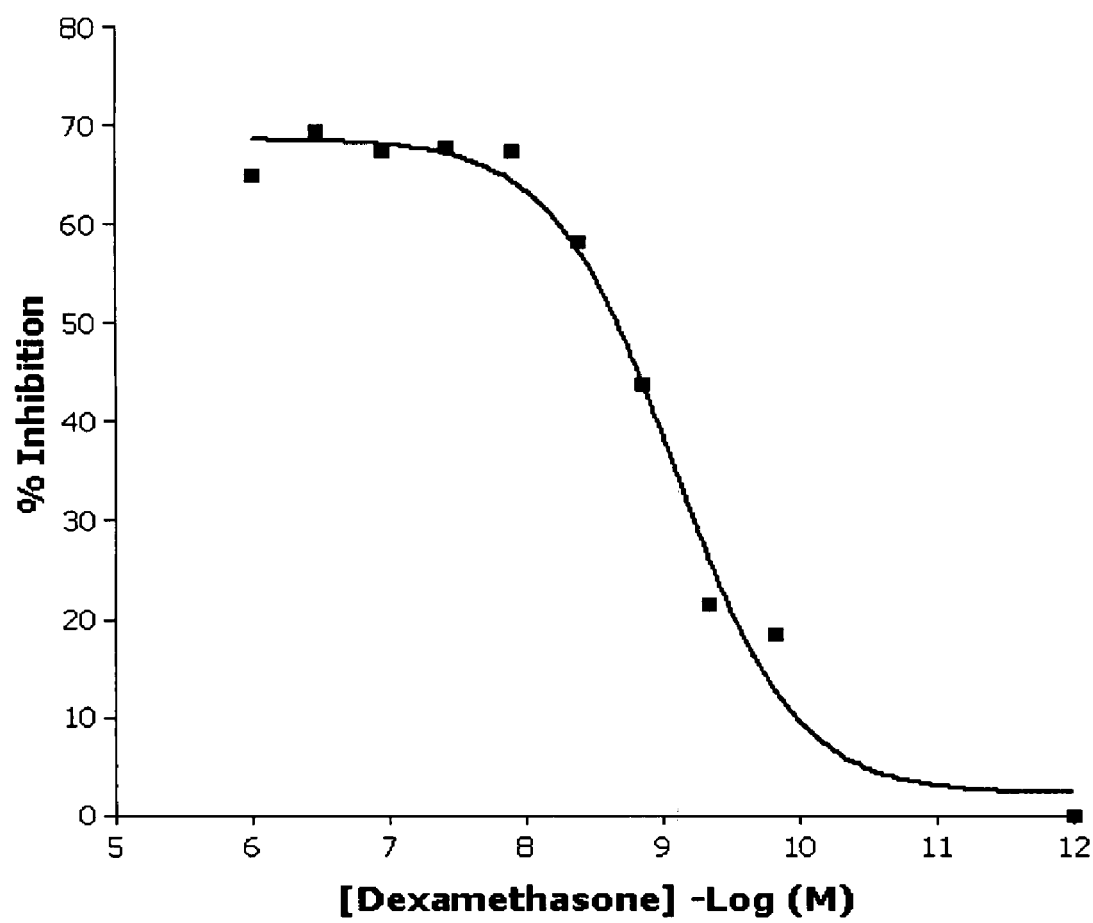
FIG. 3. This graph shows the dose-dependent inhibition of the "TNF-α-based trigger"-induced expression of MMP1 by SFs by a known anti-inflammatory compound.

Inhibition of the activation of SF by the 'complex trigger' is shown using dexamethasone, a potent anti-inflammatory agent that also strongly reduces collagen-induced arthritis in rodents (Yang et al., 2004) (FIG. 3). Dexamethasone is shown to dose-dependently reduce amounts of MMP1 produced by complex trigger activated SFs. SFs are seeded at a density of 3000 cells/well in 96 well plates. 24 hrs after seeding, increasing concentrations of dexamethasone are added to the cells. After overnight incubation, medium of every well is refreshed to supernatant of THP-1 cells treated with TNF-α (50% diluted in M199+0.5% FBS), and the same concentration of dexamethasone as added the day before. 48 hrs after treatment, the supernatant is collected and subjected to the MMP1 ELISA described above. The addition of dexamethasone clearly reduced the MMP1 expression by SFs, with an $IC_{50}$ value of about 1 nM (see FIG. 3). These data show that the MMP1 expression by activated SFs can be reduced by the addition of a physiologically relevant inhibitor and represent a proof of principle for the 'MMP assay'.

EXAMPLE 2.2

MAPKAPK5 Modulates SF 'Complex Trigger'-induced MMP1 Expression (A) Ad-siRNA Virus Functions to Knock Down MAPKAPK5 Expression.

Recombinant adenoviruses mediating the expression of siRNA's targeting MAPKAPK5 and eGFP are generated according to the procedure described in WO03/020931. The target sequence used in the recombinant adenovirus is: CGGCACTTTACAGAGAAGC (SEQ ID NO: 5) as well as ATGATGTGTGCCACACACC (SEQ ID NO: 6). The target sequence within the eGFP mRNA used in the recombinant adenovirus is: GCTGACCCTGAAGTTCATC (SEQ ID NO: 1). These sequences are cloned into the adapter plasmid using Sapl sites. dE1/dE2A adenoviruses are generated from these adapter plasmids by co-transfection of the helper plasmid pWEAd5AflII-rITR.dE2A in PER.E2A packaging cells, as described in WO99/64582.

Figure 4:
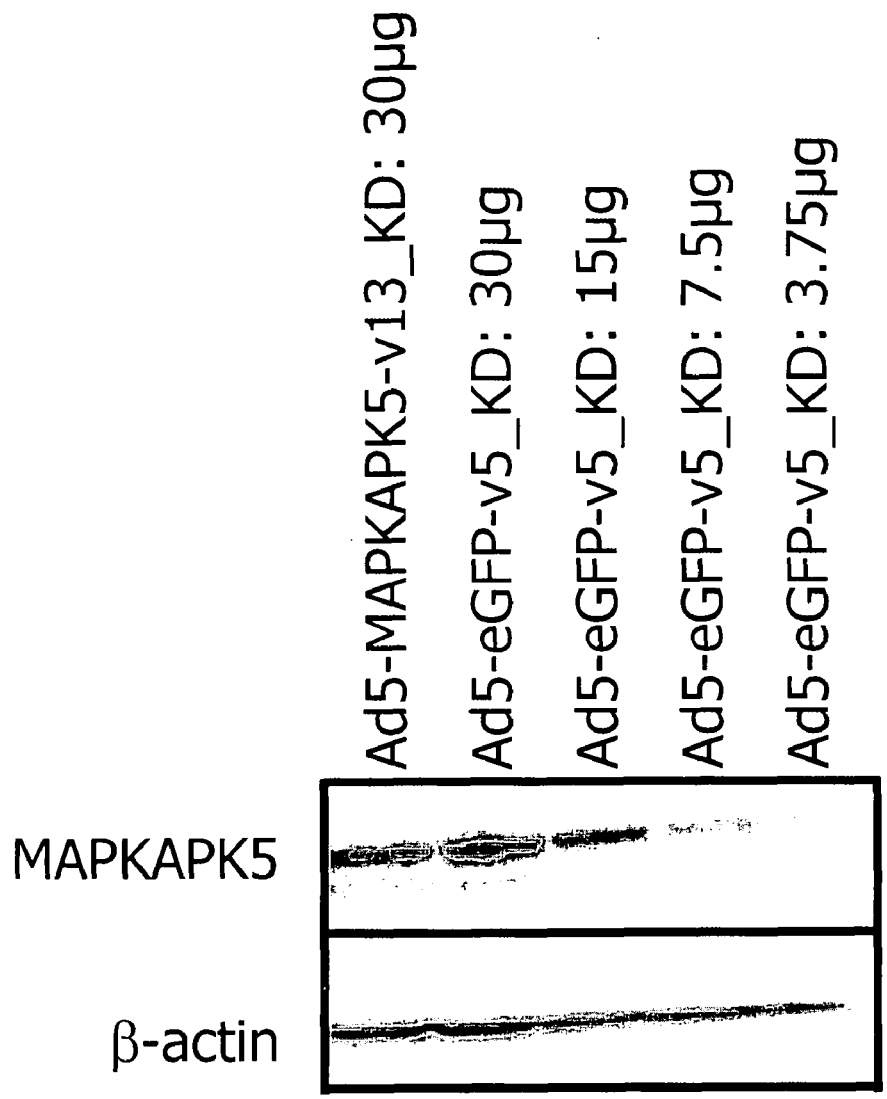
FIG. 4. This gel shows the reduction, at the protein level, of the expression of MAPKAPK5 in SFs by infection of the cells with Ad-siRNA virus targeting MAPKAPK5.

The functionality of an adenovirus targeting MAPKAPK5 is tested as follows. These adenoviruses are used to infect primary human SFs cultured in petri dishes as follows. On day 1, 500.000 SFs are seeded per petri dish. One day later, the cells are infected with Ad5-MAPKAPK5-v13_KD (1.6E9 VP/mL) or Ad5-eGFP-v5_KD (1.3E10 VP/mL) at an MOI of 4000 (based on the titers (number of virus particles per mL) defined for the viruses by Q-rt-PCR). On day 7, cells are detached from the petri dish according to standard procedure using a trypsin EDTA solution. The trypsin is then neutralized by addition of DMEM growth medium supplemented with 10% FBS. The cells are then collected by a centrifugation step (1000 rpm, 5 min). The pellet is lysed in 100 µL of fresh RIPA buffer (50 mM Tris pH7.5, 150 mM NaCl, 1% deoxycholate, 1% Triton X100, 0.1% SDS). The samples are then sonicated for 10 sec. The protein concentration of the samples is then determined using the BCA kit (Pierce, Cat N° 23227) as described by the provider, using BSA as a standard. To 30 µg of cell lysate diluted to 19.5 µl in RIPA buffer, 3.5 µL of reducing agent (NuPage reducing agent N° 10, Invitrogen NP0004) and 7.5 µL of sample buffer (NuPage LDS sample buffer, Invitrogen NP0007) are added. The 30 µL sample is then boiled for 5 min and loaded on a 10% polyacrylamide gel (Invitrogen NP0301). To allow the estimation of the level of protein knock-down, 15 µg, 7.5 µg and 3.75 µg of the lysate of the Ad5-eGFP-v5_KD infected cells are also loaded onto the gel. The gel is then run for 2 hours at 100V in 1× MOPS/SDS NuPage running buffer (Invitrogen NP001). 10 µl of Seablue Plus Prestained standard (Invitrogen LC5925) is used to estimate protein size on the gel. The proteins on the gel are then transferred onto a PVDF membrane (Invitrogen LC2002) by a wet blotting procedure using a transfer buffer prepared by mixing 100 ml Nupage Transfer buffer 20*(NP0006-1), 400 mL methanol and 1500 mL Milli Q water. Before the transfer, the membrane is first soaked in methanol and in transfer buffer. The transfer is performed at 100V for 90 minutes. The membrane is then blocked by 30 min soaking in blocking buffer (2% blocking blocking powder (Amersham, RPN 2109) prepared in PBST (PBS supplemented with 0.1% Tween 20 (Sigma, P1379)). After blocking, the immunodetection is performed using a mouse monoclonal antibody against MAPKAPK5 (BD Biosciences, Cat N° 612080) diluted 250 fold in blocking buffer. After overnight incubation with this primary antibody, the membrane is washed 3 times with PBST and incubated 1 hr with the secondary antibody ((Polyclonal goat anti-mouse Ig, HRP conjugated (DAKO P0447) diluted 50000 fold in blocking buffer. The blot is then washed 3 times in PBST and the detection is performed with ECL advance (RPN2109, Amersham) on a Kodakimager according to the manufacturers instructions. The Western Blotting revealed a lower expression level of MAPKAPK5 in the Ad5-MAPKAPK5-v13_KD infected cells compared to the cells infected with the Ad5-eGFP-v5_KD negative control virus. Comparison with the diluted Ad5-eGFP-v5_KD infected samples allowed to estimate the reduction in expression to be 2-fold. Equal loading of the 30 µg samples is demonstrated by immunodetection of β-actin after removal of the MAPKAPK5 antibody by a 'stripping procedure' (5 minutes boiling of the membrane in PBST). Immunodetection of β-actin is performed according to the method described for MAPKAPK5 detection, but using a goat polyclonal antibody against β-actin (Santa Cruz, Cat N° SC-1615) at a 1000 fold dilution as primary antibody and a rabbit anti goat antibody at a 50000 fold dilution as a secondary antibody. Results of this experiment are given in FIG. 4. Taken together, this experiment demonstrated the functionality of the Ad-siRNA virus produced to reduce the MAPKAPK5 expression levels in primary human SFs.

(B) MAPKAPK5 Knock-Down Ad-siRNA Reduces SF-Induced MMP1 Expression

Figure 5:
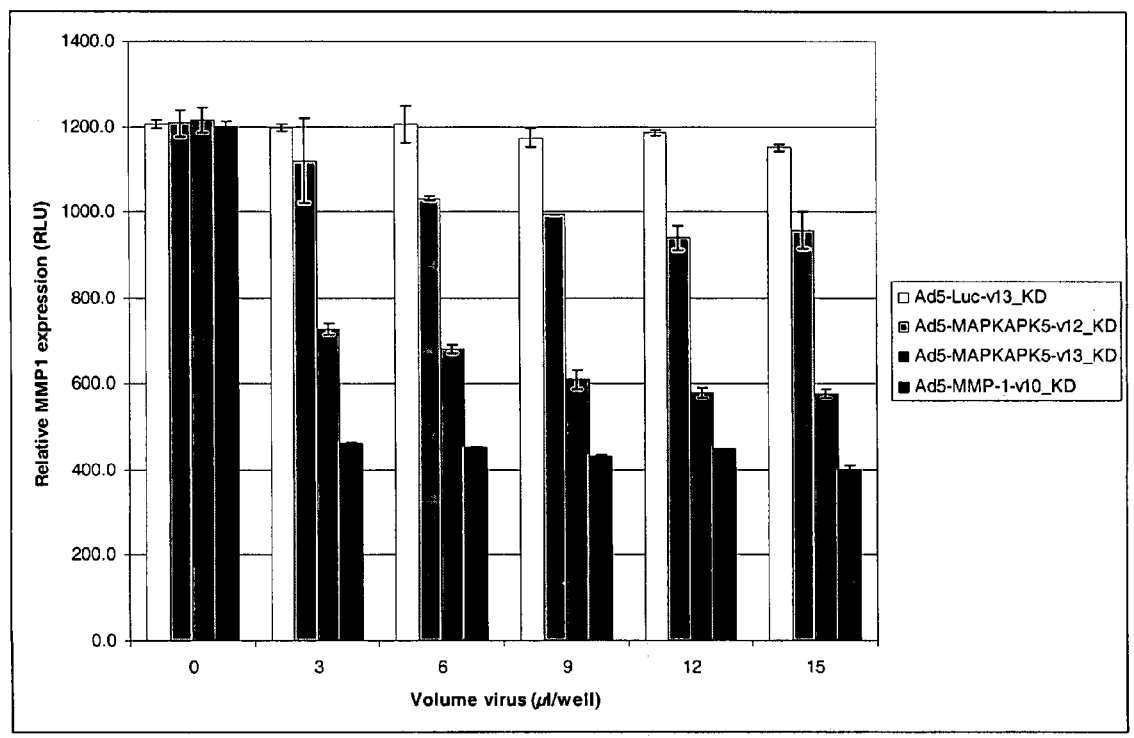
FIG. 5. This chart shows the reduction of 'complex trigger' induced levels of MMP1 expression by SFs by an Ad-siRNA virus targeting MAPKAPK5.

The efficacy of Ad5-MAPKAPK5-v13_KD virus in the 'MMP assay' is tested as follows. Day 1, SFs (passage 9 to 10) are seeded in 96 well plates at a density of 3000 cells per well in complete synovial growth medium (Cell Applications). One day later, the cells are infected with increasing amounts (3, 6; 9, 12 or 15 l) of following viruses: Ad5-eGFP-v5_KD, Ad5-MAPKAPK5-v12_KD, Ad5-MAPKAPK5-v13_KD, Ad5-MMP1-v10_KD. The virus load is corrected by addition of the neutral virus Ad5-Luc-v13_KD to bring the final virus volume on the cells to 15 µL in every well. This correction guarantees that the effects observed do not result from the virus load applied to the cells. The cells are then incubated for 5 days before the activation step. This step involves the replacement, in every well, of the growth medium by 75 µL of M199 medium supplemented with 25 µL of 'complex trigger'. 48 hrs after the activation step, the supernatant is collected and subjected to the MMP1 ELISA as described in Example 1. The results of the experiment are shown in FIG. 5. The quality of the experiment is demonstrated by the efficacy of the Ad-siRNA virus targeting MMP1 itself. This positive control virus strongly reduces the MMP1 expression by SFs, whereas the negative control virus, designed to target the expression of luciferase, does not influence the levels of MMP1 expression. Two viruses used to validate the MAPKAPK5 target (Ad5-MAPKAPK5-v12_KD and Ad5-MAPKAPK5-v13) do also lead to a clear reduction of the complex trigger induced MMP1 expression by primary human SFs. It can be concluded, from this experiment, that MAPKAPK5 represents a valuable drug target that is shown to modulate MMP1 expression in SFs. Similarly, the inhibition of MAPKAPK5 enzymatic activity by a small molecule compound is expected to reduce the 'complex cytokine' induced MMP1 expression in the 'MMP assay'. The inhibition of MAPKAPK5 enzymatic activity by a small molecule compound is also predicted to reduce the degradation of the joint associated with RA.

(C) In vitro 'MMP Assay' Testing of Compounds Inhibiting MAPKAPK5

Compounds inhibiting the MAPKAPK5 activity in a biochemical assay (i.e. cell free, using purified enzyme), are tested in the 'MMP assay' according to following protocol.

The compound master stocks (all at 10 mM concentration in 100% DMSO) are diluted 10-fold in water (Distilled water, GIBCO, DNAse and RNAse free) to obtain a 1 mM intermediate work stock in 10% DMSO. This intermediate work stock is further diluted either 3-fold (or 10-fold) in 10% DMSO to obtain an intermediate work stock of 333 µM (or 100 µM) concentration, respectively, in 10% DMSO. The 1 mM as well as 333 µM (or 100 µM) intermediate work stocks are then further diluted 10-fold in 1.1% DMSO to obtain the 10× workstocks at 100 µM and 33.3 µM (or 10 µM) concentration in 2% DMSO. This 10× work stock is then diluted 10-fold in M199 medium supplemented with 1% FBS to obtain the final '1 compound preparation' containing the compounds at 10 µM and 3.33 µM (or 1 µM) as well as 0.2% DMSO. These are the final conditions at which the compounds are tested on the cells. In parallel, the 10× work stock is diluted 10-fold in 'complex trigger' (i.e. the supernatant of TNF-α treated THP1 cells produced as described in Example 1) that is diluted 2-fold in M199 supplemented with 1% FBS to produce the '1× compound in 50% complex trigger preparation'.

At day 1, RASFs are seeded in 96 well plates (Flat bottom, tissue culture treated, Greiner) at a density of 3000 cells/well in complete synovial growth medium (Cell Applications). Day 5, the compounds are added to the cultured cells as follows. Medium is completely removed from the cells and replaced by 75 µL of the '1× compound preparations' containing the compounds at either 10 µM or 3.33 µM (or 1 µM) in M199 medium supplemented with 1% FBS and 0.2% DMSO. After an incubation period of 2 hours, which allows the compounds to equilibrate and enter the cells, 25 µL of the '1× compound in 50% complex trigger preparations' are added to the wells on top of the '1× compound preparation', in the wells containing the corresponding compounds at corresponding concentration. In this way, an 8-fold diluted complex trigger is ultimately applied to the cells. An incubation of 48 hrs is then performed and 20 µl of the cell supernatant is then processed in the MMP1 ELISA as described above, delivering raw data (RLU: relative luminescence units). Following controls are included in the experiments. A maximal signal control, in which the cells are activated by the complex trigger but only the 0.2% DMSO vehicle (and thus no compound) is added. This control indicates the maximal level of MMP1 that can be achieved in the test. A minimal signal control is also included in these experiments. Here, cells are not triggered. The medium of the cells is then changed to 100 µl M199 medium supplemented with 1% FBS at day 5. This control returns the basal MMP1 levels produced by the RASFs. The percent inhibition of the MMP1 expression achieved by the compounds is then calculated based on the RLU data returned by the ELISA with following formula: [[(maximal MMP1 levels−minimal MMP1 levels)−(MMP1 level compound X at concentration Y−minimal MMP1 levels)]/(maximal MMP1 levels−minimal MMP1 levels)]×100.

Toxicity of the compounds is assessed as follows. Day 1, SFs are seeded in white, tissue culture treated 96 well plates at a density of 3000 cells per well in 100 µL complete synovial growth medium. The compound handling, compound addition to the cells as well as activation of the cells is further performed as described above in this example for the determination of the MMP I levels. After the 48 hrs incubation period, the medium is removed from the wells, replaced by 50

µL fresh M199 medium supplemented with 1% FBS. 50 µL of substrate (Promega Celltiter Glow cell viability kit) is then added to the wells. After an incubation period of 10 min, luminescence signal is measured. A reduction of the luminescence signal by more than 50% as compared to the maximal control wells is considered to reflect significant toxicity. No toxicity is observed for the compounds tested in the 'MMP assay'.

It should be understood that factors such as the differential cell penetration capacity of the various compounds can contribute to discrepancies between the activity of the compounds in the in vitro biochemical and cellular MMP assays.

For the purpose of Table 2 below, MMP1 $EC_{50}$ of each compound, which can be determined using the assay method described herein, is expressed as follows:

TABLE 2

| Compd ID | MMP1 $EC_{50}$ (nM) |
|---|---|
| 1 | * |
| 2 | * |
| 3 | |
| 4 | *** |
| 5 | *** |
| 6 | * |
| 7 | * |
| 8 | |
| 9 | * |
| 10 | * |
| 11 | * |
| 12 | * |
| 13 | ** |
| 14 | * |
| 15 | * |
| 16 | * |
| 17 | * |
| 18 | * |
| 19 | ** |
| 20 | * |
| 21 | * |
| 22 | * |
| 23 | * |
| 24 | * |
| 25 | * |
| 26 | ** |
| 27 | * |
| 28 | ** |
| 29 | * |
| 30 | * |
| 31 | * |
| 32 | * |
| 33 | * |
| 34 | ** |
| 35 | * |
| 36 | * |
| 37 | * |
| 38 | * |
| 39 | * |
| 40 | * |
| 41 | * |
| 42 | * |
| 43 | * |
| 44 | * |
| 45 | * |
| 46 | * |
| 47 | * |
| 48 | * |
| 49 | * |
| 50 | * |
| 51 | * |
| 52 | * |
| 53 | * |
| 54 | * |
| 55 | * |
| 56 | * |
| 57 | * |
| 58 | * |
| 59 | * |
| 60 | * |
| 61 | * |
| 62 | * |
| 63 | * |
| 64 | * |
| 65 | * |
| 66 | * |
| 67 | * |
| 68 | * |
| 69 | * |
| 70 | * |
| 71 | * |
| 72 | * |
| 73 | * |
| 74 | * |
| 75 | * |
| 76 | * |
| 77 | * |
| 78 | * |
| 79 | * |
| 80 | * |
| 81 | * |
| 82 | * |
| 83 | * |
| 84 | * |
| 85 | ** |
| 86 | * |
| 87 | * |
| 88 | * |
| 89 | ** |
| 90 | *** |
| 91 | * |
| 92 | * |
| 93 | * |
| 94 | * |
| 95 | *** |
| 96 | * |
| 97 | * |
| 98 | ** |
| 99 | * |
| 100 | * |
| 101 | * |
| 102 | * |
| 103 | * |
| 104 | * |
| 105 | * |
| 106 | * |
| 107 | * |
| 108 | *** |
| 109 | * |
| 111 | * |
| 112 | *** |
| 114 | * |
| 115 | * |
| 116 | * |
| 117 | * |
| 118 | * |
| 119 | * |
| 120 | * |
| 121 | * |
| 122 | *** |
| 123 | *** |
| 124 | * |
| 125 | * |
| 126 | * |
| 127 | *** |
| 128 | * |
| 129 | * |
| 130 | * |
| 131 | * |
| 132 | * |
| 133 | *** |

TABLE 2-continued

| Compd ID | MMP1 EC$_{50}$ (nM) |
|---|---|
| 134 | *** |
| 135 | * |
| 136 | * |
| 137 | *** |
| 138 | * |
| 139 | * |
| 140 | * |
| 141 | ** |
| 142 | ** |
| 143 | ** |
| 144 | *** |
| 145 | ** |
| 146 | ** |
| 147 | *** |
| 148 | ** |
| 149 | * |
| 150 | * |
| 151 | *** |
| 152 | *** |
| 153 | *** |
| 154 | **** |
| 155 | *** |
| 156 | *** |
| 157 | * |
| 158 | * |
| 159 | *** |
| 160 | * |
| 161 | * |
| 162 | ** |
| 163 | * |
| 164 | * |
| 165 | * |
| 166 | * |
| 167 | * |
| 168 | * |
| 169 | *** |
| 170 | *** |
| 171 | *** |
| 172 | * |
| 173 | * |
| 174 | *** |
| 175 | ** |
| 176 | * |
| 177 | *** |
| 178 | *** |
| 179 | *** |
| 180 |  |
| 181 | * |
| 182 | * |
| 183 | *** |
| 184 | *** |
| 185 | ** |
| 186 | ** |
| 187 | *** |
| 188 | ** |
| 189 | ** |
| 190 | *** |
| 191 | * |
| 192 | ** |
| 193 | ** |
| 194 | ** |
| 195 | * |
| 196 | * |
| 197 | ** |
| 198 | *** |
| 199 | *** |
| 200 | *** |
| 201 | * |
| 202 | * |
| 203 | ** |
| 204 | ** |
| 205 | * |
| 206 | * |
| 207 | * |
| 208 | * |

TABLE 2-continued

| Compd ID | MMP1 EC$_{50}$ (nM) |
|---|---|
| 209 | * |
| 210 | ** |
| 211 | * |
| 212 | *** |
| 213 | *** |
| 214 | * |
| 215 | * |
| 216 | * |
| 217 | * |
| 218 | * |
| 219 | ** |
| 220 | * |
| 222 | ** |
| 224 | * |
| 225 | * |
| 226 | * |
| 227 | * |
| 228 |  |

EXAMPLE 3

Assay to Assess Effect of Compounds on Cytokine Release by Human PBMCs

Human peripheral blood mononuclear cells (PBMCs) are isolated from "buffy coats" prepared from the blood of healthy volunteers, isolated essentially according to method of Boyum (1984). In brief, buffy coat is diluted 1:1 with 1× PBS (Gibco) and 30 mL is carefully put on top of 20 mL Lymphoprep™ (Lucron Bioproducts) in 50 mL Falcon tubes. After centrifugation (35 min 400 g, 18° C.) the mononuclear cells are collected from the white interphase and washed 3 times with 1× PBS by resuspending and centrifugation (10 min, 200 g). Isolated PBMCs are finally resuspended in RPMI 1640 (Cat. No. 21875, Gibco) that is supplemented with 10% heat-inactivated FBS (Hyclone).

For the assay PBMCs are seeded at 2.5E6 cells/mL in 160 µL in 96-well plates (Nunc). Serial dilution of the test compounds are made first in DMSO (Sigma) and then diluted 50-fold in M199 medium (Gibco) containing 1% heat-inactivated FBS. Compounds are further ¹/₁₀ diluted in the assay plates to obtain final DMSO concentration of 0.2%. Cells are preincubated with the compounds for 1 hr at 37° C., 5% CO$_2$. Then, cells are stimulated with LPS (*Escherichia coli* serotype 026:B6, Cat. No. L2654, Sigma) that is added in a volume of 20 µL to a final concentration of 1 µg/mL and cells are further cultured for 24 hr. The plates are centrifuged and the supernatant is collected and stored at −80° C. until analysis of appropriate dilutions in ELISAs.

The following 384-well chemiluminescent ELISA protocol was developed to measure TNFα levels in the supernatant: White Lumitrac 600 384-well plates (Greiner) are coated with (40 µL/well) anti-TNFα capture antibody (Cat. No. 551220, BD Pharmingen) that is diluted to 1 µg/mL in 1× PBS (Gibco). After overnight incubation at 4° C., plates are washed with 1× PBS (80 g NaCl, 2 g KCl (Sigma), 11.5 g Na$_2$HPO$_4$.7H2O and 2 g KH$_2$PO$_4$ in 10 L milliQ; pH 7.4) and blocked with 100 µL/well buffer B (1× PBS containing 1% BSA (Sigma), 5% sucrose (Sigma) and 0.05% NaN$_3$ (Sigma)). After 4 hr incubation at RT, blocking buffer is removed and plates are washed once with PBST (1× PBS with 0.05% Tween-20 (Sigma)). Then, 40 µL of sample is transferred to the ELISA plates and plates are incubated at 4° C.

Next day, plates are washed 3 times (twice with PBST and once with PBS) and 35 µL/well biotinylated anti-TNFα antibody (Cat. No. 554511, BD Pharmingen) diluted first to a concentration of 250 ng/ml in buffer D (1× PBS with 1% BSA) is added. After 2 h of incubation at RT, plates are washed as described above and 35 µL/well of a ½₀₀₀ dilution of streptavidin-HRP conjugate (Cat. No. SNN2004, Biosource) in buffer D is added. After 45 min, plates are washed as described above and incubated for 5 min with 50 µL/well BM Chemiluminescence ELISA Substrate POD (Roche). Readout is performed on the Luminoscan Ascent Luminometer (Labsystems) with an integration time of 100 msec delivering raw data (RLU: relative luminescence units). The following controls are included in the experiments, a maximal signal control, in which the cells are activated by LPS but only the 0.2% DMSO vehicle (and thus no compound) is added. This control indicates the maximal level of TNFα that can be achieved in the test. A minimal signal control is also included in these experiments. Here, cells are not triggered. This control returns the basal TNFα levels produced by the PBMCs. The percent inhibition (PIN) of the TNFα release, achieved by the compounds is then calculated based on the RLU data returned by the ELISA with following formula: 100−[((TNFα level compound X at concentration Y−minimal TNFα levels)/(maximal TNFα levels−minimal TNFα levels))×100]. Where compounds are tested at 8 concentrations (⅓ serial dilution), EC50-values can be calculated by curve fitting of the means of the PIN data achieved for a compound at each test concentration.

To assay the effect of compounds on the release of IL1 and IL6 by LPS stimulated PBMC cultures, appropriate dilutions of the supernatant can be measured using the same ELISA protocol as described above. Matched pair antibodies for IL1 and IL6 ELISA (all from R&D Systems) may be used as follows: anti-IL1 capture antibody (Cat. No. MAB601) used at 0.5 µg/mL, biotinylated anti-IL1 detection antibody (Cat. No. BAF201) used at 50 ng/mL; anti-IL6 capture antibody (Cat. No. MAB206) used at 1 µg/mL; biotinylated anti-IL6 detection antibody (Cat. No. BAF206) used at 50 ng/mL.

For the purpose of Table 3 below, PBMC $EC_{50}$ of each compound, which can be determined using the assay method described herein, is expressed as follows:

TABLE 3

| Compound # | PBMC $EC_{50}$ (nM) |
|---|---|
| 1 | # |
| 11 | # |
| 13 | # |
| 14 | # |
| 26 | # |
| 32 | # |
| 35 | ## |
| 36 | # |
| 41 | # |
| 45 | # |
| 53 | # |
| 55 | # |
| 56 | # |
| 64 | # |
| 69 | ## |
| 71 | # |
| 82 | # |
| 83 | # |
| 85 | # |
| 89 | # |
| 90 | # |
| 93 | # |
| 98 | # |
| 102 | # |
| 114 | # |
| 116 | # |
| 118 | # |
| 119 | # |
| 120 | # |
| 122 | # |
| 123 | # |
| 124 | ## |
| 125 | # |
| 127 | # |
| 128 | # |
| 129 | # |
| 136 | ### |
| 137 | # |
| 138 | ### |
| 139 | # |
| 140 | # |
| 141 | # |
| 142 | # |
| 143 | # |
| 144 | #### |
| 145 | # |
| 146 | # |
| 149 | # |
| 150 | # |
| 151 | # |
| 152 | ### |
| 153 | #### |
| 155 | # |
| 156 | # |
| 158 | ### |
| 159 | # |
| 160 | # |
| 163 | # |
| 165 | # |
| 166 | # |
| 167 | #### |
| 168 | # |
| 169 | # |
| 171 | # |
| 173 | # |
| 176 | # |
| 177 | # |
| 178 | #### |
| 179 | # |
| 181 | # |
| 186 | # |
| 187 | # |
| 188 | # |
| 192 | # |
| 193 | # |
| 197 | # |
| 198 | # |
| 203 | # |
| 204 | # |
| 205 | # |
| 210 | # |
| 218 | # |

The present invention relates also to a method of treatment or prevention of inflammatory diseases, which comprises administering to a subject in need thereof, a therapeutically effective inhibitor of Mitogen-Activated Protein Kinase-Activated Protein Kinase 5 inhibiting amount of a compound according to Formula 1.

Another aspect of the present method invention relates to a method of treatment or prophylaxis of a condition characterised by abnormal matrix metallo proteinase activity, which comprises administering a therapeutically effective amount of a matrix metallo proteinase inhibiting compound according to Formula 1.

A further aspect of the present method invention is a method of treatment or prophylaxis of a condition selected from diseases involving degradation of extra-cellular matrix, which comprises administering a therapeutically effective matrix metallo proteinase inhibiting amount of a compound according to Formula 1.

A yet further aspect of the present method invention is a method of treatment or prophylaxis of a condition selected from diseases involving abnormal cellular expression of MMP1, which comprises administering a therapeutically effective matrix metallo proteinase inhibiting amount of a compound according to Formula 1.

A special embodiment of the present method invention is a method of treatment or prevention of rheumatoid arthritis, which comprises administering to a subject in need thereof, a therapeutically effective amount of a compound according to Formula 1.

This invention also relates to the use of the present compounds in the manufacture of a medicament for treatment or prophylaxis of a condition prevented, ameliorated or eliminated by administration of an inhibitor of Mitogen-Activated Protein Kinase-Activated Protein Kinase 5, or a condition characterised by abnormal collagenase activity, or a condition selected from diseases involving inflammation, most preferably in for the treatment of rheumatoid arthritis.

Administering of the compound of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The compound of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammatory, with an effective matrix metallo-protease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A preferred therapeutically effective amount of the compound of the present invention to administer to a subject patient is about 0.1 mg/kg to about 10 mg/kg administered from once to three times a day. For example, an effective regimen of the present method may administer about 5 mg to about 1000 mg of said compound of the present invention from once to three times a day. It will be understood, however, that the specific dose level for any particular subject patient will depend upon a variety of factors including the age, body weight, general health, sex, diet, time of administration, route of administration, rate of excretion, drug combination and the severity of the particular inflammatory condition. A consideration of these factors is well within the purview of the ordinarily skilled clinician for the purpose of determining the therapeutically effective or prophylactically effective dosage amount needed to prevent, counter, or arrest the progress of the condition.

Compounds of the invention can be incorporated into pharmaceutical compositions suitable for administration. Such compositions typically comprise at least one compound of the invention and at least one pharmaceutically acceptable carrier. As used herein the language "pharmaceutically acceptable carrier" is intended to include solid carriers such as lactose, magnesium stearate, terra alba, sucrose, talc, stearic acid, gelatin, agar, pectin, acacia or the like; and liquids such as vegetable oils, arachis oil and sterile water, or the like, any and all solvents, dispersion media, coatings, antibacterial and antifungal agents, isotonic and absorption delaying agents, and the like, compatible with pharmaceutical administration. This listing of pharmaceutically acceptable carriers is not to be construed as limiting. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

A compound according to an embodiment of the invention may be provided as a salt, preferably as a pharmaceutically acceptable salt of compounds of formula 1. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminum, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts of compounds according to an embodiment of the invention may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

References

Choy E H, Panayi G S. (2001). N Engl J Med. 344: 907-16.
Firestein G S. (2003). Nature. 423:356-61.
Smolen J S, Steiner G. (2003). Nat Rev Drug Discov. 2: 473-88.
Lee D M, Weinblatt M E (2001). Lancet. 358: 903-11.
Kremer J. M., Westhovens R., Leon M., Di Giorgio E., Alten R., Steinfeld S., Russell A., Dougados M., Emery P., Nuamah I. F., Williams G. R., Becker J. -C., Hagerty D. T., Moreland L. W. (2003) N Engl J Med. 349:1907-1915.
Edwards J. C. W., Szczepanski L., Szechinski J., Filipowicz-Sosnowska A., Emery P., Close D. R., Stevens R. M., Shaw T. (2004) N Engl J Med. 350:2572-2581.
O'Dell J R, Leff R, Paulsen G, Haire C, Mallek J, Eckhoff P J, Fernandez A, Blakely K, Wees S, Stoner J, Hadley S, Felt J, Palmer W, Waytz P, Churchill M, Klassen L, Moore G. (2002) Arthritis Rheum. 46:1164-70.
St Clair E W, van der Heijde D M, Smolen J S, Maini R N, Bathon J M, Emery P, Keystone E, Schiff M, Kalden J R, Wang B, Dewoody K, Weiss R, Baker D; (2004) Combination of infliximab and methotrexate therapy for early rheumatoid arthritis: a randomized, controlled trial. Arthritis Rheum. 50 :3432-43.
Gomez-Reino J J, et al. (2003). Arthritis Rheum. 48: 2122-7.
O'Dell J R. (2004) Therapeutic strategies for rheumatoid arthritis. N Engl J Med. 350(25):2591-602.
New L, Jiang Y, Han J. (2003) Regulation of PRAK subcellular location by p38 MAP kinases. Mol Biol Cell. 14(6):2603-16.
Shi Y, Kotlyarov A, Laabeta K, Gruber A D, Butt E, Marcus K, Meyer H E, Friedrich A, Volk H D, Gaestel M. (2003) Elimination of protein kinase MK5/PRAK activity by targeted homologous recombination. Mol Cell Biol. 23:7732-41.
Seternes O M, Mikalsen T, Johansen B, Michaelsen E, Armstrong C G, Morrice NA, Turgeon B, Meloche S, Moens U, Keyse S M. (2004) Activation of MK5/PRAK by the atypical MAP kinase ERK3 defines a novel signal transduction pathway. EMBO J. 23:4780-91.
Andreakos E, et al. (2003). Arthritis Rheum. 48: 1901-12.
Cunnane G, et al. (2001). Arthritis Rheum 44: 2263-74.
Coussens L M, et al. (2002). Science 295: 2387-92.
Creemers E E, et al. (2001). Circ Res. 2001 89:201-10
Gapski R, et al. (2004). J Periodontol. 75:441-52.
Reif S, Somech R, Brazovski E, Reich R, Belson A, Konikoff F M, Kessler A. (2005) Digestion. 71:124-130.
Rosenberg G A. (2002). Glia. 39:279-91.
Schanstra J P, et al. (2002). J Clin Invest. 110:371-9.
Suzuki R, et al. (2004). Treat Respir Med. 3:17-27.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using MDL's ISIS Draw Autonom Software tool and are not verified. Preferably, in the event of inconsistency, the depicted structure governs.

What is claimed is:

1. A compound according to formula IVa, IVb, or IVc:

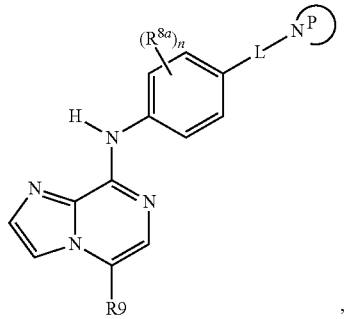
IVa

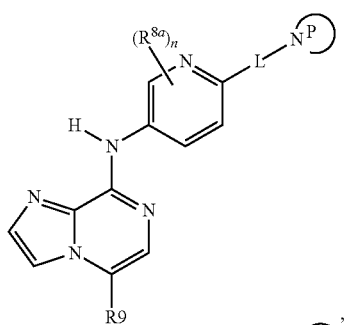
IVb

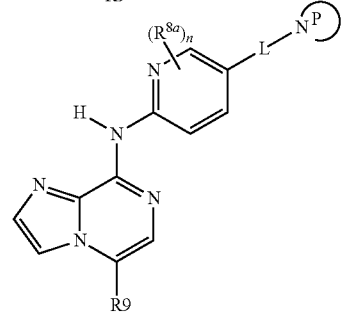
IVc wherein L is —CON(H)—CH$_2$—CH$_2$—; the ring P is substituted or unsubstituted heterocycloalkyl; the subscript n, is selected from 1-4; each R$^{8a}$ is independently selected from hydrogen, substituted or unsubstituted alkyl, alkoxy, cyano, and halo; and R$^9$ is independently selected from substituted or unsubstituted aryl and heteroaryl; or a pharmaceutically acceptable salt, thereof; or stereoisomers or tautomers thereof.

2. A compound according to formula IVa, IVb, or IVc:

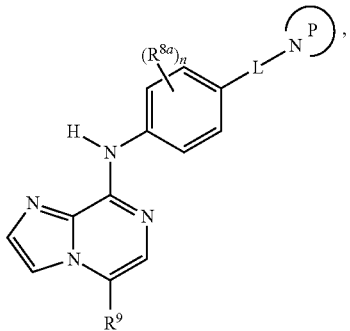
IVa

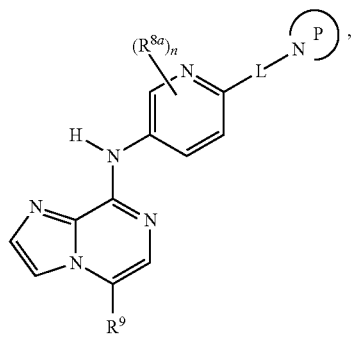
IVb

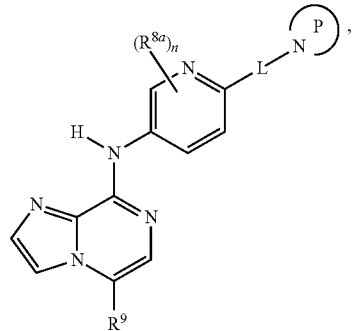
IVc wherein L is —OCH$_2$—CH$_2$— or —NHCH$_2$—CH$_2$—; the ring P is substituted or unsubstituted heterocycloalkyl; the subscript n, is selected from 1-4; each R$^{8a}$ is independently selected from hydrogen, substituted or unsubstituted alkyl, alkoxy, cyano, and halo; and R$^9$ is independently selected from substituted or unsubstituted aryl and heteroaryl; or a pharmaceutically acceptable salt, thereof; or stereoisomers or tautomers thereof.

3. A compound according to any one of claims 1 and 2, wherein the ring P is substituted or unsubstituted piperidine, morpholine or piperazine.

4. A compound according to formula III;

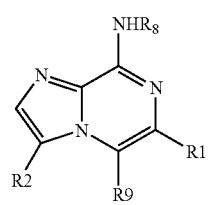
(III)

wherein

R$^1$ is H, or substituted or unsubstituted alkyl; R$^2$ is H, lower alkyl, lower cycloalkyl and lower alkyl-lower cycloalkyl, optionally substituted with one or more of F and Cl; R$^8$ is

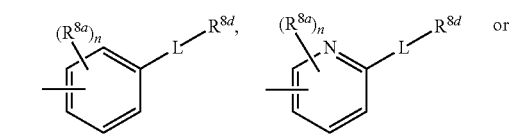

-continued

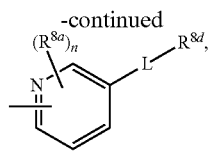

L is selected from a single bond, alkylene, —O—, —N(R$^{8e}$)—, —CO—, —CO$_2$—, —SO—, —SO$_2$—, —CON(R$^{8e}$)—, —SO$_2$N(R$^{8e}$)—, —N(R$^{8e}$)CO—, —N(R$^{8e}$)SO$_2$—, —N(R$^{8e}$)CO N(R$^{8e}$)—, —N(R$^{8e}$)SO$_2$ N(R$^{8e}$)—; —O(CR$^{8e}$$_2$)$_{m1}$—, or —CON(R$^{8e}$)(CR$^{8e}$$_2$)$_{m1}$—;

each R$^{8a}$ independently selected from hydrogen, substituted or unsubstituted alkyl, alkoxy, cyano, and halo;

R$^{8d}$ is selected from substituted or unsubstituted heterocycloalkyl;

R$^{8e}$ is selected from H, substituted or unsubstituted alkyl and substituted or unsubstituted cycloalkyl;

the subscript m1 is 1, 2, 3, or 4; the subscript n is 1, 2, 3, or 4;

and wherein R$^9$ is

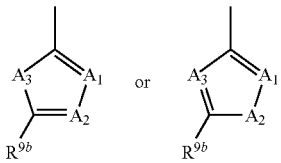

and each of A$^1$, A$^2$ and A$^3$ is independently selected from S, O, N, NR$^{9a}$, and CR$^{9a}$; each of R$^{9a}$ is independently H or substituted or unsubstituted alkyl; and R$^{9b}$ is CONH$_2$, CONHMe, or CN;

or a pharmaceutically acceptable salt, thereof; or stereoisomers or tautomers thereof.

5. A compound according to formula III;

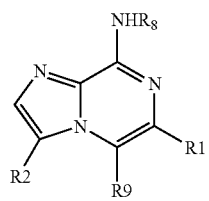

wherein

R$^1$ is H, or substituted or unsubstituted alkyl; R$^2$ is H, lower alkyl, lower cycloalkyl and lower alkyl-lower cycloalkyl, optionally substituted with one or more of F and Cl; R$^8$ is

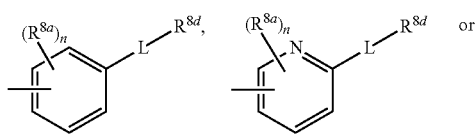

-continued

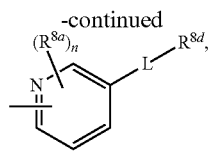

L is selected from a single bond, alkylene, —O—, —N(R$^{8e}$)—, —CO—, —CO$_2$—, —SO—, —SO$_2$—, —CON(R$^{8e}$)—, —SO$_2$N(R$^{8e}$)—, —N(R$^{8e}$)CO—, —N(R$^{8e}$)SO$_2$—, —N(R$^{8e}$)CON(R$^{8e}$)—, —N(R$^{8e}$)SO$_2$ N(R$^{8e}$)—; —O(CR$^{8e}$$_2$)$_{m1}$—, or —CON(R$^{8e}$)(CR$^{8e}$$_2$)$_{m1}$—;

each R$^{8a}$ is independently selected from hydrogen, substituted or unsubstituted alkyl, alkoxy, cyano, and halo;

R$^{8d}$ is selected from substituted or unsubstituted heterocycloalkyl;

R$^{8e}$ is selected from H, substituted or unsubstituted alkyl and substituted or unsubstituted cycloalkyl;

the subscript m1 is 1, 2, 3, or 4; the subscript n is 1, 2, 3, or 4;

and wherein R$^9$ is

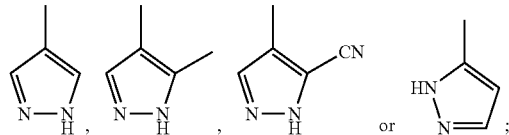

or a pharmaceutically acceptable salt, thereof; or stereoisomers or tautomers thereof.

6. A compound according to formula III:

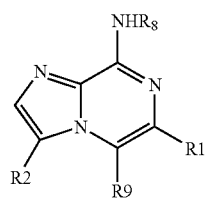

wherein

R$^1$ is H, or substituted or unsubstituted alkyl; R$^2$ is H, lower alkyl, lower cycloalkyl and lower alkyl-lower cycloalkyl, optionally substituted with one or more of F and Cl; R$^8$ is

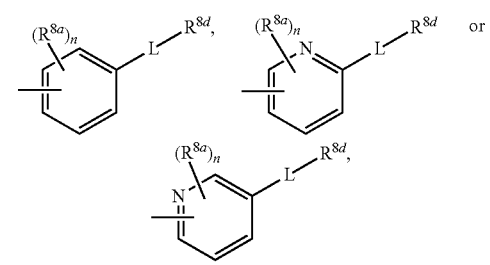

L is selected from a single bond, alkylene, —O—, —N($R^{8e}$)—, —CO—, —CO$_2$—, —SO—, —SO$_2$—, —CON($R^{8e}$)—, —SO$_2$N($R^{8e}$)—, —N($R^{8e}$)CO—, —N($R^{8e}$)SO$_2$—, —N($R^{8e}$)CO N($R^{8e}$)—, —N($R^{8e}$) SO$_2$ N($R^{8e}$)—; —O(C$R^{8e}_2$)$_{m1}$—, or —CON($R^{8e}$) (C$R^{8e}_2$)$_{m1}$—;

each $R^{8a}$ independently selected from hydrogen, substituted or unsubstituted alkyl, alkoxy, cyano, and halo;

$R^{8d}$ is selected from substituted or unsubstituted heterocycloalkyl;

$R^{8e}$ is selected from H, substituted or unsubstituted alkyl and substituted or unsubstituted cycloalkyl;

the subscript m1 is 1, 2, 3, or 4; the subscript n is 1, 2, 3, or 4;

and wherein $R^9$ is

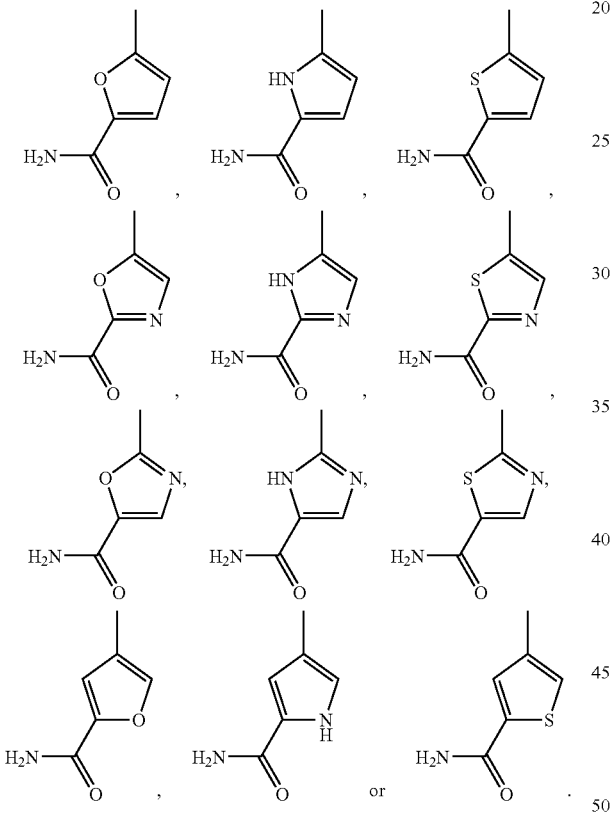

or a pharmaceutically acceptable salt, thereof; or stereoisomers or tautomers thereof.

7. A compound according to formula III:

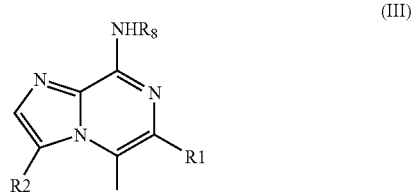

(III)

wherein
$R^1$ is H, or substituted or unsubstituted alkyl; $R^2$ is H, lower alkyl, lower cycloalkyl and lower alkyl-lower cycloalkyl, optionally substituted with one or more of F and Cl; $R^8$ is

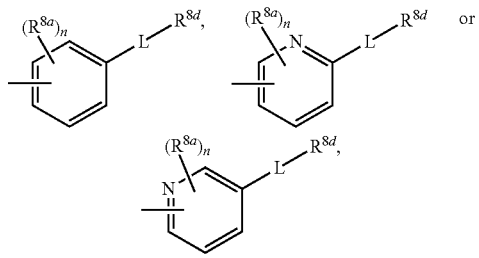

L is selected from a single bond, alkylene, —O—, —N($R^{8e}$)—, —CO—, —CO$_2$—, —SO—, —SO$_2$—, —CON($R^{8e}$)—, —SO$_2$N($R^{8e}$)—, —N($R^{8e}$)CO—, —N($R^{8e}$)SO$_2$—, —N($R^{8e}$)CO N($R^{8e}$)—, —N($R^{8e}$) SO$_2$ N($R^{8e}$)—; —O(C$R^{8e}_2$)$_{m1}$—, or —CON($R^{8e}$) (C$R^{8e}_2$)$_{m1}$—;

each $R^{8a}$ is independently selected from hydrogen, substituted or unsubstituted alkyl, alkoxy, cyano, and halo;

$R^{8d}$ is selected from substituted or unsubstituted heterocycloalkyl;

$R^{8e}$ is selected from H, substituted or unsubstituted alkyl and substituted or unsubstituted cycloalkyl;

the subscript m1 is 1, 2, 3, or 4; the subscript n is 1, 2, 3, or 4;

and wherein $R^9$ is

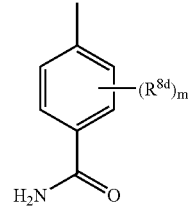

and wherein the subscript m is selected from 1-4 and each $R^{9d}$ is independently H, substituted or unsubstituted alkyl or halo; or a pharmaceutically acceptable salt, thereof; or stereoisomers or tautomers thereof.

8. A compound according to formula III:

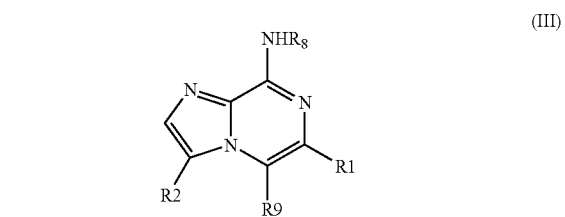

(III)

wherein
$R^1$ is H, or substituted or unsubstituted alkyl; $R^2$ is H, lower alkyl, lower cycloalkyl and lower alkyl-lower cycloalkyl, optionally substituted with one or more of F and Cl; $R^8$ is

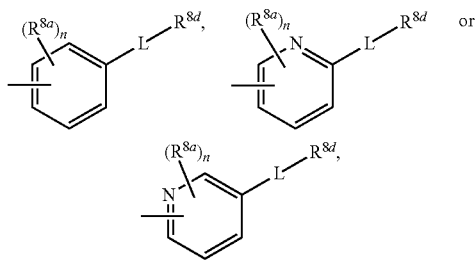

L is selected from a single bond, alkylene, —O—, —N(R$^{8e}$)—, —CO—, —CO$_2$—, —SO—, —SO$_2$—, —CON(R$^{8e}$)—, —SO$_2$N(R$^{8e}$)—, —N(R$^{8e}$)CO—, —N(R$^{8e}$)SO$_2$—, —N(R$^{8e}$)CO N(R$^{8e}$)—, —N(R$^{8e}$)SO$_2$ N(R$^{8e}$)—; —O(CR$^{8e}_2$)$_{m1}$—, or —CON(R$^{8e}$)(CR$^{8e}_2$)$_{m1}$—;

each R$^{8a}$ is independently selected from hydrogen, substituted or unsubstituted alkyl, alkoxy, cyano, and halo;

R$^{8d}$ is selected from substituted or unsubstituted heterocycloalkyl;

R$^{8e}$ is selected from H, substituted or unsubstituted alkyl and substituted or unsubstituted cycloalkyl;

the subscript m1 is 1, 2, 3, or 4; the subscript n is 1, 2, 3, or 4;

wherein R$^9$ is

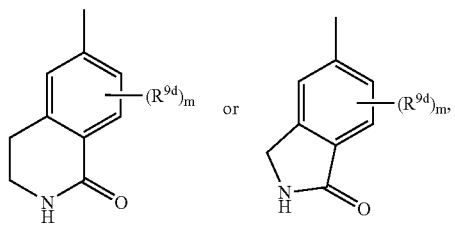

and wherein the subscript m is selected from 1-4 and each R$^{9d}$ is independently H, substituted or unsubstituted alkyl or halo; or a pharmaceutically acceptable salt, thereof; or stereoisomers or tautomers thereof.

9. A compound according to formula III:

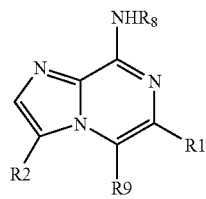

(III)

wherein

R$^1$ is H, or substituted or unsubstituted alkyl; R$^2$ is H, lower alkyl, lower cycloalkyl and lower alkyl-lower cycloalkyl, optionally substituted with one or more of F and Cl; R$^8$ is

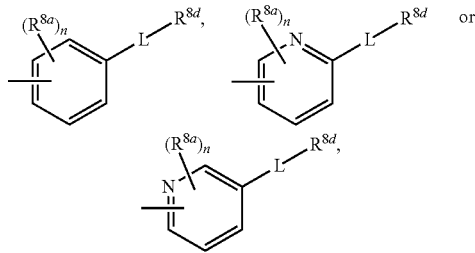

L is selected from a single bond, alkylene, —O—, —N(R$^{8e}$)—, —CO—, —CO$_2$—, —SO—, —SO$_2$—, —CON(R$^{8e}$)—, —SO$_2$N(R$^{8e}$)—, —N(R$^{8e}$)CO—, —N(R$^{8e}$)SO$_2$—, —N(R$^{8e}$)CO N(R$^{8e}$)—, —N(R$^{8e}$)SO$_2$ N(R$^{8e}$)—; —O(CR$^{8e}_2$)$_{m1}$—, or —CON(R$^{8e}$)(CR$^{8e}_2$)$_{m1}$—;

each R$^{8a}$ is independently selected from hydrogen, substituted or unsubstituted alkyl, alkoxy, cyano, and halo;

R$^{8d}$ is selected from substituted or unsubstituted heterocycloalkyl;

r$^{8e}$ is selected from H, substituted or unsubstituted alkyl and substituted or unsubstituted cycloalkyl;

the subscript m1 is 1, 2, 3, or 4; the subscript n is 1, 2, 3, or 4;

wherein R$^9$ is

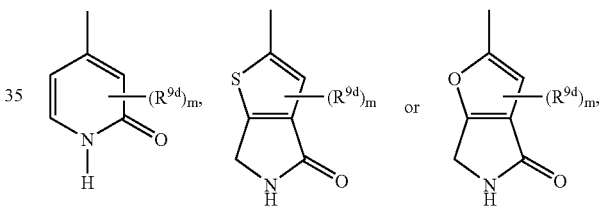

and wherein the subscript m is selected from 1-3 and each R$^{9d}$ is independently H, substituted or unsubstituted alkyl or halo; or a pharmaceutically acceptable salt, thereof; or stereoisomers or tautomers thereof.

10. A compound of formula VIa, VIb, VId, or VIe:

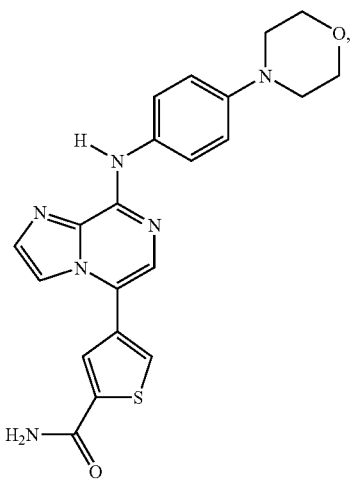

VIa

VIb
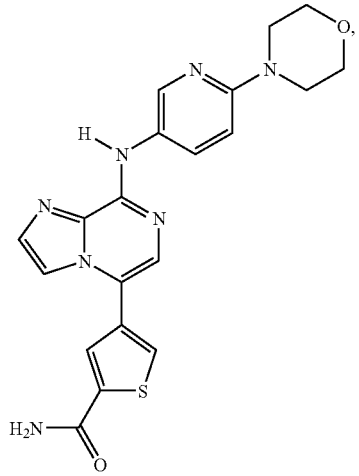
VIc
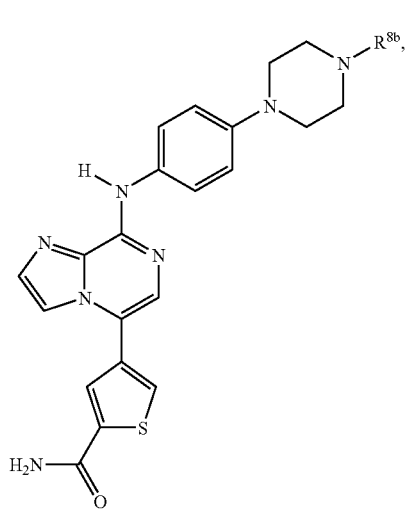
VId
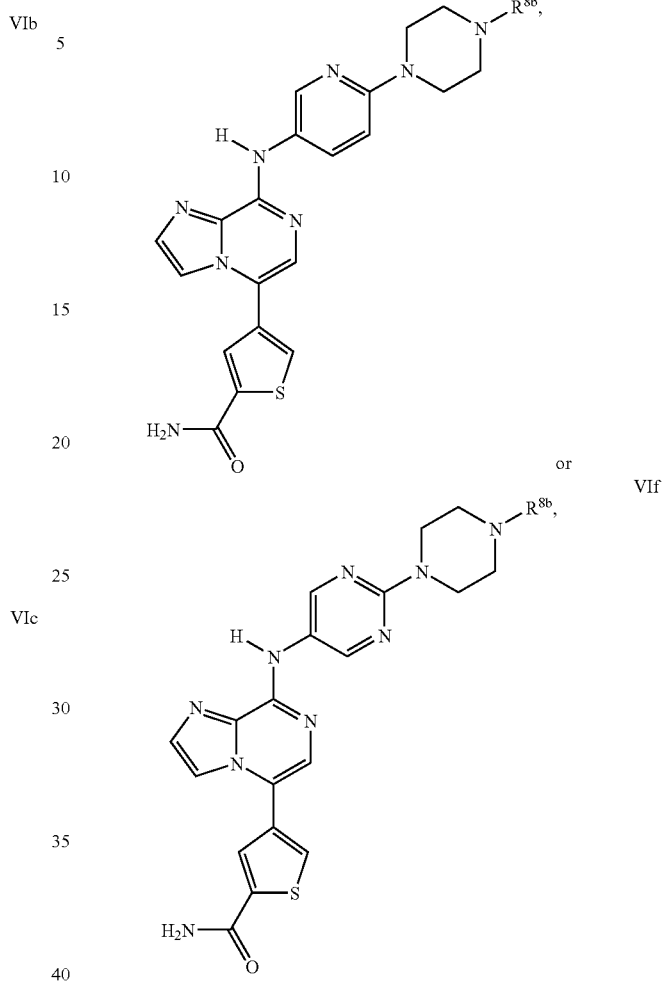
wherein $R^{8b}$ is hydrogen, substituted or unsubstituted alkyl or substituted or unsubstituted cycloalkyl.
11. A compound of formula VIIa, VIIb, VIId, or VIIe:
VIIa
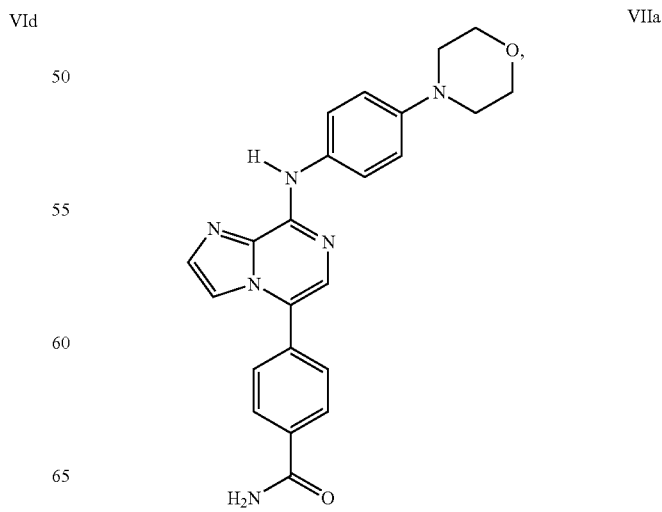

-continued
VIIb
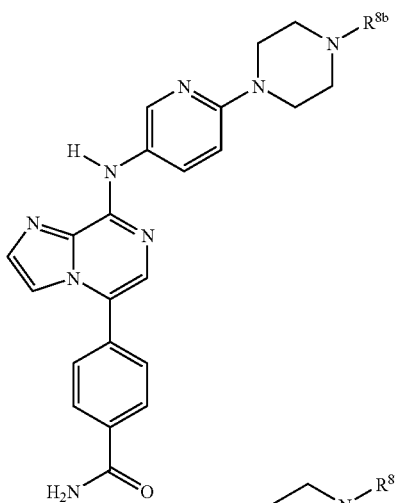
VIIc
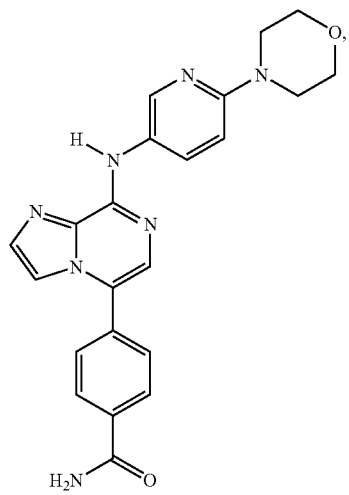
VIIe
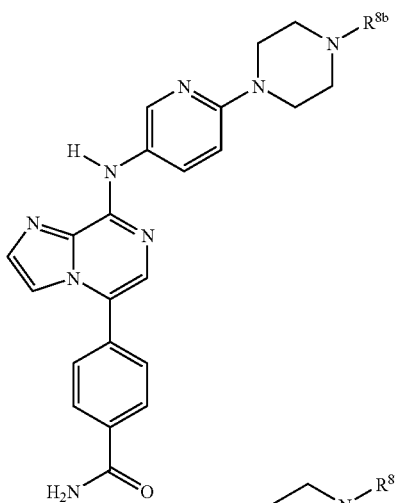
VIIf
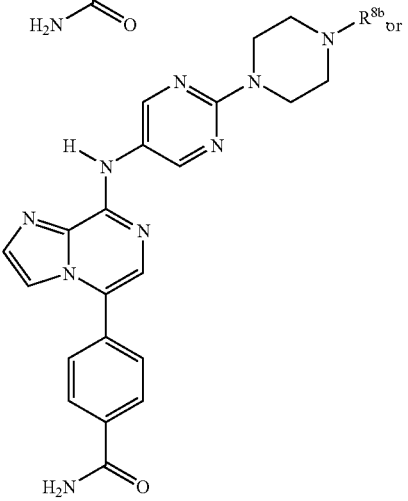
wherein $R^{8b}$ is hydrogen, substituted or unsubstituted alkyl or substituted or unsubstituted cycloalkyl.
12. A compound of formula VIIIa, VIIIb, VIIId, or VIIIe:
VIId
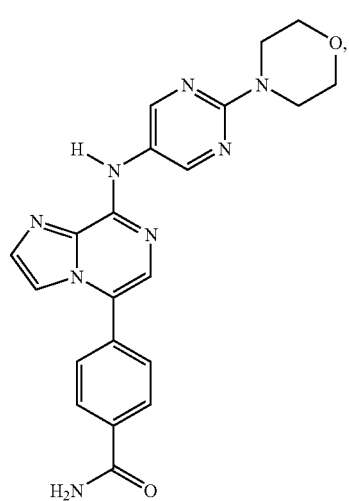
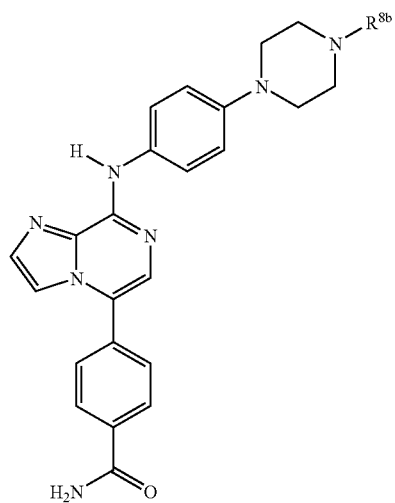
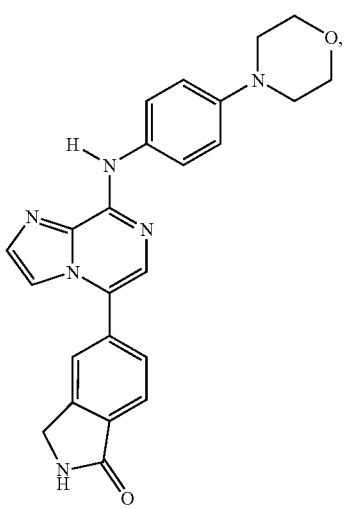

-continued
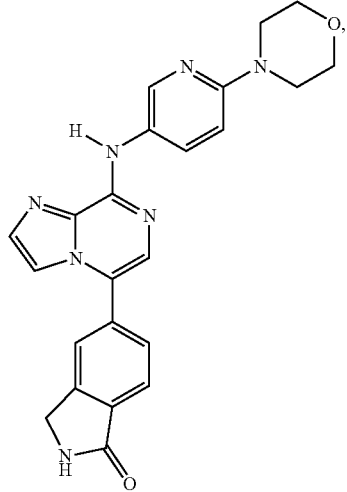
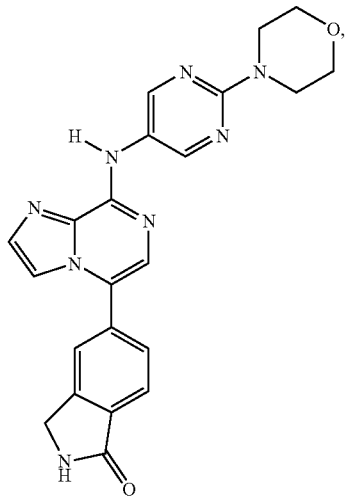
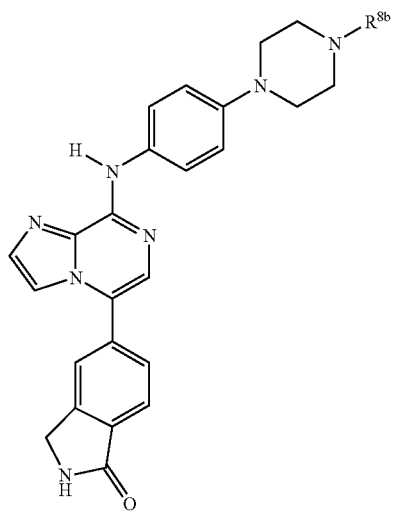
-continued
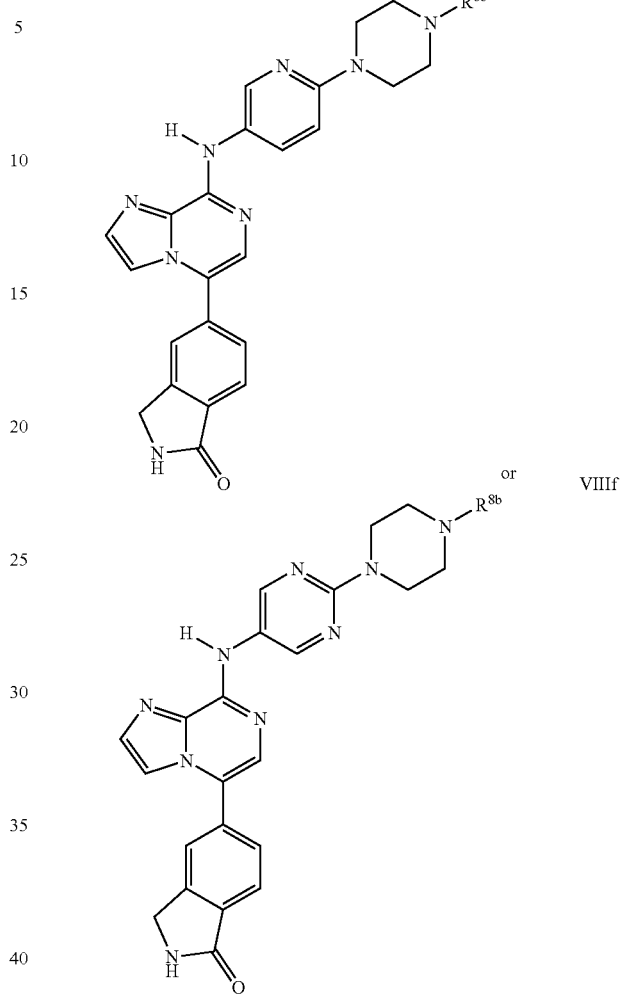
wherein $R^{8b}$ is hydrogen, substituted or unsubstituted alkyl or substituted or unsubstituted cycloalkyl.
13. A compound of formula IXa, IXb, IXd, or IXe:
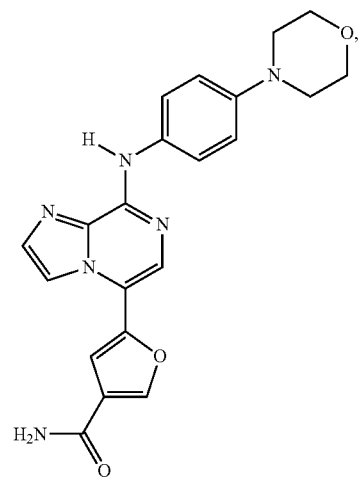

337
-continued
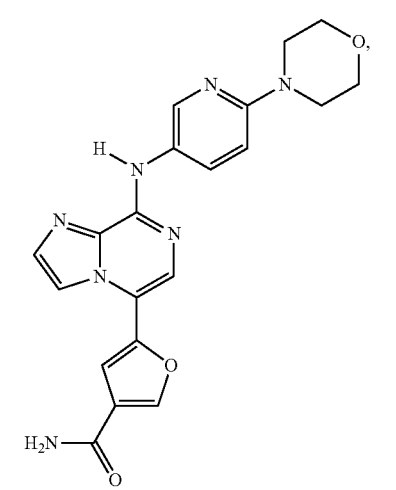
IXb
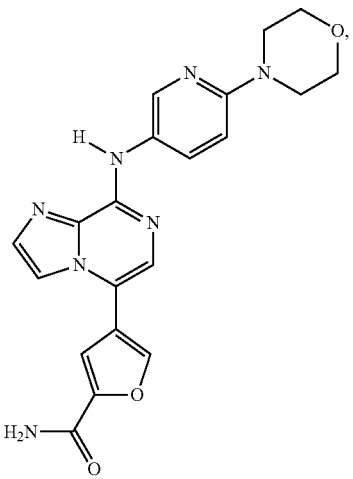
IXd
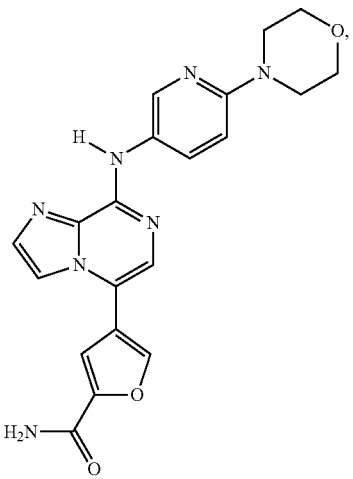
IXe
wherein R^{8b} is hydrogen, substituted or unsubstituted alkyl or substituted or unsubstituted cycloalkyl.
338
14. A compound of formula Xa, Xb, Xd, or Xe:
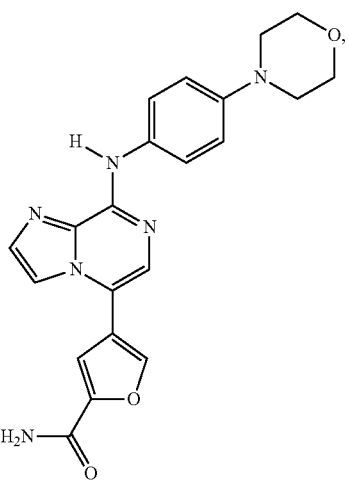
Xa
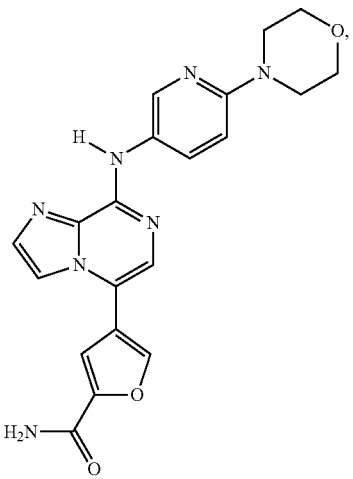
Xb
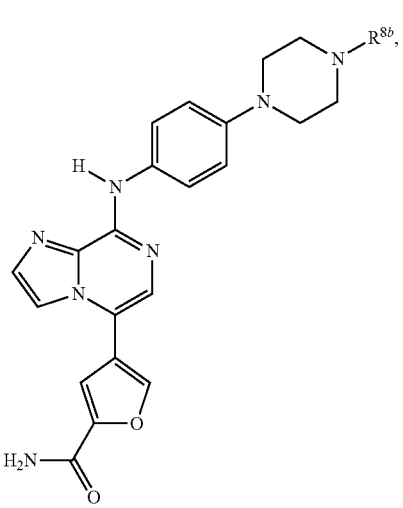
Xc -continued

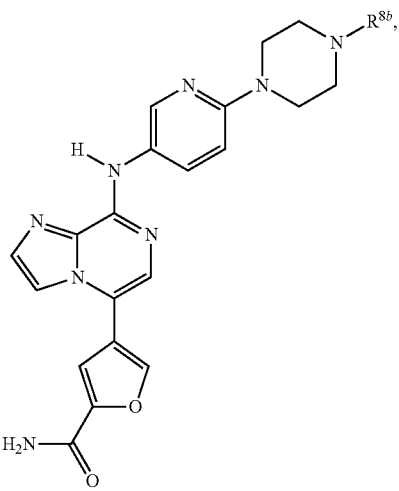

Xe wherein $R^{8b}$ is hydrogen, substituted or unsubstituted alkyl or substituted or unsubstituted cycloalkyl.

15. A compound of formula XIa, XIb, XId, or XIe:

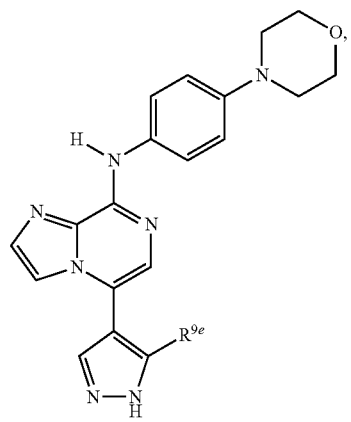

XIa

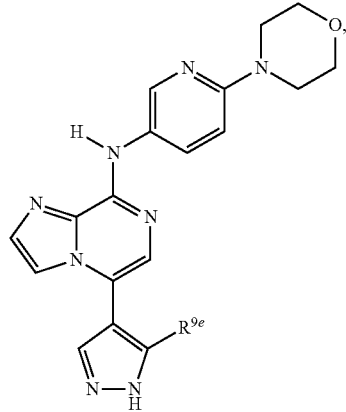

XIb

-continued

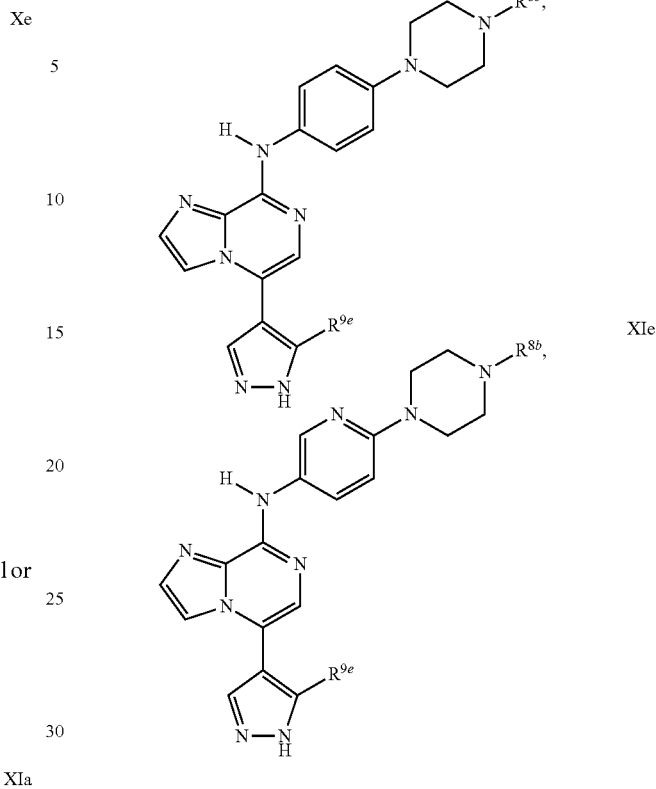

XId

XIe wherein $R^{8b}$ is hydrogen, substituted or unsubstituted alkyl or substituted or unsubstituted cycloalkyl; and $R^{9e}$ is hydrogen, Me, or CN.

16. A compound according to any one of claims 10-15, wherein $R^{8b}$ is H.

17. A compound according to any one of claims 10-15, wherein $R^{8b}$ is cycloalkyl.

18. A compound according to any one of claims 10-15, wherein $R^{8b}$ is cyclopropyl.

19. A compound according to any one of claims 10-15, wherein $R^{8b}$ is substituted or unsubstituted alkyl.

20. A compound according to any one of claims 10-15, wherein $R^{8b}$ is Me, Et, Pr, i-Pr, t-Bu, i-Bu, $CF_3$, $CH_2CF_3$, $CH_2CONH_2$, or cyclopropylmethyl.

21. A compound of formula XIIa, XIIb, XIIc or XIId:

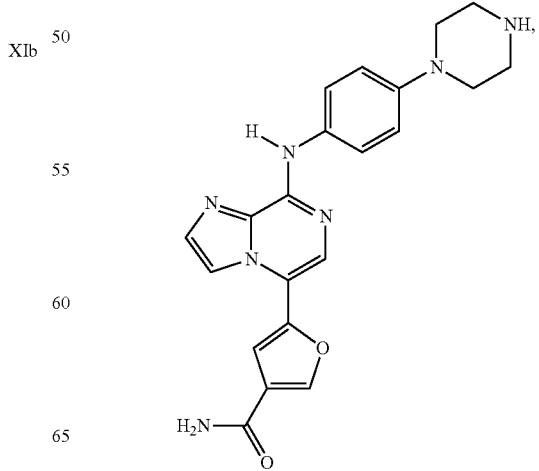

XIIa

-continued
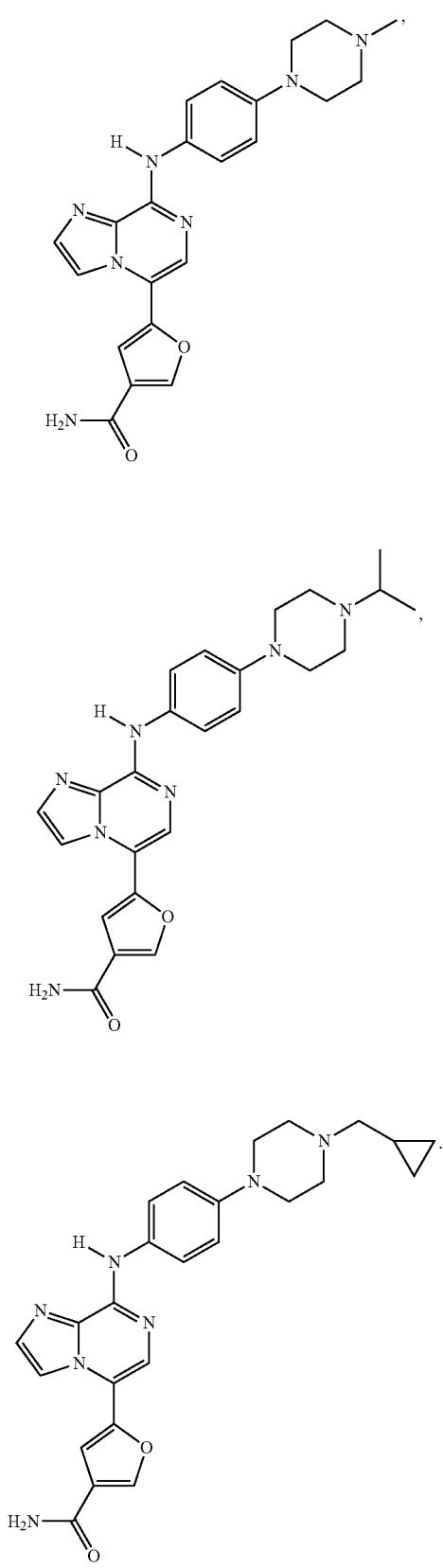
22. A compound of formula XIIIa, XIIIb, XIIIc or XIIId:
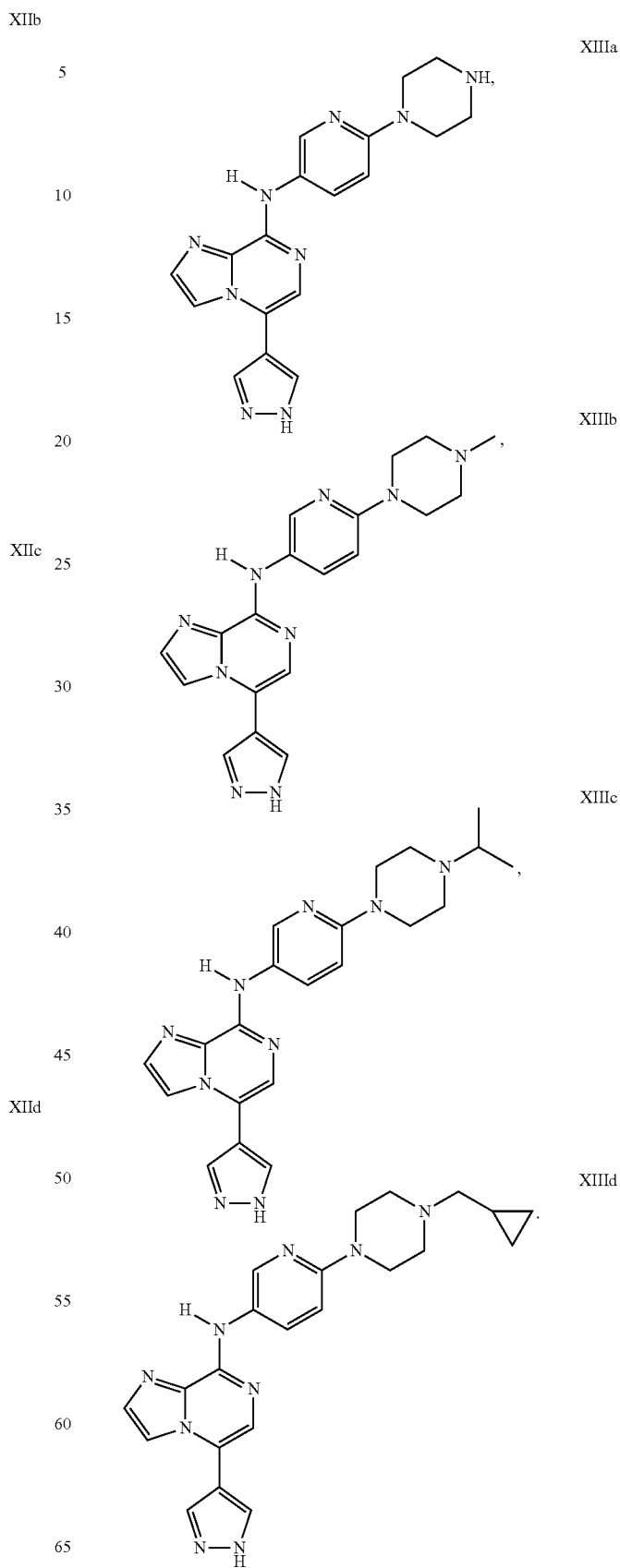

23. A compound of formula XVa, or XVb:

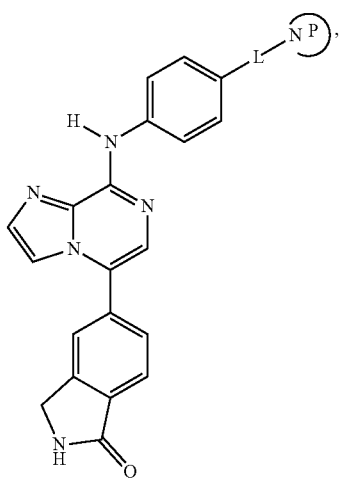

XVa

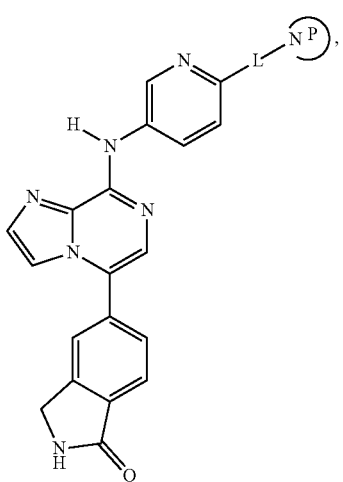

XVb wherein L is a single bond, —CO—, or —O—CH$_2$—CH$_2$—; the ring P is

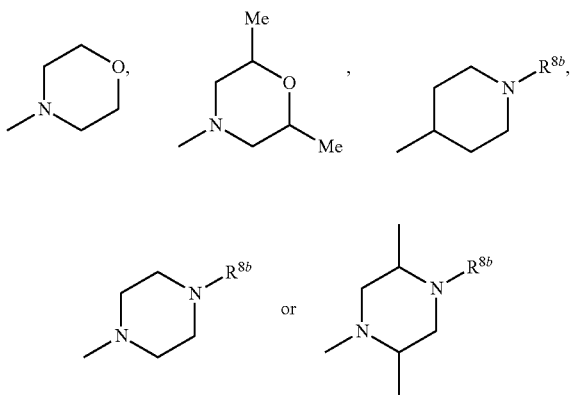

and R$^{8b}$ is H, Me, i-Pr, t-Bu, CH$_2$CONH$_2$, cyclopropylmethyl, or CH$_2$CF$_3$.

24. A compound according to claim 23, wherein L is a bond and the ring P is

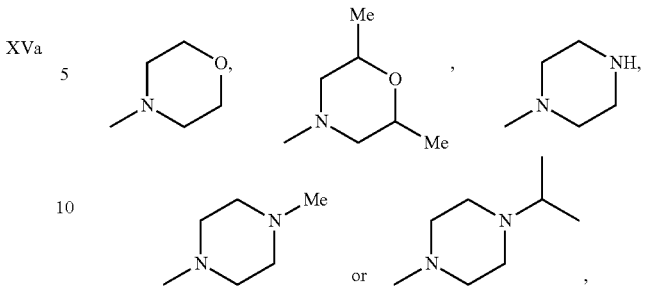

25. A compound selected from
(4-Morpholin-4-yl-phenyl)-[5-(1H-pyrazol-4-yl)-imidazo[1,2-a]pyrazin-8-yl]-amine;
4-[8-(4-Morpholin-4-yl-phenylamino)-imidazo[1,2-a]pyrazin-5-yl]-benzamide;
[4-(4-Methylpiperazin-1-yl)-phenyl]-[5-(1H-pyrazol-4-yl)-imidazo[1,2-a]pyrazin-8-yl]-amine;
4-{8-[4-(4-Methyl-piperazin-1-yl)-phenylamino]-imidazo[1,2-a]pyrazin-5-yl}-benzamide;
Morpholin-4-yl-{4-[5-(1H-pyrazol-4-yl)-imidazo[1,2-a]pyrazin-8-ylamino]-phenyl}-methanone;
N-(2-Morpholin-4-yl-ethyl)-4-[5-(1H-pyrazol-4-yl)-imidazo[1,2-a]pyrazin-8-ylamino]-benzamide;
4-{8-[4-(2-Morpholin-4-yl-ethylcarbamoyl)-phenylamino]-imidazo[1,2-a]pyrazin-5-yl}-benzoic acid;
4-[5-(1H-pyrazol-4-yl)-imidazo[1,2-a]pyrazin-8-ylamino]-N-pyrrolidin-3-yl-benzamide;
N-(1-Methyl-pyrrolidin-3-yl)-4-[5-(1H-pyrazol-4-yl)-imidazo[1,2-a]pyrazin-8-ylamino]-benzamide;
[4-(4-Methyl-piperazine-1-sulfonyl)-phenyl]-[5-(1H-pyrazol-4-yl)-imidazo[1,2-a]pyrazin-8-yl]-amine;
4-{8-[4-(4-Methyl-piperazin-1-yl)-phenylamino]-imidazo[1,2-a]pyrazin-5-yl}-1H-pyridin-2-one;
4-{8-[4-(4-Methyl-piperazin-1-yl)-phenylamino]-imidazo[1,2-a]pyrazin-5-yl}-thiophene-2-carboxylic acid amide;
[4-(4-Methyl-piperazin-1-yl)-phenyl]-[5-(5-methyl-1H-pyrazol-4-yl)-imidazo[1,2-a]pyrazin-8-yl]-amine;
3-Methyl-4-{8-[4-(4-Methyl-piperazin-1-yl)-phenylamino]-imidazo[1,2-a]pyrazin-5-yl}-benzamide;
2-Fluoro-4-{8-[4-(4-methyl-piperazin-1-yl)-phenylamino]-imidazo[1,2-a]pyrazin-5-yl}-benzamide;
3-Fluoro-4-{8-[4-(4-methyl-piperazin-1-yl)-phenylamino]-imidazo[1,2-a]pyrazin-5-yl}-benzamide;
2-Chloro-4-{8-[4-(4-methyl-piperazin-1-yl)-phenylamino]-imidazo[1,2-a]pyrazin-5-yl}-benzamide;
5-{8-[4-(4-Methyl-piperazin-1-yl)-phenylamino]-imidazo[1,2-a]pyrazin-5-yl}-thiophene-2-carboxylic acid amide;
4-(8-(3-chloro-4-(4-methylpiperazin-1-yl)phenylamino)imidazo[1,2-a]pyrazin-5-yl)benzamide;
4-(8-(4-((2R,5S)-2,4,5-trimethylpiperazin-1-yl)phenylamino)imidazo[1,2-a]pyrazin-5-yl) benzamide;
5-(8-(4-(4-methylpiperazin-1-yl)phenylamino)imidazo[1,2-a]pyrazin-5-yl)furan-2-carboxamide;
2,6-difluoro-4-(8-(4-(4-methylpiperazin-1-yl)phenylamino)imidazo[1,2-a]pyrazin-5-yl)benzamide;
4-(8(4-(4-isopropylpiperazin-1-yl)phenylamino)imidazo[1,2-a]pyrazin-5-yl)benzamide;
4-(8-(6-(4-methylpiperazin-1-yl)pyridin-3-ylamino)imidazo[1,2-a]pyrazin-5-yl)benzamide;

5-(8-(4-(4-methylpiperazin- 1-yl)phenylamino)imidazo[1,2-a]pyrazin-5-yl)thiophene-3-carboxamide;
5-(8-(4-(4-methylpiperazin-1-yl)phenylamino)imidazo[1,2-a]pyrazin-5-yl)furan-3-carboxamide;
2-fluoro-4-(8-(4-(2-morpholinoethoxy)phenylamino)imidazo[1,2-a]pyrazin-5-yl)benzamide;
N-(4-(2-morpholinoethoxy)phenyl)-5-(1H-pyrazol-4-yl)imidazo[1,2-a]pyrazin-8-amine;
5-(8-(4-morpholinophenylamino)imidazo[1,2-a]pyrazin-5-yl)thiophene-2-carboxamide;
4-(8-(4-((3S,5R)-3,4,5-trimethylpiperazin-1-yl)phenylamino)imidazo[1,2-a]pyrazin-5-yl)benzamide;
4-(8-(4-(4-(2-hydroxyethyl)piperazin-1-yl)phenylamino)imidazo[1,2-a]pyrazin-5-yl)benzamide;
2-(8-(4-morpholinophenylamino)imidazo[1,2-a]pyrazin-5-yl)thiazole-5-carboxamide;
2,6-Difluoro-4-[8-(4-morpholin-4-yl-phenylamino)-imidazo[1,2-a]pyrazin-5-yl]-benzamide;
4-(8-(3-fluoro-4-(4-methylpiperazin-1-yl)phenylamino)imidazo[1,2-a]pyrazin-5-yl)benzamide;
4-(8-(3-morpholinophenylamino)imidazo[1,2-a]pyrazin-5-yl)benzamide;
4-(8-(3-carbamoyl-4-morpholinophenylamino)imidazo[1,2-a]pyrazin-5-yl)-2,6-difluorobenzamide;
5-(5-methyl-1H-pyrazol-4-yl)-N-(4-morpholinophenyl)imidazo[1,2-a]pyrazin-8-amine;
4-(8-(4-morpholinophenylamino)imidazo[1,2-a]pyrazin-5-yl)thiophene-2-carboxamide;
5-(8-(4-morpholinophenylamino)imidazo[1,2-a]pyrazin-5-yl)isoindolin-1-one;
5-(8-(4-morpholinophenylamino)imidazo[1,2-a]pyrazin-5-yl)furan-3-carboxamide;
2,6-difluoro-4-(8-(4-((2S,5R)-2,4,5-trimethylpiperazin-1-yl)phenylamino)imidazo[1,2-a]pyrazin-5-yl)benzamide;
2-methyl-4-(8-(4-morpholinophenylamino)imidazo[1,2-a]pyrazin-5-yl)benzamide;
4-(8-(4((2S,5R)-2,4,5-trimethylpiperazin-1-yl)phenylamino)imidazo[1,2-a]pyrazin-5-yl)thiophene-2-carboxamide;
5-(8-(4((2S,5R)-2,4,5-trimethylpiperazin-1-yl)phenylamino)imidazo[1,2-a]pyrazin-5-yl)furan-3-carboxamide;
5-[8-(4-Piperazin-1-yl-phenylamino)-imidazo[1,2-a]pyrazin-5-yl]-furan-3-carboxylic acid amide;
2,6-difluoro-4-(8-(4-(4-isopropylpiperazin-1-yl)phenylamino)imidazo[1,2-a]pyrazin-5-yl)benzamide;
5-{8-[4-(4-Isopropyl-piperazin-1-yl)-phenylamino]-imidazo[1,2-a]pyrazin-5-yl}-2,3-dihydro-isoindol-1-one;
4-{8-[4-(4-Isopropyl-piperazin-1-yl)-phenylamino]-imidazo[1,2-a]pyrazin-5-yl}-furan-2-carboxylic acid amide;
4-[8-(4-Morpholin-4-yl-phenylamino)-imidazo[1,2-a]pyrazin-5-yl]-furan-2-carboxylic acid amide;
[6-(4-Isopropyl-piperazin-1-yl)-pyridin-3-yl]-[5-(1H-pyrazol-4-yl)-imidazo[1,2-a]pyrazin-8-yl]-amine;
(5-Morpholin-4-yl-pyridin-2-yl)-[5-(1H-pyrazol-4-yl)-imidazo[1,2-a]pyrazin-8-yl]-amine;
5-[8-(5-Morpholin-4-yl-pyridin-2-ylamino)-imidazo[1,2-a]pyrazin-5-yl]-2,3-dihydro-isoindol-1-one;
4-[8-(4-Morpholin-4-yl-phenylamino)-imidazo[1,2-a]pyrazin-5-yl]-2H-pyrazole-3-carbonitrile;
5-{8-[6-(4-Isopropyl-piperazin-1-yl)-pyridin-3-ylamino]-imidazo[1,2-a]pyrazin-5-yl}-2,3-dihydro-isoindol-1-one;
4-{8-[6-(4-Isopropyl-piperazin-1-yl)-pyridin-3-ylamino]-imidazo[1,2-a]pyrazin-5-yl}-furan-2-carboxylic acid amide; and
pharmaceutically acceptable salts thereof 26. A compound selected from
4-[3-Methyl-8-(4-morpholin-4-yl-phenylamino)-imidazo[1,2-a]pyrazin-5-yl]-benzamide;
[3-Methyl-5-(1H-pyrazol-4-yl)-imidazo[1,2-a]pyrazin-8-yl]-(4-morpholin-4-yl-phenyl)-amine;
4-[3-Methyl-8-(4-morpholin-4-yl-phenylamino)-imidazo[1,2-a]pyrazin-5-yl]-1H-pyridin-2-one;
4-[3-Ethyl-8-(4-morpholin-4-yl-phenylamino)-imidazo[1,2-a]pyrazin-5-yl]-benzamide;
4-[3-Ethyl-8-(4-morpholin-4-yl-phenylamino)-imidazo[1,2-a]pyrazin-5-yl]-1H-pyridin-2-one;
[3-Ethyl-5-(1H-pyrazol-4-yl)-imidazo[1,2-a]pyrazin-8-yl]-(4-morpholin-4-yl-phenyl)-amine;
[6-(4-Isopropyl-piperazin-1-yl)-pyridin-3-yl]-[5-(1H-pyrazol-4-yl)-imidazo[1,2-a]pyrazin-8-yl]-amine;
5-[8-(6-Morpholin-4-yl-pyridin-3-ylamino)-imidazo[1,2-a]pyrazin-5-yl]-2,3-dihydro-isoindol-1-one;
2,6-Difluoro-4-{8-[4-(2-morpholin-4-yl-ethoxy)-phenylamino]-imidazo[1,2-a]pyrazin-5-yl}-benzamide;
2-[8-(4-Morpholin-4-yl-phenylamino)-imidazo[1,2-a]pyrazin-5-yl]-5,6-dihydro-furo[2,3-c]pyrrol-4-one;
(3-Dimethylaminomethyl-4-morpholin-4-yl-phenyl)-[5-(1H-pyrazol-4-yl)-imidazo[1,2-a]pyrazin-8-yl]-amine;
7-Fluoro-5-{8-[4-(4-isopropyl-piperazin-1-yl)-phenylamino]-imidazo[1,2-a]pyrazin-5-yl}-2,3-dihydro-isoindol-1-one;
2-{8-[4-(4-Isopropyl-piperazin-1-yl)-phenylamino]-imidazo[1,2-a]pyrazin-5-yl}-5,6-dihydro-furo[2,3-c]pyrrol-4-one;
5-{8-[4-(4-Isopropyl-piperazin-1-yl)-phenylamino]-imidazo[1,2-a]pyrazin-5-yl}-3,3-dimethyl-2,3-dihydro-isoindol-1-one;
2-{8-[4-(4-Isopropyl-piperazin-1-yl)-phenylamino]-imidazo[1,2-a]pyrazin-5-yl}-4,5-dihydro-thieno[2,3-c]pyrrol-6-one; and
pharmaceutically acceptable salts thereof.

27. A compound selected from
(4-Morpholin-4-yl-phenyl)-[5-(1H-pyrazol-4-yl)-imidazo[1,2-a]pyrazin-8-yl]-amine;
Morpholin-4-yl-{4-[5-(1H-pyrazol-4-yl)-imidazo[1,2-a]pyrazin-8-ylamino]-phenyl}-methanone;
N-(2-Morpholin-4-yl-ethyl)-4-[5-(1H-pyrazol-4-yl)-imidazo[1,2-a]pyrazin-8-ylamino]-benzamide;
[4-(4-Methyl-piperazine-1-sulfonyl)-phenyl]-[5-(1H-pyrazol-4-yl)-imidazo[1,2-a]pyrazin-8-yl]-amine;
4-[8-(4-Morpholin-4-yl-phenylamino)-imidazo[1,2-a]pyrazin-5-yl]-1H-pyridin-2-one;
4-{8-[4-(4-Methyl-piperazin-1-yl)-phenylamino]-imidazo[1,2-a]pyrazin-5-yl}-1H-pyridin-2-one;
4-{8-[4-(4-Methyl-piperazin-1-yl)-phenylamino]-imidazo[1,2-a]pyrazin-5-yl}-thiophene-2-carboxylic acid amide;
[4-(4-Methyl-piperazin-1-yl)-phenyl]-[5-(5-methyl-1H-pyrazol-4-yl)-imidazo[1,2-a]pyrazin-8-yl]-amine;
2-Fluoro-4-{8-[4-(4-methyl-piperazin-1-yl)-phenylamino]-imidazo[1,2-a]pyrazin-5-yl}-benzamide;
3-Fluoro-4-{8-[4-(4-methyl-piperazin-1-yl)-phenylamino]-imidazo[1,2-a]pyrazin-5-yl}-benzamide;
5-{8-[4-(4-Methyl-piperazin-1-yl)-phenylamino]-imidazo[1,2-a]pyrazin-5-yl}-thiophene-2-carboxylic acid amide; and
pharmaceutically acceptable salts thereof.

28. A pharmaceutical composition comprising a pharmaceutically acceptable carrier and a pharmaceutically effective amount of a compound of any one of claims 25, 26 and 27.

29. The pharmaceutical composition of claim 28, wherein the carrier is a parenteral carrier.

30. The pharmaceutical composition of claim 28, wherein the carrier is an oral carrier.

31. The pharmaceutical composition of claim 28, wherein the carrier is a topical carrier.

32. A compound according to claim 4, wherein $R^8$ is

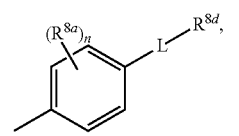

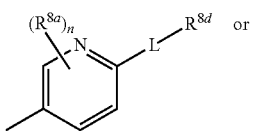

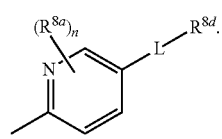

33. A compound according to formula IVa, IVb, or IVc:

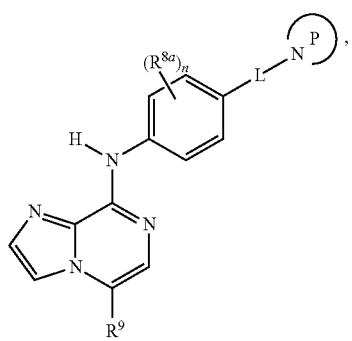

IVa

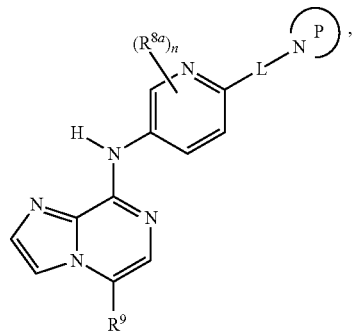

IVb

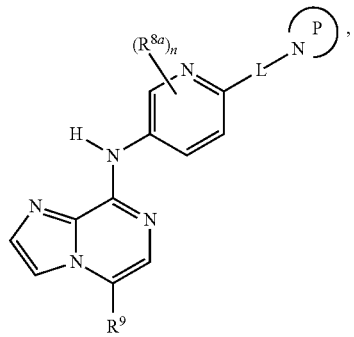

IVc and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each $R^{8a}$ is independently selected from hydrogen, substituted or unsubstituted alkyl, alkoxy, cyano, and halo; and $R^9$ is and each of $A^1$, $A^2$ and $A^3$ is independently selected from S, O, N, NR$^{9a}$, and CR$^{9a}$; each of R$^{9a}$ is independently H or substituted or unsubstituted alkyl; and R$^{9b}$ is CONH$_2$, CONHMe, or CN; or a pharmaceutically acceptable salt, thereof; or stereoisomers or tautomers thereof.

34. A compound according to claim 4, wherein the compound is according to formula Va, Vb, Vd, or Ve:

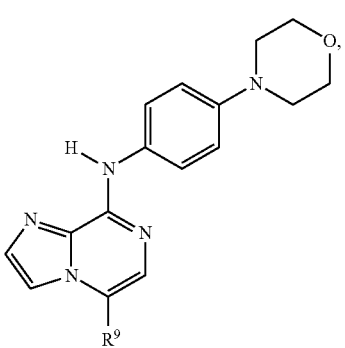

Va

-continued

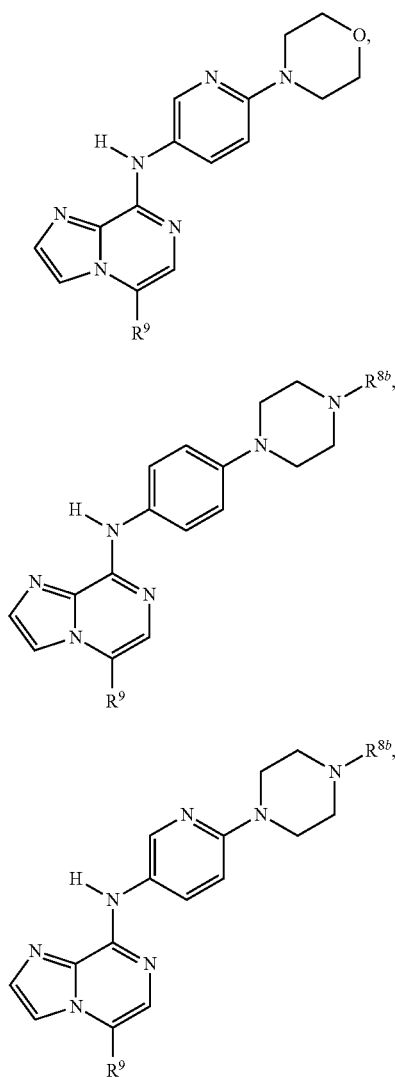

and wherein $R^{8b}$ is hydrogen, substituted or unsubstituted alkyl or substituted or unsubstituted cycloalkyl.

35. A compound according to claim 5, wherein $R^8$ is

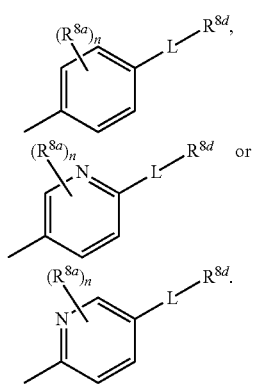

36. A compound according to formula IVa, IVb, or IVc:

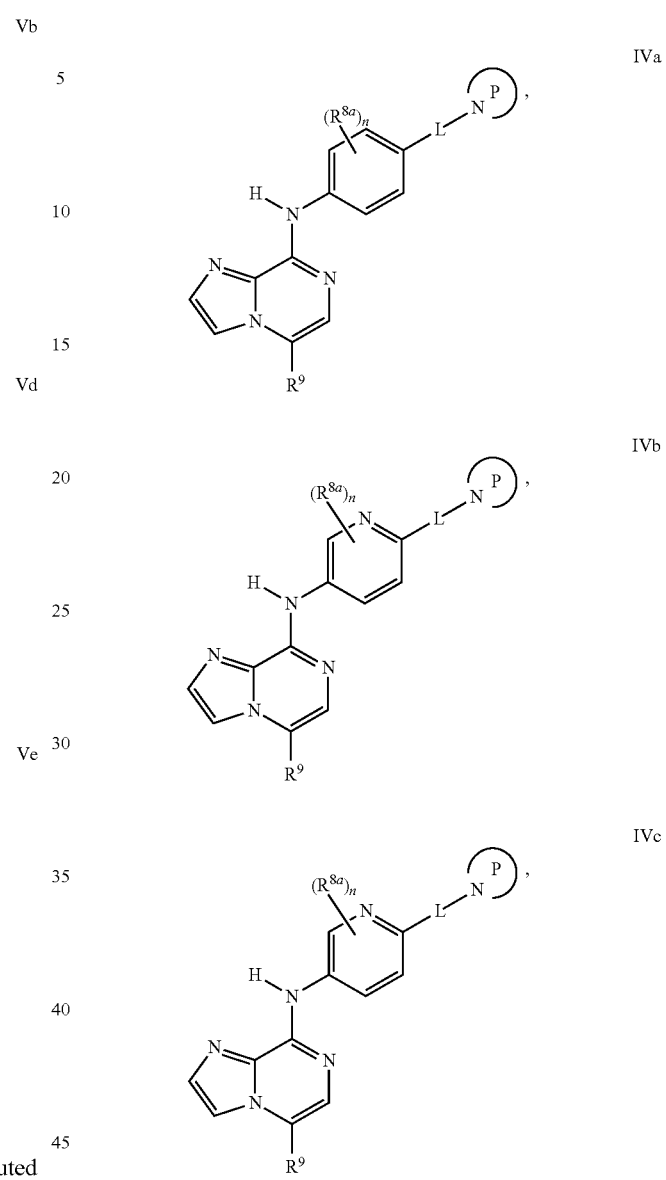

and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each $R^{8a}$ independently selected from hydrogen, substituted or unsubstituted alkyl, alkoxy, cyano, and halo; and $R^9$ is

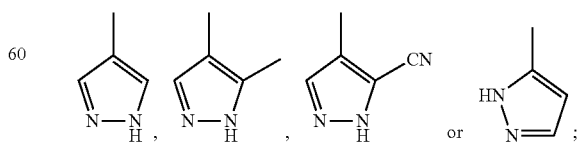

or a pharmaceutically acceptable salt, thereof; or stereoisomers or tautomers thereof.

37. A compound according to claim 5, wherein the compound is according to formula Va, Vb, Vd, or Ve:

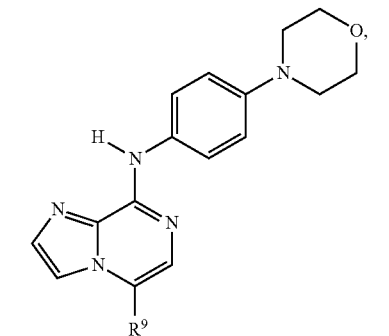

Va

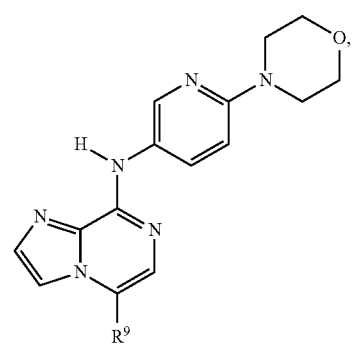

Vb

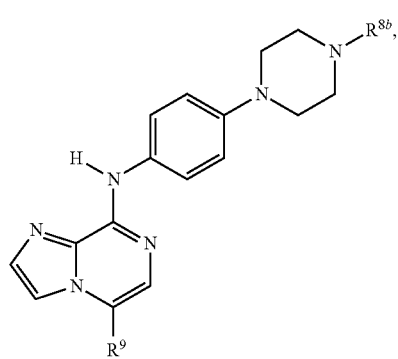

Vd

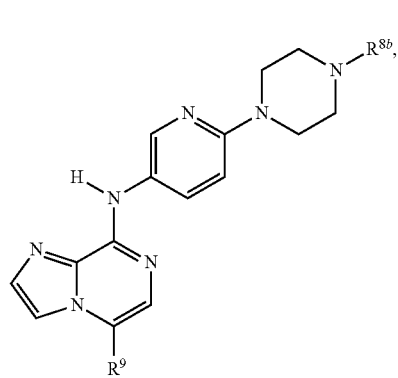

Ve and wherein $R^{8b}$ is hydrogen, substituted or unsubstituted alkyl or substituted or unsubstituted cycloalkyl.

38. A compound according to claim 6, wherein $R^8$ is

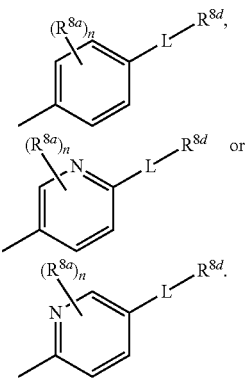

39. A compound according to formula IVa, IVb, or IVc:

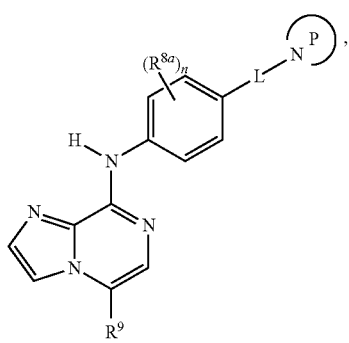

IVa

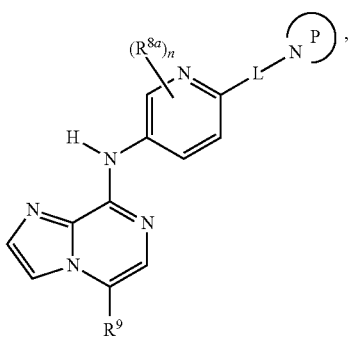

IVb

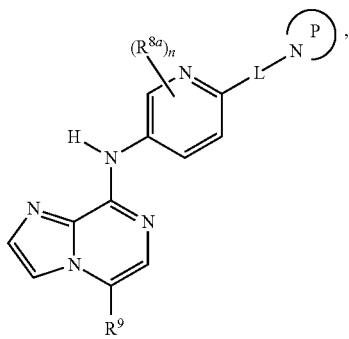

IVc and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each $R^{8a}$ is independently selected from hydrogen, substituted or unsubstituted alkyl, alkoxy, cyano, and halo; and $R^9$ is

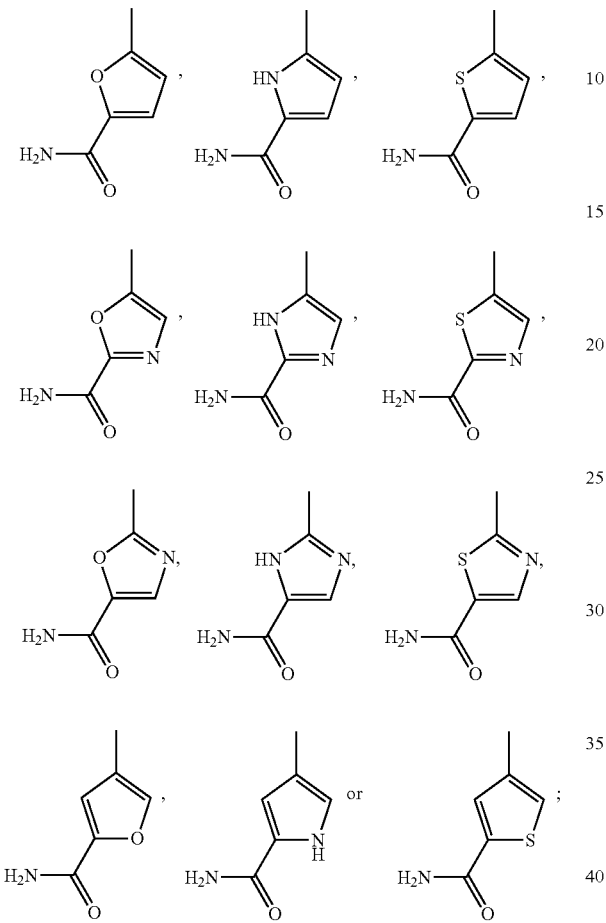

or a pharmaceutically acceptable salt, thereof; or stereoisomers or tautomers thereof.

40. A compound according to claim 6, wherein the compound is according to formula Va, Vb, Vd, or Ve:

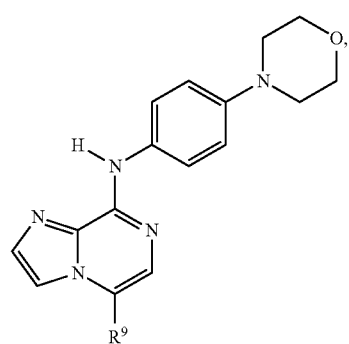
Va

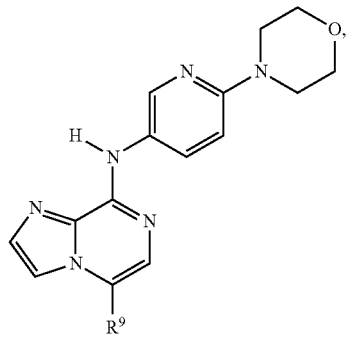
Vb

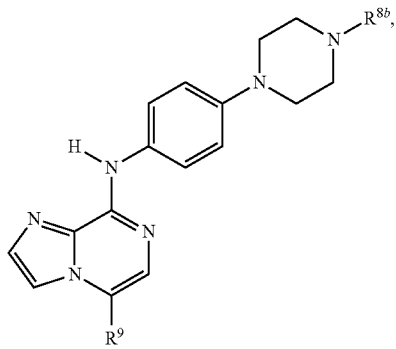
Vd

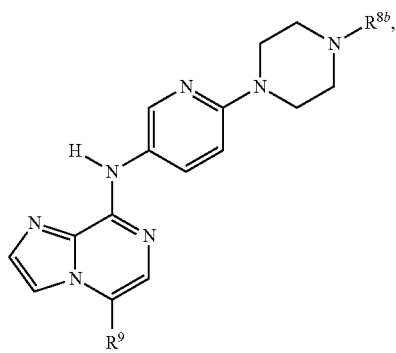
Ve and wherein $R^{8b}$ is hydrogen, substituted or unsubstituted alkyl or substituted or unsubstituted cycloalkyl.

41. A compound according to claim 7, wherein $R^8$ is

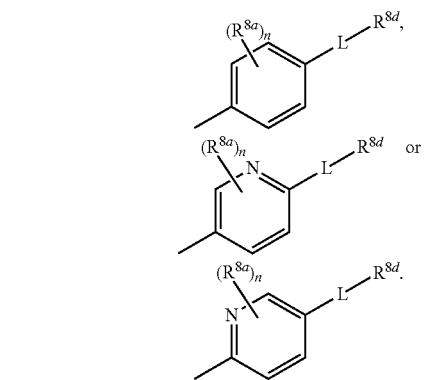

42. A compound according to formula IVa, IVb, or IVc:

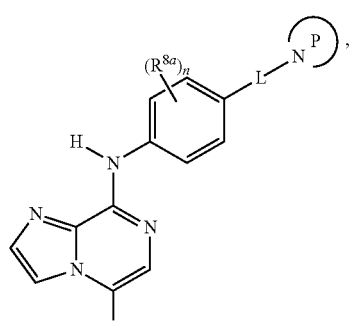

IVa

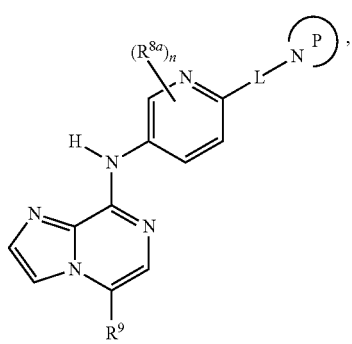

IVb

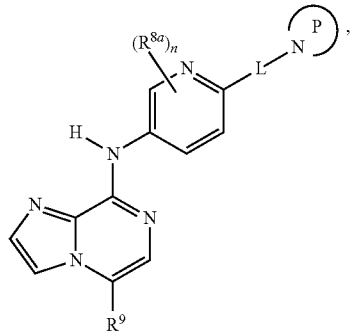

IVc and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each R$^{8a}$ is independently selected from hydrogen, substituted or unsubstituted alkyl, alkoxy, cyano, and halo; and R$^9$ is

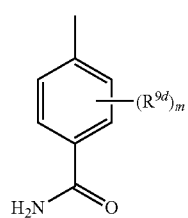

and wherein the subscript m is selected from 1-4 and each R$^{9d}$ is independently H, substituted or unsubstituted alkyl or halo; or a pharmaceutically acceptable salt, thereof; or stereoisomers or tautomers thereof.

43. A compound according to claim 7, wherein the compound is according to formula Va, Vb, Vd, or Ve:

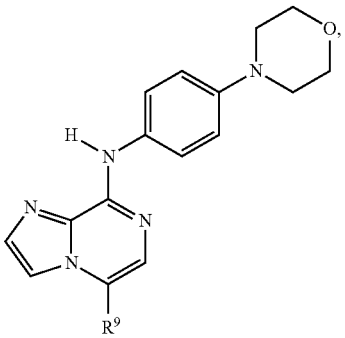

Va

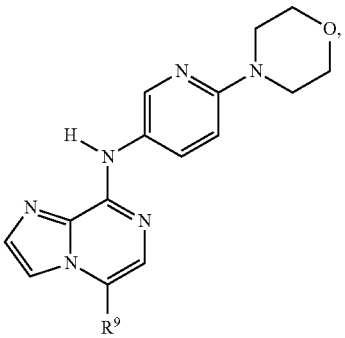

Vb

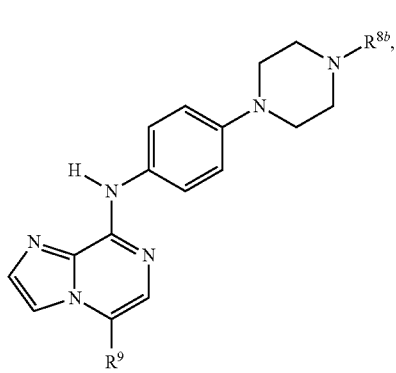

Vd

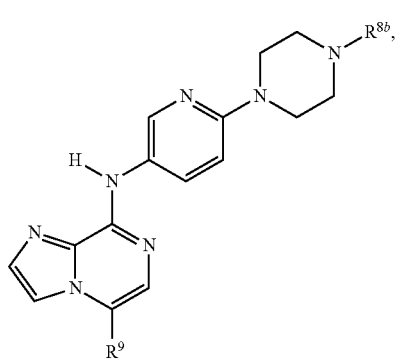

Ve and wherein R$^{8b}$ is hydrogen, substituted or unsubstituted alkyl or substituted or unsubstituted cycloalkyl.

44. A compound according to claim 8, wherein $R^8$ is

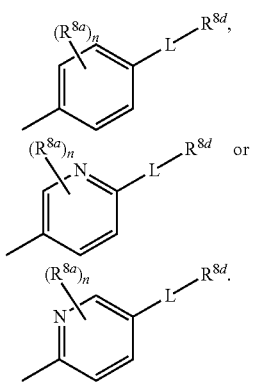

45. A compound according to formula IVa, IVb, or IVc:

IVa

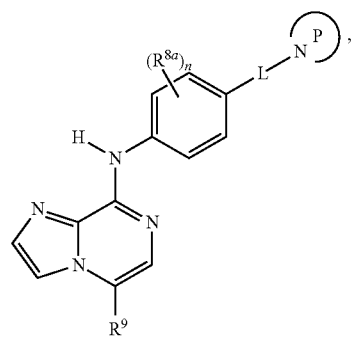

IVb

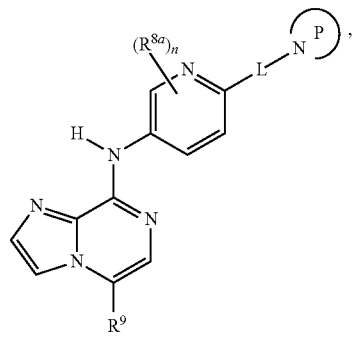

IVc

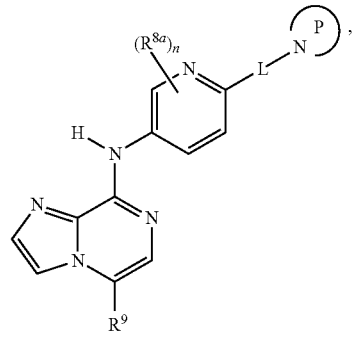

and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each $R^{8a}$ is independently selected from hydrogen, substituted or unsubstituted alkyl, alkoxy, cyano, and halo; and $R^9$ is

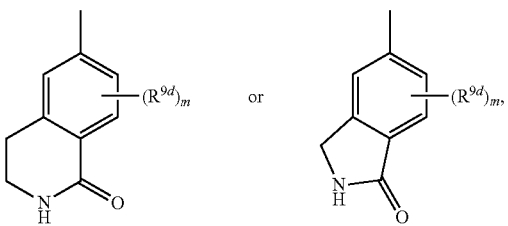

and wherein the subscript m is selected from 1-4 and each $R^{9d}$ is independently H, substituted or unsubstituted alkyl or halo; or a pharmaceutically acceptable salt, thereof; or stereoisomers or tautomers thereof.

46. A compound according to claim 8, wherein the compound is according to formula Va, Vb, Vd, or Ve:

Va

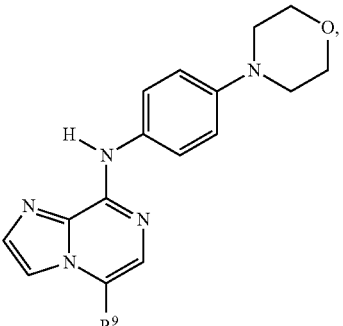

Vb

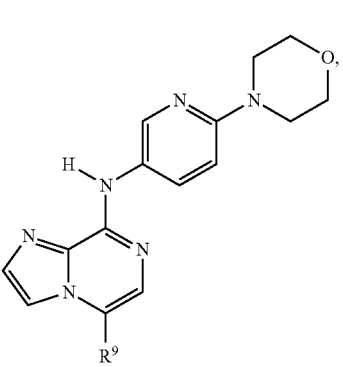

Vd

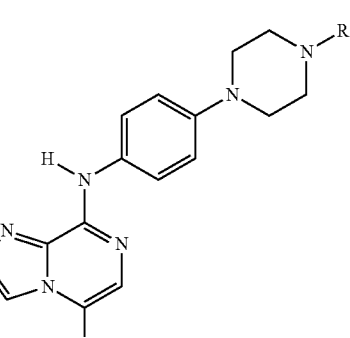

-continued

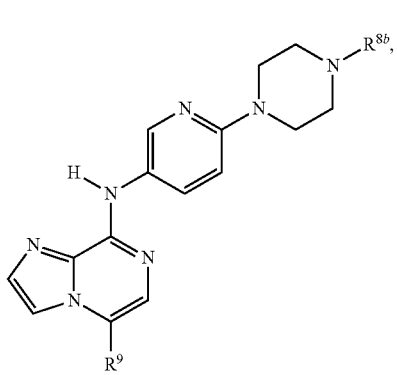
Ve and wherein $R^{8b}$ is hydrogen, substituted or unsubstituted alkyl or substituted or unsubstituted cycloalkyl.

47. A compound according to claim 9, wherein $R^8$ is

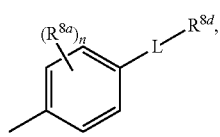

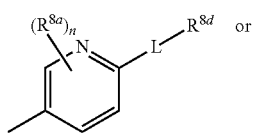 or

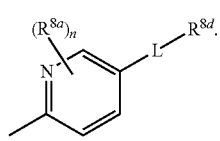

48. A compound according to formula IVa, IVb, or IVc:

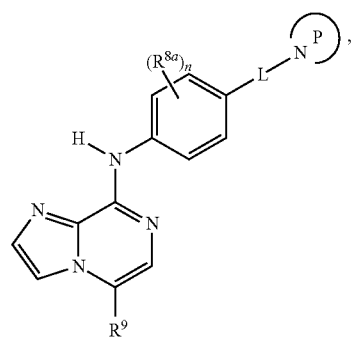
IVa

-continued

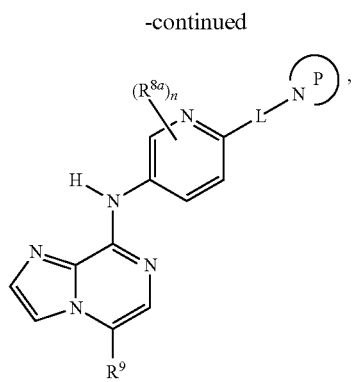
IVb

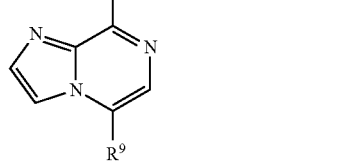
IVc

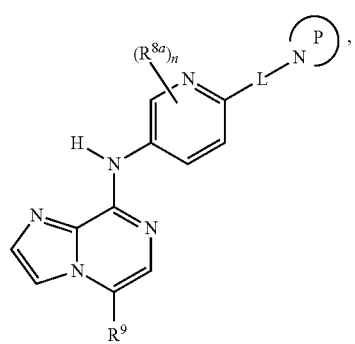

and wherein L is a single bond, —CO—, —O(CH$_2$)$_{m1}$—, —CON(H)(CH$_2$)$_{m1}$—, or —NHCO—; the subscript m1 is selected from 1-4; the ring P is substituted or unsubstituted heterocycloalkyl; the subscript n, is selected from 1-4; each $R^{8a}$ is independently selected from hydrogen, substituted or unsubstituted alkyl, alkoxy, cyano, and halo; and $R^9$ is

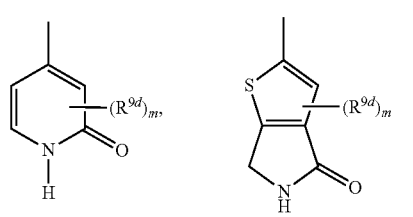 or

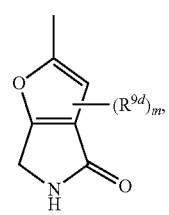

and wherein the subscript m is selected from 1-3 and each $R^{9d}$ is independently H, substituted or unsubstituted alkyl or halo; or a pharmaceutically acceptable salt, thereof; or stereoisomers or tautomers thereof.

49. A compound according to claim 9, wherein the compound is according to formula Va, Vb, Vd, or Ve:

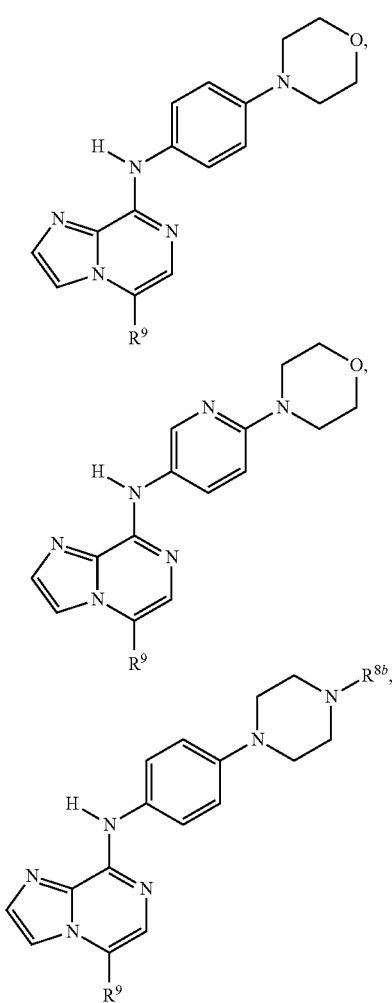

and wherein $R^{8b}$ is hydrogen, substituted or unsubstituted alkyl or substituted or unsubstituted cycloalkyl.

50. A compound according to any one of claims 7, 41, 42 and 43, wherein each $R^{9d}$ is H.

51. A compound according to any one of claims 7, 41, 42 and 43, wherein m is 1 or 2 and each $R^{9d}$ is Me, Cl or F.

52. A compound according to any one of claims 8, 44, 45 and 46, wherein each $R^{9d}$ is H.

53. A compound according to any one of claims 9, 47, 48 and 49, wherein each $R^{9d}$ is H.

54. A compound according to any one of claims 8, 44, 45 and 46, wherein m is 1 or 2 and each $R^{9d}$ is Me, Cl or F.

55. A compound according to any one of claims 9, 47, 48 and 49, wherein m is 1 or 2 and each $R^{9d}$ is Me, Cl or F.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: artificial
<220> FEATURE:
<223> OTHER INFORMATION: Knock-down sequence

<400> SEQUENCE: 1
```

-continued

```
gctgaccctg aagttcatc                                               19

<210> SEQ ID NO 2
<211> LENGTH: 19
<212> TYPE: DNA
<213> ORGANISM: artificial
<220> FEATURE:
<223> OTHER INFORMATION: Knock-down sequence

<400> SEQUENCE: 2
ggttacctaa gggtgtggc                                               19

<210> SEQ ID NO 3
<211> LENGTH: 19
<212> TYPE: DNA
<213> ORGANISM: Artificial
<220> FEATURE:
<223> OTHER INFORMATION: Knock-down sequence

<400> SEQUENCE: 3
ctctgagtgc agtgaaatc                                               19

<210> SEQ ID NO 4
<211> LENGTH: 19
<212> TYPE: DNA
<213> ORGANISM: Artificial
<220> FEATURE:
<223> OTHER INFORMATION: Knock-down sequence

<400> SEQUENCE: 4
acaagagcaa gatgtggac                                               19

<210> SEQ ID NO 5
<211> LENGTH: 19
<212> TYPE: DNA
<213> ORGANISM: artificial
<220> FEATURE:
<223> OTHER INFORMATION: Knock-down sequence

<400> SEQUENCE: 5
cggcacttta cagagaagc                                               19

<210> SEQ ID NO 6
<211> LENGTH: 19
<212> TYPE: DNA
<213> ORGANISM: Artificial
<220> FEATURE:
<223> OTHER INFORMATION: Knock-down sequence

<400> SEQUENCE: 6
atgatgtgtg ccacacacc                                               19
```